United States Patent
Accetta et al.

(10) Patent No.: US 10,501,461 B2
(45) Date of Patent: Dec. 10, 2019

(54) TYROSINE AMIDE DERIVATIVES AS RHO-KINASE INHIBITORS

(71) Applicant: CHIESI FARMACEUTICI S.P.A., Parma (IT)

(72) Inventors: Alessandro Accetta, Parma (IT); Fabio Rancati, Parma (IT); Anna Maria Capelli, Parma (IT); David Edward Clark, Saffron Walden (GB); Patrizia Tisselli, Saffron Walden (GB); Christine Edwards, Saffron Walden (GB); Gurdip Bhalay, Saffron Walden (GB); Arnaud Jean Francois Auguste Cheguillaume, Saffron Walden (GB)

(73) Assignee: CHIESI FARMACEUTICI S.P.A., Parma (IT)

( * ) Notice: Subject to any disclaimer, the term of this patent is extended or adjusted under 35 U.S.C. 154(b) by 34 days.

(21) Appl. No.: 15/883,729

(22) Filed: Jan. 30, 2018

(65) Prior Publication Data

US 2018/0215758 A1    Aug. 2, 2018

(30) Foreign Application Priority Data

Jan. 30, 2017   (EP) .................................... 17153785

(51) Int. Cl.
| | | |
|---|---|---|
| *C07D 471/04* | (2006.01) |
| *A61K 9/00* | (2006.01) |
| *A61K 31/437* | (2006.01) |
| *A61K 31/4375* | (2006.01) |
| *A61K 31/439* | (2006.01) |
| *A61K 31/444* | (2006.01) |
| *A61K 31/4725* | (2006.01) |
| *A61K 31/496* | (2006.01) |
| *A61K 31/498* | (2006.01) |
| *A61K 31/4985* | (2006.01) |
| *A61K 31/501* | (2006.01) |
| *A61K 31/519* | (2006.01) |
| *A61K 31/5377* | (2006.01) |
| *A61K 31/5383* | (2006.01) |
| *C07D 471/08* | (2006.01) |
| *C07D 498/04* | (2006.01) |
| *C07D 487/04* | (2006.01) |
| *C07D 519/00* | (2006.01) |

(52) U.S. Cl.
CPC .......... *C07D 471/04* (2013.01); *A61K 9/0073* (2013.01); *A61K 31/437* (2013.01); *A61K 31/439* (2013.01); *A61K 31/4375* (2013.01); *A61K 31/444* (2013.01); *A61K 31/4725* (2013.01); *A61K 31/496* (2013.01); *A61K 31/498* (2013.01); *A61K 31/4985* (2013.01); *A61K 31/501* (2013.01); *A61K 31/519* (2013.01); *A61K 31/5377* (2013.01); *A61K 31/5383* (2013.01); *C07D 471/08* (2013.01); *C07D 487/04* (2013.01); *C07D 498/04* (2013.01); *C07D 519/00* (2013.01)

(58) Field of Classification Search
CPC .. C07D 471/04; C07D 519/00; A61K 9/0073; A61K 31/5383; A61K 31/5377; A61K 31/519
USPC ..................................................... 1/1; 424/45
See application file for complete search history.

(56) References Cited

U.S. PATENT DOCUMENTS

2008/0139595 A1*  6/2008 Schirok ................ C07D 471/04
                                                              514/275

FOREIGN PATENT DOCUMENTS

| WO | 2005/097790 | 10/2005 |
| WO | 2006/009889 | 1/2006 |

OTHER PUBLICATIONS

European Search Report in Application No. 17153785 dated Mar. 27, 2017.
Schirok et al., Organic Process Research & Development, vol. 14, (2010) pp. 168-173.
Kast et al., British Journal of Pharmacology, vol. 152, (2007) pp. 1070-1080.
International Search Report dated Mar. 21, 2018 in PCT/EP2018/052009, 7 pages.

* cited by examiner

*Primary Examiner* — Yanzhi Zhang
(74) *Attorney, Agent, or Firm* — Oblon, McClelland, Maier & Neustadt, L.L.P.

(57) ABSTRACT

Tyrosine amide compounds of formula I described herein inhibit Rho Kinase and may be used for the treatment of many disorders associated with ROCK enzymes mechanisms, such as pulmonary diseases including asthma, chronic obstructive pulmonary disease (COPD), idiopathic pulmonary fibrosis (IPF) and pulmonary arterial hypertension (PAH).

14 Claims, No Drawings

TYROSINE AMIDE DERIVATIVES AS RHO-KINASE INHIBITORS

CROSS REFERENCES TO RELATED APPLICATIONS

This application claims priority to European Patent Application No. 17153785.5 filed on Jan. 30, 2017, which is incorporated herein by reference in its entirety.

BACKGROUND OF THE INVENTION

Field of the Invention

The present invention relates to compounds which inhibit Rho Kinase (hereinafter ROCK Inhibitors). The present invention also relates to methods of preparing such a compound, pharmaceutical compositions which contain such a compound, and therapeutic uses of such a compound.

Discussion of the Background

Rho-associated coiled-coil forming protein kinase (ROCK) belongs to the AGC (PKA/PKG/PKC) family of serine-threonine kinases. Two human isoforms of ROCK have been described, ROCK-I (also referred to as p160 ROCK or ROKβ) and ROCK-II (ROKα) are approximately 160 kDa proteins containing an N-terminal Ser/Thr kinase domain, followed by a coiled-coil structure, a pleckstrin homology domain, and a cysteine-rich region at the C-terminus (see Riento, K.; Ridley, A. J. Rocks: multifunctional kinases in cell behaviour. Nat. Rev. Mol. Cell Biol. 2003, 4, 446-456, which is incorporated herein by reference in its entirety).

Both ROCK-II and ROCK-I are expressed in many human and rodent tissues including the heart, pancreas, lung, liver, skeletal muscle, kidney and brain (see Riento, K.; Ridley, A. J. Rocks: multifunctional kinases in cell behaviour. Nat. Rev. Mol. Cell Biol. 2003, 4, 446-456, which is incorporated herein by reference in its entirety). ROCK has been identified as an effector molecule of RhoA, and is involved in a variety of cell functions, including actin organization, cell adhesion, cell migration and cytokinesis (see Riento, K.; Ridley, A. J. Rocks: multifunctional kinases in cell behaviour. Nat. Rev. Mol. Cell Biol. 2003, 4, 446-456; and Feng Y, LoGrasso P V, Defert O, Li R. Rho Kinase (ROCK) Inhibitors and Their Therapeutic Potential. J Med Chem. 2016; 59(6):2269-300, which are incorporated herein by reference in their entireties). It is also involved in regulating smooth muscle contraction, through the phosphorylation of effectors such as myosin light chain phosphatase (MLC). Indeed ROCK plays an important role in signal transduction initiated by several agents regulating smooth muscle cell contraction in blood vessels and/or airways, including serotonin, angiotensin II, endothelin I, platelet derived growth factor (PDGF) and urotensin II (see Li Q, Xu Y, Li X, Guo Y, Liu G. Inhibition of Rho-kinase ameliorates myocardial remodeling and fibrosis in pressure overload and myocardial infarction: role of TGF-β1-TAK1. Toxicol Lett. 2012; 211(2):91-7; and Shi J, Wei L. Rho kinases in cardiovascular physiology and pathophysiology: the effect of fasudil. J Cardiovasc Pharmacol. 2013; 62(4):341-54, which are incorporated herein by reference in their entireties). To date only two ROCK inhibitors have been approved for clinical use, in Japan and/or in China: Fasudil (see Suzuki Y, Shibuya M, Satoh S, Sugiyama H, Seto M, Takakura K. Safety and efficacy of fasudil monotherapy and fasudil-ozagrel combination therapy in patients with subarachnoid hemorrhage: sub-analysis of the post-marketing surveillance study. Neurol Med Chir (Tokyo). 2008; 48(6):241-7, which is incorporated herein by reference in its entirety) was approved in 1995 for the treatment of cerebral vasospasm, and ripasudil (see Tanihara H, Inoue T, Yamamoto T, Kuwayama Y, Abe H, Fukushima A, Suganami H, Araie M; K-115 Clinical Study Group. One-year clinical evaluation of 0.4% ripasudil (K-115) in patients with open-angle glaucoma and ocular hypertension. Acta Ophthalmol. 2016; 94(1):e26-34, which is incorporated herein by reference in its entirety) was approved in 2014 for the treatment of glaucoma.

ROCK mediate vasoconstriction and endothelial dysfunction are two key components of several cardiovascular diseases, including, hypertensive heart disease, coronary artery diseases, atherosclerosis, restenosis, Raynaud phenomenon, stroke and glaucoma (see Hartmann S, Ridley A J, Lutz S. The Function of Rho-Associated Kinases ROCK1 and ROCK2 in the Pathogenesis of Cardiovascular Disease. Front Pharmacol. 2015 Nov. 20; 6:276, which is incorporated herein by reference in its entirety). In particular, pharmacological data from clinical trials show that ROCK inhibitors decrease intraocular pressure and demonstrate beneficial effects in glaucoma patients (see Inoue T, Tanihara H. Rho-associated kinase inhibitors: a novel glaucoma therapy. Prog Retin Eye Res. 2013; 37:1-12, which is incorporated herein by reference in its entirety). In patients with pulmonary hypertension, ROCK activity is significantly higher in both lung tissues and circulating neutrophils as compared with controls (see Duong-Quy S, Bei Y, Liu Z, Dinh-Xuan A T. Role of Rho-kinase and its inhibitors in pulmonary hypertension. Pharmacol Ther. 2013; 137(3): 352-64, which is incorporated herein by reference in its entirety). A significant correlation was established between neutrophil ROCK activity and the severity and duration of pulmonary hypertension (see Duong-Quy S, Bei Y, Liu Z, Dinh-Xuan A T. Role of Rho-kinase and its inhibitors in pulmonary hypertension. Pharmacol Ther. 2013; 137(3): 352-64, which is incorporated herein by reference in its entirety). ROCK can also contribute to the development of cardiac fibrosis, hypertrophy, and subsequent heart failure. Recent experimental studies using ROCK inhibitors, such as fasudil, have shown the benefits of ROCK inhibition in cardiac remodeling (see Li Q, Xu Y, Li X, Guo Y, Liu G. Inhibition of Rho-kinase ameliorates myocardial remodeling and fibrosis in pressure overload and myocardial infarction: role of TGF-β1-TAK1. Toxicol Lett. 2012; 211(2):91-7, which is incorporated herein by reference in its entirety). Mice lacking each ROCK isoform also exhibit reduced myocardial fibrosis in a variety of pathological models of cardiac remodeling (see Shimizu Ti, Liao J K. Rho Kinases and Cardiac Remodeling. Circ J. 2016; 80(7):1491-8, which is incorporated herein by reference in its entirety).

ROCK is also a promising target for the treatment of cerebral vascular disorders. Indeed, preclinical studies indicate that Rho kinase inhibition may reduce the formation/growth/rupture of both intracranial aneurysms and cerebral cavernous malformations (see Bond L M, Sellers J R, McKerracher L. Rho kinase as a target for cerebral vascular disorders. Future Med Chem. 2015; 7(8):1039-53, which is incorporated herein by reference in its entirety).

RhoA-ROCK signalling is important in maintaining a flaccid penile state, and pharmacological inhibition of ROCK signalling potentiates smooth-muscle relaxation in an NO-independent manner, suggesting that ROCK is a new therapeutic target for the treatment of erectile dysfunction (see Sopko N A, Hannan J L, Bivalacqua T J. Understanding and targeting the Rho kinase pathway in erectile dysfunction. Nat Rev Urol. 2014; 11(11):622-8, which is incorporated herein by reference in its entirety).

ROCK activity is an important signaling mechanism in leucocyte-platelet-endothelium interaction, leucocyte extravasation and oedema. Overactivation of Rho kinase in endothelial cells causes leakiness by disruption of cell-cell junctions favouring inflammatory cell recruitment. Taken together, this evidence point toward a role of ROCK in pathological conditions associated with acute and chronic inflammation as well as autoimmune diseases. In particular, contribution of the ROCK pathway to autoimmunity and autoimmune disease is emerging (see Zanin-Zhorov A, Flynn R, Waksal S D, Blazar B R. Isoform-specific targeting of ROCK proteins in immune cells. Small GTPases. 2016; 7(3):173-177, which is incorporated herein by reference in its entirety). This is supported by the demonstration of the role of ROCK signaling in T-cell development and function, including adhesion, chemotactic responses, and antigen-dependent activation, as well as the beneficial effect of ROCK inhibition in experimental models of rheumatoid arthritis and lupus (see LoGrasso, P.; Feng, Y. Rho kinase inhibitors and their application to inflammatory disorders. Curr. Top. Med. Chem. 2009; 9, 704-723; Yoshimi, E.; Kumakura, F.; Hatori, C.; Hamachi, E.; Iwashita, A.; Ishii, N.; Terasawa, T.; Shimizu, Y.; Takeshita, N. Antinociceptive effects of AS1892802, a novel rho kinase inhibitor, in rat models of inflammatory and noninflammatory arthritis. J. Pharmacol. Exp. Ther. 2010, 334, 955-963; and Stirzaker R A, Biswas P S, Gupta S, Song L, Bhagat G, Pernis A B. Administration of fasudil, a ROCK inhibitor, attenuates disease in lupus-prone NZB/W F1 female mice. Lupus. 2012 May; 21(6):656-61, which are incorporated herein by reference in their entireties). The inhibitory effect of Fasudil on T-cell migration might expand its clinical application as a new therapy for multiple sclerosis (see Yu J Z, Ding J, Ma C G, Sun C H, Sun Y F, Lu C Z, Xiao B G. Therapeutic potential of experimental autoimmune encephalomyelitis by Fasudil, a Rho kinase inhibitor. J Neurosci Res. 2010; 88(8):1664-72, which is incorporated herein by reference in its entirety). Accumulating evidence also demonstrates that ROCK plays a key role in regulating three essential factors for pathogenesis of inflammatory bowel disease (IBD): disruptions of the intestinal barrier, exposure of the luminal content to mucosal immune cells and an abnormal immune response (see Huang Y, Xiao S, and Jiang Q. Role of Rho kinase signal pathway in inflammatory bowel disease Int J Clin Exp Med. 2015; 8(3): 3089-3097, which is incorporated herein by reference in its entirety). The clinical use of ROCK inhibitors is under scrutiny also in psoriasis (see Yiu Z Z, Warren R B. Novel Oral Therapies for Psoriasis and Psoriatic Arthritis. Am J Clin Dermatol. 2016; 17(3):191-200, which is incorporated herein by reference in its entirety).

There are several lines of evidence that ROCKs play a role in the pathology of diabetes. Indeed, ROCK1 KO mice exhibit insulin resistance and can have a significant increase in glucose-induced insulin secretion, leading to hyperinsulinemia (see Lee D. H., Shi J., Jeoung N. H., Kim M. S., Zabolotny J. M., Lee S. W., et al. Targeted disruption of ROCK1 causes insulin resistance in vivo. J. Biol, Chem. 2009; 284, 11776-11780, which is incorporated herein by reference in its entirety). In addition, studies in models of type 1 and type 2 diabetes have indicated blood pressure-independent nephroprotective actions of ROCKi in diabetic kidney disease (see Komers R. Rho kinase inhibition in diabetic kidney disease. Br J Clin Pharmacol. 2013; 76(4):551-9, which is incorporated herein by reference in its entirety).

There is now substantial evidence that ROCK is involved in many of the pathways that contribute to the pathologies associated with several acute and chronic pulmonary diseases, including asthma, COPD, bronchiectasis and ARDS/ALI. Given the biological effect of ROCK, selective inhibitors have the potential to treat a number of pathological mechanisms in respiratory diseases, such as smooth muscle hyper-reactivity, bronchoconstriction, airway inflammation and airway remodeling, neuromodulation and exacerbations due to respiratory tract viral infection (see Fernandes L B, Henry P J, Goldie R G. Rho kinase as a therapeutic target in the treatment of asthma and chronic obstructive pulmonary disease. Ther Adv Respir Dis. 2007 October; 1(1):25-33, which is incorporated herein by reference in its entirety). Indeed the Rho kinase inhibitor Y-27632 causes bronchodilatation and reduces pulmonary eosinophilia trafficking and airways hyperresponsiveness (see Gosens, R.; Schaafsma, D.; Nelemans, S. A.; Halayko, A. J. Rhokinase as a drug target for the treatment of airway hyperresponsiveness in asthma. Mini-Rev. Med. Chem. 2006, 6, 339-348, which is incorporated herein by reference in its entirety). Pulmonary ROCK activation has been demonstrated in humans with idiopathic pulmonary fibrosis (IPF) and in animal models of this disease. ROCK inhibitors can prevent fibrosis in these models, and more importantly, induce the regression of already established fibrosis, thus indicating ROCK inhibitors as potential powerful pharmacological agents to halt progression of pulmonary fibrosis (see Jiang, C.; Huang, H.; Liu, J.; Wang, Y.; Lu, Z.; Xu, Z. Fasudil, a rho-kinase inhibitor, attenuates bleomycin-induced pulmonary fibrosis in mice. Int. J. Mol. Sci. 2012, 13, 8293-8307, which is incorporated herein by reference in its entirety).

Accumulating evidence supports the concept that ROCK plays important roles in tumor development and progression through regulating many key cellular functions associated with malignancy, including tumorigenicity, tumor growth, metastasis, angiogenesis, tumor cell apoptosis/survival and chemoresistance (see Wei L, Surma M, Shi S, Lambert-Cheatham N, Shi J. Novel Insights into the Roles of Rho Kinase in Cancer. Arch Immunol Ther Exp (Warsz). 2016; 64(4):259-78, which is incorporated herein by reference in its entirety). Thus, indicating ROCK inhibitors also as potential powerful pharmacological agents in cancer.

The administration of an oral ROCK inhibitor effectively ameliorates clinical manifestations in experimental models of graft-vs.-host disease (GVHD) (see Biol Blood Marrow Transplant. 2014; 20(8):1104-11; and Blood. 2016; 127(17): 2144-54, which are incorporated herein by reference in their entireties). Further findings highlight the Rho kinases as rational therapeutic targets to combat tau accumulation in Progressive Supranuclear Palsy (PSP) and Corticobasal Degeneration (CBD) (see Gentry et al., J Neurosci. 2016; 36(4):1316-23, which is incorporated herein by reference in its entirety).

In various disorders of the central nervous system there is an abnormal activation of the Rho/ROCK pathway. ROCK is activated upon injury to the adult brain and spinal cord and inhibition of ROCKs results in accelerated regeneration and enhanced functional recovery after spinal-cord injury (see Kubo T, Hata K, Yamaguchi A, Yamashita T. Rho-ROCK inhibitors as emerging strategies to promote nerve regeneration. Curr Pharm Des. 2007; 13(24):2493-9, which is incorporated herein by reference in its entirety). Inhibition of the Rho/ROCK pathway has also proved to be efficacious in animal models of stroke, inflammatory and demyelinating diseases, Alzheimer's disease and neuropathic pain (reviewed by Mueller, B. K.; Mack, H.; Teusch, N. Rho kinase, a promising drug target for neurological disorders. Nat. Rev. Drug Discovery 2005, 4, 387-398, which is incorporated herein by reference in its entirety).

Various compounds have been described in the literature as Rho Kinase Inhibitors. See e.g. WO 2004/039796; WO 2006/009889; WO 2010/032875; WO 2009/079008; and WO 2014/118133, which are incorporated herein by reference in their entireties.

There remains, however, a potential for developing novel and pharmacologically improved ROCK inhibitors in many therapeutic areas such as: cardiovascular and respiratory diseases, erectile dysfunction, fibrotic diseases, insulin resistance, kidney failure, central nervous system disorders, auto-immune diseases and oncology.

In view of the number of pathological responses which are mediated by ROCK enzymes, there is a continuing need for inhibitors of such enzymes which can be useful in the treatment of many disorders.

SUMMARY OF THE INVENTION

Accordingly, it is one object of the present invention to provide novel compounds which inhibit Rho Kinase (hereinafter ROCK Inhibitors).

It is another object of the present invention to provide novel methods of preparing such a compound.

It is another object of the present invention to provide novel pharmaceutical compositions which contain such a compound.

It is another object of the present invention to provide novel therapeutic uses of such a compound.

These and other objects, which will become apparent during the following detailed description, have been achieved by the inventors' discovery that the compounds of formula (I):

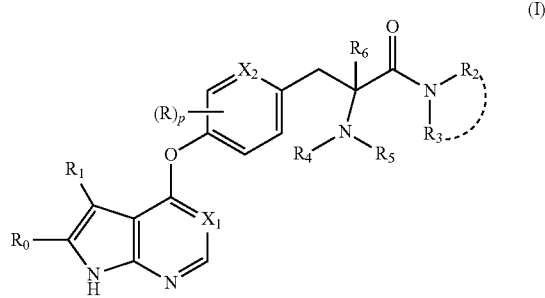

wherein $X_1$, $X_2$, R, $R_0$, $R_1$, $R_2$, $R_3$, $R_4$, $R_5$, $R_6$, and p are as reported below in the detailed description of the invention, are inhibitors of ROCK-I and ROCK-II isoforms of the Rho-associated coiled-coil forming protein kinase (ROCK).

Thus, the present invention provides novel compounds which are inhibitors of ROCK-I and ROCK-II isoforms of the Rho-associated coiled-coil forming protein kinase (ROCK) that have therapeutically desirable characteristics, particularly promising for some pulmonary diseases including asthma, chronic obstructive pulmonary disease (COPD), idiopathic pulmonary fibrosis (IPF) and pulmonary hypertension (PH) and specifically pulmonary arterial hypertension (PAH).

More particularly, the compounds of the present invention are inhibitors of the activity or function of the ROCK-I and/or ROCK-II isoforms of the Rho-associated coiled-coil forming protein kinase (ROCK).

Therefore, the compounds of the present invention may be useful in the treatment of many disorders associated with ROCK enzymes mechanisms, such as pulmonary diseases including asthma, chronic obstructive pulmonary disease (COPD), idiopathic pulmonary fibrosis (IPF) and pulmonary arterial hypertension (PAH). In one aspect the present invention provides the use of a compound of the invention for the manufacture of a medicament.

In a further aspect the present invention provides the use of a compound of the invention for the preparation of a medicament for the treatment of any disease characterized by ROCK enzyme aberrant activity and/or wherein an inhibition of activity is desirable and in particular through the selective inhibition of the ROCK enzyme isoforms over other Kinases.

Moreover the present invention provides a method for prevention and/or treatment of any disease wherein a ROCK enzyme inhibition is desirable, said method comprises administering to a patient in need of such treatment a therapeutically effective amount of a compound of the invention.

In particular the compounds of the invention alone or combined with other active ingredients may be administered for the prevention and/or treatment of a pulmonary disease including asthma, chronic obstructive pulmonary disease (COPD), idiopathic pulmonary fibrosis (IPF) and pulmonary hypertension (PH) and specifically pulmonary arterial hypertension (PAH).

DETAILED DESCRIPTION OF THE PREFERRED EMBODIMENTS

The invention is directed to a class of compounds acting as inhibitors of the Rho Kinase (ROCK).

Said class of compounds inhibits the activity or function of the ROCK enzyme and more specifically, they are inhibitors of ROCK-I and ROCK-II isoforms of the Rho-associated coiled-coil forming protein kinase (ROCK). The present invention relates to compounds of formula (I):

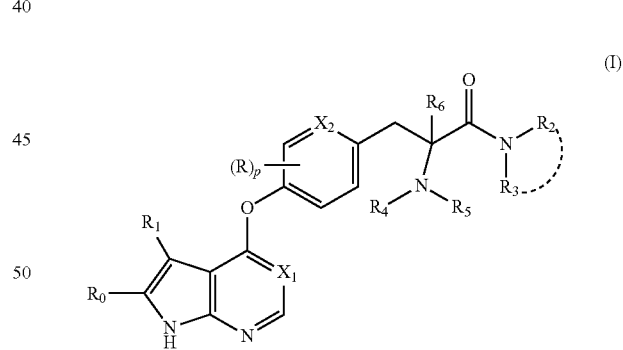

wherein $X_1$, and $X_2$ are in each occurrence independently a CH group or a nitrogen atom.

p is zero or an integer from 1 to 3;

each R, when present, is a halogen;

$R_0$ and $R_1$ are independently selected from the group consisting of

—H, halogen,

—$NR_7R_8$,

—CN, ($C_1$-$C_6$) alkyl, ($C_1$-$C_6$) haloalkyl, ($C_1$-$C_6$) hydroxyalkyl,
($C_1$-$C_6$) aminoalkyl,
($C_1$-$C_6$) alkoxy-($C_1$-$C_6$) alkyl
($C_3$-$C_{10}$) cycloalkyl,
($C_2$-$C_6$) alkenyl,
($C_5$-$C_7$) cycloalkenyl,
($C_2$-$C_6$) alkynyl,
($C_2$-$C_6$) hydroxyalkynyl,
aryl,
heteroaryl, and
($C_3$-$C_6$) heterocycloalkyl
  each of which aryl, heteroaryl and ($C_3$-$C_6$) heterocycloalkyl may be optionally and independently substituted with one or more groups selected from
halogen,
—OH,
—CN,
—$NR_7R_8$,
—$CH_2NR_7R_8$,
($C_1$-$C_6$) alkyl,
($C_1$-$C_6$) haloalkyl,
($C_1$-$C_6$) hydroxyalkyl,
($C_2$-$C_6$) alkenyl,
($C_2$-$C_6$) alkynyl,
($C_2$-$C_6$) hydroxyalkynyl;
$R_2$ and $R_3$, are the same or different, and are selected from the group consisting of
—H,
($C_1$-$C_6$) alkyl,
($C_1$-$C_6$) haloalkyl,
($C_1$-$C_6$) hydroxyalkyl,
($C_1$-$C_6$) aminoalkyl,
($C_1$-$C_6$) alkoxy ($C_1$-$C_6$) alkyl,
($C_3$-$C_{10}$)cycloalkyl,
($C_3$-$C_8$)heterocycloalkyl,
aryl,
heteroaryl,
aryl($C_1$-$C_6$)alkyl,
heteroaryl($C_1$-$C_6$)alkyl
($C_3$-$C_8$)cycloalkyl($C_1$-$C_6$)alkyl, and
($C_3$-$C_8$)heterocycloalkyl-($C_1$-$C_6$)alkyl,
  each of said aryl, heteroaryl, cycloalkyl, heterocycloalkyl may be optionally substituted by one or more groups selected independently from
halogen,
—CN,
—OH,
($C_1$-$C_8$)alkyl,
($C_1$-$C_6$) haloalkyl,
($C_1$-$C_{10}$)alkoxy,
aryl,
aryl($C_1$-$C_6$)alkyl,
carbamoyl,
($C_1$-$C_6$) aminoalkyl, and
($C_1$-$C_6$) hydroxyalkyl;
or
  $R_2$ and $R_3$, in the alternative, are taken together with the nitrogen atom they are linked to, to form a mono- or bi-cyclic saturated or partially saturated heterocyclic radical, preferably a 4 to 6 membered monocyclic radical, at least one further ring carbon atom in the said heterocyclic radical is optionally replaced by at least one further heteroatom independently selected from N, S, or O and/or may bear an -oxo (=O) substituent group, said heterocyclic radical is further optionally including spiro disubstitution as well as substitution on two adjacent or vicinal atoms forming an additional 5 to 6 membered cyclic or heterocyclic, saturated, partially saturated or aromatic ring;
    said heterocyclic radical being optionally in its turn further substituted with one or more groups selected from the group consisting of
halogen,
hydroxyl,
—$NR_7R_8$,
—$CH_2NR_7R_8$,
($C_1$-$C_6$) alkyl,
($C_1$-$C_6$) haloalkyl,
($C_1$-$C_6$) hydroxyalkyl,
($C_2$-$C_6$) alkenyl,
($C_2$-$C_6$) alkynyl,
($C_2$-$C_6$) hydroxyalkynyl,
($C_1$-$C_6$) alkoxy ($C_1$-$C_6$) alkyl,
($C_1$-$C_6$) alkanoyl,
carbamoyl,
($C_3$-$C_6$) cycloalkyl-carbonyl,
($C_3$-$C_6$) heterocycloalkyl-carbonyl,
aryl($C_1$-$C_6$)alkyl,
aryl alkanoyl,
arylsulfonyl,
heteroaryl($C_1$-$C_6$)alkyl,
heteroaryl-carbonyl
heteroaryloxyl,
($C_3$-$C_6$) cycloalkyl,
($C_3$-$C_8$)cycloalkyl($C_1$-$C_6$)alkyl
($C_3$-$C_6$) heterocycloalkyl-($C_1$-$C_6$) alkyl,
aryl, and
heteroaryl,
  each of said cycloalkyl, aryl, and heteroaryl may be optionally substituted by halogen, ($C_1$-$C_8$)alkyl, ($C_1$-$C_{10}$)alkoxy, ($C_1$-$C_6$)alkylthio, ($C_1$-$C_6$)aminoalkyl, ($C_1$-$C_6$) aminoalkoxyl, carbamoyl, or ($C_1$-$C_6$)alkyl-sulfonyl;
$R_4$ and $R_5$ are in each occurrence independently selected in the group consisting of
H,
($C_1$-$C_6$) alkyl,
($C_1$-$C_6$) haloalkyl,
($C_1$-$C_6$) hydroxyalkyl,
($C_1$-$C_6$) aminoalkyl,
($C_1$-$C_6$) alkoxyl,
($C_1$-$C_6$) alkoxy-($C_1$-$C_6$) alkyl,
($C_3$-$C_6$) cycloalkyl-($C_1$-$C_6$) alkyl
($C_3$-$C_6$) heterocycloalkyl-($C_1$-$C_6$) alkyl,
($C_3$-$C_6$) cycloalkyl-carbonyl
($C_3$-$C_6$) heterocycloalkyl-carbonyl
aryl,
heteroaryl, and
($C_3$-$C_6$) heterocycloalkyl;
  wherein any of said ($C_3$-$C_6$) cycloalkyl, aryl, heteroaryl and ($C_3$-$C_6$) heterocycloalkyl may be optionally and independently substituted with one or more groups selected from
halogen,
—OH,
($C_1$-$C_6$) alkyl;
$R_6$ is selected from the group consisting of —H, ($C_1$-$C_6$) alkyl, and ($C_1$-$C_6$) haloalkyl;
$R_7$ and $R_8$ are in each occurrence independently selected from the group
H,
($C_1$-$C_6$) alkyl,
($C_1$-$C_6$) haloalkyl,
($C_1$-$C_6$) hydroxyalkyl, ($C_1$-$C_6$) aminoalkyl,
($C_1$-$C_6$) alkoxyl,
($C_1$-$C_6$) alkoxy-($C_1$-$C_6$) alkyl,
($C_3$-$C_6$) heterocycloalkyl-($C_1$-$C_6$) alkyl,
aryl,
heteroaryl, and
($C_3$-$C_6$) heterocycloalkyl;
wherein any of said aryl, heteroaryl and ($C_3$-$C_6$) heterocycloalkyl in its turn is optionally and independently substituted with one or more groups selected from
halogen,
—OH, and
($C_1$-$C_6$) alkyl;
or
$R_7$ and $R_8$ are taken together with the nitrogen atom they are linked to, to form a 4 to 6 membered heterocyclic radical, wherein at least one further ring carbon atom in the said heterocyclic radical may be replaced by at least one group selected from N, S or O; said heterocyclic radical can be further optionally substituted by a group selected from
H,
—CN,
halogen,
oxo,
—$NR_7R_8$
($C_1$-$C_6$) alkyl,
($C_1$-$C_6$) haloalkyl,
($C_1$-$C_6$) hydroxyalkyl,
($C_1$-$C_6$) aminoalkyl,
($C_1$-$C_6$) alkoxyl,
($C_1$-$C_6$) alkoxy-($C_1$-$C_6$) alkyl, and
alkanoyl;
and pharmaceutically acceptable salts and solvates thereof.

The term "pharmaceutically acceptable salts", as used herein, refers to derivatives of compounds of formula (I) wherein the parent compound is suitably modified by converting any of the free acid or basic group, if present, into the corresponding addition salt with any base or acid conventionally intended as being pharmaceutically acceptable.

Suitable examples of said salts may thus include mineral or organic acid addition salts of basic residues such as amino groups, as well as mineral or organic basic addition salts of acid residues such as carboxylic groups.

Cations of inorganic bases which can be suitably used to prepare salts within the invention comprise ions of alkali or alkaline earth metals such as potassium, sodium, calcium or magnesium.

Those obtained by reacting the main compound, functioning as a base, with an inorganic or organic acid to form a salt comprise, for example, salts of hydrochloric acid, hydrobromic acid, sulfuric acid, phosphoric acid, methane sulfonic acid, camphor sulfonic acid, acetic acid, oxalic acid, maleic acid, fumaric acid, succinic acid and citric acid.

The term "halogen" or "halogen atoms" as used herein includes fluorine, chlorine, bromine, and iodine atom, preferably chlorine or fluorine; meaning fluoro, chloro, bromo, iodo as substituent.

The term "($C_1$-$C_6$) alkyl" refers to straight-chained or branched alkyl groups wherein the number of constituent carbon atoms is in the range 1 to 6. Particular alkyl groups are methyl, ethyl, n-propyl, isopropyl and t-butyl.

The expressions "($C_1$-$C_6$) haloalkyl" refer to the above defined "($C_1$-$C_6$)alkyl" groups wherein one or more hydrogen atoms are replaced by one or more halogen atoms, which can be the same or different from each other.

Examples of said ($C_1$-$C_6$) haloalkyl groups may thus include halogenated, poly-halogenated and fully halogenated alkyl groups wherein all of the hydrogen atoms are replaced by halogen atoms, e.g. trifluoromethyl or difluoro methyl groups.

By way of analogy, the terms "($C_1$-$C_6$) hydroxyalkyl" or "($C_1$-$C_6$) aminoalkyl" refer to the above defined "($C_1$-$C_6$) alkyl" groups wherein one or more hydrogen atoms are replaced by one or more hydroxy (OH) or amino group respectively. Non-limiting examples being respectively hydroxymethyl and aminomethyl and the like.

In the present description, unless otherwise provided, the definition of aminoalkyl encompasses alkyl groups (i.e. "($C_1$-$C_6$) alkyl" groups) substituted by one or more amino group ($NR_7R_8$). Thus, an example of aminoalkyl is a mono-aminoalkyl group such as $R_7R_8N$—($C_1$-$C_6$) alkyl.

With reference to the substituent $R_7$ and $R_8$ as above defined and below, it is here further explained that when $R_7$ and $R_8$ are taken together with the nitrogen atom they are linked to form a 4 to 6 membered heterocyclic radical, at least one further ring carbon atom in the said heterocyclic radical is optionally replaced by at least one heteroatom (e.g. N, S or O) and/or may bear -oxo (=O) substituent groups. It is understood that the said heterocyclic radical might be further optionally substituted on any available points in the ring, namely on a carbon atom, or on any heteroatom available for substitution. Substitution on a carbon atom includes spiro disubstitution as well as substitution on two adjacent carbon atoms, in both cases thus form an additional 5 to 6 membered heterocyclic ring. Thus, examples of said heterocycle radicals are 1-pyrrolidinyl, 1-piperidinyl, 1-piperazinyl, 4-morpholinyl, piperazin-4yl-2-one, 4-methylpiperazine-1-yl, 4-methylpiperazine-1-yl-2-one, 7-methyl-2,7-diazaspiro[3.5]nonan-2-yl, 2-methyl-2,9-diazaspiro[5.5]undecan-9-yl, 9-methyl-3,9-diazaspiro[5.5]undecan-3-yl, and (3aR,6aS)-5-methyl-octahydropyrrolo[3,4-c]pyrrol-2-yl, 8-methyl-2,8-diazaspiro[4,5]decane-2-yl, 5-methyloctahydropyrrolo[3,4-c]pyrrole-2-yl, and 1,1-dioxidothiomorpholin-4yl.

The term "($C_3$-$C_{10}$) cycloalkyl" likewise "($C_3$-$C_6$) cycloalkyl" refers to saturated cyclic hydrocarbon groups containing the indicated number of ring carbon atoms. Non-limiting examples include cyclopropyl, cyclobutyl, cyclopentyl, cyclohexyl and cycloheptyl, and polycyclic ring systems such as adamantan-yl.

The term "($C_2$-$C_6$) alkenyl" refers to straight or branched carbon chains with one or more double bonds, conjugated or not conjugated, in cis or trans configuration, wherein the number atoms is in the range 2 to 6.

By way of analogy, the terms "($C_5$-$C_7$) cycloalkenyl" refers to cyclic hydrocarbon groups containing from 5 to 7 ring carbon atoms and one or two double bonds.

The term "($C_2$-$C_6$) alkynyl" refers to straight or branched carbon chains with one or more triple bonds wherein the number atoms is in the range 2 to 6.

The term "($C_2$-$C_6$) hydroxyalkynyl" refers to the above defined "($C_1$-$C_6$) alkynyl" groups wherein one or more hydrogen atoms are replaced by one or more hydroxy (OH) group.

The term "($C_2$-$C_6$) aminoalkynyl" refers to the above defined "($C_1$-$C_6$) alkynyl" groups wherein one or more hydrogen atoms are replaced by one or more (—$NR_7R_8$) groups.

The expression "aryl" refers to mono, bi- or tri-cyclic carbon ring systems which have 6 to 20, preferably from 6 to 15 ring atoms, wherein at least one ring is aromatic. The expression "heteroaryl" refers to mono-, bi- or tri-cyclic ring systems with 5 to 20, preferably from 5 to 15 ring atoms, in which at least one ring is aromatic and in which at least one ring atom is a heteroatom (e.g. N, S, or O).

Examples of suitable aryl or heteroaryl monocyclic ring systems include, for instance, phenyl, thienyl, pyrrolyl, pyrazolyl, imidazolyl, isoxazolyl, oxazolyl, isothiazolyl, thiazolyl, pyridinyl, pyrimidinyl, pyrazinyl, triazinyl, furanyl radicals and the like.

Examples of suitable aryl or heteroaryl bicyclic ring systems include naphthalenyl, biphenylenyl, purinyl, pteridinyl, pyrazolopyrimidinyl, benzotriazolyl, benzoimidazole-yl, quinolinyl, isoquinolinyl, indolyl, isoindolyl, benzothiopheneyl, benzodioxinyl, dihydrobenzodioxinyl, indenyl, dihydro-indenyl, dihydrobenzo[1,4]dioxinyl, benzothiazole-2-yl, dihydrobenzodioxepinyl, benzooxazinyl radicals and the like.

Examples of suitable aryl or heteroaryl tricyclic ring systems include fluorenyl radicals as well as benzocondensed derivatives of the aforementioned heteroaryl bicyclic ring systems.

In an analogous manner, the expressions "arylene" and "heteroarylene" refer to divalent groups, such a phenylene, biphenylene and thienylene. Such groups are also commonly named as "arenediyl" or "heteroarenediyl" groups. For example o-phenylene is also named benzene-1,2-diyl. Thienyl-ene is alternatively named thiophenediyl.

The derived expression "$(C_3-C_6)$ heterocycloalkyl" refers to saturated or partially unsaturated monocyclic $(C_3-C_6)$ cycloalkyl groups in which at least one ring carbon atom is replaced by at least one heteroatom (e.g. N, S, or O) or may bear an -oxo (=O) substituent group. The said heterocycloalkyl (i.e. heterocyclic radical or group) might be further optionally substituted on the available points in the ring, namely on a carbon atom, or on an heteroatom available for substitution. Substitution on a carbon atom includes Spiro disubstitution as well as substitution on two adjacent carbon atoms, in both cases thus form additional condensed 5 to 6 membered heterocyclic ring. Non-limiting examples of $(C_3-C_6)$ heterocycloalkyl are represented by: pyrrolidinyl, imidazolidinyl, thiazolidinyl, piperazinyl, piperidinyl, morpholinyl, thiomorpholinyl, dihydro- or tetrahydro-pyridinyl, tetrahydropyranyl, pyranyl, 2H- or 4H-pyranyl, dihydro- or tetrahydrofuranyl, dihydroisoxazolyl, pyrrolidin-2-one-yl, dihydropyrrolyl radicals and the like.

Specific examples of said heterocycle radicals are 1-pyrrolidinyl, 1-methyl-2-pyrrolidinyl, 1-piperidinyl, 1-piperazinyl, 4-morpholinyl, piperazin-4yl-2-one, 4-methylpiperazine-1-yl, 1-methylpiperidin-4yl, 4-methylpiperazine-1-yl-2-one, 7-methyl-2,7-diazaspiro[3.5]nonan-2-yl, 2-methyl-2,9-diazaspiro[5.5]undecan-9-yl, 9-methyl-3,9-diazaspiro[5.5]undecan-3-yl, and (3aR,6aS)-5-methyl-octahydropyrrolo[3,4-c]pyrrol-2-yl.

The term "aryl $(C_1-C_6)$ alkyl" refers to an aryl ring linked to a straight-chained or branched alkyl groups wherein the number of constituent carbon atoms is in the range from 1 to 6, e.g. phenylmethyl (i.e. benzyl), phenylethyl, or phenylpropyl.

Likewise the term "heteroaryl $(C_1-C_6)$ alkyl" refers to an heteroaryl ring linked to a straight-chained or branched alkyl groups wherein the number of constituent carbon atoms is in the range from 1 to 6, e.g. furanylmethyl.

The term "alkanoyl", refers to HC(O)— or to alkylcarbonyl groups (e.g. $(C_1-C_6)$alkylC(O)— wherein the group "alkyl" has the meaning above defined. Non-limiting examples include formyl, acetyl, propanoyl, and butanoyl.

Likewise "$(C_1-C_6)$alkyl-sulfonyl" refers to a"$(C_1-C_6)$ alkyl-S(O)$_2$ group wherein alkyl has the meaning above defined. Non-limiting examples are represented by methylsulfonyl.

The term "carbamoyl" refers to amino carbonyl derived groups —C(O)NR$_7$R$_8$, wherein R$_7$ and R$_8$ are as defined above in the definition of aminoalkyl groups and including substituted (preferred aminoalkyl substituted) and Spiro substituted derivatives. Non-limiting examples of such carbamoyl groups being aminocarbonyl, piperazine-1-carbonyl, morpholine-N-carbonyl, morpholine-N-carbonyl and N-(2-(dimethylamino)ethyl)aminocarbonyl, N-(2-(dimethylamino)ethyl)-N-methylaminocarbonyl, N-(3-(dimethylamino)propyl)-N-methylaminocarbonyl, 4-methylpiperazine-1-carbonyl, 4-(dimethylamino)piperidin-1-carbonyl, N-(2-(4-methylpiperazin-1-yl)ethyl)aminocarbonyl, (2 morpholino-ethyl) aminocarbonyl, N-methyl-N-(2 morpholino-ethyl) aminocarbonyl, N-(2-(piperidin-1-yl)ethyl) aminocarbonyl, N-methyl-N-(2-(piperidin-1-yl)ethyl)aminocarbonyl, N-(1-methylpiperidin-4-yl-methyl) aminocarbonyl, N-methyl-N-(1-methylpiperidin-4-yl)aminocarbonyl, N-methyl-N-(1-methylpiperidin-4-yl)aminocarbonyl, 5-methyloctahydropyrrolo[3,4-c]pyrrole-2 carbonyl.

The term "hydroxycarbonyl" refers to a terminal group HOC(O)—.

The term "$(C_1-C_{10})$ alkoxy" or "$(C_1-C_{10})$ alkoxyl", likewise "$(C_1-C_6)$ alkoxy" or "$(C_1-C_6)$ alkoxyl" etc., refers to a straight or branched hydrocarbon of the indicated number of carbons, attached to the rest of the molecule through an oxygen bridge. Likewise "$(C_1-C_6)$alkylthio" refers to the above hydrocarbon attached through a sulfur bridge.

The derived expression "$(C_1-C_6)$ haloalkoxy" or "$(C_1-C_6)$ haloalkoxyl" refers to the above defined haloalkyl, attached through an oxygen bridge. Non-limiting example being trifluoromethoxy.

By analogy, derived expressions "$(C_3-C_6)$ heterocycloalkyloxyl" and "$(C_3-C_6)$ heterocycloalkyl $(C_1-C_6)$ alkoxyl" refer to heterocycloalkyl groups attached through an oxygen bridge and chained heterocycloalkyl-alkoxyl groups respectively. Non-limiting examples of such $(C_3-C_6)$ heterocycloalkyloxyl and $(C_3-C_6)$ heterocycloalkyl $(C_1-C_6)$ alkoxyl groups are respectively (piperidin-4-yl)oxy, 1-methylpiperidin-4-yl)oxy, 2-(piperidin-4-yl)ethoxyl, 2-(1-methylpiperidin-4-yl)ethoxy, and 2-(4-morpholino)ethoxy.

The derived expressions "aryloxyl" and "aryl $(C_1-C_6)$ alkoxyl" likewise "heteroaryloxyl" and "heteroaryl $(C_1-C_6)$ alkoxyl" refer to aryl or heteroaryl groups attached through an oxygen bridge and chained aryl-alkoxyl or heteroaryl-alkoxyl groups. Non-limiting examples of such are phenyloxy and benzyloxy and pyridinyloxy respectively.

Likewise, derived expression "$(C_3-C_6)$ heterocycloalkyl-$(C_1-C_6)$ alkyl" and "$(C_3-C_6)$ cycloalkyl-$(C_1-C_6)$ alkyl" refer to the above defined heterocycloalkyl and cycloalkyl groups attached to the rest of the molecule via an alkyl group of the indicated number of carbons. Non-limiting examples being piperidin-4-yl-methyl and cyclohexylethyl.

The derived expression "$(C_1-C_6)$ alkoxy-$(C_1-C_6)$ alkyl" refers to the above defined alkoxy group attached to the rest of the molecule via an alkyl group of the indicated number of carbons. Non-limiting examples being methoxymethyl.

The derived expression "$(C_1-C_6)$ alkoxycarbonyl" refers to the above defined alkoxy group attached to the rest of the molecule via a carbonyl group. Non-limiting examples being ethoxycarbonyl.

Further derived expression like "$(C_1-C_6)$ alkoxycarbonyl-amino" refers to the above defined alkoxy group attached to the rest of the molecule via a carbonyl group followed by an amino group (—NR$_7$—). Non limiting example being tert-butoxy-carbonyl-amino-.

Thus, "(C$_1$-C$_6$) alkoxycarbonyl (C$_3$-C$_6$) heterocycloalkyl (C$_1$-C$_6$) alkyl" refers to alkoxy carbonyl heterocycloalkyl substituents enchained in the said order and attached to the rest of the molecule via an alkyl group of the indicated number of carbons. Non limiting example being (tert-butyl piperidine-1-carboxylate)-4 yl-methyl.

The derived expression "(C$_1$-C$_6$) aminoalkoxyl" refers to (C$_1$-C$_6$) aminoalkyl groups as above defined attached through an oxygen bridge. A non-limiting example is (2-(dimethylamino)ethoxy.

And the expression "(C$_1$-C$_6$) hydroxyalkoxyl" refers to hydroxyalkyl groups as above defined attached to the rest of the molecule through an oxygen bridge. A non-limiting example being hydroxyethoxy.

The derived expression "(C$_1$-C$_6$) aminoalkylcarbamoyl" refers to a "carbamoyl" group, as above defined, substituted with a (C$_1$-C$_6$) aminoalkyl group (i.e. —C(O)NR$_7$R$_8$ wherein e.g. R$_8$ is an (C$_1$-C$_6$) aminoalkyl).

A non-limiting examples being 2(dimethylamino) ethyl carbamoyl.

The term "aryl alkanoyl" refers to an arylC(O) or arylalkylcarbonyl group (e.g. aryl(C$_1$-C$_6$)alkylC(O)—] wherein aryl and alkyl have the meaning above defined. Non-limiting examples are represented by benzoyl, phenylacetyl, phenylpropanoyl or phenylbutanoyl radicals. Likewise "aryl sulfonyl'" refers to an arylS(O)$_2$ group wherein aryl has the meaning above defined. Non limiting examples are represented by phenylsulfonyl.

Further likewise, enchained substituents derive their definition from the composing fragments, like in the above provided definitions, such as "(C$_3$-C$_6$) cycloalkyl-carbonyl".

"(C$_3$-C$_6$) heterocycloalkyl-carbonyl" and "heteroaryl-carbonyl"; refer to the above defined fragments attached to the rest of the molecule via a carbonyl group. Non-limiting examples of such groups being cyclopropanecarbonyl, pyrrolidine-3-carbonyl, (pyridin-3-yl)carbonyl.

The expression "saturated, partially unsaturated or aromatic, five or six membered cycloalkane-diyl, arylene-diyl or heterocycle-diyl" refers to suitable disubstituted cycloalkane or heterocycle or aromatic residue with five or six elements including 1,2-, 1,3- or 1,4-benzene-diyl; 2,3-, 3,4-, 4,5- or 5,6-pyridine-diyl; 3,4-, 4,5- or 5,6-pyridazine-diyl; 4,5- or 5,6-pyrimidine-diyl; 2,3-pyrazinediyl; 2,3-, 3,4- or 4,5-thiophene-diyl/furane-diyl/pyrrole-diyl; 4,5-imidazole-diyl/oxazole-diyl/thiazolediyl; 3,4- or 4,5-pyrazole-diyl/isoxazolediyl/isothiazole-diyl their saturated or partially unsaturated analogues and the like. Other non-vicinal disubstituted residues (diradical) are included too, such as 4,6-pyrimidine-diyl and the like.

As used herein, the expression "ring system" refers to mono- or bicyclic or polycyclic ring systems which may be saturated, partially unsaturated or unsaturated, such as aryl, (C$_3$-C$_{10}$) cycloalkyl, (C$_3$-C$_6$) heterocycloalkyl or heteroaryl.

As used herein the terms "group", "radical" or "fragment" or "substituent" are synonymous and are intended to indicate functional groups or fragments of molecules attachable to a bond or other fragments or molecules. Thus, as an example, a "heterocyclic radical" herein refers to a mono- or bi-cyclic saturated or partially saturated heterocyclic moiety (group, radical), preferably a 4 to 6 membered monocyclic radical, at least one further ring carbon atom in the said heterocyclic radical is optionally replaced by at least one further heteroatom independently selected from N, S, or O and/or may bear an -oxo (═O) substituent group, said heterocyclic radical is further optionally including spiro disubstitution as well as substitution on two adjacent or vicinal atoms forming an additional 5 to 6 membered cyclic or heterocyclic, saturated, partially saturated or aromatic ring. Thus, Examples of said heterocycle radicals are 1-pyrrolidinyl, 1-piperidinyl, 1-piperazinyl, 4-morpholinyl, piperazin-4yl-2-one, 4-methylpiperazine-1-yl, 4-methylpiperazine-1-yl-2-one, 7-methyl-2,7-diazaspiro[3.5]nonan-2-yl, 2-methyl-2,9-diazaspiro[5.5]undecan-9-yl, 9-methyl-3,9-diazaspiro[5.5]undecan-3-yl, and (3aR,6aS)-5-methyl-octahydropyrrolo[3,4-c]pyrrol-2-yl and the like.

A dash ("-") that is not between two letters or symbols is meant to represent the point of attachment for a substituent. When graphically represented the point of attachment in a cyclic functional group is indicated with a dot ("•") localized in one of the available ring atom where the functional group is attachable to a bond or other fragment of molecules.

As used herein an oxo moiety is represented by (O) as an alternative to the other common representation, e.g. (═O). Thus, in terms of general formula, the carbonyl group is herein preferably represented as —C(O)— as an alternative to the other common representations such as —CO—, —(CO)—, or —C(═O)—. In general the bracketed group is a lateral group, not included into the chain, and brackets are used, when deemed useful, to help disambiguating linear chemical formulas; e.g. the sulfonyl group —SO$_2$— might be also represented as —S(O)$_2$— to distinguish e.g. with respect to the sulfinic group —S(O)O—.

When a numerical index is used like in the statement "p is zero or an integer from 1 to 3" the statement (value) "p is zero" means that the substituent R is absent, that is to say there is no substituent R on the ring.

Whenever basic amino or quaternary ammonium groups are present in the compounds of formula I, physiological acceptable anions, selected among chloride, bromide, iodide, trifluoroacetate, formate, sulfate, phosphate, methanesulfonate, nitrate, maleate, acetate, citrate, fumarate, tartrate, oxalate, succinate, benzoate, p-toluenesulfonate, pamoate and naphthalene disulfonate may be present. Likewise, in the presence of acidic groups such as COOH groups, corresponding physiological cation salts may be present as well, for instance including alkaline or alkaline earth metal ions.

It will be apparent to those skilled in the art that compounds of formula (I) when contain one or more stereogenic center, may exist as optical stereoisomers.

Where the compounds according to the invention have at least one stereogenic center, they may accordingly exist as enantiomers. Where the compounds according to the invention possess two or more stereogenic centers, they may additionally exist as diastereoisomers. It is to be understood that all such single enantiomers, diastereoisomers and mixtures thereof in any proportion are encompassed within the scope of the present invention. The absolute configuration (R) or (S) for carbon bearing a stereogenic center is assigned on the basis of Cahn-Ingold-Prelog nomenclature rules based on groups' priorities.

Atropisomers are resulting from hindered rotation about single bonds where the steric strain barrier to rotation is high enough to allow for the isolation of the conformers (see Bringmann G et al, Angew. Chemie Int, Ed., 44 (34), 5384-5427, 2005, doi:10.1002/anie.200462661, which is incorporated herein by reference in its entirety).

Oki defined atropisomers as conformers that interconvert with a half-life of more than 1000 seconds at a given temperature (see Oki M, Topics in Stereochemistry 14, 1-82, 1983, which is incorporated herein by reference in its entirety).

Atropisomers differ from other chiral compounds in that in many cases they can be equilibrated thermally whereas in the other forms of chirality isomerization is usually only possible chemically.

Separation of atropisomers is possible by chiral resolution methods such as selective crystallization. In an atropo-enantioselective or atroposelective synthesis one atropisomer is formed at the expense of the other. Atroposelective synthesis may be carried out by use of chiral auxiliaries like a Corey Bakshi Shibata (CBS) catalyst, an asymmetric catalyst derived from proline, or by approaches based on thermodynamic equilibration when an isomerization reaction favors one atropisomer over the other.

Racemic forms of compounds of formula (I) as well as the individual atropisomers (substantially free of its corresponding enantiomer) and stereoisomer-enriched atropisomers mixtures are included in the scope of the present invention.

The invention further concerns the corresponding deuterated derivatives of compounds of formula (I) that are included in the scope of the present invention. In the context of the present invention, the term deuterated derivatives refers to compounds in which at least one hydrogen atom is replaced with deuterium at a level above the natural abundance of deuterium. Suitably, the degree of deuteration is at least 50%, preferably at least 75%, more preferably at least 90%, even more preferably at least 95%. The degree of deuteration may be 100%, less than 100%, less than 99%, or less than 95%. Suitably, the compound is deuterated at one or more exchangeable hydrogen atoms, such as a hydroxyl hydrogen atom, a carboxyl hydrogen atom, an amino hydrogen atom, an amide hydrogen atom, or a thiol hydrogen atom.

It is to be understood that all preferred groups or embodiments described above and herebelow for compounds of formula I may be combined among each other and apply as well mutatis mutandis.

In a preferred embodiment, the present invention is directed to compounds of formula (I) as above defined wherein each of $X_1$ and $X_2$ is a CH; represented by formula Ia:

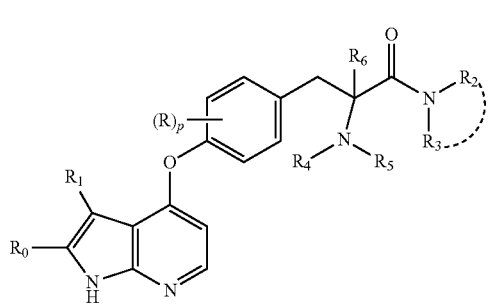

Ia

In a second preferred embodiment, the invention is directed to compounds of formula (I) as above defined wherein $R_2$ and $R_3$, are taken together with the nitrogen atom they are linked to, to form a mono-cyclic saturated heterocyclic radical, which is a piperazine ring; represented by formula Ib:

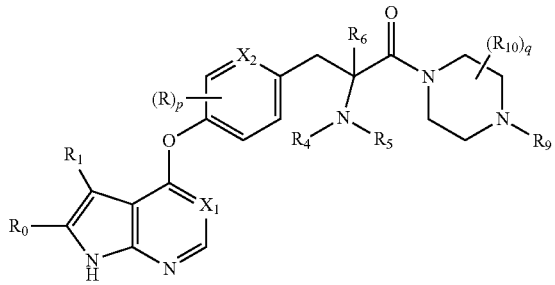

Ib wherein $R_9$ is selected from the group consisting of
$(C_1-C_6)$ alkyl,
$(C_1-C_6)$ alkoxy$(C_1-C_6)$ alkyl,
$(C_1-C_6)$ alkanoyl,
carbamoyl,
$(C_3-C_6)$ cycloalkyl-carbonyl,
$(C_3-C_6)$ heterocycloalkyl-carbonyl,
aryl$(C_1-C_6)$alkyl,
aryl alkanoyl,
arylsulfonyl,
heteroaryl$(C_1-C_6)$alkyl,
heteroaryl-carbonyl,
heteroaryloxyl,
$(C_3-C_6)$ cycloalkyl,
$(C_3-C_8)$cycloalkyl$(C_1-C_6)$alkyl
$(C_3-C_6)$ heterocycloalkyl-$(C_1-C_6)$ alkyl,
aryl, and
heteroaryl
each of said cycloalkyl, heterocycloalkyl, aryl and heteroaryl being further optionally substituted by one or more of halogen, $(C_1-C_8)$alkyl, $(C_1-C_{10})$alkoxy, $(C_1-C_6)$alkylthio, $(C_1-C_6)$ aminoalkyl, $(C_1-C_6)$ aminoalkoxyl, carbamoyl, $(C_1-C_6)$alkyl-sulfonyl;

and wherein said piperazine ring is further optionally substituted by one or more substituent group $R_{10}$ selected from the group consisting of $(C_1-C_6)$ alkyl, $(C_1-C_6)$ hydroxyalkyl, and aryl;
all the other variables being as defined above.

In a third preferred embodiment, the invention is directed to compounds of formula (I) as above defined,

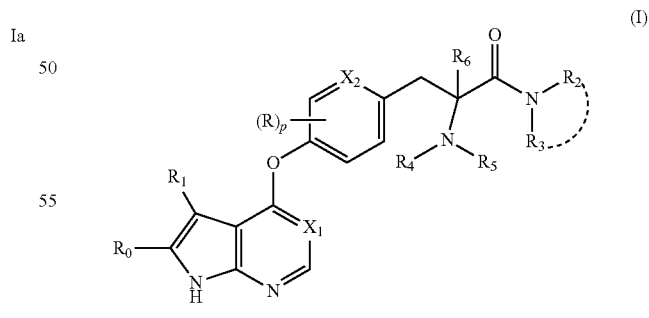

(I)

wherein
$X_1$, and $X_2$ are both a CH group;
p is zero or an integer from 1 to 3
each R, when present, is a halogen;
$R_0$ is —H, and
$R_1$ is independently selected from the group consisting of
—CN, ($C_1$-$C_6$) alkyl, and
($C_1$-$C_6$) hydroxyalkyl,
$R_2$ is —H, and
$R_3$, is selected from the group consisting of
($C_3$-$C_{10}$)cycloalkyl,
($C_3$-$C_8$)heterocycloalkyl, and
heteroaryl($C_1$-$C_6$)alkyl;
each of said heteroaryl, cycloalkyl, heterocycloalkyl is further optionally substituted by one or more ($C_1$-$C_8$)alkyl or ($C_1$-$C_6$) hydroxyalkyl;
$R_4$ and $R_5$ are both H, and
$R_6$ is —H;
and pharmaceutically acceptable salt and solvates thereof.

A preferred group of compounds according to the invention are compounds of formula (I)
wherein
$X_1$, and $X_2$ are in each occurrence independently a CH group or a nitrogen atom;
p is zero or an integer from 1 to 3;
each R, when present, is fluoro;
$R_0$ is —H or ($C_1$-$C_6$) alkyl which is methyl, and
$R_1$ is independently selected from the group consisting of
—H,
halogen which is Bromo, Chloro, Iodo, Fluoro
$NR_7R_8$,
—CN,
($C_1$-$C_6$) alkyl which is methyl,
($C_1$-$C_6$) haloalkyl,
($C_1$-$C_6$) hydroxyalkyl which is hydroxymethyl, hydroxyethyl
($C_1$-$C_6$) aminoalkyl,
($C_1$-$C_6$) alkoxy-($C_1$-$C_6$) alkyl which is methoxymethyl
($C_3$-$C_{10}$) cycloalkyl which is cyclopropyl,
($C_2$-$C_6$) alkenyl,
($C_5$-$C_7$) cycloalkenyl,
($C_2$-$C_6$) alkynyl,
($C_2$-$C_6$) hydroxyalkynyl which is hydroxypropynyl,
aryl which is phenyl or hydroxyphenyl,
heteroaryl which is isoxazolyl, N-methylimidazolyl, pyridinyl, thiazolyl, N-ethyl pyrazolyl, or thiopheneylcarbonitrile, and
($C_3$-$C_6$) heterocycloalkyl which is dihydropyrrolyl or dihydrofuranyl,
$R_2$ is —H or ($C_1$-$C_6$) alkyl which is methyl, and
$R_3$, is independently selected from the group consisting of
($C_1$-$C_6$) alkyl which is methyl,
($C_1$-$C_6$) haloalkyl,
($C_1$-$C_6$) hydroxyalkyl,
($C_1$-$C_6$) aminoalkyl which is dimethylaminoethyl, dimethylaminopropyl,
($C_1$-$C_6$) alkoxy ($C_1$-$C_6$) alkyl which is methoxypropyl,
($C_3$-$C_{10}$)cycloalkyl which is cyclohexyl, hydroxymethylcyclohexyl, hydroxyethylcyclohexyl, cyano-cyclohexyl, 4-aminocarbonyl-cyclohexane-4yl, or 4-dimethylaminomethyl-cyclohexane-4yl,
($C_3$-$C_3$)heterocycloalkyl which is N-methylpiperidinyl, (hydroxymethyl)-N-methylpiperidinyl, N-benzylpiperidinyl, N-methylazetidin-3-yl, tetrahydropyranyl, 4-hydroxymethyl-tetrahydropyran-4-yl, quinuclidinyl, aryl which is phenyl, trifluoromethylphenyl, dihydroindenyl, heteroaryl which is thiazolyl, pyridinyl, chloropyridinyl, or isoquinolinyl,
aryl($C_1$-$C_6$)alkyl which is benzyl, o-, m-, p-hydroxymethylbenzyl, or phenethyl,
heteroaryl($C_1$-$C_6$)alkyl which is (pyridinyl)ethyl, (thiophene-yl)methyl, or (N-phenyl-pyrazolyl)ethyl,
($C_3$-$C_8$)cycloalkyl($C_1$-$C_6$)alkyl which is cyclohexylmethyl,
($C_3$-$C_8$)heterocycloalkyl-($C_1$-$C_6$)alkyl which is (piperidin-4-yl)methyl, (N-benzylpiperidinyl)methyl, (N-methylpiperidin-4-yl)methyl, N-methylazetidin-3-yl-methyl, morpholinopropyl; or
$R_2$ and $R_3$, in the alternative, taken together with the nitrogen atom they are linked to, form a mono-cyclic group which is piperazin-N-yl, methylpiperazin-N-yl, phenyl-N-methylpiperazin-N-yl, N-phenyl-piperazin-N-yl, trimethylpiperazin-N-yl, 4-benzyl-3,5-dimethylpiperazin-N-yl, (hydroxymethyl)-N-methylpiperazin-N-yl, acetyl(piperazin-N-yl), phenylacetyl(piperazin-N-yl), benzoyl(piperazin-N-yl), 4-(((dimethylamino)methyl)benzoyl)piperazin-1-yl, cyclopropyl(piperazin-N-yl), cyclopropylmethyl(piperazin-N-yl), cyclopropanecarbonyl(piperazin-N-yl), cyclohexanecarbonyl(piperazin-N-yl), N-methylpiperidine-4-carbonyl(piperazin-N-yl), 4-(pyridine-3-carbonyl)piperazin-N-yl, 4-(1methyl-1H-pyrazole-4-carbonyl)piperazin-N-yl, 4-(1methyl-1H-imidazole-4-carbonyl)piperazin-N-yl, 4-(1H-thiazole-4-carbonyl)piperazin-N-yl, 4-dimethylaminocarbonyl(piperazin-N-yl), (phenylsulfonyl)piperazin-N-yl, (pyridinyl)piperazin-N-yl, (pyridinylmethyl)piperazin-N-yl, (methoxyethyl)piperazin-N-yl, (benzyl)piperazin-N-yl, (methoxybenzyl)piperazin-N-yl, (3-(dimethylaminopropoxy)benzyl)piperazin-N-yl, (fluorobenzyl)piperazin-N-yl, (methylbenzyl)piperazin-N-yl, N-(((methylaminocarbonyl)phenyl)methyl)piperazine-N-yl, N-(((methylaminocarbonyl)furanyl)methyl)piperazine-N-yl, (phenethyl)piperazin-N-yl, (pyrimidinylmethyl)piperazin-N-yl, (2(methylthio)pyrimidinylmethyl)piperazin-N-yl, (((methylsulfonyl)piperidin-4-yl)methyl)piperazin-N-yl, ((N-methyl-imidazol-5-yl)methyl)piperazin-N-yl, ((1-methyl-1H-imidazol-2-yl)methyl)piperazin-N-yl, ((methylthiazolyl)methyl)piperazin-N-yl, ((pyrazin-2-yl)methyl)piperazin-N-yl, ((1-methyl-1H-pyrazol-4-yl)methyl)piperazin-N-yl, benzo[d][1,3]dioxol-5-ylmethyl)piperazin-N-yl, (quinoxalin-2-ylmethyl)piperazin-N-yl, ((1,2,3-thiadiazol-4-yl)methyl)piperazin-N-yl, (pyridazin-4-ylmethyl)piperazin-N-yl, pyrrolidin-N-yl, phenylpyrrolidin-N-yl, (pyridinyl)pyrrolidin-N-yl, piperidin-N-yl, (dimethylamino)piperidin-N-yl, 4-((dimethylamino)methyl)piperidin-N-yl, benzylpiperidin-N-yl, benzylhydroxypiperidin-N-yl, pyridinylpiperidin-N-yl, pyridinyloxypiperidin-N-yl, (phenylsulfonyl)piperidin-N-yl, 4-phenyl-5,6-dihydropyridin-1(2H)-yl, phenylmorpholin-N-yl, 3-(dimethylamino)azetidin-N-yl, 3-(dimethylamino)methyl-azetidin-N-yl, 3-(dimethylamino)pyrrolidin-N-yl, 3-(3-methyl-1,2,4-oxadiazol-5-yl)pyrrolidin-N-yl 3-(dimethylamino)piperidin-N-yl,
or a bi-cyclic group which is 5,6-dihydroimidazo[1,5-a]pyrazin-7(8H)-yl, 3,4-dihydro-2,7-naphthyridin-2(1H)-yl), 1H-pyrrolo[3,4-c]pyridin-2(3H)-yl, hexahydropyrazino[2,1-c][1,4]oxazin-8(1H)-yl, 3,4-dihydroisoquinolin-2(1H)-yl, 5-methyl-2,5-diazabicyclo[2.2.1]heptan-2-yl, 5-benzyl-2,5-diazabicyclo[2.2.1]heptan-2-yl, 7,8-dihydropyrido[4,3-d]pyrimidin-6(5H)-yl), 2,6-diazaspiro[3.3]heptan-2-yl, 6-methyl-2,6-diazaspiro[3.3]heptan-2-yl, 7-methyl-2,7-diazaspiro[3.5]nonan-2-yl, 2-methyl-2,9-diazaspiro[5.5]undecan-9-yl, 9-methyl-3,9-diazaspiro[5.5]undecan-3-yl, octahydropyrrolo[3,4-c]pyrrol-2-yl or 5-methyl-octahydropyrrolo[3,4-c]pyrrol-2-yl;
$R_4$ is selected in the group consisting of H, ($C_1$-$C_6$) alkyl which is methyl, ($C_3$-$C_6$) cycloalkyl-($C_1$-$C_6$) which is cyclohexylmethyl, and ($C_3$-$C_6$) cycloalkyl-carbonyl which is cyclohexylcarbonyl or (pyrrolidin-3-yl)carbonyl; and
$R_5$ is independently selected in the group consisting of H, ($C_1$-$C_6$) alkyl which is methyl; and R₆ is selected from the group consisting of —H, and (C₁-C₆) alkyl which is methyl;

and pharmaceutically acceptable salt and solvates thereof.

The present invention also provides pharmaceutical compositions comprising a compound of formula I, or a pharmaceutically acceptable salt thereof in admixture with one or more pharmaceutically acceptable carrier or excipient, either alone or in combination with one or more further active ingredient.

In one aspect the present invention provides a compound according to the invention for use as a medicament.

In a further aspect the present invention provides the use of a compound of the invention, or a pharmaceutically acceptable salt thereof, in the manufacture of a medicament for the treatment of disorders associated with ROCK enzymes mechanisms, particularly for the treatment of disorders such as pulmonary diseases.

In particular the invention provides compounds according to the invention for use in the prevention and/or treatment of pulmonary disease selected from the group consisting of asthma, chronic obstructive pulmonary disease COPD, idiopathic pulmonary fibrosis (IPF), pulmonary hypertension (PH) and specifically Pulmonary Arterial Hypertension (PAH).

Moreover the present invention provides a method for the prevention and/or treatment of disorders associated with ROCK enzymes mechanisms, said method comprising administering to a patient in need of such treatment a therapeutically effective amount of a compound of the invention.

In particular the invention provides methods for the prevention and/or treatment wherein the disorder is asthma, chronic obstructive pulmonary disease COPD idiopathic pulmonary fibrosis (IPF), pulmonary hypertension (PH) and specifically Pulmonary Arterial Hypertension (PAH).

According to specific embodiments, the present invention provides the compounds listed in the table below and pharmaceutical acceptable salts thereof.

| Ex. N. | Chemical Name |
|---|---|
| 1 | (S)-2-amino-3-(3-fluoro-4-((3-methyl-1H-pyrrolo[2,3-b]pyridin-4-yl)oxy)phenyl)-N-(1-methylpiperidin-4-yl)propanamide |
| 2 | (S)-2-amino-1-(7,8-dihydropyrido[4,3-d]pyrimidin-6(5H)-yl)-3-(3-fluoro-4-((3-methyl-1H-pyrrolo[2,3-b]pyridin-4-yl)oxy)phenyl)propan-1-one |
| 3 | (S)-2-amino-3-(3-fluoro-4-((3-methyl-1H-pyrrolo[2,3-b]pyridin-4-yl)oxy)phenyl)-1-(6-methyl-2,6-diazaspiro[3.3]heptan-2-yl)propan-1-one |
| 4 | (2S)-2-amino-3-(3-fluoro-4-((3-methyl-1H-pyrrolo[2,3-b]pyridin-4-yl)oxy)phenyl)-1-(2-phenylmorpholino)propan-1-one |
| 5 | (S)-2-amino-3-(3-fluoro-4-((3-methyl-1H-pyrrolo[2,3-b]pyridin-4-yl)oxy)phenyl)-1-(4-phenylpiperazin-1-yl)propan-1-one |
| 6 | (2S)-2-amino-3-(3-fluoro-4-((3-methyl-1H-pyrrolo[2,3-b]pyridin-4-yl)oxy)phenyl)-1-(4-methyl-3-phenylpiperazin-1-yl)propan-1-one |
| 7 | (S)-2-amino-3-(3-fluoro-4-((3-methyl-1H-pyrrolo[2,3-b]pyridin-4-yl)oxy)phenyl)-1-(4-(phenylsulfonyl)piperidin-1-yl)propan-1-one |
| 8 | (2S)-2-amino-3-(3-fluoro-4-((3-methyl-1H-pyrrolo[2,3-b]pyridin-4-yl)oxy)phenyl)-1-(3-(3-methyl-1,2,4-oxadiazol-5-yl)pyrrolidin-1-yl)propan-1-one |
| 9 | (S)-2-amino-1-(4-benzyl-4-hydroxypiperidin-1-yl)-3-(3-fluoro-4-((3-methyl-1H-pyrrolo[2,3-b]pyridin-4-yl)oxy)phenyl)propan-1-one |
| 10 | (S)-2-amino-1-(3,4-dihydroisoquinolin-2(1H)-yl)-3-(3-fluoro-4-((3-methyl-1H-pyrrolo[2,3-b]pyridin-4-yl)oxy)phenyl)propan-1-one |
| 11 | (S)-2-amino-3-(3-fluoro-4-((3-methyl-1H-pyrrolo[2,3-b]pyridin-4-yl)oxy)phenyl)-1-(4-(pyridin-3-yloxy)piperidin-1-yl)propan-1-one |
| 12 | (S)-2-amino-3-(3-fluoro-4-((3-methyl-1H-pyrrolo[2,3-b]pyridin-4-yl)oxy)phenyl)-1-(4-(pyridin-4-yl)piperidin-1-yl)propan-1-one |
| 13 | (S)-2-amino-1-(4-benzylpiperidin-1-yl)-3-(3-fluoro-4-((3-methyl-1H-pyrrolo[2,3-b]pyridin-4-yl)oxy)phenyl)propan-1-one |
| 14 | (S)-2-amino-1-(4-(dimethylamino)piperidin-1-yl)-3-(3-fluoro-4-((3-methyl-1H-pyrrolo[2,3-b]pyridin-4-yl)oxy)phenyl)propan-1-one |
| 15 | (S)-2-amino-N-(3-(dimethylamino)propyl)-3-(3-fluoro-4-((3-methyl-1H-pyrrolo[2,3-b]pyridin-4-yl)oxy)phenyl)propanamide |
| 16 | (2S)-2-amino-3-(3-fluoro-4-((3-methyl-1H-pyrrolo[2,3-b]pyridin-4-yl)oxy)phenyl)-1-(hexahydropyrazino[2,1-c][1,4]oxazin-8(1H)-yl)propan-1-one |
| 17 | (S)-2-amino-3-(3-fluoro-4-((3-methyl-1H-pyrrolo[2,3-b]pyridin-4-yl)oxy)phenyl)-1-((3S,5R)-3,4,5-trimethylpiperazin-1-yl)propan-1-one |
| 18 | (S)-2-amino-3-(3-fluoro-4-((3-methyl-1H-pyrrolo[2,3-b]pyridin-4-yl)oxy)phenyl)-1-(3,3,4-trimethylpiperazin-1-yl)propan-1-one |
| 19 | 2-amino-3-(3-fluoro-4-((3-methyl-1H-pyrrolo[2,3-b]pyridin-4-yl)oxy)phenyl)-1-(4-(2-methoxyethyl)piperazin-1-yl)propan-1-one |
| 20 | (S)-2-amino-N-cyclohexyl-3-(3-fluoro-4-((3-methyl-1H-pyrrolo[2,3-b]pyridin-4-yl)oxy)phenyl)propanamide |
| 21 | (S)-2-amino-3-(3-fluoro-4-((3-methyl-1H-pyrrolo[2,3-b]pyridin-4-yl)oxy)phenyl)-1-(4-phenyl-5,6-dihydropyridin-1(2H)-yl)propan-1-one |
| 22 | (S)-2-amino-3-(3-fluoro-4-((3-methyl-1H-pyrrolo[2,3-b]pyridin-4-yl)oxy)phenyl)-1-(4-(phenylsulfonyl)piperazin-1-yl)propan-1-one |
| 23 | (S)-4-(2-amino-3-(3-fluoro-4-((3-methyl-1H-pyrrolo[2,3-b]pyridin-4-yl)oxy)phenyl)propanoyl)-N,N-dimethylpiperazine-1-carboxamide |
| 24 | (S)-2-amino-1-((1S,4S)-5-benzyl-2,5-diazabicyclo[2.2.1]heptan-2-yl)-3-(3-fluoro-4-((3-methyl-1H-pyrrolo[2,3-b]pyridin-4-yl)oxy)phenyl)propan-1-one |
| 25 | (S)-2-amino-3-(3-fluoro-4-((3-methyl-1H-pyrrolo[2,3-b]pyridin-4-yl)oxy)phenyl)-1-((1S,4S)-5-methyl-2,5-diazabicyclo[2.2.1]heptan-2-yl)propan-1-one |
| 26 | (S)-2-amino-1-((3S,5R)-4-benzyl-3,5-dimethylpiperazin-1-yl)-3-(3-fluoro-4-((3-methyl-1H-pyrrolo[2,3-b]pyridin-4-yl)oxy)phenyl)propan-1-one |

| Ex. N. | Chemical Name |
|---|---|
| 27 | (S)-2-amino-3-(3-fluoro-4-((3-methyl-1H-pyrrolo[2,3-b]pyridin-4-yl)oxy)phenyl)-1-(4-(pyridin-2-ylmethyl)piperazin-1-yl)propan-1-one |
| 28 | (S)-2-amino-3-(3-fluoro-4-((3-methyl-1H-pyrrolo[2,3-b]pyridin-4-yl)oxy)phenyl)-1-(4-(pyridin-3-ylmethyl)piperazin-1-yl)propan-1-one |
| 29 | (S)-2-amino-3-(3-fluoro-4-((3-methyl-1H-pyrrolo[2,3-b]pyridin-4-yl)oxy)phenyl)-1-(2,6-diazaspiro[3.3]heptan-2-yl)propan-1-one |
| 30 | (S)-2-amino-3-(3-fluoro-4-((3-methyl-1H-pyrrolo[2,3-b]pyridin-4-yl)oxy)phenyl)-1-((3aR,6aS)-5-methylhexahydropyrrolo[3,4-c]pyrrol-2(1H)-yl)propan-1-one |
| 31 | (S)-2-amino-3-(3-fluoro-4-((3-methyl-1H-pyrrolo[2,3-b]pyridin-4-yl)oxy)phenyl)-1-((3aR,6aS)-hexahydropyrrolo[3,4-c]pyrrol-2(1H)-yl)propan-1-one |
| 32 | (S)-2-amino-3-(3-fluoro-4-((3-methyl-1H-pyrrolo[2,3-b]pyridin-4-yl)oxy)phenyl)-N-(1-(hydroxymethyl)cyclohexyl)propanamide |
| 33 | (S)-2-amino-3-(3-fluoro-4-((3-methyl-1H-pyrrolo[2,3-b]pyridin-4-yl)oxy)phenyl)-N-(4-(hydroxymethyl)tetrahydro-2H-pyran-4-yl)propanamide |
| 34 | (S)-2-amino-N-(1-cyanocyclohexyl)-3-(3-fluoro-4-((3-methyl-1H-pyrrolo[2,3-b]pyridin-4-yl)oxy)phenyl)propanamide |
| 35 | (S)-1-(2-amino-3-(3-fluoro-4-((3-methyl-1H-pyrrolo[2,3-b]pyridin-4-yl)oxy)phenyl)propanamido)cyclohexanecarboxamide |
| 36 | (S)-2-amino-3-(3-fluoro-4-((3-methyl-1H-pyrrolo[2,3-b]pyridin-4-yl)oxy)phenyl)-N-(1-(2-hydroxyethyl)cyclohexyl)propanamide |
| 37 | (S)-2-amino-3-(3-fluoro-4-((3-methyl-1H-pyrrolo[2,3-b]pyridin-4-yl)oxy)phenyl)-N-(4-(hydroxymethyl)-1-methylpiperidin-4-yl)propanamide |
| 38 | (S)-2-amino-N-(1-((dimethylamino)methyl)cyclohexyl)-3-(3-fluoro-4-((3-methyl-1H-pyrrolo[2,3-b]pyridin-4-yl)oxy)phenyl)propanamide |
| 39 | (S)-2-amino-3-(3-fluoro-4-((3-methyl-1H-pyrrolo[2,3-b]pyridin-4-yl)oxy)phenyl)-N-methyl-N-((1-methylpiperidin-4-yl)methyl)propanamide |
| 40 | (S)-2-amino-3-(3-fluoro-4-((3-methyl-1H-pyrrolo[2,3-b]pyridin-4-yl)oxy)phenyl)-N-((1-methylpiperidin-4-yl)methyl)propanamide |
| 41 | (S)-2-amino-1-(3-(dimethylamino)azetidin-1-yl)-3-(3-fluoro-4-((3-methyl-1H-pyrrolo[2,3-b]pyridin-4-yl)oxy)phenyl)propan-1-one |
| 42 | (S)-2-amino-3-(3-fluoro-4-((3-methyl-1H-pyrrolo[2,3-b]pyridin-4-yl)oxy)phenyl)-N-(1-methylazetidin-3-yl)propanamide |
| 43 | (S)-2-amino-1-((R)-3-(dimethylamino)pyrrolidin-1-yl)-3-(3-fluoro-4-((3-methyl-1H-pyrrolo[2,3-b]pyridin-4-yl)oxy)phenyl)propan-1-one |
| 44 | (S)-2-amino-3-(3-fluoro-4-((3-methyl-1H-pyrrolo[2,3-b]pyridin-4-yl)oxy)phenyl)-N-methyl-N-(1-methylpiperidin-4-yl)propanamide |
| 45 | (S)-2-amino-1-(4-((dimethylamino)methyl)piperidin-1-yl)-3-(3-fluoro-4-((3-methyl-1H-pyrrolo[2,3-b]pyridin-4-yl)oxy)phenyl)propan-1-one |
| 46 | (S)-2-amino-3-(3-fluoro-4-((3-methyl-1H-pyrrolo[2,3-b]pyridin-4-yl)oxy)phenyl)-N-((R)-quinuclidin-3-yl)propanamide |
| 47 | (S)-2-amino-3-(3-fluoro-4-((3-methyl-1H-pyrrolo[2,3-b]pyridin-4-yl)oxy)phenyl)-N-((1-methylazetidin-3-yl)methyl)propanamide |
| 48 | (S)-2-amino-1-(3-((dimethylamino)methyl)azetidin-1-yl)-3-(3-fluoro-4-((3-methyl-1H-pyrrolo[2,3-b]pyridin-4-yl)oxy)phenyl)propan-1-one |
| 49 | (S)-2-amino-1-((S)-3-(dimethylamino)pyrrolidin-1-yl)-3-(3-fluoro-4-((3-methyl-1H-pyrrolo[2,3-b]pyridin-4-yl)oxy)phenyl)propan-1-one |
| 50 | (S)-2-amino-1-((R)-3-(dimethylamino)piperidin-1-yl)-3-(3-fluoro-4-((3-methyl-1H-pyrrolo[2,3-b]pyridin-4-yl)oxy)phenyl)propan-1-one |
| 51 | 2-amino-3-(3-fluoro-4-((3-methyl-1H-pyrrolo[2,3-b]pyridin-4-yl)oxy)phenyl)-1-(4-(pyridin-4-ylmethyl)piperazin-1-yl)propan-1-one |
| 52 | 2-amino-1-(4-(benzo[d][1,3]dioxol-5-ylmethyl)piperazin-1-yl)-3-(3-fluoro-4-((3-methyl-1H-pyrrolo[2,3-b]pyridin-4-yl)oxy)phenyl)propan-1-one |
| 53 | 2-amino-3-(3-fluoro-4-((3-methyl-1H-pyrrolo[2,3-b]pyridin-4-yl)oxy)phenyl)-1-(4-phenethylpiperazin-1-yl)propan-1-one |
| 54 | (S)-2-amino-3-(3-fluoro-4-((3-methyl-1H-pyrrolo[2,3-b]pyridin-4-yl)oxy)phenyl)-N-(tetrahydro-2H-pyran-4-yl)propanamide |
| 55 | (R)-2-amino-3-(3-fluoro-4-((3-methyl-1H-pyrrolo[2,3-b]pyridin-4-yl)oxy)phenyl)-N-(tetrahydro-2H-pyran-4-yl)propanamide |
| 56 | (S)-2-amino-3-(3-fluoro-4-((3-methyl-1H-pyrrolo[2,3-b]pyridin-4-yl)oxy)phenyl)-N-(2-(1-phenyl-1H-pyrazol-4-yl)ethyl)propanamide |
| 57 | 2-amino-3-(3-fluoro-4-((3-methyl-1H-pyrrolo[2,3-b]pyridin-4-yl)oxy)phenyl)-N-(2-(pyridin-4-yl)ethyl)propanamide |
| 58 | 2-amino-1-(4-(cyclopropylmethyl)piperazin-1-yl)-3-(3-fluoro-4-((3-methyl-1H-pyrrolo[2,3-b]pyridin-4-yl)oxy)phenyl)propan-1-one |
| 59 | 2-amino-3-(3-fluoro-4-((3-methyl-1H-pyrrolo[2,3-b]pyridin-4-yl)oxy)phenyl)-1-(4-methylpiperazin-1-yl)propan-1-one |
| 60 | 2-amino-1-(4-cyclopropylpiperazin-1-yl)-3-(3-fluoro-4-((3-methyl-1H-pyrrolo[2,3-b]pyridin-4-yl)oxy)phenyl)propan-1-one |
| 61 | 2-amino-3-(3-fluoro-4-((3-methyl-1H-pyrrolo[2,3-b]pyridin-4-yl)oxy)phenyl)-N-(thiophen-2-ylmethyl)propanamide |
| 62 | 2-amino-3-(3-fluoro-4-((3-methyl-1H-pyrrolo[2,3-b]pyridin-4-yl)oxy)phenyl)-N-(4-(hydroxymethyl)benzyl)propanamide |
| 63 | 2-amino-N-(2,3-dihydro-1H-inden-2-yl)-3-(3-fluoro-4-((3-methyl-1H-pyrrolo[2,3-b]pyridin-4-yl)oxy)phenyl)propanamide |

| Ex. N. | Chemical Name |
|---|---|
| 64 | 2-amino-3-(3-fluoro-4-((3-methyl-1H-pyrrolo[2,3-b]pyridin-4-yl)oxy)phenyl)-1-(2-(hydroxymethyl)-4-methylpiperazin-1-yl)propan-1-one |
| 65 | 2-amino-3-(3-fluoro-4-((3-methyl-1H-pyrrolo[2,3-b]pyridin-4-yl)oxy)phenyl)-1-(1H-pyrrolo[3,4-c]pyridin-2(3H)-yl)propan-1-one |
| 66 | 2-amino-3-(3-fluoro-4-((3-methyl-1H-pyrrolo[2,3-b]pyridin-4-yl)oxy)phenyl)-1-(3-(pyridin-4-yl)pyrrolidin-1-yl)propan-1-one |
| 67 | 2-amino-1-(3,4-dihydro-2,7-naphthyridin-2(1H)-yl)-3-(3-fluoro-4-((3-methyl-1H-pyrrolo[2,3-b]pyridin-4-yl)oxy)phenyl)propan-1-one |
| 68 | 2-amino-3-(3-fluoro-4-((3-methyl-1H-pyrrolo[2,3-b]pyridin-4-yl)oxy)phenyl)-N-(3-methoxypropyl)propanamide |
| 69 | 2-amino-3-(3-fluoro-4-((3-methyl-1H-pyrrolo[2,3-b]pyridin-4-yl)oxy)phenyl)-N-(2-(pyridin-2-yl)ethyl)propanamide |
| 70 | 2-amino-3-(3-fluoro-4-((3-methyl-1H-pyrrolo[2,3-b]pyridin-4-yl)oxy)phenyl)-N-(pyridin-3-yl)propanamide |
| 71 | 2-amino-3-(3-fluoro-4-((3-methyl-1H-pyrrolo[2,3-b]pyridin-4-yl)oxy)phenyl)-N-(pyridin-4-yl)propanamide |
| 72 | 2-amino-3-(3-fluoro-4-((3-methyl-1H-pyrrolo[2,3-b]pyridin-4-yl)oxy)phenyl)-1-(4-(4-methylbenzyl)piperazin-1-yl)propan-1-one |
| 73 | 2-amino-3-(3-fluoro-4-((3-methyl-1H-pyrrolo[2,3-b]pyridin-4-yl)oxy)phenyl)-1-(4-(3-methylbenzyl)piperazin-1-yl)propan-1-one |
| 74 | 2-amino-3-(3-fluoro-4-((3-methyl-1H-pyrrolo[2,3-b]pyridin-4-yl)oxy)phenyl)-1-(4-(4-fluorobenzyl)piperazin-1-yl)propan-1-one |
| 75 | 2-amino-3-(3-fluoro-4-((3-methyl-1H-pyrrolo[2,3-b]pyridin-4-yl)oxy)phenyl)-1-(4-(4-methoxybenzyl)piperazin-1-yl)propan-1-one |
| 76 | 2-amino-3-(3-fluoro-4-((3-methyl-1H-pyrrolo[2,3-b]pyridin-4-yl)oxy)phenyl)-N-phenethylpropanamide |
| 77 | 2-amino-3-(3-fluoro-4-((3-methyl-1H-pyrrolo[2,3-b]pyridin-4-yl)oxy)phenyl)-1-(piperidin-1-yl)propan-1-one |
| 78 | 2-amino-3-(3-fluoro-4-((3-methyl-1H-pyrrolo[2,3-b]pyridin-4-yl)oxy)phenyl)-N-(isoquinolin-5-yl)propanamide |
| 79 | 2-amino-3-(3-fluoro-4-((3-methyl-1H-pyrrolo[2,3-b]pyridin-4-yl)oxy)phenyl)-N-(3-morpholinopropyl)propanamide |
| 80 | 2-amino-3-(3-fluoro-4-((3-methyl-1H-pyrrolo[2,3-b]pyridin-4-yl)oxy)phenyl)-1-(4-(pyridin-2-yl)piperazin-1-yl)propan-1-one |
| 81 | 2-amino-1-(5,6-dihydroimidazo[1,5-a]pyrazin-7(8H)-yl)-3-(3-fluoro-4-((3-methyl-1H-pyrrolo[2,3-b]pyridin-4-yl)oxy)phenyl)propan-1-one |
| 82 | 2-amino-N-((1-benzylpiperidin-4-yl)methyl)-3-(3-fluoro-4-((3-methyl-1H-pyrrolo[2,3-b]pyridin-4-yl)oxy)phenyl)propanamide |
| 83 | 2-amino-N-(1-benzylpiperidin-4-yl)-3-(3-fluoro-4-((3-methyl-1H-pyrrolo[2,3-b]pyridin-4-yl)oxy)phenyl)propanamide |
| 84 | First eluting rac-diastereoisomer 2-amino-3-(3-fluoro-4-((3-methyl-1H-pyrrolo[2,3-b]pyridin-4-yl)oxy)phenyl)-1-(2-phenylpyrrolidin-1-yl)propan-1-one |
| 85 | Second eluting rac-diastereoisomer 2-amino-3-(3-fluoro-4-((3-methyl-1H-pyrrolo[2,3-b]pyridin-4-yl)oxy)phenyl)-1-(2-phenylpyrrolidin-1-yl)propan-1-one |
| 86 | (S)-2-amino-1-(4-benzylpiperazin-1-yl)-3-(3-fluoro-4-((2-methyl-1H-pyrrolo[2,3-b]pyridin-4-yl)oxy)phenyl)propan-1-one |
| 87 | (S)-2-amino-N-(3-methoxylpropyl)-3-(4-((3-methyl-1H-pyrrolo[2,3-b]pyridin-4-yl)oxy)phenyl)propanamide |
| 88 | (S)-2-amino-1-(4-benzylpiperazin-1-yl)-3-(4-((3-methyl-1H-pyrrolo[2,3-b]pyridin-4-yl)oxy)phenyl)propan-1-one |
| 89 | (S)-2-amino-3-(4-((3-methyl-1H-pyrrolo[2,3-b]pyridin-4-yl)oxy)phenyl)-N-(2-(pyridin-4-yl)ethyl)propanamide |
| 90 | (S)-2-amino-3-(4-((3-methyl-1H-pyrrolo[2,3-b]pyridin-4-yl)oxy)phenyl)-N-(tetrahydro-2H-pyran-4-yl)propanamide |
| 91 | 3-(4-((1H-pyrrolo[2,3-b]pyridin-4-yl)oxy)phenyl)-2-amino-N-(4-(trifluoromethyl)phenyl)propanamide |
| 92 | (S)-3-(4-((1H-pyrrolo[2,3-b]pyridin-4-yl)oxy)phenyl)-2-amino-N-(cyclohexylmethyl)-N-methylpropanamide |
| 93 | (S)-3-(4-((1H-pyrrolo[2,3-b]pyridin-4-yl)oxy)phenyl)-2-amino-N-benzyl-N-methylpropanamide |
| 94 | (S)-3-(4-((1H-pyrrolo[2,3-b]pyridin-4-yl)oxy)phenyl)-2-amino-N-(6-chloropyridin-3-yl)propanamide |
| 95 | (S)-3-(4-((1H-pyrrolo[2,3-b]pyridin-4-yl)oxy)phenyl)-2-amino-N-(2-(dimethylamino)ethyl)propanamide |
| 96 | (R)-3-(4-((1H-pyrrolo[2,3-b]pyridin-4-yl)oxy)phenyl)-2-amino-N-(2-(dimethylamino)ethyl)propanamide |
| 97 | (S)-3-(4-((1H-pyrrolo[2,3-b]pyridin-4-yl)oxy)phenyl)-2-amino-N-benzylpropanamide |
| 98 | (R)-3-(4-((1H-pyrrolo[2,3-b]pyridin-4-yl)oxy)phenyl)-2-amino-N-benzylpropanamide |
| 99 | (S)-3-(4-((1H-pyrrolo[2,3-b]pyridin-4-yl)oxy)phenyl)-2-amino-N-(tetrahydro-2H-pyran-4-yl)propanamide |
| 100 | (R)-3-(4-((1H-pyrrolo[2,3-b]pyridin-4-yl)oxy)phenyl)-2-amino-N-(tetrahydro-2H-pyran-4-yl)propanamide |

| Ex. N. | Chemical Name |
|---|---|
| 101 | (S)-3-(4-((1H-pyrrolo[2,3-b]pyridin-4-yl)oxy)phenyl)-2-amino-N-cyclohexyl-N-methylpropanamide |
| 102 | (R)-3-(4-((1H-pyrrolo[2,3-b]pyridin-4-yl)oxy)phenyl)-2-amino-N-cyclohexyl-N-methylpropanamide |
| 103 | (S)-3-(4-((1H-pyrrolo[2,3-b]pyridin-4-yl)oxy)phenyl)-2-amino-N-(1-methylpiperidin-4-yl)propanamide |
| 104 | (R)-3-(4-((1H-pyrrolo[2,3-b]pyridin-4-yl)oxy)phenyl)-2-amino-N-(1-methylpiperidin-4-yl)propanamide |
| 105 | (S)-3-(4-((1H-pyrrolo[2,3-b]pyridin-4-yl)oxy)phenyl)-2-amino-N-(thiazol-2-yl)propanamide |
| 106 | (R)-3-(4-((1H-pyrrolo[2,3-b]pyridin-4-yl)oxy)phenyl)-2-amino-N-(thiazol-2-yl)propanamide |
| 107 | (S)-3-(4-((1H-pyrrolo[2,3-b]pyridin-4-yl)oxy)phenyl)-2-amino-N-(cyclohexylmethyl)propanamide |
| 108 | (R)-3-(4-((1H-pyrrolo[2,3-b]pyridin-4-yl)oxy)phenyl)-2-amino-N-(cyclohexylmethyl)propanamide |
| 109 | (S)-3-(4-((1H-pyrrolo[2,3-b]pyridin-4-yl)oxy)phenyl)-2-amino-N-phenylpropanamide |
| 110 | (R)-3-(4-((1H-pyrrolo[2,3-b]pyridin-4-yl)oxy)phenyl)-2-amino-N-phenylpropanamide |
| 111 | (S)-3-(4-((1H-pyrrolo[2,3-b]pyridin-4-yl)oxy)phenyl)-2-amino-N-cyclohexylpropanamide |
| 112 | (R)-3-(4-((1H-pyrrolo[2,3-b]pyridin-4-yl)oxy)phenyl)-2-amino-N-cyclohexylpropanamide |
| 113 | 3-(4-((1H-pyrrolo[2,3-b]pyridin-4-yl)oxy)phenyl)-2-amino-N,N-dimethylpropanamide |
| 114 | (S)-2-amino-1-(4-benzylpiperazin-1-yl)-3-(4-((3-fluoro-1H-pyrrolo[2,3-b]pyridin-4-yl)oxy)phenyl)propan-1-one |
| 115 | (S)-2-amino-1-(4-benzylpiperazin-1-yl)-3-(3-fluoro-4-((5-methyl-7H-pyrrolo[2,3-d]pyrimidin-4-yl)oxy)phenyl)propan-1-one |
| 116 | (S)-2-amino-N-(3-(dimethylamino)propyl)-3-(3-fluoro-4-((5-methyl-7H-pyrrolo[2,3-d]pyrimidin-4-yl)oxy)phenyl)propanamide |
| 117 | (S)-2-amino-3-(3-fluoro-4-((5-methyl-7H-pyrrolo[2,3-d]pyrimidin-4-yl)oxy)phenyl)-N-(1-methylpiperidin-4-yl)propanamide |
| 118 | (S)-2-amino-3-(3-fluoro-4-((5-methyl-7H-pyrrolo[2,3-d]pyrimidin-4-yl)oxy)phenyl)-1-(4-methylpiperazin-1-yl)propan-1-one |
| 119 | (S)-2-amino-1-(4-cyclopropylpiperazin-1-yl)-3-(3-fluoro-4-((5-methyl-7H-pyrrolo[2,3-d]pyrimidin-4-yl)oxy)phenyl)propan-1-one |
| 120 | (S)-2-amino-3-(3-fluoro-4-((5-methyl-7H-pyrrolo[2,3-d]pyrimidin-4-yl)oxy)phenyl)-1-(4-(pyridin-2-ylmethyl)piperazin-1-yl)propan-1-one |
| 121 | 2-amino-3-(3-fluoro-4-((5-methyl-7H-pyrrolo[2,3-d]pyrimidin-4-yl)oxy)phenyl)-1-((1S,4S)-5-methyl-2,5-diazabicyclo[2.2.1]heptan-2-yl)propan-1-one |
| 122 | (S)-2-amino-3-(3-fluoro-4-((5-methyl-7H-pyrrolo[2,3-d]pyrimidin-4-yl)oxy)phenyl)-1-(4-(pyridin-4-yl)piperidin-1-yl)propan-1-one |
| 123 | (S)-2-amino-1-(4-benzyl-4-hydroxypiperidin-1-yl)-3-(3-fluoro-4-((5-methyl-7H-pyrrolo[2,3-d]pyrimidin-4-yl)oxy)phenyl)propan-1-one |
| 124 | (S)-2-amino-1-(3,4-dihydroisoquinolin-2(1H)-yl)-3-(3-fluoro-4-((5-methyl-7H-pyrrolo[2,3-d]pyrimidin-4-yl)oxy)phenyl)propan-1-one |
| 125 | (S)-2-amino-3-(3-fluoro-4-((5-methyl-7H-pyrrolo[2,3-d]pyrimidin-4-yl)oxy)phenyl)-N-(tetrahydro-2H-pyran-4-yl)propanamide |
| 126 | (S)-2-amino-3-(3-fluoro-4-((5-methyl-7H-pyrrolo[2,3-d]pyrimidin-4-yl)oxy)phenyl)-1-(4-(pyridin-3-yloxy)piperidin-1-yl)propan-1-one |
| 127 | (S)-2-amino-3-(3-fluoro-4-((5-methyl-7H-pyrrolo[2,3-d]pyrimidin-4-yl)oxy)phenyl)-1-(4-(phenylsulfonyl)piperidin-1-yl)propan-1-one |
| 128 | (S)-2-amino-3-(3-fluoro-4-((5-methyl-7H-pyrrolo[2,3-d]pyrimidin-4-yl)oxy)phenyl)-N-(2-(pyridin-4-yl)ethyl)propanamide |
| 129 | (S)-2-amino-3-(3-fluoro-4-((5-methyl-7H-pyrrolo[2,3-d]pyrimidin-4-yl)oxy)phenyl)-1-((3S,5R)-3,4,5-trimethylpiperazin-1-yl)propan-1-one |
| 130 | (S)-4-(4-(2-amino-3-(4-benzylpiperazin-1-yl)-3-oxopropyl)-2-fluorophenoxy)-7H-pyrrolo[2,3-d]pyrimidine-5-carbonitrile |
| 131 | (S)-3-(4-((1H-pyrrolo[2,3-b]pyridin-4-yl)oxy)phenyl)-N-cyclohexyl-2-(methylamino)propanamide |
| 132 | 2-amino-1-(4-benzylpiperazin-1-yl)-3-(3-fluoro-4-((3-methyl-1H-pyrrolo[2,3-b]pyridin-4-yl)oxy)phenyl)propan-1-one |
| 133 | 1-(4-acetylpiperazin-1-yl)-2-amino-3-(3-fluoro-4-((3-methyl-1H-pyrrolo[2,3-b]pyridin-4-yl)oxy)phenyl)propan-1-one |
| 134 | (S)-2-amino-N-cyclohexyl-N-methyl-3-(4-((3-methyl-1H-pyrrolo[2,3-b]pyridin-4-yl)oxy)phenyl)propanamide |
| 135 | (S)-2-amino-N-benzyl-3-(4-((3-methyl-1H-pyrrolo[2,3-b]pyridin-4-yl)oxy)phenyl)propanamide |
| 136 | (R)-2-amino-N-benzyl-3-(4-((3-methyl-1H-pyrrolo[2,3-b]pyridin-4-yl)oxy)phenyl)propanamide |
| 137 | (S)-2-amino-3-(4-((3-methyl-1H-pyrrolo[2,3-b]pyridin-4-yl)oxy)phenyl)-N-phenylpropanamide |
| 138 | (R)-2-amino-3-(4-((3-methyl-1H-pyrrolo[2,3-b]pyridin-4-yl)oxy)phenyl)-N-phenylpropanamide |

| Ex. N. | Chemical Name |
|---|---|
| 139 | (S)-2-amino-N-(cyclohexylmethyl)-3-(4-((3-methyl-1H-pyrrolo[2,3-b]pyridin-4-yl)oxy)phenyl)propanamide |
| 140 | (R)-2-amino-N-(cyclohexylmethyl)-3-(4-((3-methyl-1H-pyrrolo[2,3-b]pyridin-4-yl)oxy)phenyl)propanamide |
| 141 | (S)-2-amino-N-cyclohexyl-3-(4-((3-methyl-1H-pyrrolo[2,3-b]pyridin-4-yl)oxy)phenyl)propanamide |
| 142 | (R)-2-amino-N-cyclohexyl-3-(4-((3-methyl-1H-pyrrolo[2,3-b]pyridin-4-yl)oxy)phenyl)propanamide |
| 143 | (R)-3-(4-((1H-pyrrolo[2,3-b]pyridin-4-yl)oxy)phenyl)-2-amino-N-(cyclohexylmethyl)-N-methylpropanamide |
| 144 | (R)-3-(4-((1H-pyrrolo[2,3-b]pyridin-4-yl)oxy)phenyl)-2-amino-N-benzyl-N-methylpropanamide |
| 145 | (S)-2-amino-3-(3-fluoro-4-((3-methyl-1H-pyrrolo[2,3-b]pyridin-4-yl)oxy)phenyl)-N-phenylpropanamide |
| 146 | (S)-3-(4-((1H-pyrrolo[2,3-b]pyridin-4-yl)oxy)-3-fluorophenyl)-2-amino-N-cyclohexylpropanamide |
| 147 | (S)-3-(4-((1H-pyrrolo[2,3-b]pyridin-4-yl)oxy)-3-fluorophenyl)-2-amino-N-phenylpropanamide |
| 148 | (R)-2-amino-N-cyclohexyl-3-(3-fluoro-4-((3-methyl-1H-pyrrolo[2,3-b]pyridin-4-yl)oxy)phenyl)propanamide |
| 149 | (R)-2-amino-3-(3-fluoro-4-((3-methyl-1H-pyrrolo[2,3-b]pyridin-4-yl)oxy)phenyl)-N-phenylpropanamide |
| 150 | 3-(4-((1H-pyrrolo[2,3-b]pyridin-4-yl)oxy)phenyl)-2-amino-N-cyclohexyl-2-methylpropanamide |
| 151 | 3-(4-((1H-pyrrolo[2,3-b]pyridin-4-yl)oxy)phenyl)-2-amino-2-methyl-N-(tetrahydro-2H-pyran-4-yl)propanamide |
| 152 | (S)-2-amino-3-(3-fluoro-4-((3-methyl-1H-pyrrolo[2,3-b]pyridin-4-yl)oxy)phenyl)-1-(piperazin-1-yl)propan-1-one |
| 153 | (S)-2-amino-3-(3-fluoro-4-((3-methyl-1H-pyrrolo[2,3-b]pyridin-4-yl)oxy)phenyl)-1-(4-(pyridazin-4-ylmethyl)piperazin-1-yl)propan-1-one |
| 154 | (S)-2-amino-3-(3-fluoro-4-((3-methyl-1H-pyrrolo[2,3-b]pyridin-4-yl)oxy)phenyl)-1-(4-((2-(methylthio)pyrimidin-4-yl)methyl)piperazin-1-yl)propan-1-one |
| 155 | (S)-2-amino-3-(3-fluoro-4-((3-methyl-1H-pyrrolo[2,3-b]pyridin-4-yl)oxy)phenyl)-1-(4-(pyrazin-2-ylmethyl)piperazin-1-yl)propan-1-one |
| 156 | (S)-2-amino-3-(3-fluoro-4-((3-methyl-1H-pyrrolo[2,3-b]pyridin-4-yl)oxy)phenyl)-1-(4-((1-methyl-1H-imidazol-2-yl)methyl)piperazin-1-yl)propan-1-one |
| 157 | (S)-2-amino-3-(3-fluoro-4-((3-methyl-1H-pyrrolo[2,3-b]pyridin-4-yl)oxy)phenyl)-1-(4-((2-methylthiazol-4-yl)methyl)piperazin-1-yl)propan-1-one |
| 158 | (S)-2-amino-3-(3-fluoro-4-((3-methyl-1H-pyrrolo[2,3-b]pyridin-4-yl)oxy)phenyl)-1-(4-((1-methyl-1H-imidazol-5-yl)methyl)piperazin-1-yl)propan-1-one |
| 159 | (S)-2-amino-3-(3-fluoro-4-((3-methyl-1H-pyrrolo[2,3-b]pyridin-4-yl)oxy)phenyl)-1-(4-(quinoxalin-2-ylmethyl)piperazin-1-yl)propan-1-one |
| 160 | (S)-2-amino-1-(4-(4-(3-(dimethylamino)propoxy)benzyl)piperazin-1-yl)-3-(3-fluoro-4-((3-methyl-1H-pyrrolo[2,3-b]pyridin-4-yl)oxy)phenyl)propan-1-one |
| 161 | (S)-2-amino-3-(3-fluoro-4-((3-methyl-1H-pyrrolo[2,3-b]pyridin-4-yl)oxy)phenyl)-1-(4-((1-(methylsulfonyl)piperidin-4-yl)methyl)piperazin-1-yl)propan-1-one |
| 162 | (S)-2-amino-3-(3-fluoro-4-((3-methyl-1H-pyrrolo[2,3-b]pyridin-4-yl)oxy)phenyl)-1-(4-(pyrimidin-5-ylmethyl)piperazin-1-yl)propan-1-one |
| 163 | (S)-2-amino-3-(3-fluoro-4-((3-methyl-1H-pyrrolo[2,3-b]pyridin-4-yl)oxy)phenyl)-1-(4-((1-methyl-1H-pyrazol-4-yl)methyl)piperazin-1-yl)propan-1-one |
| 164 | (S)-1-(4-((1,2,3-thiadiazol-4-yl)methyl)piperazin-1-yl)-2-amino-3-(3-fluoro-4-((3-methyl-1H-pyrrolo[2,3-b]pyridin-4-yl)oxy)phenyl)propan-1-one |
| 165 | (S)-3-((4-(2-amino-3-(3-fluoro-4-((3-methyl-1H-pyrrolo[2,3-b]pyridin-4-yl)oxy)phenyl)propanoyl)piperazin-1-yl)methyl)-N-methylbenzamide |
| 166 | (S)-5-((4-(2-amino-3-(3-fluoro-4-((3-methyl-1H-pyrrolo[2,3-b]pyridin-4-yl)oxy)phenyl)propanoyl)piperazin-1-yl)methyl)-N-methylfuran-2-carboxamide |
| 167 | (S)-2-amino-1-(4-benzoylpiperazin-1-yl)-3-(3-fluoro-4-((3-methyl-1H-pyrrolo[2,3-b]pyridin-4-yl)oxy)phenyl)propan-1-one |
| 168 | (S)-2-amino-1-(4-(cyclohexanecarbonyl)piperazin-1-yl)-3-(3-fluoro-4-((3-methyl-1H-pyrrolo[2,3-b]pyridin-4-yl)oxy)phenyl)propan-1-one |
| 169 | (S)-2-amino-3-(3-fluoro-4-((3-methyl-1H-pyrrolo[2,3-b]pyridin-4-yl)oxy)phenyl)-1-(4-(2-phenylacetyl)piperazin-1-yl)propan-1-one |
| 170 | (S)-2-amino-1-(4-(cyclopropanecarbonyl)piperazin-1-yl)-3-(3-fluoro-4-((3-methyl-1H-pyrrolo[2,3-b]pyridin-4-yl)oxy)phenyl)propan-1-one |
| 171 | (S)-2-amino-3-(3-fluoro-4-((3-methyl-1H-pyrrolo[2,3-b]pyridin-4-yl)oxy)phenyl)-1-(4-(1-methylpiperidine-4-carbonyl)piperazin-1-yl)propan-1-one |
| 172 | (S)-2-amino-1-(4-(4-((dimethylamino)methyl)benzoyl)piperazin-1-yl)-3-(3-fluoro-4-((3-methyl-1H-pyrrolo[2,3-b]pyridin-4-yl)oxy)phenyl)propan-1-one |
| 173 | (S)-2-amino-1-(4-(3-((dimethylamino)methyl)benzoyl)piperazin-1-yl)-3-(3-fluoro-4-((3-methyl-1H-pyrrolo[2,3-b]pyridin-4-yl)oxy)phenyl)propan-1-one |

| Ex. N. | Chemical Name |
|---|---|
| 174 | (S)-2-amino-3-(3-fluoro-4-((3-methyl-1H-pyrrolo[2,3-b]pyridin-4-yl)oxy)phenyl)-1-(4-nicotinoylpiperazin-1-yl)propan-1-one |
| 175 | (S)-2-amino-3-(3-fluoro-4-((3-methyl-1H-pyrrolo[2,3-b]pyridin-4-yl)oxy)phenyl)-1-(4-(1-methyl-1H-pyrazole-4-carbonyl)piperazin-1-yl)propan-1-one |
| 176 | (S)-2-amino-3-(3-fluoro-4-((3-methyl-1H-pyrrolo[2,3-b]pyridin-4-yl)oxy)phenyl)-1-(4-(1-methyl-1H-imidazole-4-carbonyl)piperazin-1-yl)propan-1-one |
| 177 | (S)-2-amino-3-(3-fluoro-4-((3-methyl-1H-pyrrolo[2,3-b]pyridin-4-yl)oxy)phenyl)-1-(4-(thiazole-2-carbonyl)piperazin-1-yl)propan-1-one |
| 178 | N-(3-(4-((1H-pyrrolo[2,3-b]pyridin-4-yl)oxy)phenyl)-1-(dimethylamino)-1-oxopropan-2-yl)pyrrolidine-3-carboxamide |
| 179 | N-(3-(4-((1H-pyrrolo[2,3-b]pyridin-4-yl)oxy)phenyl)-1-oxo-1-(phenylamino)propan-2-yl)pyrrolidine-3-carboxamide |
| 180 | N-(3-(4-((1H-pyrrolo[2,3-b]pyridin-4-yl)oxy)phenyl)-1-(cyclohexylamino)-1-oxopropan-2-yl)pyrrolidine-3-carboxamide |
| 181 | N-(3-(4-((1H-pyrrolo[2,3-b]pyridin-4-yl)oxy)phenyl)-1-((2-(dimethylamino)ethyl)amino)-1-oxopropan-2-yl)cyclohexanecarboxamide |
| 182 | 3-(4-((1H-pyrrolo[2,3-b]pyridin-4-yl)oxy)phenyl)-2-(dimethylamino)-N-(tetrahydro-2H-pyran-4-yl)propanamide |
| 183 | 3-(4-((1H-pyrrolo[2,3-b]pyridin-4-yl)oxy)phenyl)-N-cyclohexyl-2-(dimethylamino)propanamide |
| 184 | (S)-N-cyclohexyl-2-(dimethylamino)-3-(4-((3-methyl-1H-pyaolo[2,3-b]pyridin-4-yl)oxy)phenyl)propanamide |
| 185 | 3-(4-((1H-pyrrolo[2,3-b]pyridin-4-yl)oxy)phenyl)-2-((cyclohexylmethyl)amino)-N-methylpropanamide |
| 186 | (S)-2-amino-3-(4-((3-bromo-1H-pyrrolo[2,3-b]pyridin-4-yl)oxy)-3-fluorophenyl)-N-cyclohexylpropanamide |
| 187 | (S)-2-amino-1-(4-benzylpiperazin-1-yl)-3-(4-((3-bromo-1H-pyrrolo[2,3-b]pyridin-4-yl)oxy)-3-fluorophenyl)propan-1-one |
| 188 | (S)-2-amino-3-(4-((3-bromo-1H-pyrrolo[2,3-b]pyridin-4-yl)oxy)phenyl)-N-cyclohexylpropanamide |
| 189 | (S)-2-amino-3-(4-((3-bromo-1H-pyrrolo[2,3-b]pyridin-4-yl)oxy)phenyl)-N-(tetrahydro-2H-pyran-4-yl)propanamide |
| 190 | (S)-2-amino-N-cyclohexyl-3-(4-((3-iodo-1H-pyrrolo[2,3-b]pyridin-4-yl)oxy)phenyl)propanamide |
| 191 | (S)-2-amino-3-(4-((3-chloro-1H-pyrrolo[2,3-b]pyridin-4-yl)oxy)phenyl)-N-cyclohexylpropanamide |
| 192 | (S)-2-amino-1-(4-benzylpiperazin-1-yl)-3-(4-((3-(pyridin-4-yl)-1H-pyrrolo[2,3-b]pyridin-4-yl)oxy)phenyl)propan-1-one |
| 193 | (S)-2-amino-1-(4-benzylpiperazin-1-yl)-3-(4-((3-(1-ethyl-1H-pyrazol-5-yl)-1H-pyrrolo[2,3-b]pyridin-4-yl)oxy)phenyl)propan-1-one |
| 194 | (S)-2-amino-1-(4-benzylpiperazin-1-yl)-3-(4-((3-(pyridin-3-yl)-1H-pyrrolo[2,3-b]pyridin-4-yl)oxy)phenyl)propan-1-one |
| 195 | (S)-5-(4-(4-(2-amino-3-(4-benzylpiperazin-1-yl)-3-oxopropyl)phenoxy)-1H-pyrrolo[2,3-b]pyridin-3-yl)thiophene-2-carbonitrile |
| 196 | (S)-2-amino-1-(4-benzylpiperazin-1-yl)-3-(4-((3-(thiazol-5-yl)-1H-pyrrolo[2,3-b]pyridin-4-yl)oxy)phenyl)propan-1-one |
| 197 | (S)-2-amino-1-(4-benzylpiperazin-1-yl)-3-(4-((3-(1-methyl-1H-imidazol-5-yl)-1H-pyrrolo[2,3-b]pyridin-4-yl)oxy)phenyl)propan-1-one |
| 198 | (S)-2-amino-1-(4-benzylpiperazin-1-yl)-3-(4-((3-(isoxazol-4-yl)-1H-pyrrolo[2,3-b]pyridin-4-yl)oxy)phenyl)propan-1-one |
| 199 | (S)-2-amino-1-(4-benzylpiperazin-1-yl)-3-(4-((3-phenyl-1H-pyrrolo[2,3-b]pyridin-4-yl)oxy)phenyl)propan-1-one |
| 200 | (S)-2-amino-1-(4-benzylpiperazin-1-yl)-3-(4-((3-(4-hydroxyphenyl)-1H-pyrrolo[2,3-b]pyridin-4-yl)oxy)phenyl)propan-1-one |
| 201 | (S)-2-amino-1-(4-benzylpiperazin-1-yl)-3-(4-((3-(2,5-dihydrofuran-3-yl)-1H-pyrrolo[2,3-b]pyridin-4-yl)oxy)phenyl)propan-1-one |
| 202 | (S)-2-amino-1-(4-benzylpiperazin-1-yl)-3-(4-((3-(2,5-dihydro-1H-pyrrol-3-yl)-1H-pyrrolo[2,3-b]pyridin-4-yl)oxy)phenyl)propan-1-one |
| 203 | (S)-2-amino-N-cyclohexyl-3-(4-((3-cyclopropyl-1H-pyrrolo[2,3-b]pyridin-4-yl)oxy)phenyl)propanamide |
| 204 | (S)-2-amino-3-(3-fluoro-4-((3-phenyl-1H-pyrrolo[2,3-b]pyridin-4-yl)oxy)phenyl)-N-(1-methylpiperidin-4-yl)propanamide |
| 205 | (S)-2-amino-3-(3-fluoro-4-((3-(thiazol-5-yl)-1H-pyrrolo[2,3-b]pyridin-4-yl)oxy)phenyl)-N-(1-methylpiperidin-4-yl)propanamide |
| 206 | (S)-2-amino-3-(4-((3-(4-hydroxyphenyl)-1H-pyrrolo[2,3-b]pyridin-4-yl)oxy)phenyl)-N-(2-(pyridin-4-yl)ethyl)propanamide |
| 207 | (S)-2-amino-1-(4-benzylpiperazin-1-yl)-3-(3-fluoro-4-((3-(hydroxymethyl)-1H-pyrrolo[2,3-b]pyridin-4-yl)oxy)phenyl)propan-1-one |
| 208 | (S)-2-amino-N-cyclohexyl-3-(3-fluoro-4-((3-(hydroxymethyl)-1H-pyrrolo[2,3-b]pyridin-4-yl)oxy)phenyl)propanamide |
| 209 | (S)-2-amino-3-(3-fluoro-4-((3-(hydroxymethyl)-1H-pyrrolo[2,3-b]pyridin-4-yl)oxy)phenyl)-N-(tetrahydro-2H-pyran-4-yl)propanamide |
| 210 | (S)-2-amino-3-(3-fluoro-4-((3-(hydroxymethyl)-1H-pyrrolo[2,3-b]pyridin-4-yl)oxy)phenyl)-N-(1-methylpiperidin-4-yl)propanamide |

-continued

| Ex. N. | Chemical Name |
|---|---|
| 211 | (S)-2-amino-3-(3-fluoro-4-((3-(hydroxymethyl)-1H-pyrrolo[2,3-b]pyridin-4-yl)oxy)phenyl)-1-((1S,4S)-5-methyl-2,5-diazabicyclo[2.2.1]heptan-2-yl)propan-1-one |
| 212 | (S)-2-amino-N-(3-(dimethylamino)propyl)-3-(3-fluoro-4-((3-(hydroxymethyl)-1H-pyrrolo[2,3-b]pyridin-4-yl)oxy)phenyl)propanamide |
| 213 | (S)-2-amino-3-(3-fluoro-4-((3-(hydroxymethyl)-1H-pyrrolo[2,3-b]pyridin-4-yl)oxy)phenyl)-1-(4-(pyridin-2-ylmethyl)piperazin-1-yl)propan-1-one |
| 214 | (S)-2-amino-3-(3-fluoro-4-((3-(methoxymethyl)-1H-pyrrolo[2,3-b]pyridin-4-yl)oxy)phenyl)-N-(tetrahydro-2H-pyran-4-yl)propanamide |
| 215 | (S)-2-amino-3-(3-fluoro-4-((3-(methoxymethyl)-1H-pyrrolo[2,3-b]pyridin-4-yl)oxy)phenyl)-1-(4-methylpiperazin-1-yl)propan-1-one |
| 216 | (S)-2-amino-1-(4-benzylpiperazin-1-yl)-3-(4-((3-(2-hydroxyethyl)-1H-pyrrolo[2,3-b]pyridin-4-yl)oxy)phenyl)propan-1-one |
| 217 | (S)-2-amino-N-cyclohexyl-3-(4-((3-(3-hydroxyprop-1-yn-1-yl)-1H-pyrrolo[2,3-b]pyridin-4-yl)oxy)phenyl)propanamide |
| 218 | (S)-2-amino-3-(4-((3-cyano-1H-pyrrolo[2,3-b]pyridin-4-yl)oxy)phenyl)-N-(tetrahydro-2H-pyran-4-yl)propanamide |
| 219 | (S)-2-amino-3-(4-((3-cyano-1H-pyrrolo[2,3-b]pyridin-4-yl)oxy)phenyl)-N-cyclohexylpropanamide |
| 220 | (S)-4-(4-(2-amino-3-(4-benzylpiperazin-1-yl)-3-oxopropyl)-2-fluorophenoxy)-1H-pyrrolo[2,3-b]pyridine-3-carbonitrile |
| 221 | (S)-2-amino-3-(4-((3-cyano-1H-pyrrolo[2,3-b]pyridin-4-yl)oxy)-3-fluorophenyl)-N-cyclohexylpropanamide |
| 222 | (S)-2-amino-3-(4-((3-cyano-1H-pyrrolo[2,3-b]pyridin-4-yl)oxy)-3-fluorophenyl)-N-(1-methylpiperidin-4-yl)propanamide |
| 223 | 4-(4-((S)-2-amino-3-((1S,4S)-5-methyl-2,5-diazabicyclo[2.2.1]heptan-2-yl)-3-oxopropyl)-2-fluorophenoxy)-1H-pyrrolo[2,3-b]pyridine-3-carbonitrile |
| 224 | (S)-4-(4-(2-amino-3-oxo-3-(4-(pyridin-2-ylmethyl)piperazin-1-yl)propyl)-2-fluorophenoxy)-1H-pyrrolo[2,3-b]pyridine-3-carbonitrile |
| 225 | (S)-3-(4-((7H-pyrrolo[2,3-d]pyrimidin-4-yl)oxy)phenyl)-2-amino-N-cyclohexylpropanamide |
| 226 | (S)-3-(4-((7H-pyrrolo[2,3-d]pyrimidin-4-yl)oxy)phenyl)-2-amino-1-(4-benzylpiperazin-1-yl)propan-1-one |
| 227 | (S)-3-(5-((1H-pyrrolo[2,3-b]pyridin-4-yl)oxy)pyridin-2-yl)-2-amino-N-cyclohexylpropanamide |
| 228 | (S)-3-(5-((1H-pyrrolo[2,3-b]pyridin-4-yl)oxy)pyridin-2-yl)-2-amino-1-(4-benzylpiperazin-1-yl)propan-1-one |
| 229 | (R)-3-(4-((1H-pyrrolo[2,3-b]pyridin-4-yl)oxy)-3,5-difluorophenyl)-2-amino-N-cyclohexylpropanamide |
| 132A | First eluting single enantiomer of 2-amino-1-(4-benzylpiperazin-1-yl)-3-(3-fluoro-4-((3-methyl-1H-pyrrolo[2,3-b]pyridin-4-yl)oxy)phenyl)propan-1-one |
| 132B | Second eluting single enantiomer of 2-amino-1-(4-benzylpiperazin-1-yl)-3-(3-fluoro-4-((3-methyl-1H-pyrrolo[2,3-b]pyridin-4-yl)oxy)phenyl)propan-1-one |
| 8A | First eluting diastereoisomer of (S)-2-amino-3-(3-fluoro-4-((3-methyl-1H-pyrrolo[2,3-b]pyridin-4-yl)oxy)phenyl)-1-(3-(3-methyl-1,2,4-oxadiazol-5-yl)pyrrolidin-1-yl)propan-1-one |
| 8B | Second eluting diastereoisomer of (S)-2-amino-3-(3-fluoro-4-((3-methyl-1H-pyrrolo[2,3-b]pyridin-4-yl)oxy)phenyl)-1-(3-(3-methyl-1,2,4-oxadiazol-5-yl)pyrrolidin-1-yl)propan-1-one |
| 91A | First eluting enantiomer of 3-(4-((1H-pyrrolo[2,3-b]pyridin-4-yl)oxy)phenyl)-2-amino-N-(4-(trifluoromethyl)phenyl)propanamide |
| 91B | Second eluting enantiomer of 3-(4-((1H-pyrrolo[2,3-b]pyridin-4-yl)oxy)phenyl)-2-amino-N-(4-(trifluoromethyl)phenyl)propanamide |
| 57A | First eluting enantiomer of 2-amino-3-(3-fluoro-4-((3-methyl-1H-pyrrolo[2,3-b]pyridin-4-yl)oxy)phenyl)-N-(2-(pyridin-4-yl)ethyl)propanamide |
| 57B | Second eluting enantiomer of 2-amino-3-(3-fluoro-4-((3-methyl-1H-pyrrolo[2,3-b]pyridin-4-yl)oxy)phenyl)-N-(2-(pyridin-4-yl)ethyl)propanamide |

The compounds of the invention, including all the compounds here-above listed, can be prepared from readily available starting materials using the following general methods and procedures or by using slightly modified processes readily available to those of ordinary skill in the art. Although a particular embodiment of the present invention may be shown or described herein, those skilled in the art will recognize that all embodiments or aspects of the present invention can be prepared using the methods described herein or by using other known methods, reagents and starting materials. When typical or preferred process conditions (i.e. reaction temperatures, times, mole ratios of reactants, solvents, pressures, etc.) are given, other process conditions can also be used unless otherwise stated. While the optimum reaction conditions may vary depending on the particular reactants or solvent used, such conditions can be readily determined by those skilled in the art by routine optimization procedures.

Thus, processes of preparation described below and reported in the following schemes should not be viewed as limiting the scope of the synthetic methods available for the preparation of the compounds of the invention.

In some cases a step is needed in order to mask or protect sensitive or reactive moieties, generally known protective groups (PG) could be employed, in accordance to general principles of chemistry (Protective Groups in Organic Synthesis, 3rd ed., T. W. Greene, P. G. M. Wuts, John Wiley & Sons (1999), which is incorporated herein by reference in its entirety).

The compounds of formula I, including all the compounds here above listed, can be generally prepared according to the procedures shown in the schemes below. Where a specific detail or step differs from the general schemes it has been detailed in the specific examples, and/or in additional schemes.

Compounds of formula I contain at least one stereogenic centre, as marked as asterisk * in the picture below.

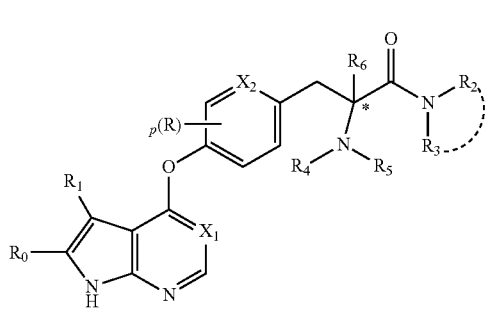

Enantiomerically pure compounds can be prepared according to the reactions described below, by means of enantiomerically pure starting materials and intermediates. Preparation of enantiomerically pure compounds of formula I on the carbon carrying —$NR_4R_5$ (which is marked with asterisk in the picture above) may be accomplished by means of enantiomerically pure intermediates IV and XII as found in the following schemes. These intermediates may be commercial available or readily produced from commercial sources by those of ordinary skill in the art.

In another approach, enantiomerically pure compounds can be prepared from the corresponding racemates by means of chiral chromatography. Whenever, in compounds of formula I, there are two or more stereogenic centres, the structure is then characterized by different stereoisomers. Stereochemically pure compounds may be obtained by chiral separation from a diastereoisomeric mixture, or stepwise by chromatographic separation of diastereoisomers followed by further chiral separation into single stereoisomers.

Compounds of formula I, wherein $R_5$ is H, may be prepared according to Scheme 1 as described hereinafter. Scheme 1 provides at least one non-limiting synthetic route for the preparation of Examples from 1 to 151 and from 225 to 229.

Typical protective groups ($PG_1$) for protection of the NH of the 5-membered ring of the bicyclic intermediate II can be 2-[(trimethylsilyl)ethoxy]methyl (SEM), 4-toluenesulfonyl (Ts) and p-methoxybenzyl (PMB), and anyhow not limiting the use of other protective groups. Intermediate III may be prepared from the corresponding intermediate II and a suitable reagent for $PG_1$ introduction, for example Ts-Cl (tosyl chloride), SEM-Cl ([2-(trimethylsilyl)ethoxy]methyl chloride) or PMB-Br (p-methoxybenzyl bromide). Reaction between said components may be carried out in a polar organic solvent such as DMF or DCM, in the presence of a strong base, such as NaH, at RT or lower.

The carboxylic acid of intermediate IV may be suitably protected as an ester with $PG_2$ (for example as the methyl ester) and the amino group protected as a carbamate with $PG_3$ (for example a Boc group). These transformations may be achieved by using generally well know methods starting from unprotected tyrosine like derivatives.

Intermediate V may be obtained from Intermediates III and IV through a palladium catalyzed O-arylation. For example, the reaction may be carried out by reacting the aryl halide intermediate III and the phenol derivative IV in a suitable organic solvent such as toluene or THF, in the presence of an inorganic base such as $K_2CO_3$, with a suitable palladium catalytic system such as $Pd_2dba_3$/XPhos or another palladium source/phosphine based ligand at high temperature (around 100° C.) for a few hours.

In a different approach, intermediate V may be obtained with a two-step synthesis starting from intermediate VIII. Ipso-substitution of the nitro group of the intermediate VIII by the phenol of intermediate IV, to give intermediate VII, may be carried out in a high boiling organic solvent such as DMSO, at a temperature equal to or higher that 100° C. and in the presence of an inorganic base such as $K_2CO_3$. Intermediate VII can be converted into intermediate V by removing the chlorine atom by means of heterogeneous palladium catalyzed hydrogenation, by reacting VII under a hydrogen atmosphere, in the presence of Pd/C and an organic base such as TEA. Intermediate VIII may be prepared similarly to intermediate III from a corresponding unprotected heterocycle as described above.

Removal of $PG_2$ (when $PG_2$ is a methyl) from intermediate V to give the intermediate VI, whilst not affecting other protections ($PG_1$: SEM, Ts or PMB and $PG_3$: Boc), may be carried out by hydrolysis, using an inorganic base such as LiOH in a mixture of methanol/water, generally at RT and for a time ranging from 1 h to overnight. In some cases, for synthetic convenience, the hydrolysis may be carried out at a temperature equal to or higher than 50° C. and may lead to concurrent $PG_1$ cleavage to give intermediate VIa. Intermediate VIa can be used in a similar way of intermediate VI.

Reaction between intermediate VI (or VIa) and intermediate IX to give the intermediate X (or Xa) may be carried out under suitable amide coupling reaction conditions. For example, intermediate VI (or VIa) and IX may be reacted in the presence of an activating agent such as COMU or HATU, with an organic base such as DIPEA or TEA, in a suitable organic solvent such as DCM or DMF, and at temperature generally around RT for a time ranging from a few hours to overnight.

Alternatively, intermediate X may be prepared from intermediate XI and intermediate III through palladium catalyzed O-arylation in a similar way to that described above for the preparation of the intermediate V. Intermediate XI may be obtained by amide coupling of the intermediate XII with intermediate IX in a similar way as described above for the preparation of intermediate X.

Removal of $PG_1$ and $PG_3$ from intermediate X (or Xa, which bears only $PG_3$), to give compounds of formula I (wherein $R_5$ is H), may be achieved stepwise or concurrently according to the cleavage conditions used (Protective group in organic syntheses, $3^{rd}$ ed. T. W. Greene, P. G. M. Wuts, which is incorporated herein by reference in its entirety). For example, an acidic cleavage using a mixture of TFA in an organic solvent such as DCM, can deprotect both Boc and PMB, while SEM may require an extra treatment in concentrated methanolic ammonia or LiOH. The tosyl group (Ts) may be hydrolysed in a solution of inorganic base such as LiOH in water/methanol at temperature equal to or higher that 50° C.

Scheme 1

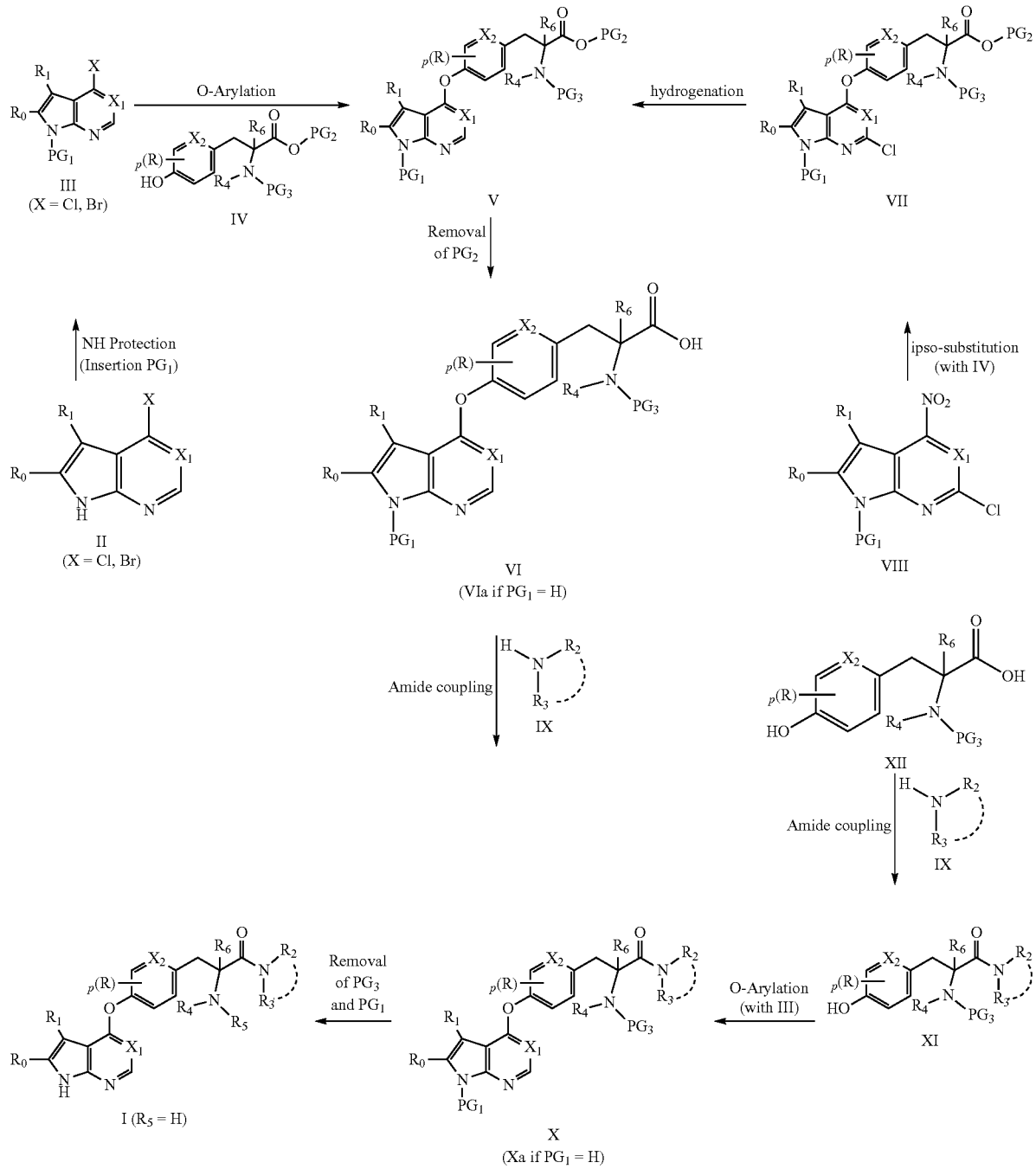

In another embodiment, compounds of formula I (wherein $R_5$ is H, and $R_2$ and $R_3$ are taken together with the nitrogen atom they are linked to form a piperazine ring, optionally substituted at the second nitrogen with an $R_9$) can be prepared according to Scheme 2, providing at least one non-limiting synthetic route for the preparation of Examples from 152 to 177.

Intermediate Xb indicates a compound of formula X wherein $R_2R_3$ are taken together to form a piperazine ring, in which the second nitrogen is protected by a suitable protective group (indicated as $PG_4$), that may be orthogonal to $PG_1$ and $PG_3$. A suitable $PG_4$ group may be represented by a carboxybenzyloxy group (Cbz). Intermediate Xb ($PG_4$ is Cbz) may be converted into intermediate XIIIa by catalytic hydrogenation in the presence of a Pd/C catalyst, in an organic solvent such as MeOH or EtOH and at temperature around RT.

Compounds of formula I (wherein $R_5$ is H, and $R_2R_3$ are taken together to form a piperazine ring) may be prepared from intermediate XIIIa by removal of $PG_3$ and $PG_1$ as described for intermediate X in Scheme 1.

Intermediate XIIIb may be prepared from intermediate XIIIa by introducing group R9 (as specified above) by means of an amide coupling or a reductive amination. For the amide coupling, intermediate XIIIa and a suitable carboxylic acid may be reacted using similar conditions to those already described in SCHEME 1 for the coupling of intermediates VI and IX. Reductive amination can be performed by reacting intermediate XIIIa and a suitable aldehyde, using a reducing agent such as NaBH(OAc)$_3$, NaBH$_3$CN or NaBH$_4$ and in a suitable organic solvent such as DCE, DCM, THF or MeOH. The reaction proceeds smoothly at room temperature over a couple of hours. It could be useful to react the amine and the aldehyde, to pre-form the imine, before adding the reducing agent.

Compounds of formula I (wherein R$_5$ is H, and R$_2$ and R$_3$ are taken together to form a piperazine ring as above said) can be obtained from intermediate XIIIb by removing PG$_1$ and PG$_3$, employing the same cleavage conditions already described in Scheme 1 for intermediate X. It will be apparent to those skilled in the art that the R9 substituent of intermediate XIIIb may be further elaborated prior to deprotection of PG$_1$ and PG$_3$ to give compounds of formula I. For example, if R$_9$ is a 3-(methoxycarbonyl)-phenyl)methyl or a methoxycarbonylheteroarylmethyl moiety (for example 5-(methoxycarbonyl)2-furanylmethyl), it can be readily converted into a corresponding amide in a two-step process including a methyl ester hydrolysis and an amide coupling.

3. Scheme 3 provides at least one non-limiting synthetic route for the preparation of Examples from 178-185.

Intermediate V (wherein R$_4$ is H) may be converted into intermediate XIV by removing PG$_3$. For example, when PG$_1$ is a Ts and PG$_3$ a Boc, the selective removal of PG$_3$ may be achieved by acidic cleavage using a mixture of TFA and an organic solvent such as DCM. Intermediate XIV may be then converted into intermediate XV by introducing R$_4$ and/or R$_5$ with an amide coupling or a reductive amination. Amide coupling may be performed by reacting intermediate XIV and a suitable carboxylic acid using similar conditions to those already described in SCHEME 1 for the coupling of intermediates VI and IX. Reductive amination can be performed by reacting intermediate XIV and a suitable aldehyde in a similar way to what described for intermediate XIIIa of Scheme 2. Alternatively, reductive amination on intermediate XIV may be performed by catalytic hydrogenation of the in situ generated imine, in the presence of a catalyst such as Pd/C and in an alcoholic solvent such as MeOH or EtOH.

Intermediate XV may be converted into intermediate XVI or XVIa by using similar conditions to those already described for the removal of PG$_2$ and PG$_1$, or converted into XVIa using selective deprotection conditions to remove PG$_2$ only.

Compounds of formula I may be obtained from an amide coupling of intermediate XVI (or XVIa) and IX, employing the same conditions already described in Scheme 1. Where

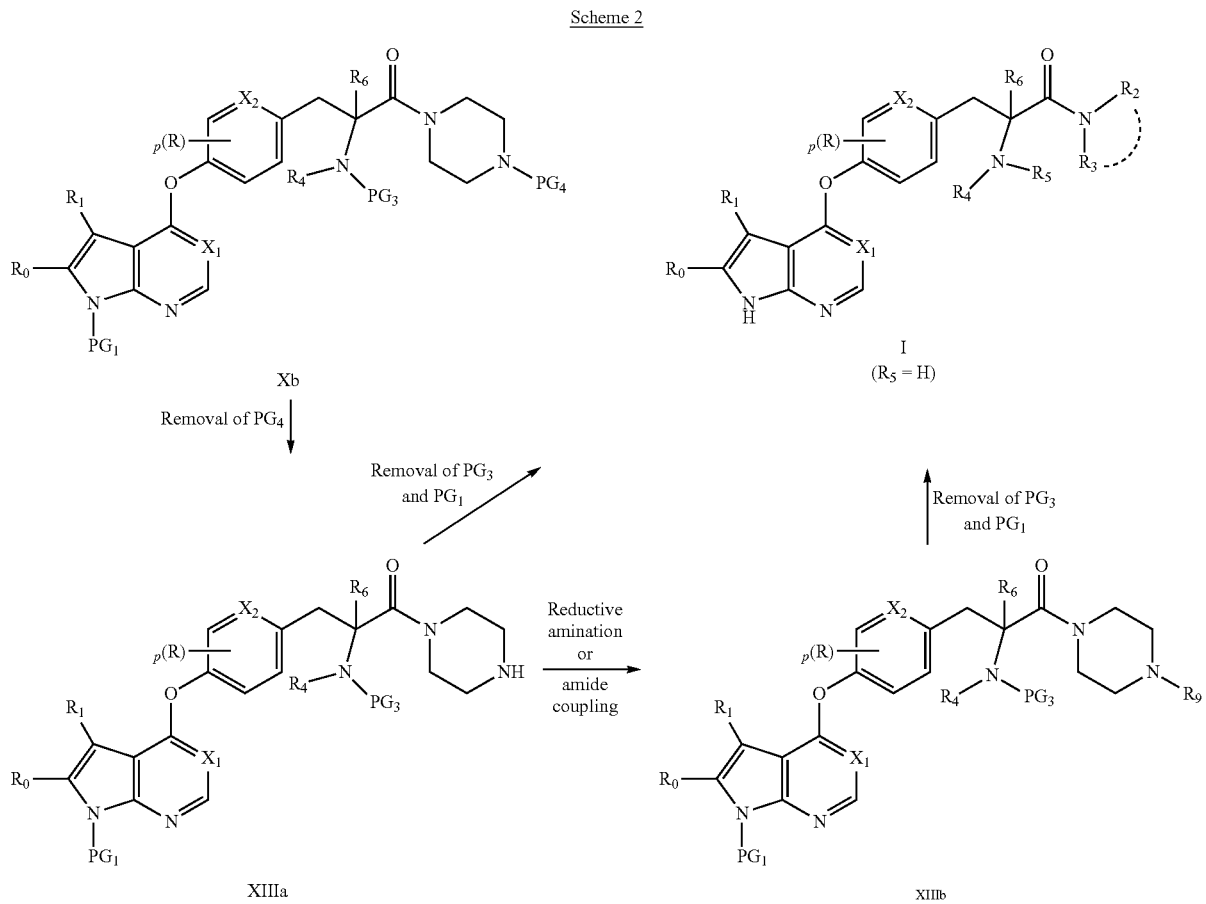

Scheme 2

In another embodiment of the present invention, compounds of formula I may be prepared according to Scheme intermediate XVIa is used in the amide coupling, it will be necessary to remove PG$_1$, as already described in Scheme 1.

Alternatively, compounds of formula I (wherein $R_4$ is an acyl moiety e.g. heterocycloalkylcarbonyl or cycloalkylcarbonyl), may be obtained by converting a corresponding compound (wherein $R_4$=H), via an amide coupling with a suitable carboxylic acid, in a similar way to what described in Scheme 1.

Intermediate VII (wherein $R_1$ is H) may be converted into the intermediate XVII by an electrophilic halogenation with the corresponding NXS (N-halo succinimide, X: Cl, Br or I) carried out in an organic solvent such as MeCN and at temperature around RT for a few hours. Intermediate XVII may be converted in a two-step synthesis into intermediate

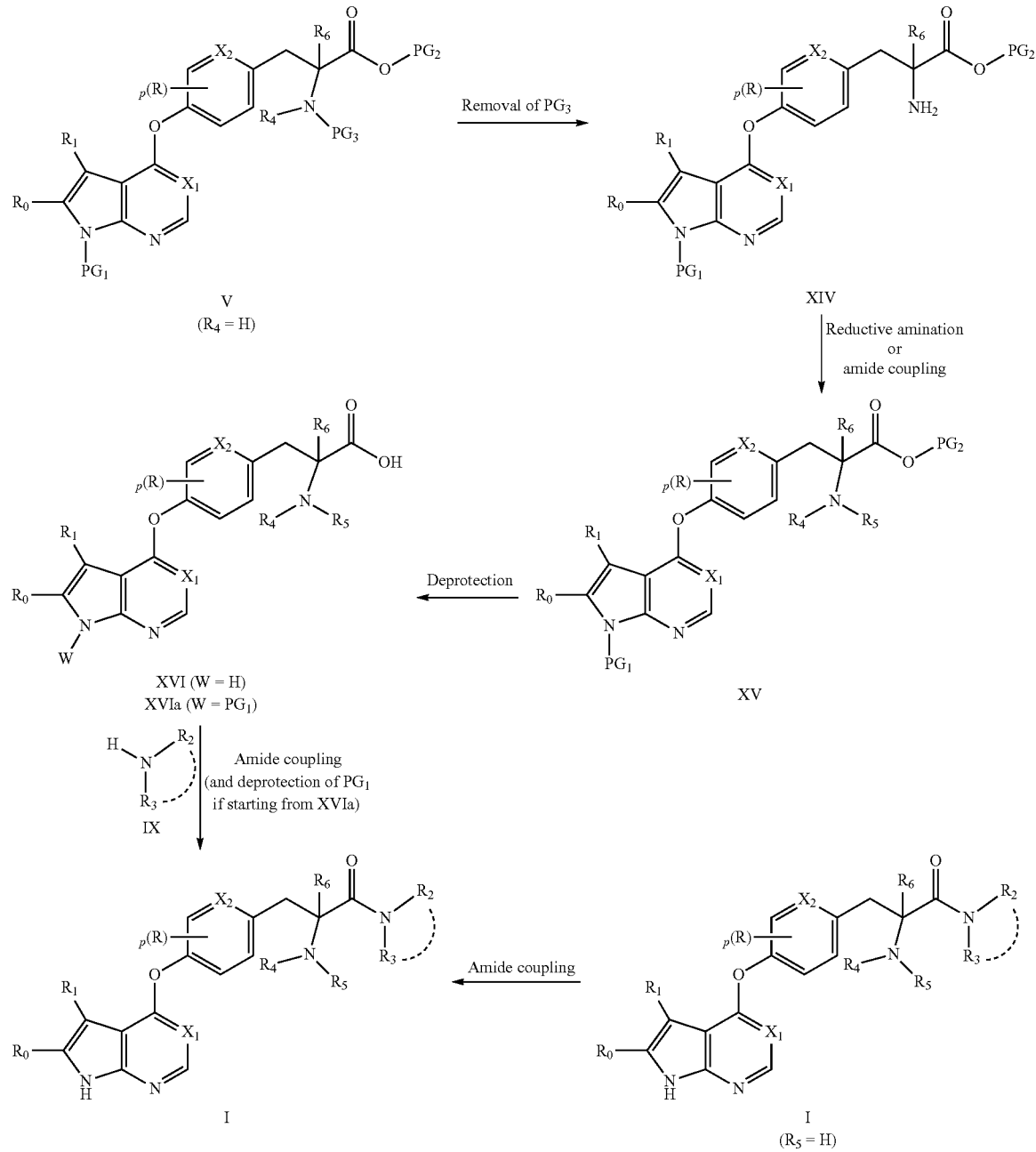

Scheme 3

In another embodiment of the present invention, compounds of formula I (wherein $R_5$=H, $R_1$ is halogen X=Cl, Br, I, or CN or e.g. aryl, heteroaryl, hydroxyalkynyl, cycloalkyl and cycloheteroalkyl and further optionally substituted), may be prepared according to Scheme 4 providing at least one non-limiting synthetic route for the preparation of Examples from 186 to 206 and from 217 to 224.

XVIII. First, $PG_2$ is removed and then the resulting carboxylic acid intermediate is coupled with amine IX under amide coupling conditions. Both removal of $PG_2$ and amide coupling may be performed using similar conditions to what has already been described in Scheme 1.

In a different approach, intermediate XVIII may be obtained from intermediate X (wherein $R_1$ is H) by halogenation, in a similar way to that already described above for conversion of VII into XVII.

Conversion of intermediate XVIII into intermediate Xc (when $R_1$ is CN) may be carried out by metal catalyzed cyanation. For example, intermediate XVIII may be reacted with zinc cyanide in the presence of a Pd catalyst, such as $Pd_2(dba)_3$/1,1'-ferrocenediylbis(diphenylphosphine), in an organic solvent such as DMF, and at a temperature higher than 100° C. for times up to overnight or longer, to give intermediate Xc.

Intermediate XVIII can be alternatively converted into intermediate Xd by introducing an $R_1$ group (aryl, heteroaryl, hydroxyalkynyl, cycloalkyl or cycloheteroalkyl) by a palladium catalyzed cross coupling reaction such as Sonogashira, Suzuki or others described in the reference hereinafter (Strategic Applications of Named Reactions in Organic Synthesis, L. Kurti, B. Czako, Ed., Academic Press (2005), which is incorporated herein by reference in its entirety). For example, a Sonogashira coupling may be performed by heating the intermediate XVIII and a suitable primary alkyne in the presence of a Pd catalyst such as $PdCl_2(dppf)_2$ DCM adduct or tetrakistriphenylphosphinepalladium (0), in the presence of copper iodide (I), and a base such as trimethylamine, in an organic solvent such as THF, at a temperature around 90° C. or higher and for a time up to overnight or longer. A Suzuki coupling can be executed for example by heating intermediate XVIII and a suitable boronic acid or pinacolate derivative in a mixture of water/organic solvent such as DME or THF, in the presence of a Pd catalyst such as $PdCl_2(dppf)_2$ DCM adduct, with an inorganic base such as an alkaline carbonate, at a temperature around 90° C. or higher and for a time up to overnight or longer.

Intermediates XVIII, Xc, and Xd may be converted into compounds of formula I, wherein respectively $R_1$ is a halogen (Cl, Br or I), or a cyano group (CN), or an aryl, heteroaryl, alkynyl, cycloalkyl or cycloheteroalkyl, by using similar methods to what has been already described in Scheme 1 for removal of $PG_1$ and $PG_3$.

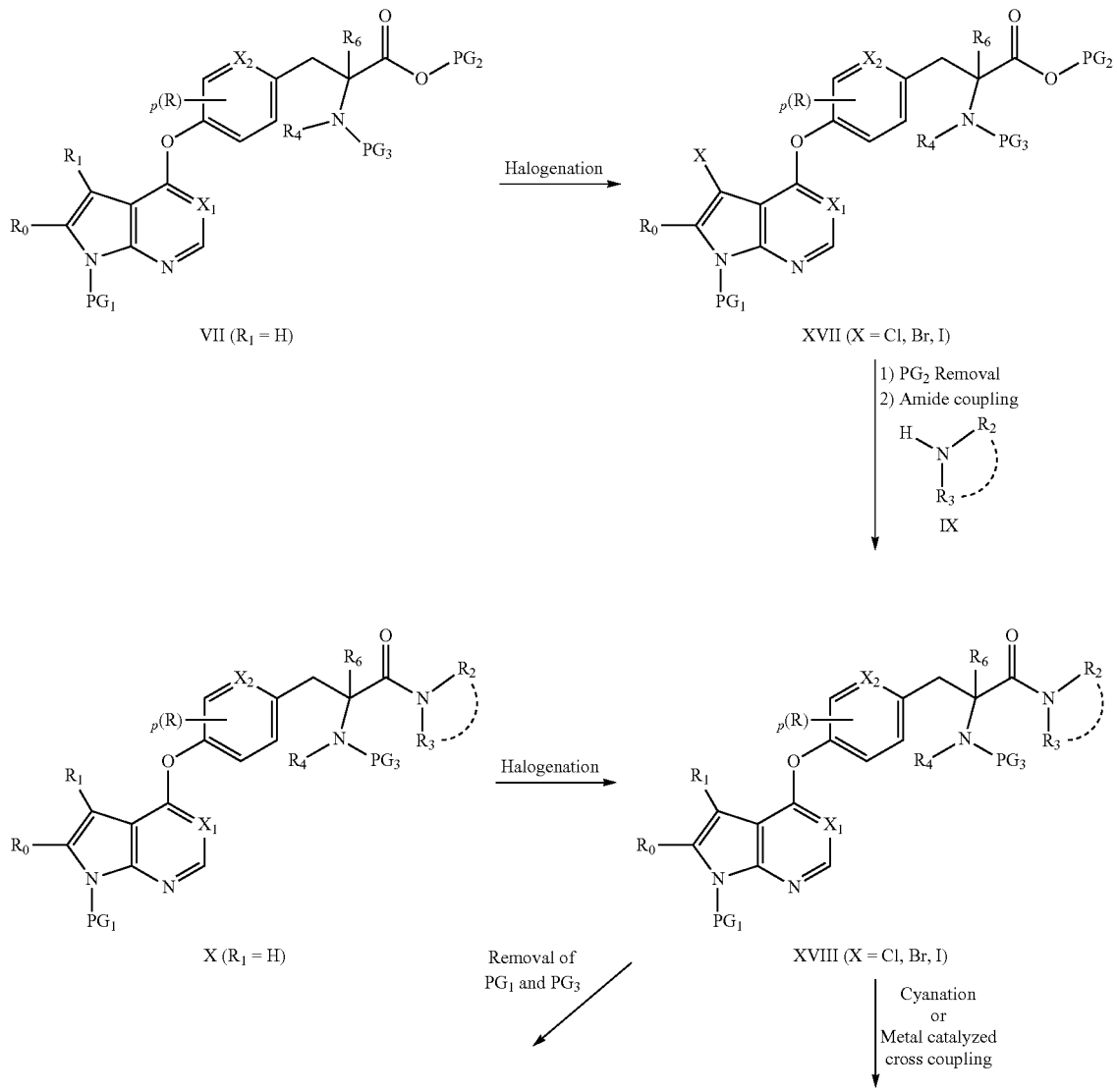

Scheme 4

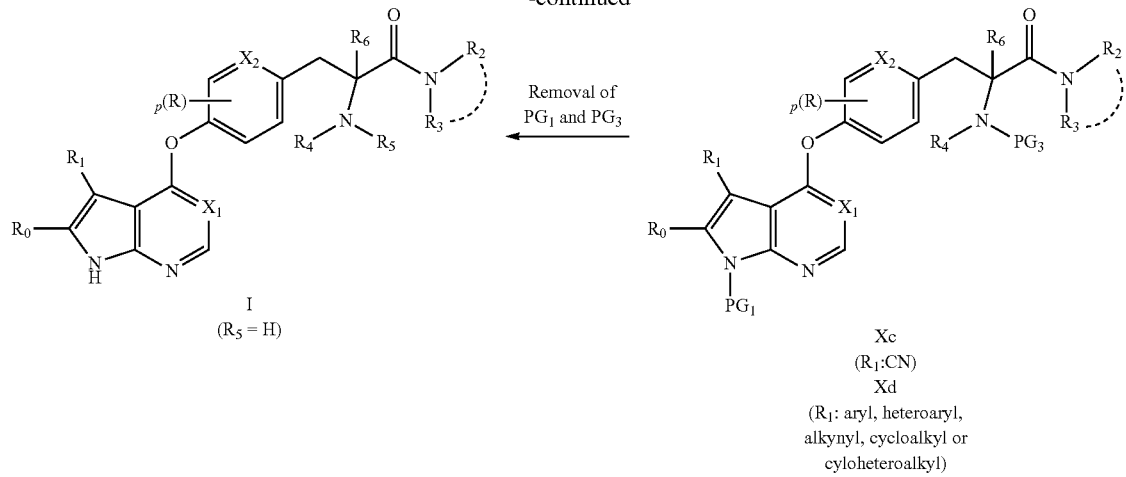

Xc
(R₁:CN)
Xd
(R₁: aryl, heteroaryl,
alkynyl, cycloalkyl or
cyloheteroalkyl)

In another embodiment, compounds of formula I (wherein R₁ is —CH₂OH or —CH₂CH₂OH) may be prepared following Scheme 5. Scheme 5 provides at least one non-limiting synthetic route for the preparation of Examples from 207 to 216 and from 225 to 229.

Compounds of formula I (wherein R₁ is —CH₂OH or —CH₂CH₂OH) may be prepared from intermediate XXIa and/or XXIb, by removal of PG₁ and PG₃, in the same way as described for intermediate X (Scheme 1). In the case of an intermediate XXIIb, which bears a protective group PG₅, the said group can be cleaved under the same conditions as PG₁ and PG₃.

Intermediate XXIa may be obtained by an amide coupling of intermediates XX and IX in a similar way to that described for intermediate X (Scheme 1). Intermediate XX may be prepared starting from intermediate IV and intermediate XIX (wherein Y is CHO) using a palladium catalyzed O-arylation, followed by PG₂ removal as described in Scheme 1. The resulting aldehyde intermediate can be reduced, for example by sodium borohydride in a mixture of organic solvents such as DCM/MeOH at RT for times up to overnight or longer, to afford intermediate XX.

Intermediate XXIb may be prepared from intermediate IV and XXII following the same synthetic sequence described for transforming III and IV into X (Scheme 1), including O-arylation of XXII with IV, followed by deprotection of PG₂ and amide coupling with IX. Intermediate XXII can be prepared from intermediate XIX by a two-step synthesis. Reduction of the carbonyl moiety included in Y can be performed in the same way as described in this scheme for intermediate XX. The resulting alcohol intermediate may be protected with PG₅ (for example TBDMS) to give intermediate XXII, by using generally known methods.

Intermediate XIX can be prepared in a similar way of intermediate III (Scheme 1).

Scheme 5

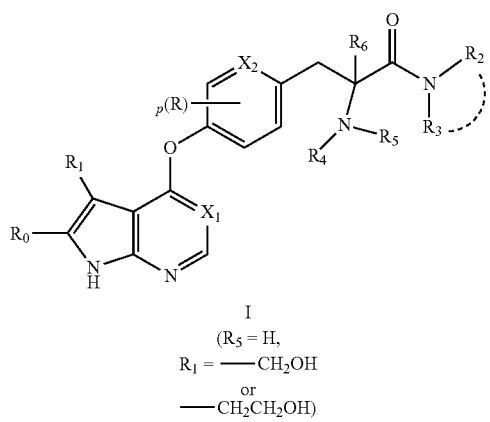

I
(R₅ = H,
R₁ = —CH₂OH
or
—CH₂CH₂OH)

-continued

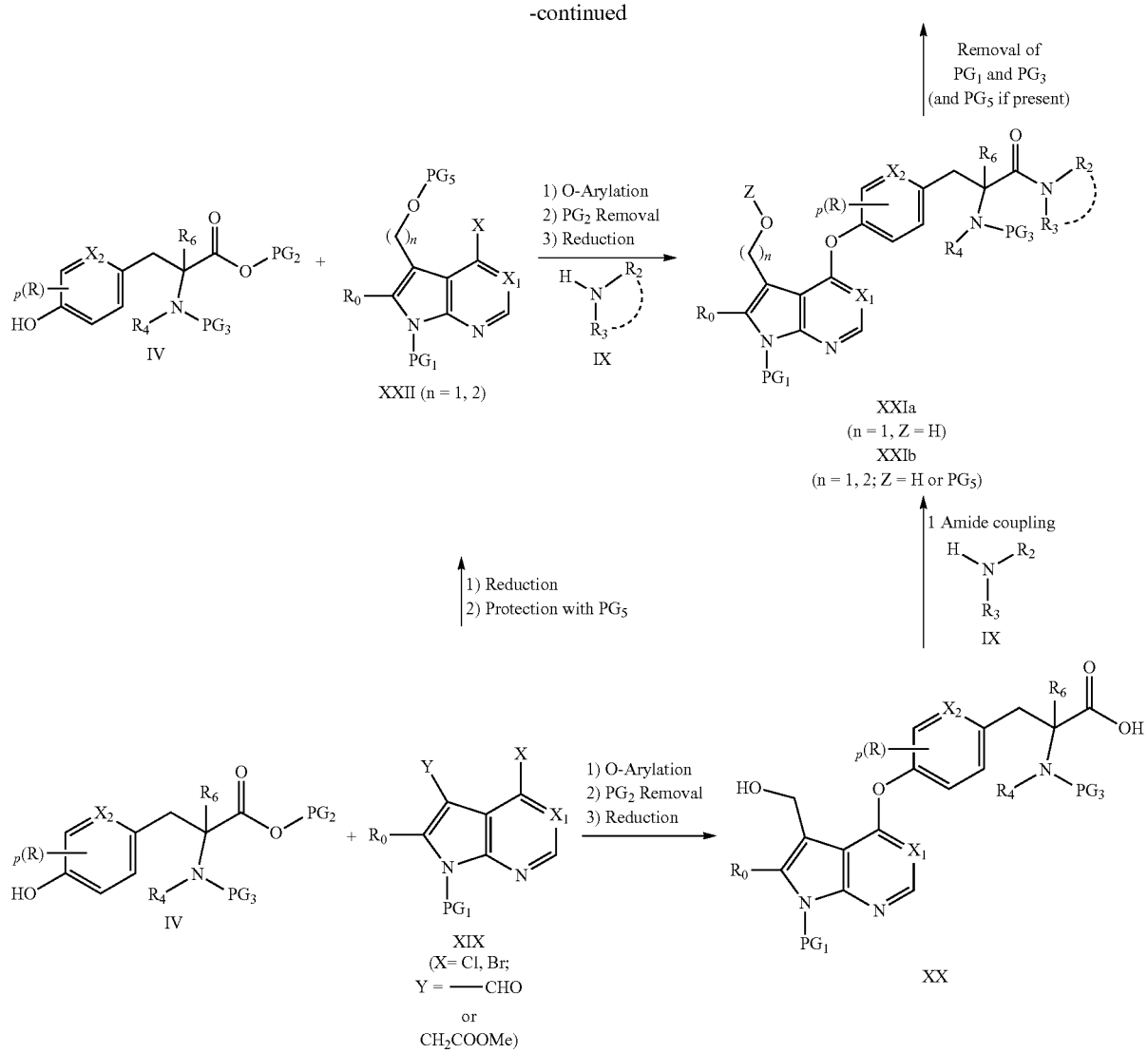

The compounds of the invention are inhibitors of kinase activity, in particular Rho-kinase activity. Generally speaking, compounds which are ROCK inhibitors may be useful in the treatment of many disorders associated with ROCK enzymes mechanisms.

In one embodiment, the disorders that can be treated by the compounds of the present invention include glaucoma, inflammatory bowel disease (IBD) and pulmonary diseases selected from asthma, chronic obstructive pulmonary disease (COPD), interstitial lung disease such as idiopathic pulmonary fibrosis (IPF) and pulmonary arterial hypertension (PAH).

In another embodiment, the disorder that can be treated by the compound of the present invention is selected from the group consisting of asthma, chronic obstructive pulmonary disease (COPD) and interstitial lung disease such as idiopathic pulmonary fibrosis (IPF) and pulmonary arterial hypertension (PAH).

In a further embodiment, the disorder is selected from idiopathic pulmonary fibrosis (IPF) and pulmonary arterial hypertension (PAH).

The methods of treatment of the invention comprise administering a safe and effective amount of a compound of formula (I) or a pharmaceutically acceptable salt thereof to a patient in need thereof. As used herein, "safe and effective amount" in reference to a compound of formula (I) or a pharmaceutically acceptable salt thereof or other pharmaceutically-active agent means an amount of the compound sufficient to treat the patient's condition but low enough to avoid serious side effects and it can nevertheless be routinely determined by the skilled artisan. The compounds of formula (I) or pharmaceutically acceptable salts thereof may be administered once or according to a dosing regimen wherein a number of doses are administered at varying intervals of time for a given period of time. Typical daily dosages may vary depending upon the particular route of administration chosen.

The invention also provides pharmaceutical compositions of compounds of formula (I) in admixture with one or more pharmaceutically acceptable carrier or excipient, for example those described in Remington's Pharmaceutical Sciences Handbook, XVII Ed., Mack Pub., N.Y., U.S.A., which is incorporated herein by reference in its entirety.

Administration of the compounds of the present invention and their pharmaceutical compositions may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and known excipients, including suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the invention, including aqueous and non-aqueous solutions, emulsions, suspensions, syrups, and elixirs. Such dosage forms can also contain suitable known inert diluents such as water and suitable known excipients such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the invention can be prepared by mixing the compound with a suitable excipient such as cocoa butter, salicylates and polyethylene glycols.

Formulations for vaginal administration can be in the form of cream, gel, paste, foam, or spray formula containing, in addition to the active ingredient, such as suitable carriers, are also known.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

For the treatment of the diseases of the respiratory tract, the compounds according to the invention are preferably administered by inhalation.

Inhalable preparations include inhalable powders, propellant-containing metering aerosols or propellant-free inhalable formulations.

For administration as a dry powder, single- or multi-dose inhalers known from the prior art may be utilized. In that case the powder may be filled in gelatine, plastic or other capsules, cartridges or blister packs or in a reservoir.

A diluent or carrier, generally non-toxic and chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in form of solutions or suspensions in an aqueous, alcoholic or hydroalcoholic medium and they may be delivered by jet or ultrasonic nebulizers known from the prior art or by soft-mist nebulizers such as Respimat®.

The compounds of the invention can be administered as the sole active agent or in combination (i.e. as co-therapeutic agents administered in fixed dose combination or in combined therapy of separately formulated active ingredients) with other pharmaceutical active ingredients selected from organic nitrates and NO donors; inhaled NO; stimulator of soluble guanylate cyclase (sGC); prostaciclin analogue PGI2 and agonist of prostacyclin receptors; compounds that inhibit the degradation of cyclic guanosine monophosphate (cGMP) and/or cyclic adenosine monophosphate (cAMP), such as inhibitors of phosphodiesterases (PDE) 1, 2, 3, 4 and/or 5, especially PDE 5 inhibitors; human neutrophilic elastase inhibitors; compounds inhibiting the signal transduction cascade, such as tyrosine kinase and/or serine/threonine kinase inhibitors; antithrombotic agents, for example platelet aggregation inhibitors, anticoagulants or profibrinolytic substances; active substances for lowering blood pressure, for example calcium antagonists, angiotensin II antagonists, ACE inhibitors, endothelin antagonists, renin inhibitors, aldosterone synthase inhibitors, alpha receptor blockers, beta receptor blockers, mineralocorticoid receptor antagonists; neutral endopeptidase inhibitor; osmotic agents; ENaC blockers; anti-inflammatory including corticosteroids and antagonists of chemokine receptors; bronchodilators for example beta2agonist and muscarinic antagonists; antihistamine drug; anti-tussive drug; antibiotic such as macrolide and DNase drug substance and selective cleavage agents such as recombinant human deoxyribonuclease I (rhDNase); agents that inhibit ALK5 and/or ALK4 phosphorylation of Smad2 and Smad3; tryptophan hydroylase 1 (TPH1) inhibitors and multi-kinase inhibitors.

In a preferred embodiment, the compounds of the invention are dosed in combination with phosphodiesterase V such as sildenafil, vardenafil and tadalafil; organic nitrates and NO donors (for example sodium nitroprusside, nitroglycerin, isosorbide mononitrate, isosorbide dinitrate, molsidomine or SIN-1, and inhaled NO); synthetic prostaciclin analogue PGI2 such as iloprost, treprostinil, epoprostenol and beraprost; agonist of prostacyclin receptors such as selexipag and compounds of WO 2012/007539; stimulator of soluble guanylate cyclase (sGC) like riociguat and tyrosine kinase like imatinib, sorafenib and nilotinib and endothelin antagonist (for example macitentan, bosentan, sitaxentan and ambrisentan).

The dosages of the compounds of the invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of formula (I) can be administered for example, at a dosage of 0.001 to 1000 mg/day, preferably 0.1 to 500 mg/day.

When the compounds of formula (I) are administered by inhalation route, they are preferably given at a dosage of 0.001 to 500 mg/day, preferably 0.1 to 100 mg/day.

A pharmaceutical composition comprising a compound of the invention suitable to be administered by inhalation, such as inhalable powders, propellant-containing metering aerosols or propellant-free inhalable formulations is preferred.

The present invention is also directed to a device comprising the pharmaceutical composition comprising a compound according to the invention, which may be a single- or multi-dose dry powder inhaler, a metered dose inhaler and a soft mist nebulizer.

Other features of the invention will become apparent in the course of the following descriptions of exemplary embodiments which are given for illustration of the invention and are not intended to be limiting thereof.

EXAMPLES

Preparation of Intermediates and Examples

General Experimental Details

Reactions were not carried out under an inert atmosphere unless specified and all solvents and commercial reagents were used as received.

Purification by chromatography refers to purification using the CombiFlash® Companion purification system or the Biotage SP1 purification system. Where products were purified using an Isolute® SPE Si II cartridge, Isolute SPE Si cartridge' refers to a pre-packed polypropylene column containing unbonded activated silica with irregular particles with average size of 50 μm and nominal 60 Å porosity. Fractions containing the required product (identified by TLC and/or LCMS analysis) were pooled and concentrated in vacuo. Where an SCX-2 cartridge was used, 'SCX-2 cartridge' refers to an Isolute® pre-packed polypropylene column containing a non-end-capped propylsulphonic acid functionalised silica strong cation exchange sorbent. Where HPLC was used for purification (Purification by MDAP) fractions containing the required product (identified by TLC and/or LCMS analysis) were pooled and the solvent removed using a Biotage EV10 Evaporator. Alternatively the pooled product fraction was lyophilized.

NMR spectra were obtained on a Varian Unity Inova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 300 spectrometer with a standard 5 mm dual frequency probe operating at 300 MHz or on a Bruker Fourier 300 spectrometer with a 5 mm dual probe operating at 300 MHz. Shifts are given in ppm relative to tetramethylsilane.

Chemical Names for examples and intermediates were generated with Structure To Name Enterprise 12.0 CambridgeSoft (Perkin Elmer).

Solutions of common inorganic salts used in workups are aqueous solutions. Brine refers to a saturated aqueous solution of NaCl. Unless otherwise specified.

LC-MS Method 1

Waters Micromass ZQ2000 mass spectrometer with a C18-reverse-phase column (100×2.1 mm Acquity BEH with 1.7 μm particle size) maintained at 40° C., elution with A: water+0.1% formic acid; B: MeCN+0.1% formic acid.
Gradient:

| Gradient - Time | flow (mL/min) | % A | % B |
|---|---|---|---|
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection-MS, UV PDA

MS ionization method-Electrospray (positive/negative ion).

LC-MS Method 2

Waters Micromass ZQ2000 mass spectrometer with a C18-reverse-phase column (100×2.1 mm Acquity BEH with 1.7 μm particle size) maintained at 40° C., elution with A: water+0.1% aqueous ammonia; B: MeCN+0.1% aqueous ammonia.
Gradient:

| Gradient - Time | flow (mL/min) | % A | % B |
|---|---|---|---|
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection-MS, UV PDA

MS ionization method-Electrospray (positive/negative ion).

LC-MS Method 3

Quattro Micro Mass Spectrometer with a C18-reverse-phase column (100×2.1 mm Acquity BEH with 1.7 μm particle size) maintained at 40° C., elution with A: water+0.1% formic acid; B: MeCN+0.1% formic acid.
Gradient:

| Gradient - Time | flow (mL/min) | % A | % B |
|---|---|---|---|
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection-MS, UV PDA

MS ionization method-Electrospray (positive/negative ion).

LC-MS Method 4

QDa Mass Spectrometer with a C18-reverse-phase column (50×2.1 mm Acquity CSH with 1.7 μm particle size) maintained at 40° C., elution with A: water+0.1% formic acid; B: MeCN+0.1% formic acid.
Gradient:

| Gradient - Time | flow (mL/min) | % A | % B |
|---|---|---|---|
| 0.00 | 1 | 97 | 3 |
| 1.50 | 1 | 1 | 99 |
| 1.90 | 1 | 1 | 99 |
| 2.00 | 1 | 97 | 3 |
| 2.50 | 1 | 97 | 3 |

Detection-MS, UV PDA

MS ionization method-Electrospray (positive/negative ion).

LC-MS Method 5

QDa Mass Spectrometer with a C18-reverse-phase column (50×2.1 mm Acquity BEH with 1.7 μm particle size) maintained at 40° C., elution with A: water+0.1% formic acid; B: MeCN+0.1% formic acid.

Gradient:

| Gradient - Time | flow (mL/min) | % A | % B |
| --- | --- | --- | --- |
| 0.00 | 1 | 97 | 3 |
| 1.50 | 1 | 1 | 99 |
| 1.90 | 1 | 1 | 99 |
| 2.00 | 1 | 97 | 3 |
| 2.50 | 1 | 97 | 3 |

Detection-MS, UV PDA

MS ionization method-Electrospray (positive/negative ion).

LC-MS Method 6

QDa Mass Spectrometer with a C18-reverse-phase column (50×2.1 mm Acquity BEH with 1.7 µm particle size) maintained at 50° C., elution with A: water+0.1% formic acid; B: MeCN+0.1% formic acid.

Gradient:

| Gradient - Time | flow (mL/min) | % A | % B |
| --- | --- | --- | --- |
| 0.00 | 1 | 97 | 3 |
| 1.50 | 1 | 1 | 99 |
| 1.90 | 1 | 1 | 99 |
| 2.00 | 1 | 97 | 3 |
| 2.50 | 1 | 97 | 3 |

Detection-MS, UV PDA

MS ionisation method-Electrospray (positive/negative ion).

LC-MS Method 7

Waters Platform LC with a C18-reverse-phase column (30×4.6 mm Phenomenex Luna 3 µm particle size), elution with A: water+0.1% formic acid; B: acetonitrile+0.1% formic acid.

Gradient:

| Gradient - Time | flow (mL/min) | % A | % B |
| --- | --- | --- | --- |
| 0.00 | 2 | 95 | 5 |
| 0.50 | 2 | 95 | 5 |
| 4.50 | 2 | 5 | 95 |
| 5.50 | 2 | 5 | 95 |
| 6.00 | 2 | 95 | 5 |

Detection-MS, ELS, UV (100 µl split to MS with in-line UV detector)

MS ionization method-Electrospray (positive and negative ion).

LC-MS Method 8

QDa Mass Spectrometer with a C18-reverse-phase column (50×2.1 mm Acquity BEH with 1.7 µm particle size) maintained at 50° C., elution with A: water+0.1% formic acid; B: MeCN+0.1% formic acid.

Gradient:

| Gradient - Time | flow (mL/min) | % A | % B |
| --- | --- | --- | --- |
| 0.00 | 1 | 97 | 3 |
| 1.50 | 1 | 1 | 99 |
| 1.90 | 1 | 1 | 99 |
| 2.00 | 1 | 97 | 3 |
| 2.50 | 1 | 97 | 3 |

Detection-MS, UV PDA

MS ionization method-Electrospray (positive/negative ion).

LC-MS Method 9

QZ Mass Spectrometer with a C18-reverse-phase column (30×4.6 mm Phenomenex Luna with 3 µm particle size), elution with A: water+0.1% formic acid; B: MeCN+0.1% formic acid.

Gradient:

| Gradient - Time | flow (mL/min) | % A | % B |
| --- | --- | --- | --- |
| 0.0 | 2 | 95 | 05 |
| 0.3 | 2 | 95 | 05 |
| 4.3 | 2 | 05 | 95 |
| 5.3 | 2 | 05 | 95 |
| 5.8 | 2 | 95 | 05 |
| 6.0 | 2 | 95 | 05 |

Detection-MS, UV PDA

MS ionization method-Electrospray (positive/negative ion).

MDAP Method (Acidic)

Agilent Technologies 1260 Infinity purification system with an XSELECT CSH Prep C18 column (19×250 mm, 5 µm OBD) maintained at RT Mobile Phase A: 0.1% aqueous formic acid Mobile Phase B: 0.1% formic acid in acetonitrile Flow Rate: 20 ml/min Gradient Program: 10%-95%, 22 min, centered around a specific focused gradient Sample: Injection of a 20-60 mg/ml solution in DMSO (+optional formic acid and water)

MDAP Method (Basic)

Agilent Technologies 1260 Infinity purification system with an XBridge Prep C18 OBD column (19×250 mm, 5 µm OBD) maintained at RT Mobile Phase A: 0.1% aqueous ammonia Mobile Phase B: 0.1% ammonia in acetonitrile Flow Rate: 20 ml/min Gradient Program: 10%-95%, 22 min, centered around a specific focused gradient Sample: Injection of a 20-60 mg/ml solution in DMSO+ optional formic acid and water)

SFC Methods

Supercritical Fluid Chromatography (SFC) was carried out using either a Waters Thar Prep100 preparative SFC system (P200 $CO_2$ pump, 2545 modifier pump, 2998 UV/VIS detector, 2767 liquid handler with Stacked Injection Module) or a Waters Thar Investigator semi preparative system (Waters Fluid Delivery Module, 2998 UV/VIS detector, Waters Fraction Collection Module). The column and isocratic method used is indicated for each compound and the single enantiomers were analyzed using the methods given. Some of the compounds may have gone through a second purification process in order to achieve the required % ee purity.

Preparative HPLC Method (Acidic Conditions)

Where compounds were purified by HPLC they were carried out on a C18-reverse-phase column (250×21.2 mm Phenomenex Kinetex with 5 µm particle size). Specific eluting mixtures are described and, unless otherwise stated, peaks were detected by UV (254 nm). Fractions containing the pure product were generally combined and freeze-dried to give a solid.

Preparative HPLC Method (Basic Conditions)

Where compounds were purified by HPLC they were carried out on a C18-reverse-phase column (250×21.2 mm Phenomenex Kinetex EVO with 5 µm particle size). Specific eluting mixtures are described and, unless otherwise stated, peaks were detected by UV (254 nm). Fractions containing the pure product were generally combined and freeze-dried to give a solid.
Chiral HPLC (Method A)
Enantiomers were separated by chiral HPLC using a Chiralpak IC column (21×250 mm, 5 μM) and eluting with 15% ethanol in heptane (with 0.5% DEA) at a flow rate of 18 mL/min.
Abbreviations Used in the Experimental Section
COMU (1-cyano-2-ethoxy-2-oxoethylidenaminooxy)dimethylaminomorpholino-carbenium hexafluorophosphate
DCE 1,2-dichloroethane
DCM dichloromethane
DEA diethylamine
DIPEA di-isopropylethylamine
DME 1,2-dimethoxyethane
DMF N,N-dimethylformamide
DMSO dimethylsuiphoxide
h hour(s)
HATU (1-[bis(dimethylamino)methylene]-1H-1,2,3-triazolo[4,5-b]pyridinium 3-oxid hexafluorophosphate)
HPLC high performance liquid chromatography
IMS industrial methylated spirits
LCMS liquid chromatography-mass spectrometry
MDAP mass-directed autopurification
MeCN acetonitrile
NBS N-bromosuccinimide
NCS N-chlorosuccinimide
NIS N-iodosuccinimide
$Pd_2(dba)_3$ tris(dibenzylideneacetone)dipalladium(0)
$Pd_2(dppf)_2$. [1,1'-bis(diphenylphosphino)ferrocene]dichloropalladium(II)
Rt retention time
RT room temperature
SFC supercritical fluid chromatography
TFA trifluoroacetic acid
THF tetrahydrofuran
XPhos 2-dicyclohexylphosphino-2',4',6'-triisopropylbiphenyl In the procedures that follow, some of the starting materials are identified through an "Intermediate" or "Example" number with indications on step number. This is provided merely for assistance to the skilled chemist.

When reference is made to the use of a "similar" or "analogous" procedure, as will be appreciated by those skilled in the art, such a procedure may involve minor variations, for example reaction temperature, reagent/solvent amount, reaction time, work-up conditions or chromatographic purification conditions.

The stereochemistry of the compounds in the Examples, where indicated, has been assigned on the assumption that absolute configuration at resolved stereogenic centers of starting materials is maintained throughout any subsequent reaction conditions.

The ee % (enantiomeric excess) was measured by chiral LC or SFC methods described for Examples 8, 55, 57, 91 and 132. These methods are considered non limiting examples for the analytical methods to be used for the determination of ee %. Unless otherwise stated, where absolute configuration (R) or (S) is reported in the compound name, ee % has to be considered equal or greater than 90%. For those Examples having a measured value of ee % less than 90, the exact value was reported. Wherein the measure of ee % has not been determined, they were marked as n.d. (not determined).

Example 1

Step A. Methyl (S)-2-amino-3-(3-fluoro-4-hydroxyphenyl)propanoate (Intermediate 1A-a)

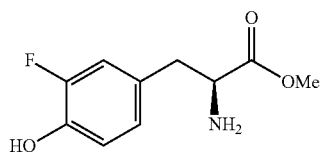 [SMILES: COC(=O)[C@@H](N)Cc1ccc(O)c(F)c1]

3-Fluoro-L-tyrosine (6.0 g, 30.12 mmol) was suspended in methanol (120 mL) and the mixture was cooled in an ice bath. Thionyl chloride (11 mL, 150.6 mmol) was added dropwise. The mixture was allowed to warm to RT and then stirred overnight. The solvent was evaporated and the residue dissolved in water (50 mL). After basifying the mixture using saturated aqueous sodium hydrogen carbonate, the product was extracted into ethyl acetate (4×40 mL). The combined organic extracts were dried ($Na_2SO_4$) and evaporated to give the desired product as a beige solid (4.55 g).
LCMS (Method 4): Rt=0.65 min, m/z 214.1 $[M+H]^+$ Step B. Methyl (S)-2-((tert-butoxycarbonyl)amino)-3-(3-fluoro-4-hydroxyphenyl)-propanoate (Intermediate 1B-a)

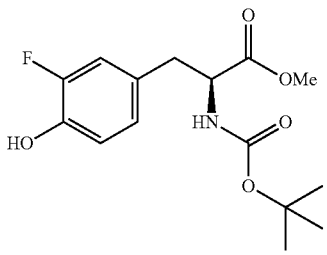 [SMILES: COC(=O)[C@H](Cc1ccc(O)c(F)c1)NC(=O)OC(C)(C)C]

Intermediate 1A-a (4.55 g, 21.34 mmol) was suspended in a mixture of DCM (153 mL) and THF (77 mL). The mixture was cooled in an ice bath and di-tert-butyl dicarbonate (5.12 g, 23.47 mmol) was added. The reaction mixture was allowed to warm to RT and stirred for 4 h. The solvent was evaporated in vacuo and the crude product was chromatographed on a 120 g Si cartridge eluting with 0-10% 2M methanolic ammonia in DCM. Intermediate 1B-a was obtained as a yellow gum (5.96 g).
LCMS (Method 4): Rt=1.29 min, m/z 336.2 $[M+Na]^+$ Step C. 4-Bromo-3-methyl-1-((2-(trimethylsilyl)ethoxy)methyl)-1H-pyrrolo[2,3-b]pyridine (Intermediate 1C-a)

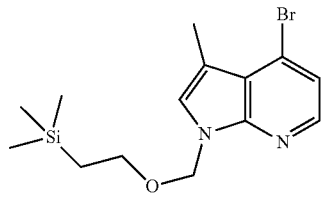 [SMILES: Cc1cn(COCC[Si](C)(C)C)c2nccc(Br)c12]

4-Bromo-3-methyl-7-azaindole (4.0 g, 18.95 mmol) was dissolved in DMF (37 mL) and the solution was cooled in an ice bath. Sodium hydride (60% on mineral oil, 1.14 g, 28.43 mmol) was added and the mixture was stirred under a stream of nitrogen for 1 h. 2-(Trimethylsilyl)ethoxymethyl chloride (4.0 mL, 22.74 mmol) was added dropwise and then the reaction mixture was stirred for a further 30 min. After quenching with water (20 mL), the product was extracted into ethyl acetate (3×20 mL). The combined extracts were dried (Na$_2$SO$_4$) and evaporated. The residue was chromatographed on a 120 g Si cartridge eluting with 0-25% ethyl acetate in cyclohexane to give Intermediate 1C-a as a colourless oil (3.78 g).

LCMS (Method 6): Rt=1.90 min, m/z 341.1/343.0 [M+H]$^+$

Step D. Methyl (S)-2-((tert-butoxycarbonyl)amino)-3-(3-fluoro-4-((3-methyl-1-((2-(trimethylsilyl)ethoxy)methyl)-1H-pyrrolo[2,3-b]pyridin-4-yl)oxy)phenyl)-propanoate (Intermediate 1D-a)

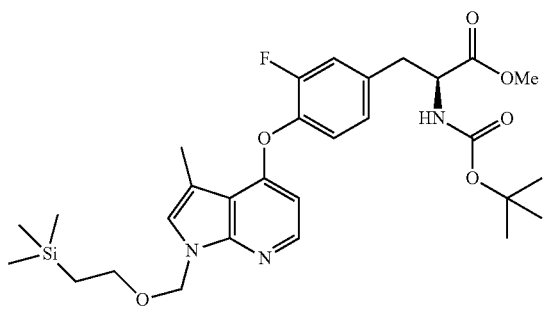 [SMILES: COC(=O)[C@H](Cc1ccc(Oc2ccnc3c2c(C)cn3COCC[Si](C)(C)C)c(F)c1)NC(=O)OC(C)(C)C]

A mixture of Intermediates 1B-a (5.96 g, 19.02 mmol) and 1C-a (6.09 g, 17.84 mmol), Pd$_2$(dba)$_3$ (0.82 g, 0.89 mmol), XPhos (0.85 g, 1.78 mmol), and potassium carbonate (5.42 g, 39.25 mmol) in toluene (224 mL) was sonicated for 5 min under a blanket of argon. The mixture was heated at 100° C. for 3 h, and then allowed to cool to RT before filtering through Celite®. The solvent was evaporated and the residue was taken up into water (40 mL) and extracted with ethyl acetate (3×30 mL). The combined organic extracts were washed with brine (30 mL), dried (Na$_2$SO$_4$) and evaporated. The crude product was chromatographed on a 300 g Si cartridge eluting with 0-50% ethyl acetate in cyclohexane. The product was obtained as a beige solid (4.85 g).

LCMS (Method 4): Rt=1.88 min, m/z 574.4 [M+H]$^+$

Step E. (S)-2-((tert-Butoxycarbonyl)amino)-3-(3-fluoro-4-((3-methyl-1-((2-(trimethylsilyl)ethoxy)methyl)-1H-pyrrolo[2,3-b]pyridin-4-yl)oxy)phenyl)propanoic acid (Intermediate 1E-a)

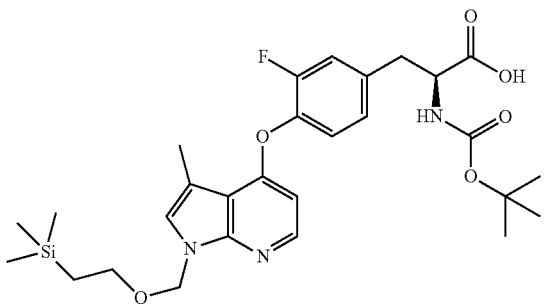 [SMILES: Cc1cn(COCC[Si](C)(C)C)c2nccc(Oc3ccc(C[C@H](NC(=O)OC(C)(C)C)C(=O)O)cc3F)c12]

Intermediate 1D-a (4.85 g, 8.45 mmol) was dissolved in a mixture of methanol (42 mL), water (42 mL) and THF (21 mL). Lithium hydroxide hydrate (1.06 g, 25.35 mmol) was added and the reaction mixture was stirred at RT for 10 min. The solvent was reduced and the product was extracted into ethyl acetate (3×20 mL). The combined organic extracts were washed with brine (30 mL), dried (Na$_2$SO$_4$) and evaporated to give a beige solid (4.74 g).

LCMS (Method 6): Rt=1.79 min, m/z 560.4 [M+H]$^+$

Step F. tert-Butyl (S)-(3-(3-fluoro-4-((3-methyl-1-((2-(trimethylsilyl)ethoxy)methyl)-1H-pyrrolo[2,3-b]pyridin-4-yl)oxy)phenyl)-1-((1-methylpiperidin-4-yl)amino)-1-oxopropan-2-yl)carbamate (Intermediate 1F-a)

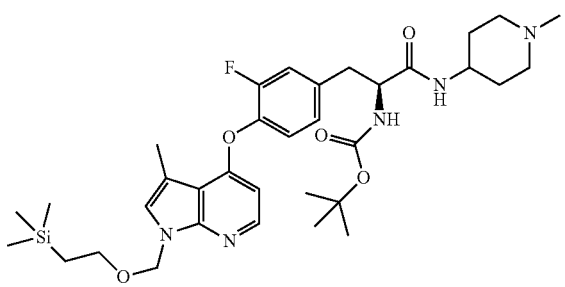

Intermediate 1E-a (500 mg, 0.89 mmol), 1-methylpiperidin-4-amine (112 mg, 0.98 mmol) and COMU (457 mg, 1.07 mmol) were dissolved in DCM (15 mL) and DIPEA (0.35 mL, 1.96 mmol) was added. The reaction was stirred at RT for 2.5 h and then a further amount of 4-amino-1-methylpiperidine (55 mg, 0.49 mmol) was added. Stirring was continued for a further 2 h. Water (15 mL) was added and the DCM layer was separated. The aqueous was further extracted with DCM (2×10 mL) and the combined organic extracts were dried (Na$_2$SO$_4$) and evaporated. The product was purified by chromatography on a 40 g Si cartridge eluting with 0-10% 2M methanolic ammonia in DCM. Intermediate 1F-a was obtained as a yellow solid (418 mg).

LCMS (Method 4): Rt=1.27 min, m/z 656.3 [M+H]$^+$

Step G. (S)-2-amino-3-(3-fluoro-4-((3-methyl-1H-pyrrolo[2,3-b]pyridin-4-yl)oxy)phenyl)-N-(1-methylpiperidin-4-yl)propanamide (Example 1)

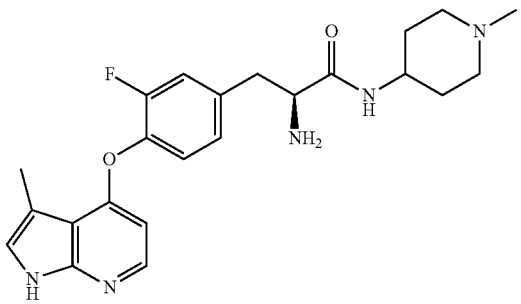 [SMILES: Cc1c[nH]c2nccc(Oc3ccc(C[C@H](N)C(=O)NC4CCN(C)CC4)cc3F)c12]

Intermediate 1F-a (418 mg, 0.64 mmol) was dissolved in a mixture of DCM (7.1 mL) and TFA (7.1 mL), and the reaction was stirred at RT for 4 h. The mixture was diluted with methanol and passed down a 10 g SCX-2 cartridge eluting with methanol and then 2M methanolic ammonia. After standing for 18 h, the ammonia solution was evaporated to give a residue which was purified by HPLC eluting with a gradient of 10-98% acetonitrile in water (0.1% NH₄OH added). Example 1 was obtained as a white solid (111 mg).

LCMS (Method 1): Rt=1.69 min, m/z 425.9 [M+H]⁺

¹H NMR (400 MHz, d6-DMSO) δ 11.38 (s, 1H), 7.97 (d, J=5.4 Hz, 1H), 7.64 (d, J=7.8 Hz, 1H), 7.28-7.20 (m, 2H), 7.13 (d, J=1.6 Hz, 1H), 7.08 (dd, J=1.3, 8.3 Hz, 1H), 6.16 (d, J=4.8 Hz, 1H), 3.53-3.42 (m, 1H), 3.41-3.35 (m, 1H), 2.87 (dd, J=5.9, 13.3 Hz, 1H), 2.74-2.54 (m, 3H), 2.38 (d, J=1.0 Hz, 3H), 2.12 (s, 3H), 1.97-1.86 (m, 2H), 1.79-1.69 (s, 2H), 1.68-1.57 (m, 2H), 1.43-1.26 (m, 2H).

Examples 2 to 130

The following Examples were prepared in a similar way to Example 1 by replacing at each step the appropriate starting materials.

Preparation of Intermediates 1B-b to 1B-e

The following intermediates were prepared in a similar manner to Intermediate 1B-a by replacing in Step A of Example 1 the tyrosine with the indicated starting materials.

| Intermediate | Starting material | Starting material | LC-MS |
|---|---|---|---|
| 1B-b | *(structure)* | 3-Fluoro-DL-tyrosine | Rt = 1.21 min, m/z 336.2 [M + Na]⁺ (Method 6) |
| 1B-c | *(structure)* | L-Tyrosine | Rt = 3.03 min, m/z 296.1 [M + H]⁺ (Method 7) |
| 1B-d | *(structure)* | D-Tyrosine | Rt = 1.19 min, m/z 294.0 [M − H]⁻ (Method 6) |

Preparation of Intermediates from 1C-b to 1C-f

The following intermediates were prepared in a similar manner to Intermediate 1C-a from the indicated starting materials.

Preparation of Intermediates from 1D-b to 1D-j

The following intermediates were prepared in a similar manner to Intermediate 1D-a from the indicated starting materials.

| Intermediate | Structure | Starting materials | LC-MS |
|---|---|---|---|
| 1C-b | 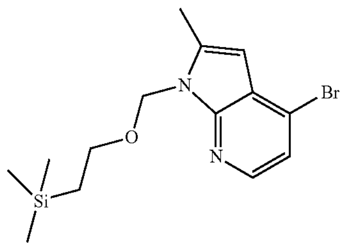 [SMILES: Cc1cc2c(Br)ccnc2n1COCC[Si](C)(C)C] | 4-Bromo-2-methyl-7-azaindole | Rt = 4.60 min, m/z 340.9/342.9 [M + H]+ (Method 9) |
| 1C-c | 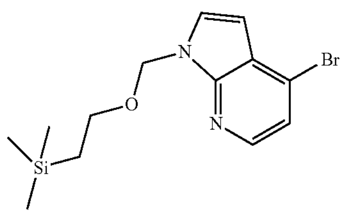 [SMILES: C[Si](C)(C)CCOCn1ccc2c(Br)ccnc21] | 4-Bromo-7-azaindole | Rt = 1.80 min, m/z 326.9/328.9 [M + H]+ (Method 6) |
| 1C-d | 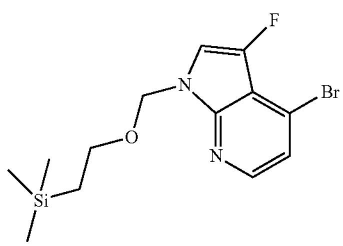 [SMILES: C[Si](C)(C)CCOCn1cc(F)c2c(Br)ccnc21] | 4-Bromo-3-fluoro-7-azaindole | Rt = 1.77 min, m/z 344.9/346.9 [M + H]+ (Method 6) |
| 1C-e | 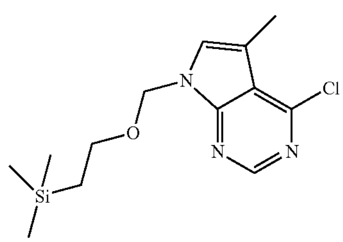 [SMILES: Cc1cn(COCC[Si](C)(C)C)c2ncnc(Cl)c12] | 4-Chloro-5-methyl-7H-pyrrolo[2,3-d]pyrimidine | Rt = 2.35 min, m/z 298.1 [M + H]+ (Method 4) |
| 1C-f | 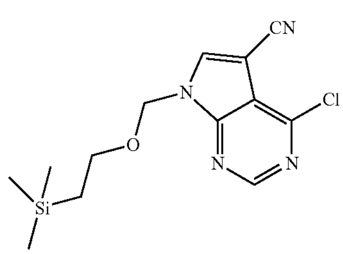 [SMILES: C[Si](C)(C)CCOCn1cc(C#N)c2c(Cl)ncnc21] | 4-Chloro-5-cyano-7H-pyrrolo[2,3-d]pyrimidine | Rt = 3.81 min, m/z 309.0 [M + H]+ (Method 9) |

| Intermediate | Structure | Starting materials | LC-MS |
|---|---|---|---|
| 1D-b | 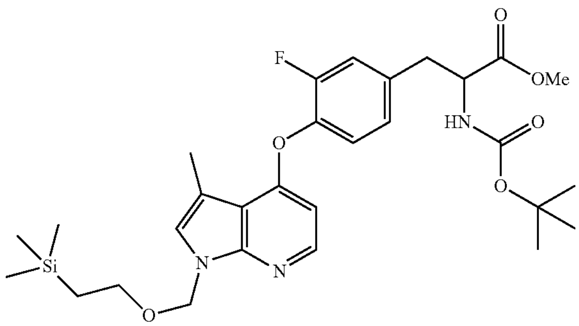 [SMILES: COC(=O)C(Cc1ccc(Oc2ccnc3c2c(C)cn3COCC[Si](C)(C)C)c(F)c1)NC(=O)OC(C)(C)C] | 1B-b and 1C-a | Rt = 1.83 min, m/z 574.3 [M + H]+ (Method 6) |
| 1D-c | 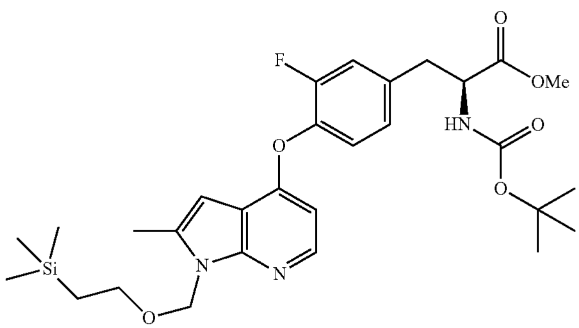 [SMILES: COC(=O)[C@H](Cc1ccc(Oc2ccnc3c2cc(C)n3COCC[Si](C)(C)C)c(F)c1)NC(=O)OC(C)(C)C] | 1B-a and 1C-b | Rt = 1.87 min, m/z 574.2 [M + H]+ (Method 6) |
| 1D-d | 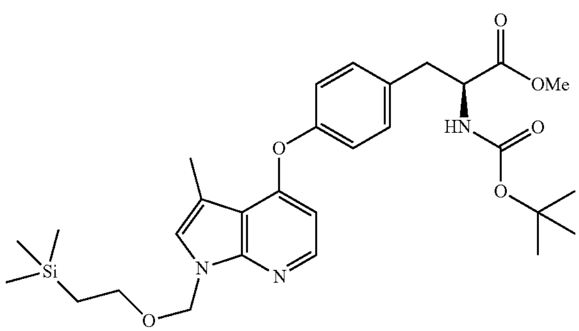 [SMILES: COC(=O)[C@H](Cc1ccc(Oc2ccnc3c2c(C)cn3COCC[Si](C)(C)C)cc1)NC(=O)OC(C)(C)C] | 1B-c and 1C-a | Rt = 1.86 min, m/z 556.2 [M + H]+ (Method 4) |
| 1D-e | 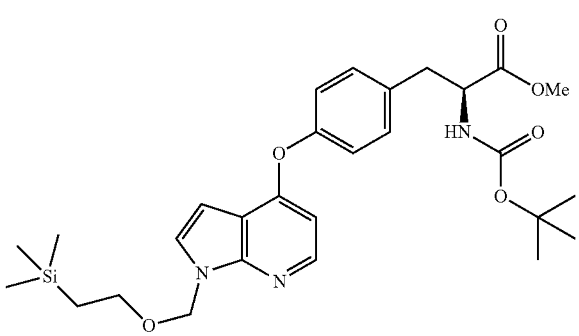 [SMILES: COC(=O)[C@H](Cc1ccc(Oc2ccnc3c2ccn3COCC[Si](C)(C)C)cc1)NC(=O)OC(C)(C)C] | 1B-c and 1C-c | Rt = 4.67 min, m/z 542.3 [M + H]+ (Method 7) |

-continued

| Intermediate | Structure | Starting materials | LC-MS |
|---|---|---|---|
| 1D-f | 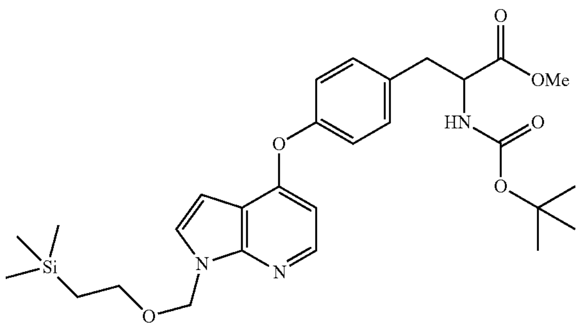 [SMILES: COC(=O)C(Cc1ccc(Oc2ccnc3c2ccn3COCC[Si](C)(C)C)cc1)NC(=O)OC(C)(C)C] | Methyl (tert-butoxycarbonyl)-tyrosinate and -1C-c | Rt = 4.69 min, m/z 542.2 [M + H]⁺ (Method 7) |
| 1D-g | 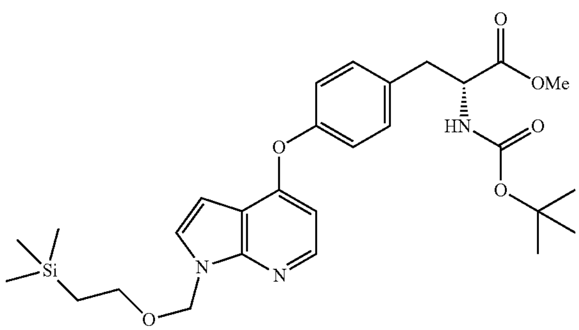 | 1B-d and 1C-c | Rt = 4.67 min, m/z 542.4 [M + H]⁺ (Method 7) |
| 1D-h | 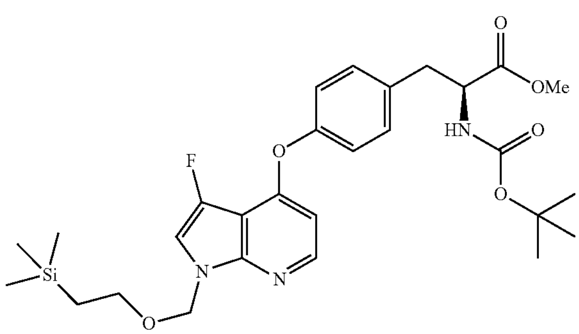 [SMILES: COC(=O)[C@H](Cc1ccc(Oc2ccnc3c2c(F)cn3COCC[Si](C)(C)C)cc1)NC(=O)OC(C)(C)C] | 1B-c and 1C-d | Rt = 1.84 min, m/z 560.2 [M + H]⁺ (Method 4) |
| 1D-i | 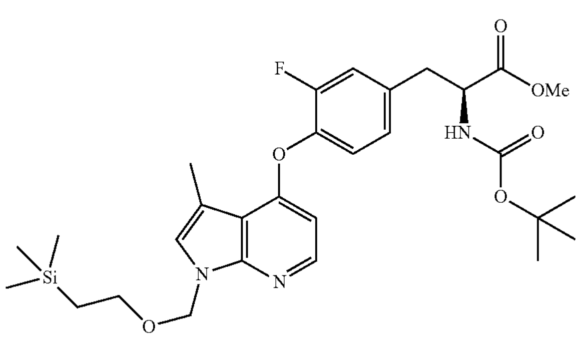 | 1B-a and 1C-e | Rt = 2.48 min, m/z 575.3 [M + H]⁺ (Method 6) |

-continued

| Intermediate | Structure | Starting materials | LC-MS |
|---|---|---|---|
| 1D-j | 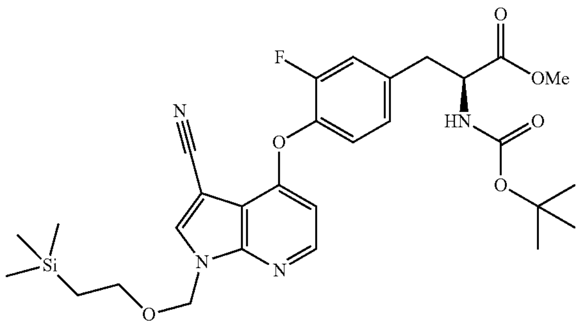 [SMILES: COC(=O)[C@H](Cc1ccc(Oc2ccnc3c2c(C#N)cn3COCC[Si](C)(C)C)c(F)c1)NC(=O)OC(C)(C)C] | 1B-a and 1C-f | Rt = 2.40 min, m/z 586.3 [M − H]⁻ (Method 6) |

Preparation of Intermediates from 1E-b to 1E-p

The following intermediates were prepared in a similar manner to Intermediate 1E-a from the indicated starting materials.

| Intermediate | Structure | Starting materials | LC-MS |
|---|---|---|---|
| 1E-b | 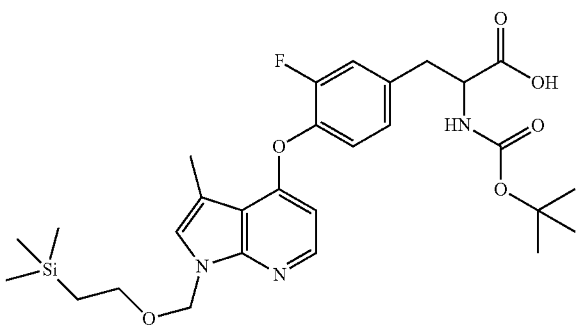 [SMILES: Cc1cn(COCC[Si](C)(C)C)c2nccc(Oc3ccc(CC(NC(=O)OC(C)(C)C)C(=O)O)cc3F)c12] | 1D-b | Rt = 1.75 min, m/z 560.3 [M + H]⁺ (Method 6) |
| 1E-c | 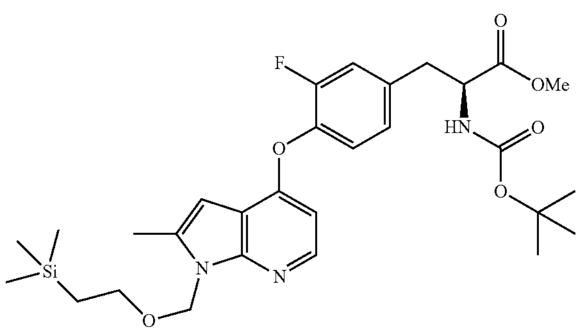 | 1D-c | Rt = 1.79 min, m/z 560.2 [M + H]⁺ (Method 6) |
| 1E-d | 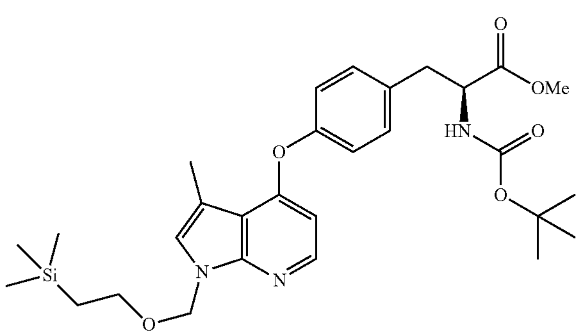 | 1D-d | Rt = 1.77 min, m/z 542.2 [M + H]⁺ (Method 4) |

-continued

| Intermediate | Structure | Starting materials | LC-MS |
|---|---|---|---|
| 1E-e | 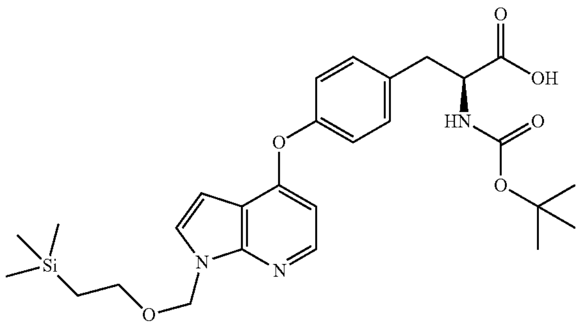 [SMILES: CC(C)(C)OC(=O)N[C@@H](Cc1ccc(Oc2ccnc3c2ccn3COCC[Si](C)(C)C)cc1)C(=O)O] | 1D-e | Rt = 4.24 min, m/z 528.4 [M + H]$^+$ (Method 7) |
| 1E-f | 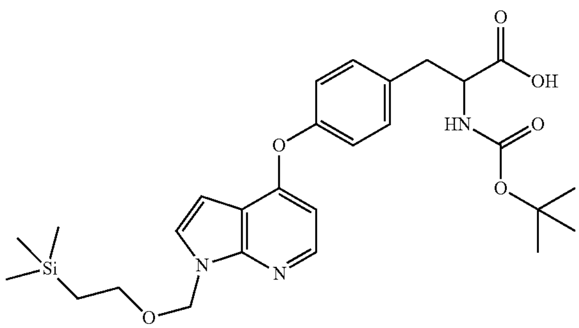 [SMILES: CC(C)(C)OC(=O)NC(Cc1ccc(Oc2ccnc3c2ccn3COCC[Si](C)(C)C)cc1)C(=O)O] | 1D-f | Rt = 4.26 min, m/z 528.2 [M + H]$^+$ (Method 7) |
| 1E-g | 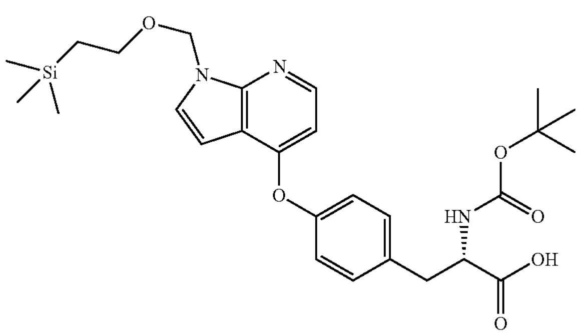 [SMILES: CC(C)(C)OC(=O)N[C@@H](Cc1ccc(Oc2ccnc3c2ccn3COCC[Si](C)(C)C)cc1)C(=O)O] | 1D-g | Rt = 1.74 min, m/z 528.4 [M + H]$^+$ (Method 6) |
| 1E-h | 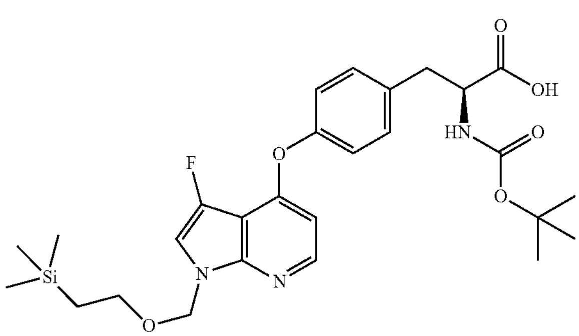 [SMILES: CC(C)(C)OC(=O)N[C@@H](Cc1ccc(Oc2ccnc3c2c(F)cn3COCC[Si](C)(C)C)cc1)C(=O)O] | 1D-h | Rt = 1.75 min, m/z 546.1 [M + H]$^+$ (Method 4) |

-continued

| Intermediate | Structure | Starting materials | LC-MS |
|---|---|---|---|
| 1E-i | 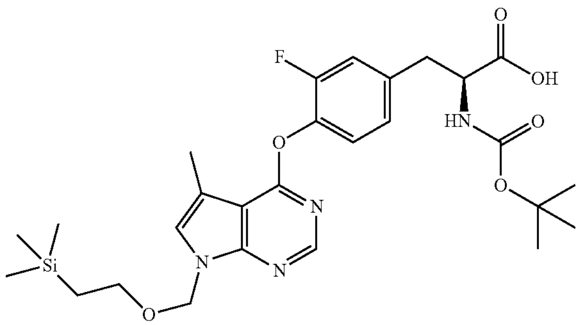 [SMILES: Cc1cn(COCC[Si](C)(C)C)c2ncnc(Oc3ccc(C[C@H](NC(=O)OC(C)(C)C)C(=O)O)cc3F)c12] | 1D-i | Rt = 1.71 min, m/z 561.3 [M + H]$^+$ (Method 4) |
| 1E-j | 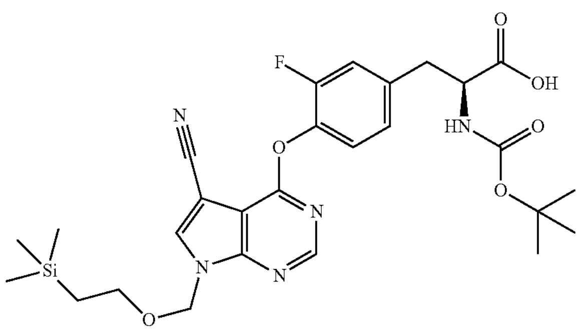 [SMILES: CC(C)(C)OC(=O)N[C@@H](Cc1ccc(Oc2ncnc3c2c(C#N)cn3COCC[Si](C)(C)C)c(F)c1)C(=O)O] | 1D-j | Rt = 1.68 min, m/z 570.2 [M − H]$^-$ (Method 6) |

Preparation of Examples

The following examples were prepared in a similar manner to Example 1, following the same synthetic sequence, by replacing in Step F the indicated Intermediate 1E and amine starting materials in the table below.

| Ex | Structure/Name | Intermediate 1E/Amine | 1H NMR | LC-MS |
|---|---|---|---|---|
| 2 | (S)-2-amino-1-(7,8-dihydropyrido[4,3-d]pyrimidin-6(5H)-yl)-3-(3-fluoro-4-((3-methyl-1H-pyrrolo[2,3-b]pyridin-4-yl)oxy)phenyl)propan-1-one | 1E-a/5,6,7,8-tetrahydro-pyrido[4,3-d]-pyrimidine | $^1$H NMR (400 MHz, d6-DMSO) δ 11.38 (s, 1H), 8.95-8.93 (m, 1H), 8.71-8.41 (m, 1H), 7.95 (dd, J = 5.6, 5.6 Hz, 1H), 7.35-7.05 (m, 4H), 6.12-6.01 (m, 1H), 4.79-4.62 (m, 2H), 4.09-3.60 (m, 3H), 3.00-2.67 (m, 4H), 2.38 (d, J = 6.9 Hz, 3H), 1.80 (s, 2H). | Rt = 1.96 min, m/z 446.9 [M + H]$^+$ (Method 1) |

-continued

| Ex | Structure/Name | Intermediate 1E/Amine | 1H NMR | LC-MS |
|---|---|---|---|---|
| 3 | 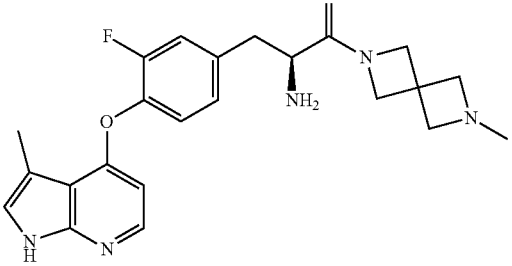<br>(S)-2-amino-3-(3-fluoro-4-((3-methyl-1H-pyrrolo[2,3-b]pyridin-4-yl)oxy)phenyl)-1-(6-methyl-2,6-diazaspiro[3.3]heptan-2-yl)propan-1-one | 1E-a/2-methyl-2,6-diaza-spiro[3.3]-heptane | ¹H NMR (400 MHz, d6-DMSO) δ 11.40 (s, 1H), 7.99 (d, J = 5.4 Hz, 1H), 7.30-7.23 (m, 2H), 7.14 (s, 1H), 7.09 (dd, J = 1.3, 8.3 Hz, 1H), 6.16 (d, J = 5.0 Hz, 1H), 4.15 (d, J = 9.0 Hz, 1H), 3.87 (d, J = 10.2 Hz, 1H), 3.79 (d, J = 10.2 Hz, 1H), 3.65 (d, J = 9.0 Hz, 1H), 3.39 (dd, J = 7.1, 7.1 Hz, 1H), 3.19-3.10 (m, 3H), 3.02 (d, J = 7.2 Hz, 1H), 2.77-2.64 (m, 2H), 2.38 (d, J = 1.0 Hz, 3H), 2.12 (s, 3H), 1.69 (s, 2H). | Rt = 1.63 min, m/z 424.0 [M + H]⁺ (Method 1) |
| 4 | 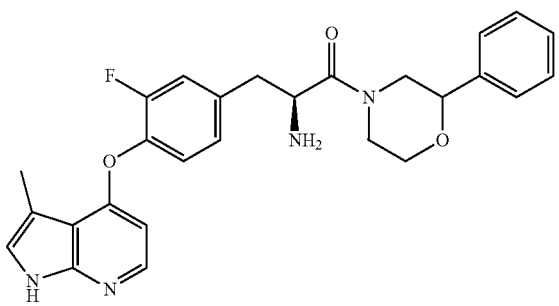<br>(2S)-2-amino-3-(3-fluoro-4-((3-methyl-1H-pyrrolo[2,3-b]pyridin-4-yl)oxy)phenyl)-1-(2-phenylmorpholino)propan-1-one | 1E-a/rac-2-phenyl-morpholine | ¹H NMR (400 MHz, d6-DMSO) δ 11.39 (s, 1H), 8.00-7.82 (m, 1H), 7.42-7.06 (m, 9H), 6.17-6.08 (m, 1H), 4.50-4.15 (m, 2H), 4.09-3.87 (m, 3H), 3.76-3.50 (m, 1H), 3.10-2.54 (m, 4H), 2.39-2.34 (m, 3H), 1.81 (s, 2H). | Rt = 2.77/2.81 min, m/z 475.0 [M + H]⁺ (Method 1) |
| 5 | 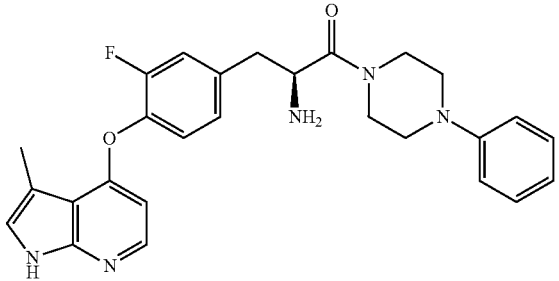<br>(S)-2-amino-3-(3-fluoro-4-((3-methyl-1H-pyrrolo[2,3-b]pyridin-4-yl)oxy)phenyl)-1-(4-phenylpiperazin-1-yl)propan-1-one | 1E-a/1-phenyl-piperazine | ¹H NMR (400 MHz, d6-DMSO) δ 11.37 (s, 1H), 7.82 (d, J = 5.4 Hz, 1H), 7.34 (dd, J = 1.9, 11.9 Hz, 1H), 7.25-7.19 (m, 3H), 7.15-7.11 (m, 2H), 6.93 (d, J = 7.9 Hz, 2H), 6.81 (dd, J = 7.3, 7.3 Hz, 1H), 6.08 (d, J = 5.3 Hz, 1H), 4.01 (dd, J = 6.9, 6.9 Hz, 1H), 3.72-3.49 (m, 4H), 3.15 (d, J = 4.7 Hz, 2H), 2.95-2.90 (m, 1H), 2.87-2.69 (m, 3H), 2.34 (d, J = 0.9 Hz, 3H), 1.81-1.72 (m, 2H). | Rt = 2.78 min, m/z 474.1 [M + H]⁺ (Method 1) |
| 6 | 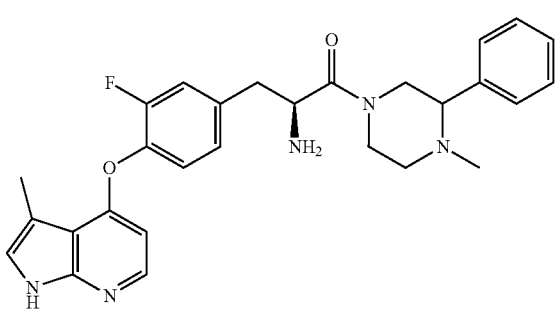<br>(2S)-2-amino-3-(3-fluoro-4-((3-methyl-1H-pyrrolo[2,3-b]pyridin-4-yl)oxy)phenyl)-1-(4-methyl-3-phenylpiperazin-1-yl)propan-1-one | 1E-a/rac-1-methyl-2-phenyl-piperazine | ¹H NMR (400 MHz, d6-DMSO) δ 11.40 (s, 1H), 8.00-7.91 (m, 1H), 7.39-7.01 (m, 9H), 6.22-6.11 (m, 1H), 4.48-4.16 (m, 1H), 4.03-3.93 (m, 1H), 3.85-3.59 (m, 1H), 3.01-2.53 (m, 6H), 2.40-2.33 (m, 3H), 2.23-2.03 (m, 1H), 1.90-1.81 (m, 3H), 1.82-1.74 (m, 2H). | Rt = 2.16 min, m/z 488.1 [M + H]⁺ (Method 1) |

-continued

| Ex | Structure/Name | Intermediate 1E/Amine | 1H NMR | LC-MS |
|---|---|---|---|---|
| 7 | 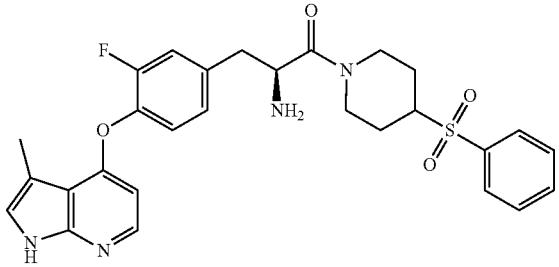<br>(S)-2-amino-3-(3-fluoro-4-((3-methyl-1H-pyrrolo[2,3-b]pyridin-4-yl)oxy)phenyl)-1-(4-(phenylsulfonyl)piperidin-1-yl)propan-1-one | 1E-a/4-(phenyl-sulfonyl)-piperidine | $^{1}$H NMR (400 MHz, d6-DMSO) δ 11.39 (s, 1H), 7.99 (dd, J = 5.4, 11.7 Hz, 1H), 7.87-7.82 (m, 2H), 7.78 (q, J = 7.9 Hz, 1H), 7.73-7.64 (m, 2H), 7.31 (dd, J = 1.2, 11.8 Hz, 1H), 7.21 (dd, J = 8.4, 8.4 Hz, 1H), 7.13 (s, 1H), 7.10 (d, J = 2.9 Hz, 1H), 6.20-6.11 (m, 1H), 4.48 (d, J = 12.3 Hz, 1H), 4.07-4.01 (m, 1H), 3.90 (q, J = 6.3 Hz, 1H), 3.60-3.51 (m, 1H), 3.04-2.76 (m, 2H), 2.69-2.54 (m, 2H), 2.38 (d, J = 7.9 Hz, 3H), 1.90-1.66 (m, 4H), 1.60-1.12 (m, 2H). | Rt = 2.62 min, m/z 537.1 [M + H]$^+$ (Method 1) |
| 8 | 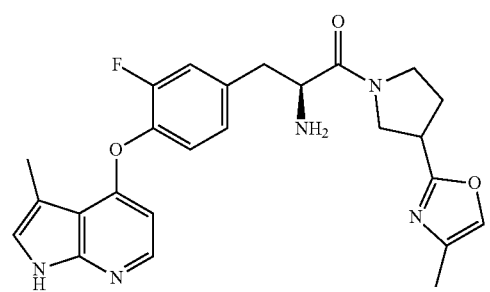<br>(2S)-2-amino-3-(3-fluoro-4-((3-methyl-1H-pyrrolo[2,3-b]pyridin-4-yl)oxy)phenyl)-1-(3-(3-methyl-1,2,4-oxadiazol-5-yl)pyrrolidin-1-yl)propan-1-one | 1E-a/3-methyl-5-(pyrrolidin-3-yl)-1,2,4-oxadiazole | $^{1}$H NMR (400 MHz, d6-DMSO) δ 11.39 (s, 1H), 8.00-7.94 (m, 1H), 7.38-7.18 (m, 2H), 7.15-7.09 (m, 2H), 6.16-6.11 (m, 1H), 3.88-3.66 (m, 3H), 3.57-3.57 (m, 1H), 2.91-2.80 (m, 1H), 2.72-2.62 (m, 1H), 2.38-2.28 (m, 6H), 2.27-1.96 (m, 2H), 1.74 (s, 2H). | Rt = 2.38 min, m/z 465.0 [M + H]$^+$ (Method 1) |
| 9 | 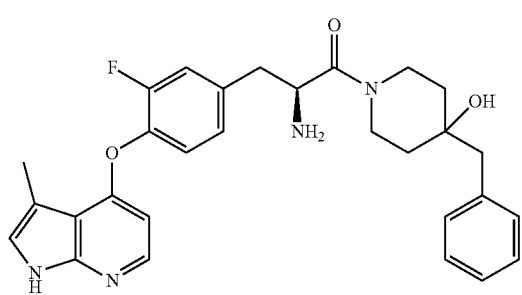<br>(S)-2-amino-1-(4-benzyl-4-hydroxypiperidin-1-yl)-3-(3-fluoro-4-((3-methyl-1H-pyrrolo[2,3-b]pyridin-4-yl)oxy)phenyl)propan-1-one | 1E-a/4-benzyl-piperidin-4-ol | $^{1}$H NMR (400 MHz, d6-DMSO) δ 11.38 (s, 1H), 7.98 (d, J = 5.4 Hz, 1H), 7.32-7.06 (m, 9H), 6.16-6.12 (m, 1H), 4.46-4.37 (m, 1H), 4.14-4.08 (m, 1H), 3.97-3.91 (m, 1H), 3.69-3.60 (m, 1H), 3.57-3.56 (m, 1H), 3.23-2.96 (m, 1H), 2.84-2.65 (m, 4H), 2.40-2.29 (m, 3H), 1.72 (s, 2H), 1.52-1.21 (m, 3H), 0.94 (m, 1H). | Rt = 2.70 min, m/z 503.1 [M + H]$^+$ (Method 1) |
| 10 | 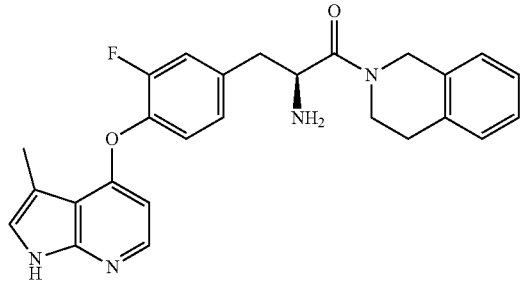<br>(S)-2-amino-1-(3,4-dihydroisoquinolin-2(1H)-yl)-3-(3-fluoro-4-((3-methyl-1H-pyrrolo[2,3-b]pyridin-4-yl)oxy)phenyl)propan-1-one | 1E-a/1,2,3,4-tetrahydro-isoquinoline | $^{1}$H NMR (400 MHz, d6-DMSO) δ 11.37 (s, 1H), 7.94-7.88 (m, 1H), 7.37-7.26 (m, 1H), 7.20-7.10 (m, 7H), 6.10-5.99 (m, 1H), 4.79-4.48 (m, 2H), 4.08-3.98 (m, 1H), 3.79-3.71 (m, 1H), 3.66-3.58 (m, 1H), 2.91-2.66 (m, 4H), 2.37 (s, 3H), 1.79 (s, 2H). | Rt = 2.69 min, m/z 445.0 [M + H]$^+$ (Method 1) |

| Ex | Structure/Name | Intermediate 1E/Amine | 1H NMR | LC-MS |
|---|---|---|---|---|
| 11 | 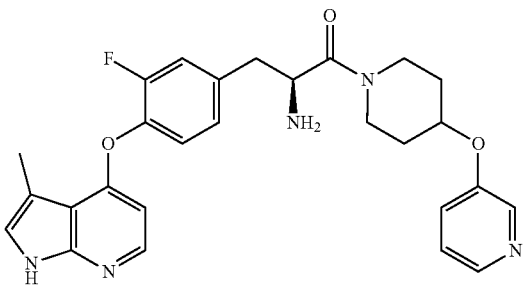<br>(S)-2-amino-3-(3-fluoro-4-((3-methyl-1H-pyrrolo[2,3-b]pyridin-4-yl)oxy)phenyl)-1-(4-(pyridin-3-yloxy)piperidin-1-yl)propan-1-one | 1E-a/3-(piperidin-4-yloxy)pyridine | $^1$H NMR (400 MHz, d6-DMSO) δ 11.39 (s, 1H), 8.33-8.25 (m, 1H), 8.18-8.15 (m, 1H), 8.01-7.91 (m, 1H), 7.48-7.39 (m, 1H), 7.37-7.29 (m, 2H), 7.27-7.21 (m, 1H), 7.16-7.09 (m, 2H), 6.16 (t, J = 4.1 Hz, 1H), 4.71-4.63 (m, 1H), 4.02-3.87 (m, 2H), 3.85-3.64 (m, 1H), 3.28-3.19 (m, 2H), 2.88-2.79 (m, 1H), 2.74-2.64 (m, 1H), 2.38 (d, J = 2.3 Hz, 3H), 2.00-1.68 (m, 4H), 1.69-1.48 (m, 1H), 1.46-1.17 (m, 1H). | Rt = 2.19 min, m/z 490.1 [M + H]$^+$ (Method 1) |
| 12 | 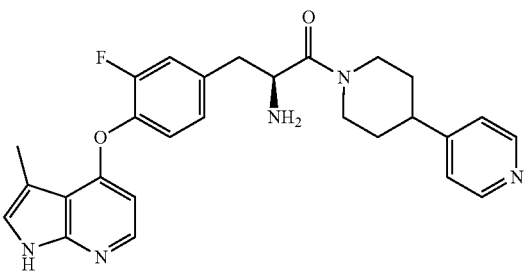<br>(S)-2-amino-3-(3-fluoro-4-((3-methyl-1H-pyrrolo[2,3-b]pyridin-4-yl)oxy)phenyl)-1-(4-(pyridin-4-yl)piperidin-1-yl)propan-1-one | 1E-a/4-(piperidin-4-yl)pyridine | $^1$H NMR (400 MHz, d6-DMSO) δ 11.38 (s, 1H), 8.53-8.36 (m, 2H), 8.02-7.86 (m, 1H), 7.37-7.11 (m, 5H), 6.18-6.05 (m, 1H), 4.59-4.53 (m, 1H) 4.13-3.98 (m, 2H), 3.57-3.57 (m, 2H), 3.17-2.90 (m, 1H), 2.89-2.34 (m, 4H), 2.39-2.33 (2xs, 3H), 1.88-1.69 (m, 3H), 1.68-1.39 (m, 1H), 1.36-0.92 (m, 1H). | Rt = 1.93 min, m/z 474.0 [M + H]$^+$ (Method 1) |
| 13 | 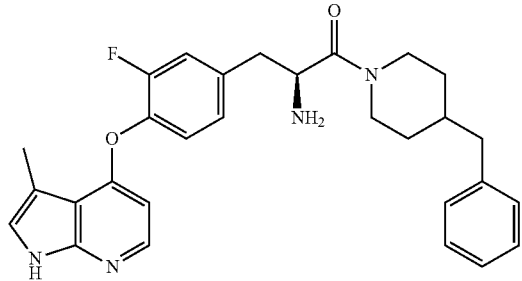<br>(S)-2-amino-1-(4-benzylpiperidin-1-yl)-3-(3-fluoro-4-((3-methyl-1H-pyrrolo[2,3-b]pyridin-4-yl)oxy)phenyl)propan-1-one | 1E-a/4-benzyl-piperidine | $^1$H NMR (400 MHz, d6-DMSO) δ 11.39 (s, 1H), 7.97 (dd, J = 5.4, 11.2 Hz, 1H), 7.33-7.09 (m, 9H), 6.14 (dd, J = 5.4, 14.3 Hz, 1H), 4.38 (t, J = 12.3 Hz, 1H), 3.98-3.83 (m, 2H), 3.57 (s, 3H), 2.89-2.57 (m, 3H), 2.39-2.35 (m, 4H), 1.69 (s, 2H), 1.61-1.34 (m, 2H), 1.24-0.95 (m, 1H), 0.84-0.28 (m, 1H). | Rt = 3.17 min, m/z 487.1 [M + H]$^+$ (Method 1) |
| 14 | 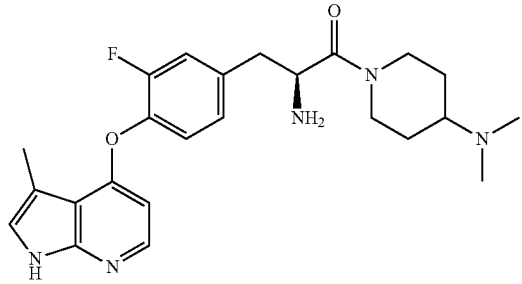<br>(S)-2-amino-1-(4-(dimethylamino)piperidin-1-yl)-3-(3-fluoro-4-((3-methyl-1H-pyrrolo[2,3-b]pyridin-4-yl)oxy)phenyl)propan-1-one | 1E-a/N,N-dimethyl-piperidine-4-amine | $^1$H NMR (400 MHz, d6-DMSO) δ 11.36 (s, 1H), 8.00-7.95 (m, 1H), 7.35-7.19 (m, 2H), 7.15-7.08 (m, 2H), 6.15-6.14 (m, 1H), 4.41-4.32 (m, 1H), 4.02-3.85 (m, 2H), 2.97-2.87 (m, 1H), 2.78 (m, 2H), 2.69-2.57 (m, 1H), 2.38 (d, J = 4.8 Hz, 3H), 2.31-2.20 (m, 1H), 2.16 (s, 3H), 2.11 (s, 3H), 1.70-1.66 (m, 4H), 1.38-1.13 (m, 1H), 1.05-0.53 (m, 1H). | Rt = 1.67 min, m/z 440.3 [M + H]$^+$ (Method 1) |

-continued

| Ex | Structure/Name | Intermediate 1E/Amine | 1H NMR | LC-MS |
|---|---|---|---|---|
| 15 | 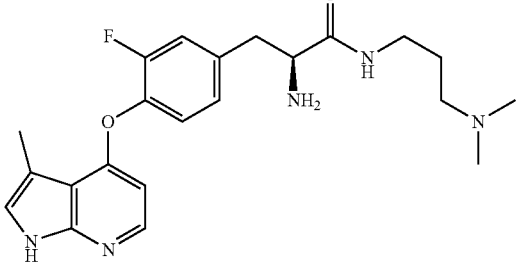<br>(S)-2-amino-N-(3-(dimethylamino)propyl)-3-(3-fluoro-4-((3-methyl-1H-pyrrolo[2,3-b]pyridin-4-yl)oxy)phenyl)propanamide | 1E-a/N,N-dimethyl-propane-1,3-diamine | $^1$H NMR (400 MHz, d6-DMSO) δ 11.36 (s, 1H), 7.97 (d, J = 5.4 Hz, 1H), 7.85 (t, J = 5.7 Hz, 1H), 7.29-7.20 (m, 2H), 7.15-7.12 (m, 1H), 7.12-7.06 (m, 1H), 6.16 (d, J = 4.9 Hz, 1H), 3.41-3.36 (m, 1H), 3.12-2.99 (m, 2H), 2.90 (dd, J = 5.7, 13.3 Hz, 1H), 2.71 (dd, J = 7.5, 13.2 Hz, 1H), 2.38 (d, J = 0.9 Hz, 3H), 2.12 (t, J = 7.1 Hz, 2H), 2.08 (s, 6H), 1.75 (s, 2H), 1.51-1.41 (m, 2H). | Rt = 3.27 min, m/z 414.0 [M + H]$^+$ (Method 1) |
| 16 | 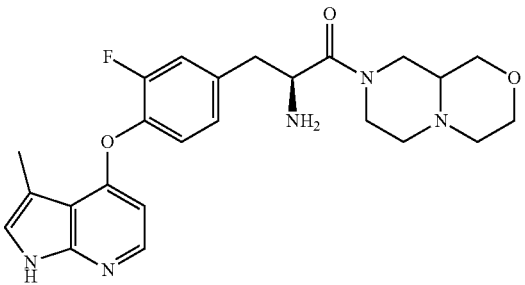<br>(2S)-2-amino-3-(3-fluoro-4-((3-methyl-1H-pyrrolo[2,3-b]pyridin-4-yl)oxy)phenyl)-1-(hexahydropyrazino[2,1-c][1,4]oxazin-8(1H)-yl)propan-1-one | 1E-a/rac-octahydro-pyrazino[2,1-c][1,4]oxazine | $^1$H NMR (400 MHz, d6-DMSO) δ 11.38 (s, 1H), 8.01-7.97 (m, 1H), 7.35-7.20 (m, 2H), 7.15-7.07 (m, 2H), 6.24-6.13 (m, 1H), 4.42-4.14 (m, 1H), 4.01-3.93 (m, 1H), 3.88-3.58 (m, 3H), 3.54-3.43 (m, 1H), 3.11-3.00 (m, 1H), 2.83-2.54 (m, 6H), 2.38 (s, 3H), 2.20-1.94 (m, 3H), 1.74 (s, 2H). | Rt= 1.87/1.91 min, m/z 454.3 [M + H]$^+$ (Method 1) |
| 17 | 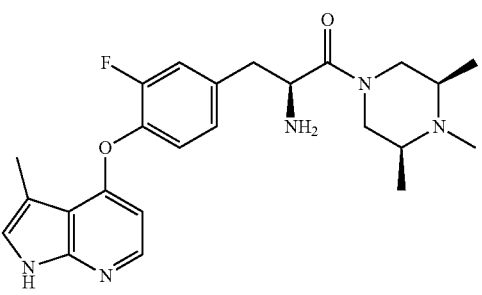<br>(S)-2-amino-3-(3-fluoro-4-((3-methyl-1H-pyrrolo[2,3-b]pyridin-4-yl)oxy)phenyl)-1-((3S,5R)-3,4,5-trimethylpiperazin-1-yl)propan-1-one | 1E-a/(2S,6R)-1,2,6-trimethyl-piperazine | $^1$H NMR (400 MHz, DMSO) δ 11.39 (s, 1H), 7.99-7.96 (m, 1H), 7.34-7.27 (m, 1H), 7.27-7.20 (m, 1H), 7.16-7.12 (m, 1H), 7.11-7.06 (m, 1H), 6.19-6.13 (m, 1H), 4.23-4.16 (m, 1H), 4.12-3.96 (m, 1H), 3.83-3.65 (m, 1H), 2.79-2.65 (m, 3H), 2.38 (d, J = 4.1 Hz, 3H), 2.30-2.20 (m, 1H), 2.06 (s, 3H), 1.98-1.88 (m, 1H), 1.77-1.66 (m, 2H), 1.27-1.21 (m, 1H), 1.03-0.91 (m, 6H). | Rt = 1.67 min, m/z 440.2 [M + H]$^+$ (Method 1) |
| 18 | 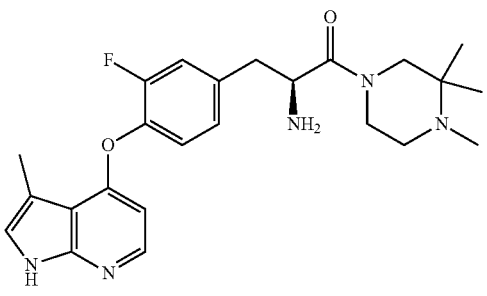<br>(S)-2-amino-3-(3-fluoro-4-((3-methyl-1H-pyrrolo[2,3-b]pyridin-4-yl)oxy)phenyl)-1-(3,3,4-trimethylpiperazin-1-yl)propan-1-one | 1E-a/1,2,2-trimethyl-piperazine | $^1$H NMR (400 MHz, d6-DMSO) δ 11.40 (s, 1H), 7.98 (d, J = 5.4 Hz, 1H), 7.36-7.28 (m, 1H), 7.26-7.19 (m, 1H), 7.14-7.13 (m, 1H), 7.11-7.07 (m, 1H), 6.15 (t, J = 5.9 Hz, 1H), 4.03-3.90 (m, 1H), 3.52-3.37 (m, 2H), 3.06 (dd, J = 3.1, 12.4 Hz, 1H), 2.83 (dd, J = 13.2 Hz, 1H), 2.69 (dd, J = 7.2, 13.2 Hz, 1H), 2.39-2.37 (m, 6H), 2.09 (s, 3H), 1.73 (s, 2H), 0.91 (d, J = 7.3 Hz, 3H), 0.83 (s, 1H), 0.76 (s, 2H). | Rt = 1.69 min, m/z 440.3 [M + H]$^+$ (Method 1) |

| Ex | Structure/Name | Intermediate 1E/Amine | 1H NMR | LC-MS |
|----|----------------|----------------------|--------|-------|
| 19 | 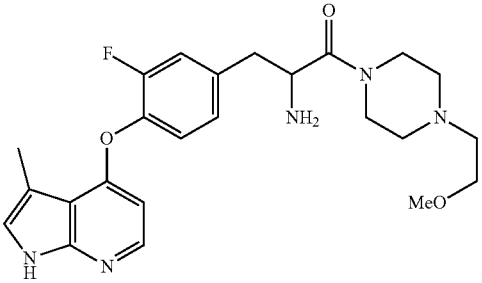<br>2-amino-3-(3-fluoro-4-((3-methyl-1H-pyrrolo[2,3-b]pyridin-4-yl)oxy)phenyl)-1-(4-(2-methoxyethyl)piperazin-1-yl)propan-1-one | 1E-b/1-(2-methoxy-ethyl)piperazine | $^1$H NMR (400 MHz, d6-DMSO) δ 11.40 (s, 1H), 7.98 (d, J = 5.4 Hz, 1H), 7.30 (dd, J = 1.9, 11.9 Hz, 1H), 7.24 (t, J = 8.5 Hz, 1H), 7.14-7.08 (m, 2H), 6.16 (d, J = 4.8 Hz, 1H), 3.94 (t, J = 7.0 Hz, 1H), 3.54-3.48 (m, 1H), 3.43-3.39 (m, 2H), 3.38-3.32 (m, 5H), 3.22 (s, 3H), 2.79 (dd, J = 6.7, 13.2 Hz, 1H), 2.68 (dd, J = 7.2, 13.1 Hz, 1H), 2.43 (t, J = 5.9 Hz, 2H), 2.38 (d, J = 1.0 Hz, 3H), 2.23-2.17 (m, 1H), 2.07-1.99 (m, 1H), 1.76-1.76 (m, 2H). | Rt = 1.73 min. m/z 456.2 [M + H]$^+$ (Method 1) |
| 20 | 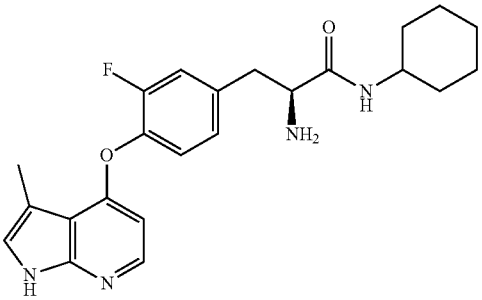<br>(S)-2-amino-N-cyclohexyl-3-(3-fluoro-4-((3-methyl-1H-pyrrolo[2,3-b]pyridin-4-yl)oxy)phenyl)propanamide | 1E-a/cyclohexanamine | $^1$H NMR (400 MHz, d6-DMSO) δ 11.38 (s, 1H), 7.97 (d, J = 5.4 Hz, 1H), 7.60 (d, J = 8.1 Hz, 1H), 7.28-7.20 (m, 2H), 7.15-7.06 (m, 2H), 6.15 (d, J = 4.8 Hz, 1H), 3.55-3.46 (m, 1H), 3.38 (t, J = 6.7 Hz, 1H), 2.86 (dd, J = 6.0, 13.2 Hz, 1H), 2.71 (dd, J = 7.3, 13.0 Hz, 1H), 2.38 (d, J = 1.0 Hz, 3H), 1.77 (d, J = 1.2 Hz, 2H), 1.69-1.52 (m, 5H), 1.29-1.16 (m, 2H), 1.15-1.02 (m, 3H). | Rt = 2.72 min, m/z 411.3 [M + H]$^+$ (Method 3) |
| 21 | 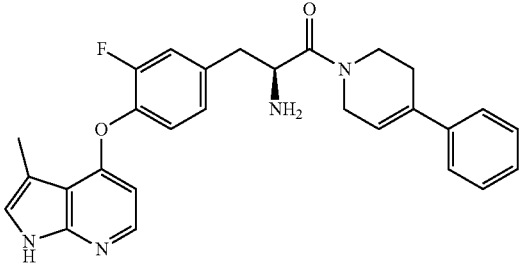<br>(S)-2-amino-3-(3-fluoro-4-((3-methyl-1H-pyrrolo[2,3-b]pyridin-4-yl)oxy)phenyl)-1-(4-phenyl-5,6-dihydropyridin-1(2H)-yl)propan-1-one | 1E-a/4-phenyl-piperidin-4-ol | $^1$H NMR (400 MHz, d6-DMSO) δ 11.37 (s, 1H), 7.90-7.87 (m, 1H), 7.45-7.11 (m, 9H), 6.21-6.05 (m, 2H), 4.30-4.23 (m, 1H), 4.13-3.92 (m, 3H), 3.71-3.62 (m, 2H), 2.90-2.80 (m, 1H), 2.75-2.66 (m, 1H), 2.44-2.43 (m, 1H), 2.37-2.33 (m, 3H), 1.78 (s, 2H). | Rt = 2.92 min, m/z 471.0 [M + H]$^+$ (Method 1) |
| 22 | 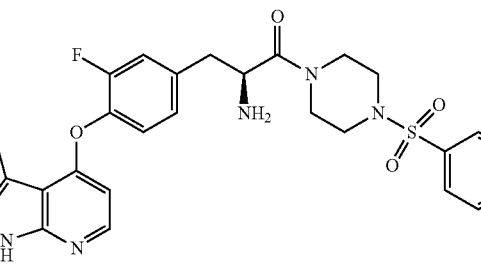<br>(S)-2-amino-3-(3-fluoro-4-((3-methyl-1H-pyrrolo[2,3-b]pyridin-4-yl)oxy)phenyl)-1-(4-(phenylsulfonyl)piperazin-1-yl)propan-1-one | 1E-a/1-(phenyl-sulfonyl)piperazine | $^1$H NMR (400 MHz, d6-DMSO) δ 11.40 (s, 1H), 7.99 (d, J = 5.4 Hz, 1H), 7.74-7.62 (m, 5H), 7.28 (dd, J = 1.9, 11.9 Hz, 1H), 7.20-7.14 (m, 2H), 7.06 (q, J = 7.8 Hz, 1H), 6.13 (dd, J = 0.8, 5.4 Hz, 1H), 3.83 (dd, J = 5.8, 7.7 Hz, 1H), 3.73-3.62 (m, 2H), 3.44-3.37 (m, 2H), 3.00-2.93 (m, 2H), 2.85-2.71 (m, 3H), 2.59 (dd, J = 8.0, 13.5 Hz, 1H), 2.38 (d, J = 1.1 Hz, 3H), 1.67 (s, 2H). | Rt = 2.73 min, m/z 538.0 [M + H]$^+$ (Method 1) |

| Ex | Structure/Name | Intermediate 1E/Amine | 1H NMR | LC-MS |
|---|---|---|---|---|
| 23 | (S)-4-(2-amino-3-(3-fluoro-4-((3-methyl-1H-pyrrolo[2,3-b]pyridin-4-yl)oxy)phenyl)propanoyl)-N,N-dimethylpiperazine-1-carboxamide | 1E-a/N,N-dimethyl-piperazine-1-carboxamide | $^1$H NMR (400 MHz, d6-DMSO) δ 11.39 (s, 1H), 7.97 (d, J = 5.4 Hz, 1H), 7.33 (dd, J = 1.9, 11.9 Hz, 1H), 7.24 (dd, J = 8.4, 8.4 Hz, 1H), 7.14-7.10 (m, 2H), 6.14 (d, J = 5.3 Hz, 1H), 3.95 (dd, J = 6.8, 6.8 Hz, 1H), 3.55-3.35 (m, 4H), 3.12-3.06 (m, 2H), 3.01-2.78 (m, 3H), 2.74 (s, 6H), 2.68 (dd, J = 7.4, 13.3 Hz, 1H), 2.38 (d, J = 1.0 Hz, 3H), 1.74 (s, 2H). | Rt = 2.28 min, m/z 469.1 [M + H]$^+$ (Method 1) |
| 24 | (S)-2-amino-1-((1S,4S)-5-benzyl-2,5-diazabicyclo[2.2.1]heptan-2-yl)-3-(3-fluoro-4-((3-methyl-1H-pyrrolo[2,3-b]pyridin-4-yl)oxy)phenyl)propan-1-one | 1E-a/(1S,4S)-2-benzyl-2,5-diazabi-cyclo[2.2.1]heptane | $^1$H NMR (400 MHz, d6-DMSO) δ 11.38 (d, J = 0.6 Hz, 1H), 8.00-7.91 (m, 1H), 7.38-7.11 (m, 9H), 6.14 (dd, J = 3.4, 5.0 Hz, 1H), 4.50-4.38 (m, 1H), 3.74-3.56 (m, 2H), 3.50-3.34 (m, 3H), 3.23-3.04 (m, 1H), 2.86-2.68 (m, 3H), 2.39-2.28 (m, 3H), 1.81-1.75 (m, 2H), 1.50-1.38 (m, 1H). | Rt = 2.00 min, m/z 500.1 [M + H]$^+$ (Method 1) |
| 25 | (S)-2-amino-3-(3-fluoro-4-((3-methyl-1H-pyrrolo[2,3-b]pyridin-4-yl)oxy)phenyl)-1-((1S,4S)-5-methyl-2,5-diazabicyclo[2.2.1]heptan-2-yl)propan-1-one | 1E-a/(1S,4S)-2-methyl-2,5-diazabi-cyclo[2.2.1]heptane | $^1$H NMR (400 MHz, d6-DMSO) δ 11.40 (s, 1H), 7.99 (dd, J = 3.5, 5.4 Hz, 1H), 7.35-7.20 (m, 2H), 7.15-7.09 (m, 2H), 6.25-6.15 (m, 1H), 4.44-4.35 (m, 1H), 3.70-3.60 (m, 1H), 3.37-3.33 (m, 2H), 3.15-2.98 (m, 1H), 2.80-2.66 (m, 3H), 2.38 (s, 3H), 2.27 (s, 1H), 2.13 (s, 2H), 1.76-1.69 (m, 2H), 1.44-1.35 (m, 1H). | Rt = 1.66 min, m/z 424.0 [M + H]$^+$ (Method 1) |

-continued

| Ex | Structure/Name | Intermediate 1E/Amine | 1H NMR | LC-MS |
|---|---|---|---|---|
| 26 | 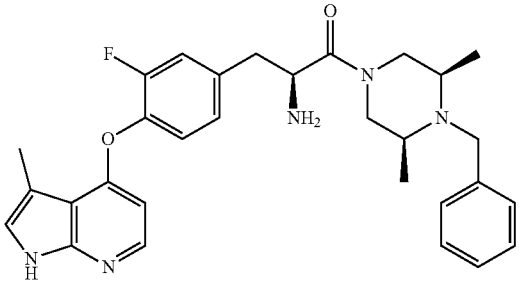<br>(S)-2-amino-1-((3S,5R)-4-benzyl-3,5-dimethylpiperazin-1-yl)-3-(3-fluoro-4-((3-methyl-1H-pyrrolo[2,3-b]pyridin-4-yl)oxy)phenyl)propan-1-one | 1E-a/(2R,6S)-1-benzyl-2,6-dimethyl-piperazine | $^1$H NMR (400 MHz, d6-DMSO) δ 11.41 (s, 1H), 7.98 (dd, J = 5.5, 7.8 Hz, 1H), 7.37-7.08 (m, 9H), 6.17 (dd, J = 5.5, 10.0 Hz, 1H), 4.18-4.15 (m, 1H), 3.99 (q, J = 6.3 Hz, 1H), 3.81-3.55 (m, 3H), 2.84-2.54 (m, 3H), 2.43-2.38 (m, 4H), 2.25-2.20 (m, 1H), 1.86-1.80 (m, 1H), 0.98-0.86 (m, 6H). | Rt = 2.26 min, m/z 516.1 [M + H]$^+$ (Method 1) |
| 27 | 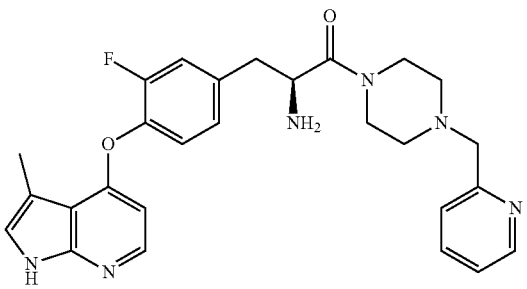<br>(ee % n.d.)<br>(S)-2-amino-3-(3-fluoro-4-((3-methyl-1H-pyrrolo[2,3-b]pyridin-4-yl)oxy)phenyl)-1-(4-(pyridin-2-ylmethyl)piperazin-1-yl)propan-1-one | 1E-a/1-(pyrimidin-2-ylmethyl)-piperazine | $^1$H NMR (400 MHz, d6-DMSO) δ 11.40 (s, 1H), 8.50-8.48 (m, 1H), 7.99 (d, J = 5.4 Hz, 1H), 7.76 (dt, J = 1.8, 7.7 Hz, 1H), 7.43 (d, J = 7.8 Hz, 1H), 7.34-7.21 (m, 3H), 7.17-7.13 (m, 1H), 7.11 (d, J = 8.7 Hz, 1H), 6.18 (d, J = 5.4 Hz, 1H), 3.94 (t, J = 6.9 Hz, 1H), 3.57 (s, 2H), 3.56-3.38 (m, 4H), 2.80 (dd, J = 6.4, 13.2 Hz, 1H), 2.68 (dd, J = 7.3, 13.1 Hz, 1H), 2.41-2.36 (m, 5H), 2.27-2.22 (m, 1H), 2.12-2.07 (m, 1H), 1.90-1.88 (m, 2H). | Rt = 1.90 min, m/z 489.3 [M + H]$^+$ (Method 1) |
| 28 | 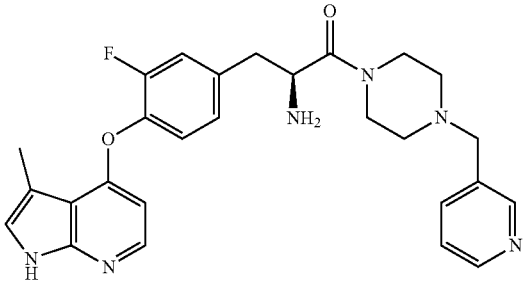<br>(S)-2-amino-3-(3-fluoro-4-((3-methyl-1H-pyrrolo[2,3-b]pyridin-4-yl)oxy)phenyl)-1-(4-(pyridin-3-ylmethyl)piperazin-1-yl)propan-1-one | 1E-a/1-(pyridin-3-ylmethyl)-piperazine | $^1$H NMR (400 MHz, d6-DMSO) δ 11.40 (s, 1H), 8.47 (dd, J = 1.7, 4.7 Hz, 2H), 7.98 (d, J = 5.4 Hz, 1H), 7.69 (td, J = 1.9, 7.8 Hz, 1H), 7.36 (dd, J = 4.8, 7.8 Hz, 1H), 7.31 (dd, J = 2.0, 12.0 Hz, 1H), 7.25 (t, J = 8.4 Hz, 1H), 7.16-7.13 (m, 1H), 7.10 (d, J = 8.2 Hz, 1H), 6.16 (d, J = 5.0 Hz, 1H), 3.93 (t, J = 6.9 Hz, 1H), 3.50-3.45 (m, 7H), 2.80 (dd, J = 6.4, 13.2 Hz, 1H), 2.67 (dd, J = 7.3, 13.3 Hz, 1H), 2.39 (d, J = 0.9 Hz, 3H), 2.37-2.30 (m, 2H), 2.25-2.16 (m, 1H), 2.10-2.04 (m, 1H), 1.87 (s, 1H). | Rt = 1.89 min, m/z 489.2 [M + H]$^+$ (Method 1) |

-continued

| Ex | Structure/Name | Intermediate 1E/Amine | 1H NMR | LC-MS |
|---|---|---|---|---|
| 29 | (ee % n.d.)<br>(S)-2-amino-3-(3-fluoro-4-((3-methyl-1H-pyrrolo[2,3-b]pyridin-4-yl)oxy)phenyl)-1-(2,6-diazaspiro[3.3]heptan-2-yl)propan-1-one | 1E-a/tert-butyl 2,6 diazaspiro[3.3]-heptane-2-carboxylate | ¹H NMR (400 MHz, DMSO) δ 11.41 (s, 1H), 7.99 (d, J = 5.4 Hz, 1H), 7.31-7.21 (m, 2H), 7.14 (s, 1H), 7.08 (d, J = 7.2 Hz, 1H), 6.15 (d, J = 5.1 Hz, 1H), 4.14 (d, J = 9.0 Hz, 1H), 3.87 (d, J =10.1 Hz, 1H), 3.83-3.77 (m, 1H), 3.64 (d, J = 9.1 Hz, 1H), 3.38 (t, J = 6.7 Hz, 2H), 3.20-3.10 (m, 2H), 3.03 (d, J = 7.6 Hz, 1H), 2.88 (s, 1H), 2.77-2.63 (m, 2H), 2.37 (s, 3H), 1.69 (s, 2H). | Rt = 1.63 min, m/z 410.1 [M + H]⁺ (Method 1) |
| 30 | (S)-2-amino-3-(3-fluoro-4-((3-methyl-1H-pyrrolo[2,3-b]pyridin-4-yl)oxy)phenyl)-1-((3aR,6aS)-5-methylhexahydropyrrolo[3,4-c]pyrrol-2(1H)-yl)propan-1-one | 1E-a/ (3aR,6aS)-2-methyloctahydropyrrolo[3,4-c]pyrrole | ¹H NMR (400 MHz, DMSO) δ 11.38 (s, 1H), 7.98 (dd, J = 1.2, 5.4 Hz, 1H), 7.30 (ddd, J = 1.8, 5.0, 11.9 Hz, 1H), 7.27-7.20 (m, 1H), 7.15-7.09 (m, 2H), 6.14 (dd, J = 3.1, 5.2 Hz, 1H), 3.75-3.65 (m, 2H), 3.57-3.39 (m, 2H), 3.27-3.03 (m, 2H), 2.85-2.59 (m, 3H), 2.47-2.38 (m, 6H), 2.23-2.09 (m, 4H), 1.78 (s, 2H). | Rt = 1.69 min, m/z 438.1 [M + H]⁺ (Method 1) |
| 31 | (ee % n.d.)<br>(S)-2-amino-3-(3-fluoro-4-((3-methyl-1H-pyrrolo[2,3-b]pyridin-4-yl)oxy)phenyl)-1-((3aR,6aS)-hexahydropyrrolo[3,4-c]pyrrol-2(1H)-yl)propan-1-one | 1E-a/tert-butyl (3aR,6aS)-hexahydro-pyrrolo[3,4-c]-pyrrole-2(1H)-carboxylate | ¹H NMR (400 MHz, DMSO) δ 11.40 (s, 1H), 8.01-7.97 (m, 1H), 7.35-7.27 (m, 1H), 7.23 (dd, J = 8.4, 8.4 Hz, 1H), 7.15-7.08 (m, 2H), 6.20-6.11 (m, 1H), 3.80-3.55 (m, 2H), 3.53-3.43 (m, 1H), 3.19 (dd, J = 4.1, 12.2 Hz, 3H), 3.11-2.95 (m, 2H), 2.89-2.78 (m, 3H), 2.75-2.56 (m, 4H), 2.46-2.41 (m, 1H), 2.38 (s, 3H). | Rt = 1.71 min, m/z 424.1 [M + H]⁺ (Method 1) |

-continued

| Ex | Structure/Name | Intermediate 1E/Amine | 1H NMR | LC-MS |
|---|---|---|---|---|
| 32 | 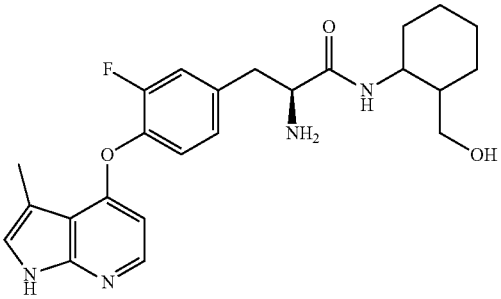<br>(S)-2-amino-3-(3-fluoro-4-((3-methyl-1H-pyrrolo[2,3-b]pyridin-4-yl)oxy)phenyl)-N-(1-(hydroxymethyl)cyclohexyl)propanamide | 1E-a/(1-aminocyclo-hexyl)methanol | $^1$H NMR (400 MHz, DMSO) δ 11.39 (s, 1H), 7.97 (d, J = 5.4 Hz, 1H), 7.35-7.21 (m, 3H), 7.15-7.11 (m, 2H), 6.16 (d, J = 5.4 Hz, 1H), 4.71 (t, J = 5.8 Hz, 1H), 3.48 (dd, J = 5.1, 7.9 Hz, 1H), 3.43 (d, J = 5.8 Hz, 2H), 2.95 (dd, J = 5.3, 13.4 Hz, 1H), 2.70 (dd, J = 7.8, 13.2 Hz, 1H), 2.38 (d, J = 1.0 Hz, 3H), 2.01-1.90 (m, 2H), 1.46-1.39 (m, 3H), 1.34-1.14 (m, 6H). | Rt = 2.51 min, m/z 441.3 [M + H]$^+$ (Method 1) |
| 33 | 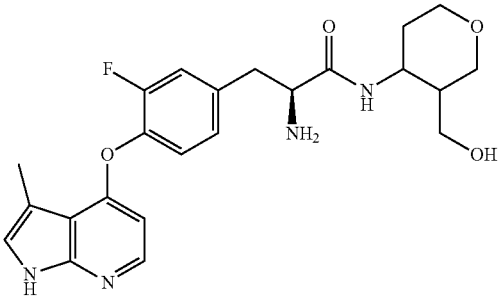<br>(S)-2-amino-3-(3-fluoro-4-((3-methyl-1H-pyrrolo[2,3-b]pyridin-4-yl)oxy)phenyl)-N-(4-(hydroxymethyl)tetrahydro-2H-pyran-4-yl)propanamide | 1E-a/(4-aminotetra-hydro-2H-pyran-4-yl)methanol | $^1$H NMR (400 MHz, DMSO) δ 11.38-11.38 (m, 1H), 7.97 (d, J = 5.4 Hz, 1H), 7.42 (s, 1H), 7.32 (dd, J = 1.9, 11.9 Hz, 1H), 7.24 (dd, J = 8.4, 8.4 Hz, 1H), 7.15-7.11 (m, 2H), 6.17 (d, J = 5.3 Hz, 1H), 4.74 (dd, J = 5.9, 5.9 Hz, 1H), 3.64-3.55 (m, 2H), 3.50-3.36 (m, 4H), 3.29 (dd, J = 2.5, 11.1 Hz, 1H), 2.93 (dd, J = 5.7, 13.5 Hz, 1H), 2.70 (dd, J = 7.8, 13.5 Hz, 1H), 2.39 (s, 3H), 1.99-1.88 (m, 4H), 1.59-1.48 (m, 2H). | Rt = 2.09 min, m/z 443.4 [M + H]$^+$ (Method 3) |
| 34 | 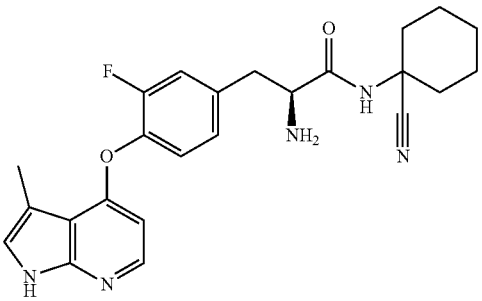<br>(ee % = 56%)<br>(S)-2-amino-N-(1-cyanocyclohexyl)-3-(3-fluoro-4-((3-methyl-1H-pyrrolo[2,3-b]pyridin-4-yl)oxy)phenyl)propanamide | 1E-a/1-amino-cyclohexane-1-carbonitrile | $^1$H NMR (400 MHz, DMSO) δ 11.39 (s, 1H), 7.97 (d, J = 5.4 Hz, 1H), 7.29 (dd, J = 2.5, 12.0 Hz, 1H), 7.23 (dd, J = 8.4, 8.4 Hz, 1H), 7.15-7.09 (m, 2H), 6.16 (d, J = 5.3 Hz, 1H), 3.47 (t, J = 7.2 Hz, 1H), 2.89 (dd, J = 6.1, 13.3 Hz, 1H), 2.77-2.66 (m, 1H), 2.38 (d, J = 1.0 Hz, 3H), 2.16-2.12 (m, 2H), 1.84 (s, 2H), 1.66-1.22 (m, 9H). | Rt = 2.59 min, m/z 436.4 [M + H]$^+$ (Method 3) |

-continued

| Ex | Structure/Name | Intermediate 1E/Amine | 1H NMR | LC-MS |
|---|---|---|---|---|
| 35 | 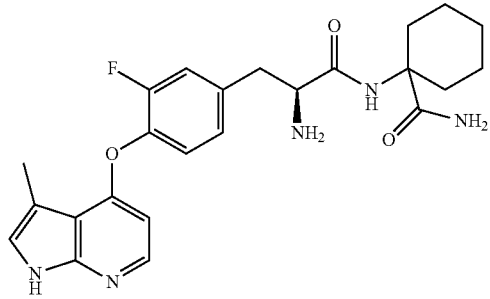<br>(S)-1-(2-amino-3-(3-fluoro-4-((3-methyl-1H-pyrrolo[2,3-b]pyridin-4-yl)oxy)phenyl)propanamido)cyclohexanecarboxamide | 1E-a/1-amido-cyclohexane-1-carboxamide | $^1$H NMR (400 MHz, DMSO) δ 11.39 (s, 1H), 7.98 (d, J = 5.5 Hz, 1H), 7.67 (s, 1H), 7.33 (dd, J = 1.8, 12.2 Hz, 1H), 7.24 (dd, J = 8.4, 8.4 Hz, 1H), 7.15-7.13 (m, 2H), 6.92 (s, 1H), 6.79 (s, 1H), 6.17 (d, J = 5.3 Hz, 1H), 3.53 (dd, J = 5.7, 7.8 Hz, 1H), 2.97 (dd, J = 5.4, 13.5 Hz, 1H), 2.73-2.66 (m, 1H), 2.38 (s, 3H), 2.07-1.92 (m, 4H), 1.64-1.56 (m, 2H), 1.48-1.29 (m, 4H), 1.18-1.12 (m, 2H). | Rt = 2.40 min, m/z 454.4 [M + H]$^+$ (Method 3) |
| 36 | 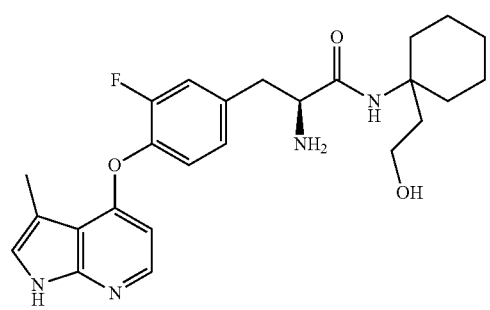<br>(S)-2-amino-3-(3-fluoro-4-((3-methyl-1H-pyrrolo[2,3-b]pyridin-4-yl)oxy)phenyl)-N-(1-(2-hydroxyethyl)cyclohexyl)propanamide | 1E-a/2-(1-aminocyclo-hexyl)ethan-1-ol | $^1$H NMR (400 MHz, DMSO) δ 11.36 (s, 1H), 7.97 (d, J = 5.4 Hz, 1H), 7.33 (dd, J = 1.8, 11.6 Hz, 1H), 7.28-7.21 (m, 2H), 7.16-7.13 (m, 2H), 6.17 (d, J = 5.3 Hz, 1H), 4.22 (dd, J = 5.1, 5.1 Hz, 1H), 3.40 (dd, J = 7.3, 12.3 Hz, 3H), 2.95 (dd, J = 5.3, 13.3 Hz, 1H), 2.69-2.63 (m, 1H), 2.39 (s, 3H), 2.08-2.01 (m, 2H), 1.88-1.77 (m, 4H), 1.45-1.33 (m, 3H), 1.27-1.21 (m, 5H). | Rt = 2.59 min, m/z 455.5 [M + H]$^+$ (Method 3) |
| 37 | 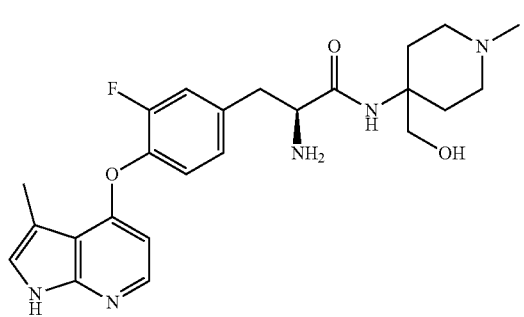<br>(S)-2-amino-3-(3-fluoro-4-((3-methyl-1H-pyrrolo[2,3-b]pyridin-4-yl)oxy)phenyl)-N-(4-(hydroxymethyl)-1-methylpiperidin-4-yl)propanamide | 1E-a/(4-amino-1-methyl-piperidin-4-yl)methanol | $^1$H NMR (400 MHz, DMSO) δ 11.39 (s, 1H), 7.98 (d, J = 5.4 Hz, 1H), 7.32 (dd, J = 2.0, 12.2 Hz, 1H), 7.29-7.21 (m, 2H), 7.15-7.11 (m, 2H), 6.17 (d, J = 5.2 Hz, 1H), 4.71 (dd, J = 5.9, 5.9 Hz, 1H), 3.49-3.41 (m, 3H), 2.93 (dd, J = 5.6, 13.5 Hz, 1H), 2.74-2.66 (m, 1H), 2.43-2.38 (m, 5H), 2.08 (s, 3H), 2.01-1.79 (m, 6H), 1.53-1.43 (m, 2H). | Rt = 3.03 min, m/z 456.3 [M + H]$^+$ (Method 2) |

-continued

| Ex | Structure/Name | Intermediate 1E/Amine | 1H NMR | LC-MS |
|---|---|---|---|---|
| 38 | 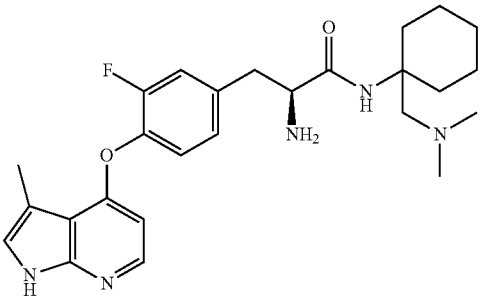<br>(S)-2-amino-N-(1-((dimethylamino)methyl)cyclohexyl)-3-(3-fluoro-4-((3-methyl-1H-pyrrolo[2,3-b]pyridin-4-yl)oxy)phenyl)propanamide | 1E-a/1-((dimethyl-amino)-methyl)-cyclohexan-1-amine | $^1$H NMR (400 MHz, DMSO) δ 11.39 (s, 1H), 7.97 (d, J = 5.4 Hz, 1H), 7.36-7.31 (m, 2H), 7.23 (dd, J = 8.4, 8.4 Hz, 1H), 7.15-7.13 (m, 2H), 6.16 (d, J = 5.4 Hz, 1H), 3.44 (dd, J = 5.6, 7.7 Hz, 1H), 2.95 (dd, J = 5.4, 13.4 Hz, 1H), 2.69-2.62 (m, 1H), 2.47-2.39 (m, 2H), 2.38 (s, 3H), 2.18 (s, 6H), 2.06-2.01 (m, 2H), 1.80-1.80 (m, 2H), 1.47-1.12 (m, 8H). | Rt = 2.11 min, m/z 468.4 [M + H]$^+$ (Method 1) |
| 39 | 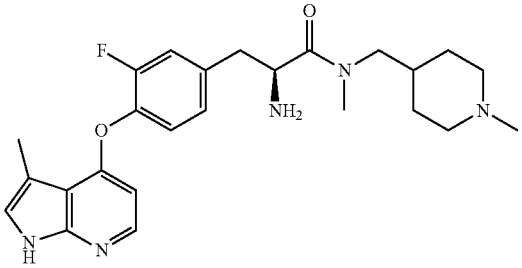<br>(S)-2-amino-3-(3-fluoro-4-((3-methyl-1H-pyrrolo[2,3-b]pyridin-4-yl)oxy)phenyl)-N-methyl-N-((1-methylpiperidin-4-yl)methyl)propanamide | 1E-a/N-methyl-1-(1-methyl-piperidin-4-yl)methanamine | $^1$H NMR (400 MHz, DMSO) δ 11.40 (s, 1H), 7.99-7.96 (m, 1H), 7.26-7.19 (m, 1H), 7.13-7.07 (m, 2H), 6.12 (d, J = 5.4 Hz, 1H), 3.94-3.75 (m, 1H), 3.37 (dd, J = 7.5, 12.9 Hz, 2H), 3.21-2.98 (m, 1H), 2.93 (s, 2H), 2.91-2.79 (m, 2H), 2.78 (s, 1H), 2.68 (dd, J = 6.7, 13.0 Hz, 3H), 2.38 (s, 3H), 2.09 (d, J = 5.4 Hz, 3H), 1.75-1.66 (m, 3H), 1.47-1.31 (m, 3H), 1.15-0.96 (m, 2H). | Rt = 1.78 min, m/z 454.2 [M + H]$^+$ (Method 1) |
| 40 | 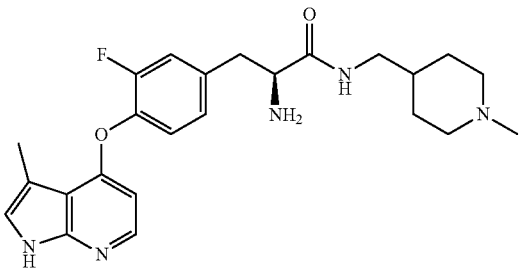<br>(S)-2-amino-3-(3-fluoro-4-((3-methyl-1H-pyrrolo[2,3-b]pyridin-4-yl)oxy)phenyl)-N-((1-methylpiperidin-4-yl)methyl)propanamide | 1E-a/(1-methyl-piperidin-4-yl)methanamine | $^1$H NMR (400 MHz, DMSO) δ 11.39 (s, 1H), 7.97 (d, J = 5.5 Hz, 1H), 7.80 (dd, J = 6.0, 6.0 Hz, 1H), 7.28-7.20 (m, 2H), 7.14 (d, J = 0.9 Hz, 1H), 7.08 (dd, J = 1.4, 8.1 Hz, 1H), 6.14 (d, J = 5.7 Hz, 1H), 3.41 (dd, J = 6.6, 6.6 Hz, 1H), 3.00-2.65 (m, 7H), 2.39 (d, J = 0.9 Hz, 3H), 2.08 (s, 3H), 1.74-1.68 (m, 3H), 1.44-1.44 (m, 2H), 1.23-1.18 (m, 1H), 1.07-0.97 (m, 2H). | Rt = 1.69 min, m/z 440.2 [M + H]$^+$ (Method 1) |
| 41 | 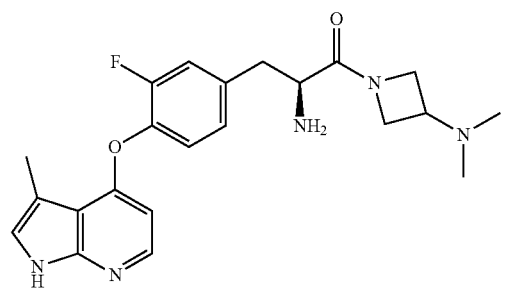<br>(S)-2-amino-1-(3-(dimethylamino)azetidin-1-yl)-3-(3-fluoro-4-((3-methyl-1H-pyrrolo[2,3-b]pyridin-4-yl)oxy)phenyl)propan-1-one | 1E-a/N,N-dimethyl-azetidin-3-amine | $^1$H NMR (400 MHz, DMSO) δ 11.39 (s, 1H), 7.98 (dd, J = 2.2, 5.4 Hz, 1H), 7.33-7.22 (m, 2H), 7.15-7.09 (m, 2H), 6.17 (dd, J = 5.3, 14.4 Hz, 1H), 4.15-3.94 (m, 1H), 3.86-3.42 (m, 4H), 3.04-2.85 (m, 1H), 2.81-2.63 (m, 2H), 2.39 (s, 3H), 2.04 (d, J = 10.4 Hz, 6H), 1.71 (s, 2H). | Rt = 1.59 min, m/z 412.2 [M + H]$^+$ (Method 1) |

-continued

| Ex | Structure/Name | Intermediate 1E/Amine | 1H NMR | LC-MS |
|---|---|---|---|---|
| 42 | 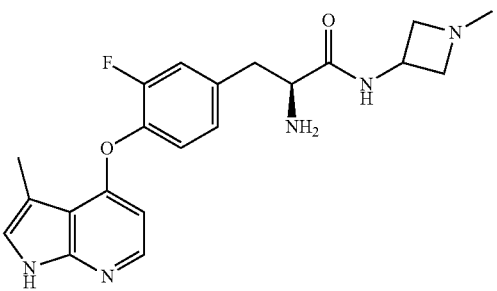<br>(S)-2-amino-3-(3-fluoro-4-((3-methyl-1H-pyrrolo[2,3-b]pyridin-4-yl)oxy)phenyl)-N-(1-methylazetidin-3-yl)propanamide | 1E-a/1-methylazetidin-3-amine | ¹H NMR (400 MHz, DMSO) δ 11.39 (s, 1H), 8.15 (d, J = 7.7 Hz, 1H), 7.98 (d, J = 5.4 Hz, 1H), 7.27-7.20 (m, 2H), 7.13 (s, 1H), 7.07 (d, J = 7.8 Hz, 1H), 6.18 (d, J = 5.3 Hz, 1H), 4.22-4.17 (m, 1H), 3.44 (dd, J = 6.7, 14.1 Hz, 2H), 3.36 (t, J = 6.9 Hz, 1H), 2.86 (dd, J = 5.9, 13.3 Hz, 1H), 2.78-2.66 (m, 3H), 2.38 (s, 3H), 2.18 (s, 3H), 1.81 (s, 2H). | Rt = 1.60 min, m/z 398.1 [M + H]⁺ (Method 1) |
| 43 | 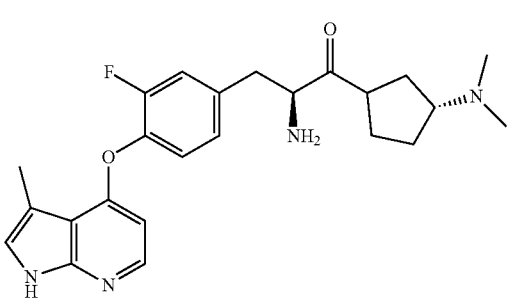<br>(S)-2-amino-1-((R)-3-(dimethylamino)pyrrolidin-1-yl)-3-(3-fluoro-4-((3-methyl-1H-pyrrolo[2,3-b]pyridin-4-yl)oxy)phenyl)propan-1-one | 1E-a/(R)-N,N-dimethyl-pyrrolidin-3-amine | ¹H NMR (400 MHz, DMSO) δ 11.39 (s, 1H), 7.98 (dd, J = 2.3, 5.4 Hz, 1H), 7.34-7.21 (m, 2H), 7.15-7.09 (m, 2H), 6.15 (dd, J = 5.5, 8.6 Hz, 1H), 3.71-3.41 (m, 3H), 3.18-3.08 (m, 1H), 2.94-2.67 (m, 3H), 2.60-2.52 (m, 1H), 2.39 (d, J = 1.6 Hz, 3H), 2.11 (d, J = 3.4 Hz, 6H), 2.05-1.91 (m, 1H), 1.76-1.74 (m, 2H), 1.60-1.50 (m, 1H). | Rt = 1.61 min, m/z 426.2 [M + H]⁺ (Method 1) |
| 44 | 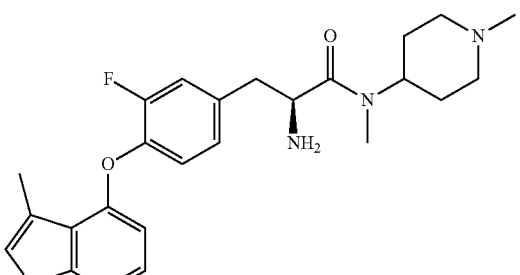<br>(S)-2-amino-3-(3-fluoro-4-((3-methyl-1H-pyrrolo[2,3-b]pyridin-4-yl)oxy)phenyl)-N-methyl-N-(1-methylpiperidin-4-yl)propanamide | 1E-a/N,1-dimethyl-piperidin-4-amine | ¹H NMR (400 MHz, DMSO) δ 11.39 (s, 1H), 8.00-7.97 (m, 1H), 7.33-7.27 (m, 1H), 7.25-7.19 (m, 1H), 7.15-7.08 (m, 2H), 6.15-6.11 (m, 1H), 4.25-3.50 (m, 2H), 2.82-2.67 (m, 6H), 2.37 (s, 3H), 2.13 (d, J = 1.8 Hz, 3H), 1.97-1.81 (m, 3H), 1.76-1.54 (m, 4H), 1.39-1.02 (m, 2H). | Rt = 1.72 min, m/z 440.2 [M + H]⁺ (Method 1) |
| 45 | 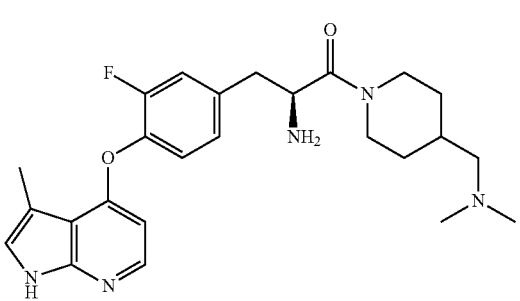<br>(S)-2-amino-1-(4-((dimethylamino)methyl)piperidin-1-yl)-3-(3-fluoro-4-((3-methyl-1H-pyrrolo[2,3-b]pyridin-4-yl)oxy)phenyl)propan-1-one | 1E-a/N,N-dimethyl-1-(piperidin-4-yl)methanamine | ¹H NMR (400 MHz, DMSO) δ 11.39 (s, 1H), 7.98 (d, J = 5.4 Hz, 1H), 7.33-7.21 (m, 2H), 7.14 (s, 1H), 7.10 (d, J = 8.3 Hz, 1H), 6.14 (d, J = 5.5 Hz, 1H), 4.37 (t, J = 15.2 Hz, 1H), 3.97-3.84 (m, 2H), 2.96-2.60 (m, 3H), 2.38 (s, 3H), 2.08 (d = 16.4 Hz, 6H), 2.03 (d, J = 6.8 Hz, 1H), 1.91 (d, J = 6.7 Hz, 1H), 1.75-1.56 (m, 5H), 1.09-0.29 (m, 3H). | Rt = 1.80 min, m/z 454.2 [M + H]⁺ (Method 1) |

-continued

| Ex | Structure/Name | Intermediate 1E/Amine | 1H NMR | LC-MS |
|---|---|---|---|---|
| 46 | 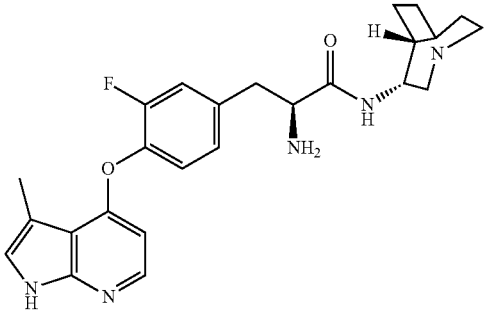<br>(S)-2-amino-3-(3-fluoro-4-((3-methyl-1H-pyrrolo[2,3-b]pyridin-4-yl)oxy)phenyl)-N-((R)-quinuclidin-3-yl)propanamide | 1E-a/(3R)-quinuclidin-3-amine | $^1$H NMR (400 MHz, DMSO) δ 11.39 (s, 1H), 7.97 (d, J = 5.4 Hz, 1H), 7.79 (d, J = 7.2 Hz, 1H), 7.27-7.19 (m, 2H), 7.14 (s, 1H), 7.07 (dd, J = 1.4, 8.3 Hz, 1H), 6.15 (d, J = 5.3 Hz, 1H), 3.69 (d, J = 7.0 Hz, 1H), 3.44 (t, J = 7.1 Hz, 1H), 3.05-2.98 (m, 1H), 2.84 (dd, J = 6.9, 13.2 Hz, 1H), 2.76-2.62 (m, 5H), 2.40-2.32 (m, 5H), 1.58-1.43 (m, 4H), 1.24-1.16 (m, 2H). | Rt = 1.84 min, m/z 438.2 [M + H]$^+$ (Method 1) |
| 47 | 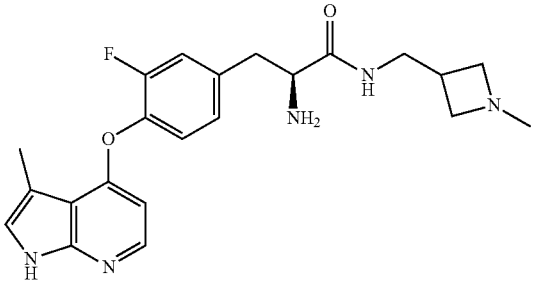<br>(S)-2-amino-3-(3-fluoro-4-((3-methyl-1H-pyrrolo[2,3-b]pyridin-4-yl)oxy)phenyl)-N-((1-methylazetidin-3-yl)methyl)propanamide | 1E-a/(1-methylazetidin-3-yl)-methanamine | $^1$H NMR (400 MHz, DMSO) δ 11.39 (s, 1H), 7.98 (d, J = 5.4 Hz, 1H), 7.90 (dd, J = 5.7, 5.7 Hz, 1H), 7.28-7.20 (m, 2H), 7.14 (s, 1H), 7.08 (dd, J = 1.3, 8.2 Hz, 1H), 6.17 (d, J = 5.4 Hz, 1H), 3.42-3.06 (m, 6H), 2.93-2.69 (m, 5H), 2.39-2.30 (m, 4H), 2.13 (s, 3H). | Rt = 1.70 min, m/z 412.2 [M + H]$^+$ (Method 1) |
| 48 | 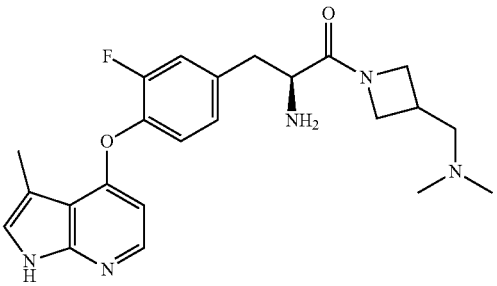<br>(S)-2-amino-1-(3-((dimethylamino)methyl)azetidin-1-yl)-3-(3-fluoro-4-((3-methyl-1H-pyrrolo[2,3-b]pyridin-4-yl)oxy)phenyl)propan-1-one | 1E-a/3-(azetidin-3-yl)-N,N-dimethyl-methanamine | $^1$H NMR (400 MHz, DMSO) δ 11.40 (s, 1H), 7.98 (d, J = 5.4 Hz, 1H), 7.33-7.23 (m, 2H), 7.15-7.09 (m, 2H), 6.14 (dd, J = 2.5, 5.4 Hz, 1H), 4.15-3.41 (m, 4H), 3.30-3.11 (m, 1H), 2.80-2.58 (m, 3H), 2.43-2.35 (s, 4H), 2.22-2.13 (m, 1H), 2.08 (d, J = 18.4 Hz, 6H), 1.76-1.76 (m, 2H). | Rt = 1.68 min, m/z 426.2 [M + H]$^+$ (Method 1) |
| 49 | 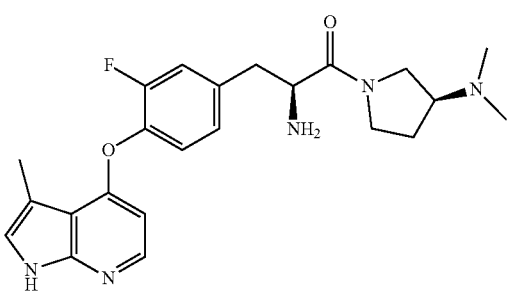<br>(S)-2-amino-1-((S)-3-(dimethylamino)pyrrolidin-1-yl)-3-(3-fluoro-4-((3-methyl-1H-pyrrolo[2,3-b]pyridin-4-yl)oxy)phenyl)propan-1-one | 1E-a/(S)-N,N-dimethyl-pyrrolidin-3-amine | $^1$H NMR (400 MHz, DMSO) δ 11.39 (d, J = 6.0 Hz, 1H), 7.98 (dd, J = 5.4, 10.4 Hz, 1H), 7.31-7.21 (m, 2H), 7.15-7.08 (m, 2H), 6.21-6.10 (m, 1H), 3.80-3.63 (m, 2H), 3.56-3.40 (m, 1H), 3.23-2.92 (m, 2H), 2.81-2.59 (m, 3H), 2.44-2.31 (m, 4H), 2.12 (d, J = 2.3 Hz, 6H), 2.01-1.98 (m, 1H), 1.72-1.39 (m, 2H). | Rt = 1.69 min, m/z 426.2 [M + H]$^+$ (Method 1) |

| Ex | Structure/Name | Intermediate 1E/Amine | 1H NMR | LC-MS |
|---|---|---|---|---|
| 50 | 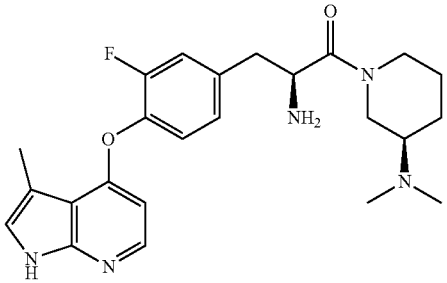<br>(S)-2-amino-1-((R)-3-(dimethylamino)piperidin-1-yl)-3-(3-fluoro-4-((3-methyl-1H-pyrrolo[2,3-b]pyridin-4-yl)oxy)phenyl)propan-1-one | 1E-a/(R)-N,N-dimethyl-piperidin-3-amine | $^1$H NMR (400 MHz, DMSO) δ 11.39 (s, 1H), 7.98 (dd, J = 5.0, 5.0 Hz, 1H), 7.36-7.07 (m, 4H), 6.14 (dd, J = 6.2, 6.2 Hz, 1H), 4.36-4.16 (m, 1H), 3.99-3.72 (m, 2H), 2.92-2.61 (m, 4H), 2.38 (d J = 3.2 Hz, 3H), 2.17 (d, J = 20.3 Hz, 6H), 1.80-1.63 (m, 4H), 1.46-0.98 (m, 3H). | Rt = 1.78 min, m/z 440.2 [M + H]$^+$ (Method 1) |
| 51 | 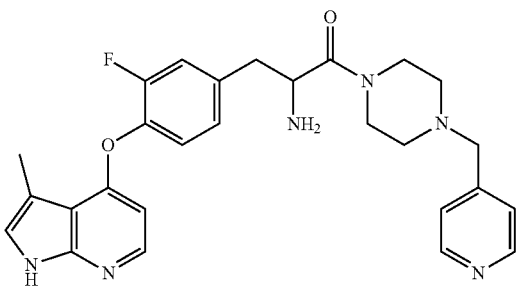<br>2-amino-3-(3-fluoro-4-((3-methyl-1H-pyrrolo[2,3-b]pyridin-4-yl)oxy)phenyl)-1-(4-(pyridin-4-ylmethyl)piperazin-1-yl)propan-1-one | 1E-b/1-(pyridin-4-ylmethyl)-piperazine | $^1$H NMR (400 MHz, d6-DMSO) δ 11.39 (s, 1H), 8.52-8.50 (m, 2H), 7.98 (d, J = 5.5 Hz, 1H), 7.34-7.28 (m, 3H), 7.24 (t, J = 8.4 Hz, 1H), 7.15-7.09 (m, 2H), 6.16 (d, J = 5.4 Hz, 1H), 3.94 (t, J = 6.9 Hz, 1H), 3.51-3.47 (m, 6H), 2.80 (dd, J = 6.4, 13.1 Hz, 1H), 2.67 (dd, J = 7.3, 13.2 Hz, 1H), 2.39 (d, J = 1.0 Hz, 3H), 2.38-2.33 (m, 2H), 2.23-2.18 (m, 1H), 2.11-2.03 (m, 1H), 1.78-1.74 (m, 2H). | Rt = 1.86 min, m/z 489.3 [M + H]$^+$ (Method 1) |
| 52 | 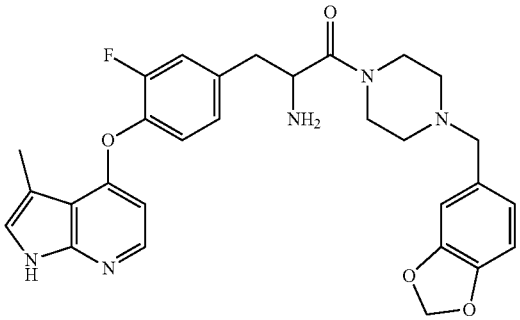<br>2-amino-1-(4-(benzo[d][1,3]dioxol-5-ylmethyl)piperazin-1-yl)-3-(3-fluoro-4-((3-methyl-1H-pyrrolo[2,3-b]pyridin-4-yl)oxy)phenyl)propan-1-one | 1E-b/1-(benzo[d][1,3]dioxol-5-ylmethyl)-piperazine | $^1$H NMR (400 MHz, d6-DMSO) δ 11.39 (s, 1H), 7.98 (d, J = 5.4 Hz, 1H), 7.31 (dd, J = 2.1, 11.9 Hz, 1H), 7.24 (t, J = 8.4 Hz, 1H), 7.16-7.12 (m, 1H), 7.10 (dd, J = 1.3, 8.3 Hz, 1H), 6.84 (dd, J = 3.1, 4.7 Hz, 2H), 6.72 (dd, J = 1.5, 7.9 Hz, 1H), 6.16 (d, J = 5.4 Hz, 1H), 5.98 (s, 2H), 3.93 (t, J = 6.8 Hz, 1H), 3.36-3.33 (m, 6H), 2.79 (dd, J = 6.4, 13.1 Hz, 1H), 2.68 (dd, J = 6.8, 12.9 Hz, 1H), 2.39 (d, J = 1.0 Hz, 3H), 2.36-2.26 (m, 2H), 2.21-2.12 (m, 1H), 2.05-1.96 (m, 1H), 1.77 (s, 2H). | Rt = 2.09 min, m/z 532.4 [M + H]$^+$ (Method 1) |
| 53 | 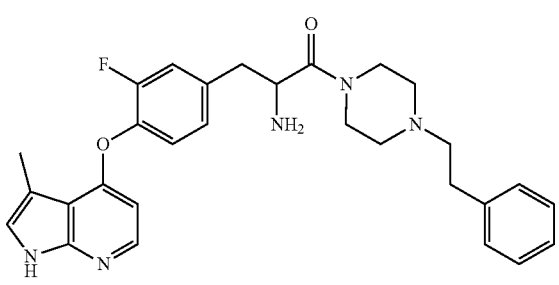<br>2-amino-3-(3-fluoro-4-((3-methyl-1H-pyrrolo[2,3-b]pyridin-4-yl)oxy)phenyl)-1-(4-phenethylpiperazin-1-yl)propan-1-one | 1E-b/1-phenethyl-piperazine | $^1$H NMR (400 MHz, d6-DMSO) δ 11.38 (s, 1H), 7.96 (d, J = 5.4 Hz, 1H), 7.33-7.09 (m, 9H), 6.15 (d, J = 4.8 Hz, 1H), 3.96 (t, J = 6.9 Hz, 1H), 3.59-3.51 (m, 1H), 3.42-3.36 (m, 3H), 2.80 (dd, J = 6.8, 13.1 Hz, 1H), 2.75-2.65 (m, 3H), 2.49-2.39 (m, 4H), 2.34 (d, J = 1.0 Hz, 3H), 2.27-2.17 (m, 1H), 2.09-1.98 (m, 1H), 1.76 (s, 2H). | Rt = 2.17 min, m/z 502.3 [M + H]$^+$ (Method 1) |

| Ex | Structure/Name | Intermediate 1E/Amine | 1H NMR | LC-MS |
|---|---|---|---|---|
| 54 | (S)-2-amino-3-(3-fluoro-4-((3-methyl-1H-pyrrolo[2,3-b]pyridin-4-yl)oxy)phenyl)-N-(tetrahydro-2H-pyran-4-yl)propanamide | 1E-a/ tetrahydro-2H-pyran-4-amine | $^1$H NMR (400 MHz, d6-DMSO) δ 11.38 (s, 1H), 7.97 (d, J = 5.4 Hz, 1H), 7.76 (d, J = 7.8 Hz, 1H), 7.29-7.20 (m, 2H), 7.16-7.12 (m, 1H), 7.11-7.06 (m, 1H), 6.16 (d, J = 4.8 Hz, 1H), 3.83-3.71 (m, 3H), 3.43-3.37 (m, 1H), 3.37-3.35 (m, 1H), 2.88 (dd, J = 6.0, 13.2 Hz, 1H), 2.73 (dd, J = 7.5, 13.1 Hz, 1H), 2.38 (d, J = 1.0 Hz, 3H), 2.17 (s, 2H), 1.66-1.56 (m, 2H), 1.44-1.22 (m, 3H). | Rt = 2.20 min. m/z 413.0 [M + H]$^+$ (Method 1) |
| 55 | (Separated by chiral HPLC Method A) (R)-2-amino-3-(3-fluoro-4-((3-methyl-1H-pyrrolo[2,3-b]pyridin-4-yl)oxy)phenyl)-N-(tetrahydro-2H-pyran-4-yl)propanamide | 1E-b/ tetrahydro-2H-pyran-4-amine | $^1$H NMR (400 MHz, d6-DMSO) δ 11.40 (s, 1H), 7.97 (d, J = 5.4 Hz, 1H), 7.75 (d, J = 7.8 Hz, 1H), 7.29-7.20 (m, 2H), 7.16-7.12 (m, 1H), 7.11-7.06 (m, 1H), 6.16 (d, J = 5.4 Hz, 1H), 3.83-3.70 (m, 3H), 3.44-3.35 (m, 2H), 2.88 (dd, J = 6.0, 13.2 Hz, 1H), 2.72 (dd, J = 7.5, 13.3 Hz, 1H), 2.38 (d, J = 1.1 Hz, 3H), 2.09 (s, 2H), 1.66-1.56 (m, 2H), 1.44-1.22 (m, 3H). | Rt = 2.17 min, m/z 413.2 [M + H]$^+$ (Method 1) |
| 56 | (S)-2-amino-3-(3-fluoro-4-((3-methyl-1H-pyrrolo[2,3-b]pyridin-4-yl)oxy)phenyl)-N-(2-(1-phenyl-1H-pyrazol-4-yl)ethyl)propanamide | 1E-a/2-(1-phenyl-1H-pyrazol-4-yl)ethan-1-amine | $^1$H NMR (400 MHz, d6-DMSO) δ 11.39 (s, 1H), 8.30 (s, 1H), 8.02 (t, J = 5.8 Hz, 1H), 7.96 (d, J = 5.5 Hz, 1H), 7.81-7.76 (m, 2H), 7.59 (s, 1H), 7.49-7.44 (m, 2H), 7.31-7.20 (m, 3H), 7.16-7.12 (m, 1H), 7.09 (d, J = 8.1 Hz, 1H), 6.15 (d, J = 4.8 Hz, 1H), 3.41 (dd, J = 5.3, 7.9 Hz, 1H), 3.31-3.25 (m, 2H), 2.94 (dd, J = 5.2, 13.4 Hz, 1H), 2.69 (dd, J = 8.0, 13.5 Hz, 1H), 2.61 (t, J = 7.2 Hz, 2H), 2.37 (d, J = 1.0 Hz, 3H), 1.81 (s, 2H). | Rt = 2.70 min, m/z 499.3 [M + H]$^+$ (Method 1) |
| 57 | 2-amino-3-(3-fluoro-4-((3-methyl-1H-pyrrolo[2,3-b]pyridin-4-yl)oxy)phenyl)-N-(2-(pyridin-4-yl)ethyl)propanamide | 1E-b/2-(pyridin-4-yl)ethan-1-amine | $^1$H NMR (400 MHz, d6-DMSO) δ 11.40 (s, 1H), 8.46-8.44 (m, 2H), 8.01-7.93 (m, 2H), 7.29-7.19 (m, 4H), 7.14-7.05 (m, 2H), 6.16 (d, J = 4.8 Hz, 1H), 3.41-3.36 (m, 3H), 2.90 (dd, J = 5.3, 13.3 Hz, 1H), 2.70 (t, J = 7.3 Hz, 2H), 2.65 (dd, J = 8.2, 13.2 Hz, 1H), 2.38 (d, J = 1.0 Hz, 3H), 1.96 (s, 2H). | Rt = 1.81 min, m/z 434.0 [M + H]$^+$ (Method 1) |

| Ex | Structure/Name | Intermediate 1E/Amine | 1H NMR | LC-MS |
|---|---|---|---|---|
| 58 | 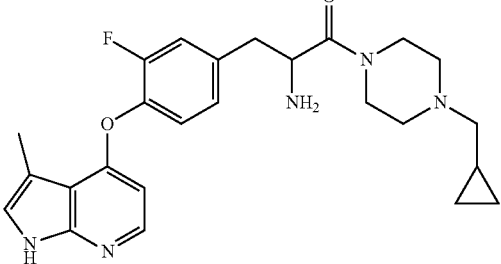<br>2-amino-1-(4-(cyclopropylmethyl)piperazin-1-yl)-3-(3-fluoro-4-((3-methyl-1H-pyrrolo[2,3-b]pyridin-4-yl)oxy)phenyl)propan-1-one | 1E-b/1-(cyclopropyl-methyl)-piperazine | $^1$H NMR (400 MHz, d6-DMSO) δ 11.39 (s, 1H), 7.97 (d, J = 5.4 Hz, 1H), 7.31 (dd, J = 1.9, 11.7 Hz, 1H), 7.25 (t, J = 8.4 Hz, 1H), 7.15-7.08 (m, 2H), 6.15 (d, J = 5.6 Hz, 1H), 3.96 (t, J = 7.0 Hz, 1H), 3.59-3.54 (m, 1H), 3.44-3.37 (m, 2H), 3.36-3.29 (m, 1H), 2.79 (dd, J = 6.8, 13.1 Hz, 1H), 2.70 (dd, J = 6.9, 12.9 Hz, 1H), 2.47-2.39 (m, 2H), 2.38 (d, J = 1.0 Hz, 3H), 2.19-2.10 (m, 3H), 1.98-1.93 (m, 1H), 1.73 (s, 2H), 0.84-0.75 (m, 1H), 0.48-0.42 (m, 2H), 0.07-0.01 (m, 2H). | Rt = 1.78 min, m/z 452.3 [M + H]$^+$ (Method 1) |
| 59 | 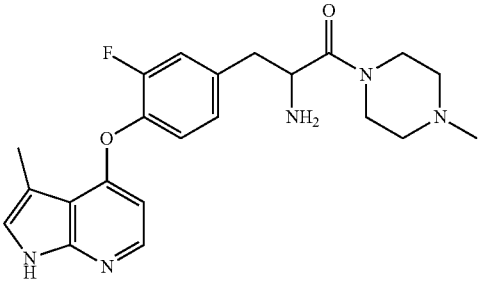<br>2-amino-3-(3-fluoro-4-((3-methyl-1H-pyrrolo[2,3-b]pyridin-4-yl)oxy)phenyl)-1-(4-methylpiperazin-1-yl)propan-1-one | 1E-b/1-methyl-piperazine | $^1$H NMR (400 MHz, d6-DMSO) δ 11.39 (s, 1H), 7.99-7.97 (m, 1H), 7.31 (dd, J = 2.0, 11.9 Hz, 1H), 7.24 (t, J = 8.5 Hz, 1H), 7.15-7.08 (m, 2H), 6.16 (d, J = 4.8 Hz, 1H), 3.95 (t, J = 6.9 Hz, 1H), 3.54-3.44 (m, 1H), 3.43-3.34 (m, 3H), 2.79 (dd, J = 6.6, 13.1 Hz, 1H), 2.69 (dd, J = 7.1, 13.1 Hz, 1H), 2.38 (d, J = 1.0 Hz, 3H), 2.33-2.23 (m, 2H), 2.13 (s, 3H), 2.11-2.04 (m, 1H), 1.94-1.89 (m, 1H), 1.75-1.72 (m, 2H). | Rt = 1.60 min, m/z 412.2 [M + H]$^+$ (Method 1) |
| 60 | 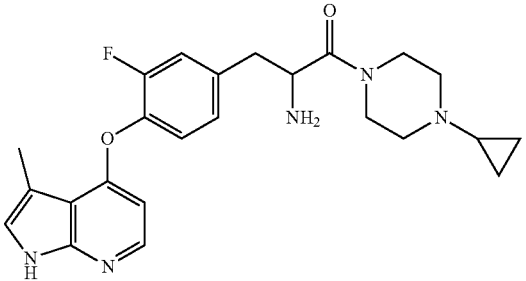<br>2-amino-1-(4-cyclopropylpiperazin-1-yl)-3-(3-fluoro-4-((3-methyl-1H-pyrrolo[2,3-b]pyridin-4-yl)oxy)phenyl)propan-1-one | 1E-b/1-cyclopropyl-piperazine | $^1$H NMR (400 MHz, d6-DMSO) δ 11.39 (s, 1H), 7.97 (d, J = 5.5 Hz, 1H), 7.31 (dd, J = 2.0, 11.6 Hz, 1H), 7.25 (t, J = 8.4 Hz, 1H), 7.14-7.09 (m, 2H), 6.16 (d, J = 5.4 Hz, 1H), 3.95 (t, J = 6.9 Hz, 1H), 3.52-3.45 (m, 1H), 3.41-3.24 (m, 5H), 2.80 (dd, J = 6.8, 13.1 Hz, 1H), 2.70 (dd, J = 7.1, 13.2 Hz, 1H), 2.37 (d, J = 1.0 Hz, 3H), 2.34-2.28 (m, 1H), 2.14-2.10 (m, 1H), 1.73 (s, 2H), 1.57-1.50 (m, 1H), 0.44-0.37 (m, 2H), 0.31 (m, 2H). | Rt = 1.87 min, m/z 438.3 [M + H]$^+$ (Method 1) |
| 61 | 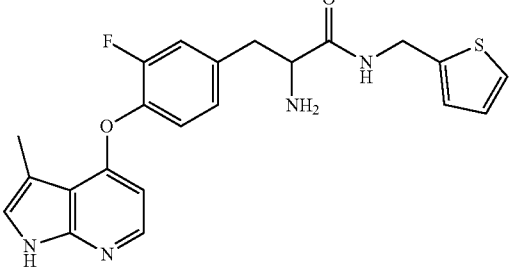<br>2-amino-3-(3-fluoro-4-((3-methyl-1H-pyrrolo[2,3-b]pyridin-4-yl)oxy)phenyl)-N-(thiophen-2-ylmethyl)propanamide | 1E-b/thiophen-2-ylmethanamine | $^1$H NMR (400 MHz, d6-DMSO) δ 11.38 (br. s., 1H), 8.52 (br. s., 1H), 8.16 (s, 1H), 7.98 (d, J = 5.5 Hz, 1H), 7.02-7.41 (m, 5H), 6.93 (d, J = 3.5 Hz, 2H), 6.16 (d, J = 5.1 Hz, 1H), 4.45 (dd, J = 8.2, 5.9 Hz, 2H), 3.44-3.67 (m, 1H), 2.97 (m, 1H), 2.75 (dd, J = 13.5, 8.0 Hz, 1H), 2.39 (s, 3H). | Rt = 2.46 min, m/z 425.1 [M + H]$^+$ (Method 1) |

-continued

| Ex | Structure/Name | Intermediate 1E/Amine | 1H NMR | LC-MS |
|---|---|---|---|---|
| 62 | 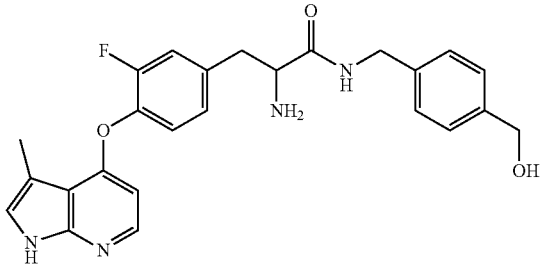<br>2-amino-3-(3-fluoro-4-((3-methyl-1H-pyrrolo[2,3-b]pyridin-4-yl)oxy)phenyl)-N-(4-(hydroxymethyl)benzyl)propanamide | 1E-b/(4-(aminomethyl)-phenyl)-methanol | $^1$H NMR (400 MHz, d6-DMSO) δ 11.39 (s, 1H), 8.36-8.26 (m, 1H), 7.97 (d, J = 5.4 Hz, 1H), 7.31-7.20 (m, 4H), 7.15-7.07 (m, 4H), 6.16 (d, J = 5.4 Hz, 1H), 5.11-5.11 (m, 1H), 4.44 (s, 2H), 4.32-4.18 (m, 2H), 3.49 (dd, J = 5.8, 7.7 Hz, 1H), 2.96 (dd, J = 5.7, 13.3 Hz, 1H), 2.74 (dd, J = 8.1, 13.1 Hz, 1H), 2.40 (d, J = 1.0 Hz, 3H). | Rt = 2.18 min, m/z 449.2 [M + H]$^+$ (Method 1) |
| 63 | 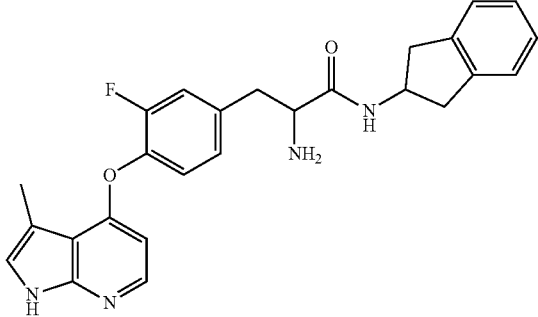<br>2-amino-N-(2,3-dihydro-1H-inden-2-yl)-3-(3-fluoro-4-((3-methyl-1H-pyrrolo[2,3-b]pyridin-4-yl)oxy)phenyl)propanamide | 1E-b/2,3-dihydro-1H-inden-2-amine | $^1$H NMR (400 MHz, d6-DMSO) δ 11.39 (br. s., 1H), 8.21 (d, J = 7.0 Hz, 1H), 8.15 (s, 1H), 7.95 (d, J = 5.7 Hz, 1H), 6.97-7.33 (m, 8H), 6.16 (d, J = 5.7 Hz, 1H), 4.34-4.63 (m, 1H), 3.55 (m, 1H), 3.15 (m, 2H), 2.78 (m, 4H), 2.39 (s, 3H). | Rt = 2.71 min, m/z 445.2 [M + H]$^+$ (Method 1) |
| 64 | 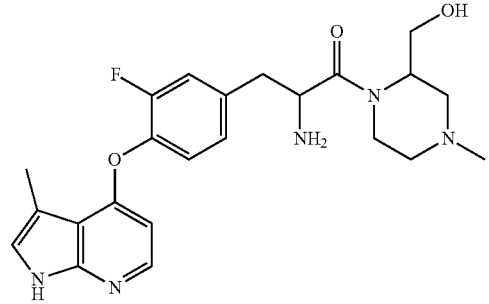<br>2-amino-3-(3-fluoro-4-((3-methyl-1H-pyrrolo[2,3-b]pyridin-4-yl)oxy)phenyl)-1-(2-(hydroxymethyl)-4-methylpiperazin-1-yl)propan-1-one | 1E-b/(4-methyl-piperazin-2-yl)-methanol | $^1$H NMR (400 MHz, d6-DMSO) δ 11.50 (br. s., 1 H), 10.07-11.04 (m, 1 H), 8.32 (br. s., 3 H), 8.03 (d, J = 5.3 Hz, 1 H), 7.03-7.61 (m, 4 H), 6.28 (m, 1 H), 2.64-4.92 (m, 15 H), 2.39 (br. s., 3 H). | Rt = 1.58 min, m/z 442.3 [M + H]$^+$ (Method 1) |
| 65 | 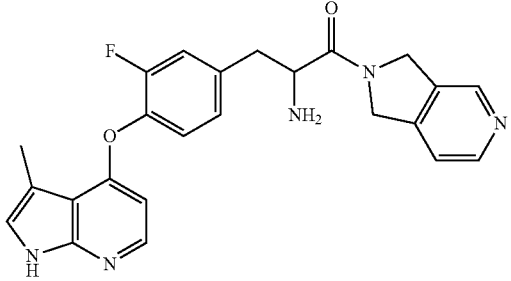<br>2-amino-3-(3-fluoro-4-((3-methyl-1H-pyrrolo[2,3-b]pyridin-4-yl)oxy)phenyl)-1-(1H-pyrrolo[3,4-c]pyridin-2(3H)-yl)propan-1-one | 1E-b/2,3-dihydro-1H-pyrrolo[3,4-c]pyridine | $^1$H NMR (400 MHz, d6-DMSO) δ 11.38 (s, 1H), 8.59 (d, J = 9.9 Hz, 1H), 8.50 (d, J = 5.0 Hz, 1H), 7.83 (d, J = 5.4 Hz, 1H), 7.44-7.35 (m, 2H), 7.27-7.15 (m, 2H), 7.12 (s, 1H), 5.95 (d, J = 5.1 Hz, 1H), 5.07-5.01 (m, 1H), 4.78-4.59 (m, 3H), 3.81-3.75 (m, 1H), 2.91 (dd, J = 6.2, 13.2 Hz, 1H), 2.74 (dd, J = 7.9, 13.3 Hz, 1H), 2.35 (d, J = 1.0 Hz, 3H), 1.83 (s, 2H). | Rt = 1.96 min, m/z 432.2 [M + H]$^+$ (Method 1) |

-continued

| Ex | Structure/Name | Intermediate 1E/Amine | 1H NMR | LC-MS |
|---|---|---|---|---|
| 66 | 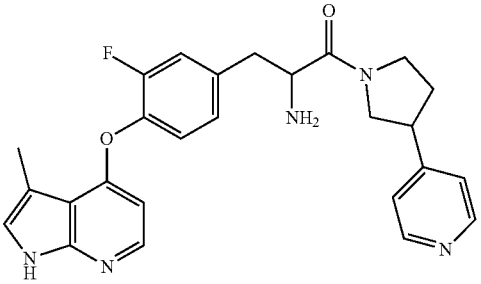<br>2-amino-3-(3-fluoro-4-((3-methyl-1H-pyrrolo[2,3-b]pyridin-4-yl)oxy)phenyl)-1-(3-(pyridin-4-yl)pyrrolidin-1-yl)propan-1-one | 1E-b/rac-4-(pyrrolidin-3-yl)pyridine | $^1$H NMR (400 MHz, d6-DMSO) δ 11.40 (s, 1H), 8.53-8.49 (m, 1H), 8.48-8.42 (m, 1H), 7.99-7.90 (m, 1H), 7.75-7.55 (m, 1H), 7.39-7.12 (m, 5H), 6.16-6.08 (m, 1H), 3.93-3.37 (m, 4H), 3.29-3.10 (m, 2H), 2.90-2.81 (m, 1H), 2.74-2.66 (m, 1H), 2.38-2.36 (m, 3H), 2.32-2.18 (m, 1H), 2.08-1.65 (m, 3H). | Rt = 1.97 min, m/z 460.3 [M + H]$^+$ (Method 1) |
| 67 | 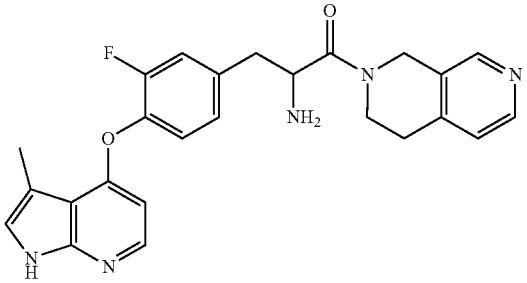<br>2-amino-1-(3,4-dihydro-2,7-naphthyridin-2(1H)-yl)-3-(3-fluoro-4-((3-methyl-1H-pyrrolo[2,3-b]pyridin-4-yl)oxy)phenyl)propan-1-one | 1E-b/1,2,3,4-tetra-hydro-2,7-naphthyridine | $^1$H NMR (400 MHz, d6-DMSO) δ 11.38 (s, 1H), 8.44-8.28 (m, 2H), 7.95-7.91 (m, 1H), 7.36-7.25 (m, 1H), 7.19-7.07 (m, 4H), 6.10-6.01 (m, 1H), 4.80-4.58 (m, 2H), 4.13-3.99 (m, 1H), 3.86-3.73 (m, 1H), 3.69-3.50 (m, 1H), 2.92-2.62 (m, 4H), 2.37 (d, J = 2.4 Hz, 3H), 1.85 (s, 2H). | Rt = 1.82 min, m/z 446.2 [M + H]$^+$ (Method 1) |
| 68 | 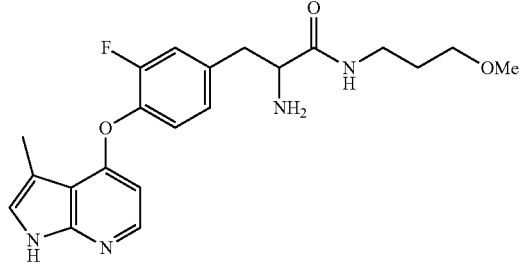<br>2-amino-3-(3-fluoro-4-((3-methyl-1H-pyrrolo[2,3-b]pyridin-4-yl)oxy)phenyl)-N-(3-methoxypropyl)propanamide | 1E-b/3-methoxypropan-1-amine | $^1$H NMR (400 MHz, d6-DMSO) δ 11.39 (s, 1H), 7.98 (d, J = 5.4 Hz, 1H), 7.85 (t, J = 5.7 Hz, 1H), 7.29-7.21 (m, 2H), 7.14-7.07 (m, 2H), 6.16 (d, J = 5.4 Hz, 1H), 3.42-3.37 (m, 1H), 3.24 (t, J = 6.3 Hz, 2H), 3.20 (s, 3H), 3.18-3.02 (m, 4H), 2.91 (dd, J = 5.7, 13.3 Hz, 1H), 2.71 (dd, J = 7.6, 13.3 Hz, 1H), 2.38 (d, J = 1.0 Hz, 3H), 1.62-1.53 (m, 2H). | Rt = 2.21 min, m/z 401.2 [M + H]$^+$ (Method 1) |
| 69 | 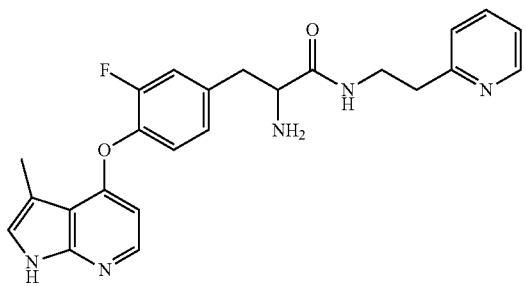<br>2-amino-3-(3-fluoro-4-((3-methyl-1H-pyrrolo[2,3-b]pyridin-4-yl)oxy)phenyl)-N-(2-(pyridin-2-yl)ethyl)propanamide | 1E-b/2-(pyridin-2-yl)ethan-1-amine | $^1$H NMR (400 MHz, d6-DMSO) δ 11.39 (s, 1H), 8.49 (dd, J = 2.1, 5.3 Hz, 1H), 8.05 (t, J = 5.7 Hz, 1H), 7.95 (d, J = 5.4 Hz, 1H), 7.69 (dt, J = 1.9, 7.7 Hz, 1H), 7.30-7.19 (m, 4H), 7.14-7.06 (m, 2H), 6.16 (dd, J = 0.8, 5.4 Hz, 1H), 3.48-3.37 (m, 3H), 2.93 (dd, J = 5.3, 13.4 Hz, 1H), 2.83 (t, J = 7.3 Hz, 2H), 2.70 (dd, J = 8.1, 13.7 Hz, 1H), 2.38 (d, J = 1.0 Hz, 3H). | Rt = 1.92 min, m/z 434.2 [M + H]$^+$ (Method 1) |

-continued

| Ex | Structure/Name | Intermediate 1E/Amine | 1H NMR | LC-MS |
|---|---|---|---|---|
| 70 | 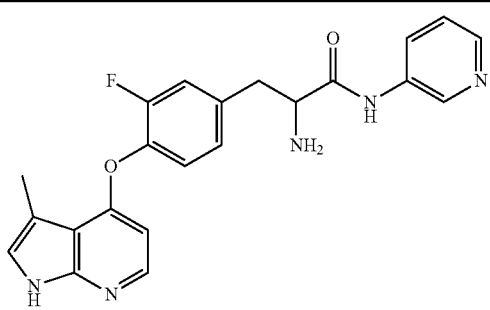<br>2-amino-3-(3-fluoro-4-((3-methyl-1H-pyrrolo[2,3-b]pyridin-4-yl)oxy)phenyl)-N-(pyridin-3-yl)propanamide | 1E-b/pyridin-3-amine | $^1$H NMR (400 MHz, d6-DMSO) δ 11.38 (s, 1H), 8.76-8.75 (m, 1H), 8.26 (dd, J = 1.5, 4.7 Hz, 1H), 8.08-8.04 (m, 1H), 7.94 (d, J = 5.4 Hz, 1H), 7.36-7.31 (m, 2H), 7.23 (t, J = 8.4 Hz, 1H), 7.16-7.12 (m, 2H), 6.08 (d, J = 4.8 Hz, 1H), 3.63 (dd, J = 5.7, 7.9 Hz, 1H), 3.03 (dd, J = 5.6, 13.4 Hz, 1H), 2.82 (dd, J = 8.0, 13.4 Hz, 1H), 2.37 (d, J = 1.0 Hz, 3H). | Rt = 2.05 min, m/z 406.2 [M + H]$^+$ (Method 1) |
| 71 | 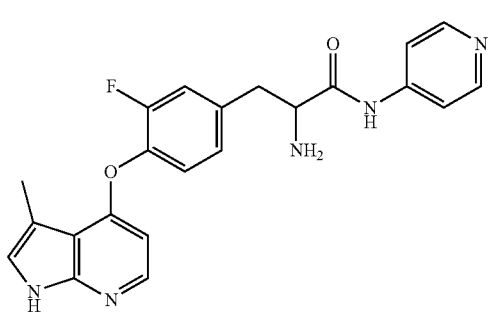<br>2-amino-3-(3-fluoro-4-((3-methyl-1H-pyrrolo[2,3-b]pyridin-4-yl)oxy)phenyl)-N-(pyridin-4-yl)propanamide | 1E-b/pyridin-4-amine | $^1$H NMR (400 MHz, d6-DMSO) δ 11.40 (s, 1H), 8.44-8.41 (m, 2H), 7.94 (d, J = 5.5 Hz, 1H), 7.62-7.59 (m, 2H), 7.34 (dd, J = 1.8, 11.9 Hz, 1H), 7.23 (t, J = 8.4 Hz, 1H), 7.15-7.11 (m, 2H), 6.07 (d, J = 4.8 Hz, 1H), 3.63 (dd, J = 5.7, 8.0 Hz, 1H), 3.01 (dd, J = 5.6, 13.4 Hz, 1H), 2.81 (dd, J = 8.1, 13.4 Hz, 1H), 2.36 (d, J = 1.0 Hz, 3H), NH and NH$_2$ not observed. | Rt = 1.81 min, m/z 406.2 [M + H]$^+$ (Method 1) |
| 72 | 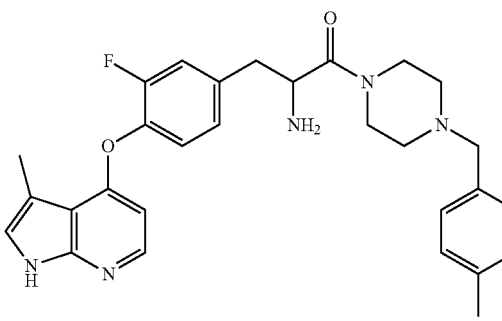<br>2-amino-3-(3-fluoro-4-((3-methyl-1H-pyrrolo[2,3-b]pyridin-4-yl)oxy)phenyl)-1-(4-(4-methylbenzyl)piperazin-1-yl)propan-1-one | 1E-b/1-(4-methyl-benzyl)-piperazine | $^1$H NMR (400 MHz, d6-DMSO) δ 11.39 (s, 1H), 7.99-7.97 (m, 1H), 7.31 (dd, J = 1.7, 11.9 Hz, 1H), 7.24 (t, J = 8.5 Hz, 1H), 7.18-7.07 (m, 6H), 6.16 (dd, J = 0.7, 5.4 Hz, 1H), 3.93 (t, J = 6.9 Hz, 1H), 3.40-3.35 (m, 6H), 2.79 (dd, J = 6.5, 13.1 Hz, 1H), 2.67 (dd, J = 7.2, 13.2 Hz, 1H), 2.39 (d, J = 1.0 Hz, 3H), 2.34-2.29 (m, 2H), 2.27 (s, 3H), 2.19-2.07 (m, 1H), 2.02-1.95 (m, 1H), 1.75 (s, 2H). | Rt = 2.22 min, m/z 502.3 [M + H]$^+$ (Method 1) |
| 73 | 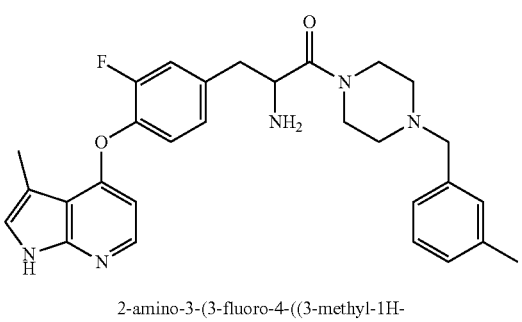<br>2-amino-3-(3-fluoro-4-((3-methyl-1H-pyrrolo[2,3-b]pyridin-4-yl)oxy)phenyl)-1-(4-(3-methylbenzyl)piperazin-1-yl)propan-1-one | 1E-b/1-(3-methyl-benzyl)-piperazine | $^1$H NMR (400 MHz, d6-DMSO) δ 11.39 (s, 1H), 7.98 (d, J = 5.4 Hz, 1H), 7.33-7.04 (m, 8H), 6.16 (d, J = 5.4 Hz, 1H), 3.94 (t, J = 6.9 Hz, 1H), 3.56-3.34 (m, 6H), 2.79 (dd, J = 6.5, 13.1 Hz, 1H), 2.68 (dd, J = 7.2, 13.1 Hz, 1H), 2.39 (s, 3H), 2.37-2.30 (m, 2H), 2.29 (s, 3H), 2.20-2.12 (m, 1H), 1.98 (t, J = 7.5 Hz, 1H), 1.73 (s, 2H). | Rt = 2.25 min, m/z 502.3 [M + H]$^+$ (Method 1) |

| Ex | Structure/Name | Intermediate 1E/Amine | 1H NMR | LC-MS |
|---|---|---|---|---|
| 74 | 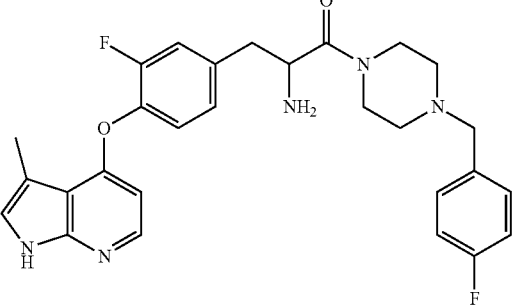<br>2-amino-3-(3-fluoro-4-((3-methyl-1H-pyrrolo[2,3-b]pyridin-4-yl)oxy)phenyl)-1-(4-(4-fluorobenzyl)piperazin-1-yl)propan-1-one | 1E-b/1-(4-fluoro-benzyl) piperazine | $^1$H NMR (400 MHz, d6-DMSO) δ 11.40 (s, 1H), 7.98 (d, J = 5.4 Hz, 1H), 7.34-7.22 (m, 4H), 7.17-7.11 (m, 4H), 6.16 (d, J = 4.8 Hz, 1H), 3.94 (t, J = 6.9 Hz, 1H), 3.55-3.37 (m, 6H), 2.79 (dd, J = 6.4, 13.1 Hz, 1H), 2.67 (dd, J = 7.3, 13.1 Hz, 1H), 2.39 (d, J = 1.0 Hz, 3H), 2.37-2.28 (m, 2H), 2.19-2.13 (m, 1H), 2.06-1.76 (m, 3H). | Rt = 2.18 min, m/z 506.3 [M + H]$^+$ (Method 1) |
| 75 | 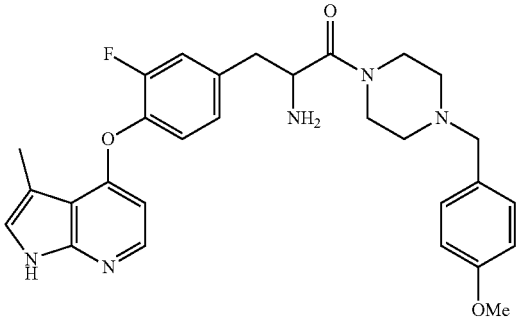<br>2-amino-3-(3-fluoro-4-((3-methyl-1H-pyrrolo[2,3-b]pyridin-4-yl)oxy)phenyl)-1-(4-(4-methoxybenzyl)piperazin-1-yl)propan-1-one | 1E-b/1-(4-methoxy-benzyl) piperazine | $^1$H NMR (400 MHz, d6-DMSO) δ 11.38 (s, 1H), 7.98 (d, J = 5.4 Hz, 1H), 7.33-7.08 (m, 6H), 6.87 (d, J = 8.7 Hz, 2H), 6.16 (d, J = 5.4 Hz, 1H), 3.93 (t, J = 7.0 Hz, 1H), 3.73 (s, 3H), 3.54-3.34 (m, 6H), 2.79 (dd, J = 6.5, 13.1 Hz, 1H), 2.67 (dd, J = 7.3, 13.2 Hz, 1H), 2.39 (d, J = 1.0 Hz, 3H), 2.36-2.30 (m, 2H), 2.16-2.11 (m, 1H), 2.02-1.92 (m, 1H), 1.71 (s, 2H). | Rt = 2.12 min, m/z 518.3 [M + H]$^+$ (Method 1) |
| 76 | 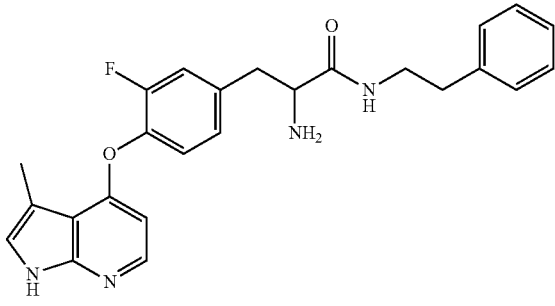<br>2-amino-3-(3-fluoro-4-((3-methyl-1H-pyrrolo[2,3-b]pyridin-4-yl)oxy)phenyl)-N-phenethylpropanamide | 1E-b/2-phenylethan-1-amine | $^1$H NMR (400 MHz, d6-DMSO) δ 11.38 (s, 1H), 7.94 (d, J = 5.5 Hz, 2H), 7.30-7.06 (m, 9H), 6.17-6.15 (m, 1H), 3.39 (dd, J = 5.4, 7.8 Hz, 1H), 3.31-3.24 (m, 2H), 2.91 (dd, J = 5.3, 13.4 Hz, 1H), 2.71-2.64 (m, 3H), 2.38 (d, J = 1.0 Hz, 3H), 1.76 (s, 2H). | Rt = 2.73 min, m/z 433.3 [M + H]$^+$ (Method 1) |
| 77 | 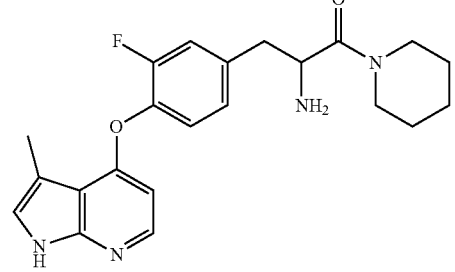<br>2-amino-3-(3-fluoro-4-((3-methyl-1H-pyrrolo[2,3-b]pyridin-4-yl)oxy)phenyl)-1-(piperidin-1-yl)propan-1-one | 1E-b/piperidine | $^1$H NMR (400 MHz, d6-DMSO) δ 11.40 (s, 1H), 7.98 (d, J = 5.4 Hz, 1H), 7.32 (dd, J = 1.8, 11.9 Hz, 1H), 7.23 (dd, J = 8.4, 8.4 Hz, 1H), 7.14-7.09 (m, 2H), 6.14 (dd, J = 0.8, 5.4 Hz, 1H), 3.94 (t, J = 6.9 Hz, 1H), 3.55-3.45 (m, 1H), 3.42-3.35 (m, 3H), 2.80 (dd, J = 6.3, 13.2 Hz, 1H), 2.66 (dd, J = 7.3, 13.2 Hz, 1H), 2.38 (d, J = 0.9 Hz, 3H), 1.74 (s, 2H), 1.58-1.42 (m, 4H), 1.37-1.28 (m, 1H), 1.25-1.15 (m, 1H). | Rt = 2.48 min, m/z 397.3 [M + H]$^+$ (Method 1) |

-continued

| Ex | Structure/Name | Intermediate 1E/Amine | 1H NMR | LC-MS |
|---|---|---|---|---|
| 78 | 2-amino-3-(3-fluoro-4-((3-methyl-1H-pyrrolo[2,3-b]pyridin-4-yl)oxy)phenyl)-N-(isoquinolin-5-yl)propanamide | 1E-b/ isoquinolin-5-amine | $^1$H NMR (400 MHz, d6-DMSO) δ 11.40 (s, 1H), 9.33 (s, 1H), 8.51 (d, J = 6.0 Hz, 1H), 8.06 (d, J = 7.6 Hz, 1H), 7.95 (d, J = 8.2 Hz, 1H), 7.87 (d, J = 5.5 Hz, 1H), 7.68 (t, J = 7.9 Hz, 2H), 7.39 (dd, J =1.6, 11.9 Hz, 1H), 7.29-7.13 (m, 3H), 6.06 (d, J = 4.8 Hz, 1H), 3.85 (t, J = 6.5 Hz, 1H), 3.11 (dd, J = 5.5, 13.6 Hz, 1H), 2.93 (dd, J =7.7, 13.4 Hz, 1H), 2.38 (d, J = 1.0 Hz, 3H), NH and NH$_2$ not observed. | Rt = 2.09 min, m/z 456.2 [M + H]$^+$ (Method 1) |
| 79 | 2-amino-3-(3-fluoro-4-((3-methyl-1H-pyrrolo[2,3-b]pyridin-4-yl)oxy)phenyl)-N-(3-morpholinopropyl)propanamide | 1E-b/3-morpholino-propan-1-amine | $^1$H NMR (400 MHz, d6-DMSO) δ 11.38 (s, 1H), 7.98 (d, J = 5.4 Hz, 1H), 7.89 (t, J = 5.7 Hz, 1H), 7.29-7.20 (m, 2H), 7.14-7.07 (m, 2H), 6.16 (d, J = 4.8 Hz, 1H), 3.56-3.51 (m, 4H), 3.39 (dd, J = 5.7, 7.4 Hz, 1H), 3.11-3.03 (m, 2H), 2.91 (dd, J = 5.6, 13.3 Hz, 1H), 2.72 (dd, J = 7.3, 13.2 Hz, 1H), 2.38 (d, J =1.0 Hz, 3H), 2.32-2.25 (m, 4H), 2.21 (t, J = 7.0 Hz, 2H), 1.84 (s, 2H), 1.54-1.45 (m, 2H). | Rt = 1.73 min, m/z 456.3 [M + H]$^+$ (Method 1) |
| 80 | 2-amino-3-(3-fluoro-4-((3-methyl-1H-pyrrolo[2,3-b]pyridin-4-yl)oxy)phenyl)-1-(4-(pyridin-2-yl)piperazin-1-yl)propan-1-one | 1E-b/1-(pyridin-2-yl)piperazine | $^1$H NMR (400 MHz, d6-DMSO) δ 11.37 (s, 1H), 8.12 (dd, J = 1.3, 4.9 Hz, 1H), 7.80 (d, J = 5.4 Hz, 1H), 7.58-7.52 (m, 1H), 7.34 (dd, J = 1.9, 11.9 Hz, 1H), 7.23 (t, J = 8.4 Hz, 1H), 7.15-7.10 (m, 2H), 6.83 (d, J = 8.6 Hz, 1H), 6.67 (dd, J = 5.0, 6.6 Hz, 1H), 6.08 (d, J = 4.9 Hz, 1H), 4.01 (t, J = 6.9 Hz, 1H), 3.65-3.46 (m, 6H), 3.31-3.24 (m, 1H), 3.19-3.11 (m, 1H), 2.84 (dd, J = 6.5, 13.1 Hz, 1H), 2.72 (dd, J = 7.3, 13.2 Hz, 1H), 2.33 (d, J = 1.0 Hz, 3H), 1.77 (s, 2H). | Rt = 2.04 min, m/z 475.3 [M + H]$^+$ (Method 1) |
| 81 | 2-amino-1-(5,6-dihydroimidazo[1,5-a]pyrazin-7(8H)-yl)-3-(3-fluoro-4-((3-methyl-1H-pyrrolo[2,3-b]pyridin-4-yl)oxy)phenyl)propan-1-one | 1E-b/5,6,7,8-tetra-hydroimidazo[1,5-a]pyrazine | $^1$H NMR (400 MHz, d6-DMSO) δ 11.39 (s, 1H), 7.96 (m, 1H), 7.58 (s, 1H), 7.39-7.29 (m, 1H), 7.23-7.07 (m, 3H), 6.74 (m, 1H), 6.09 (m, 1H), 4.88-4.55 (m, 2H), 4.14-3.75 (m, 5H), 2.92-2.79 (m, 1H), 2.74-2.66 (m, 1H), 2.37 (d, J = 1.0 Hz, 3H), 1.78 (br s, 2H). | Rt = 1.66 min, m/z 435.2 [M + H]$^+$ (Method 1) |

| Ex | Structure/Name | Intermediate 1E/Amine | 1H NMR | LC-MS |
|---|---|---|---|---|
| 82 | 2-amino-N-((1-benzylpiperidin-4-yl)methyl)-3-(3-fluoro-4-((3-methyl-1H-pyrrolo[2,3-b]pyridin-4-yl)oxy)phenyl)propanamide | 1E-b/(1-benzylpiperidin-4-yl)methanamine | $^1$H NMR (400 MHz, d6-DMSO) δ 11.39 (s, 1H), 7.97 (d, J = 5.4 Hz, 1H), 7.81 (t, J = 5.9 Hz, 1H), 7.32-7.18 (m, 6H), 7.14-7.06 (m, 2H), 6.14 (d, J = 5.5 Hz, 1H), 3.42 (d, J = 6.8 Hz, 1H), 3.39 (s, 2H), 3.01-2.82 (m, 3H), 2.76-2.68 (m, 3H), 2.37 (d, J = 1 Hz, 3H), 1.86-1.76 (m, 4H), 1.49-1.44 (m, 2H), 1.33-1.23 (m, 1H), 1.11-0.99 (m, 2H). | Rt = 2.10 min, m/z 516.4 [M + H]$^+$ (Method 1) |
| 83 | 2-amino-N-(1-benzylpiperidin-4-yl)-3-(3-fluoro-4-((3-methyl-1H-pyrrolo[2,3-b]pyridin-4-yl)oxy)phenyl)propanamide | 1E-b/1-benzyl-piperidin-4-amine | $^1$H NMR (400 MHz, d6-DMSO) δ 11.39 (s, 1H), 7.94 (d, J = 5.4 Hz, 1H), 7.66 (d, J = 7.9 Hz, 1H), 7.32-7.19 (m, 6H), 7.13-7.05 (m, 2H), 6.14 (d, J = 5.0 Hz, 1H), 3.58-3.47 (m, 1H), 3.43 (s, 2H), 3.38 (t, J = 6.8 Hz, 2H), 2.86 (dd, J = 6.1, 13.2 Hz, 1H), 2.75-2.63 (m, 3H), 2.37 (d, J = 0.9 Hz, 3H), 2.04-1.95 (m, 2H), 1.77 (s, 2H), 1.67-1.55 (m, 2H), 1.45-1.25 (m, 2H) | Rt = 2.08 min, m/z 502.3 [M + H]$^+$ (Method 1) |
| 84 | First eluting rac-diastereoisomer (Diastereoisomer A) 2-amino-3-(3-fluoro-4-((3-methyl-1H-pyrrolo[2,3-b]pyridin-4-yl)oxy)phenyl)-1-(2-phenylpyrrolidin-1-yl)propan-1-one | 1E-b/rac-2-phenyl-pyrrolidine | Diastereoisomer A $^1$H NMR (400 MHz, d6-DMSO) δ 11.41 (s, 1H), 8.00-7.96 (m, 1H), 7.39-7.03 (m, 7H), 6.95-6.92 (m, 1H), 6.17-6.15 (m, 1H), 5.10-4.69 (m, 1H), 4.02-3.83 (m, 1H), 3.82-3.53 (m, 2H), 3.50-3.24 (m, 1H), 3.04-2.78 (m, 1H), 2.72-2.61 (m, 1H), 2.42-2.38 (m, 3H), 2.25-2.01 (m, 2H), 1.91-1.67 (m, 4H). | Rt = 2.87 min, m/z 459.3 [M + H]$^+$ (Method 1) |

| Ex | Structure/Name | Intermediate 1E/Amine | 1H NMR | LC-MS |
|---|---|---|---|---|
| 85 | 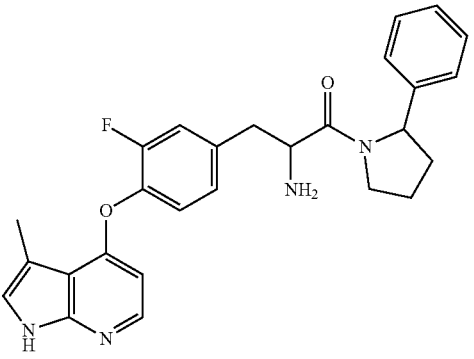<br>Second eluting rac-diastereoisomer (Diastereoisomer B)<br>2-amino-3-(3-fluoro-4-((3-methyl-1H-pyrrolo[2,3-b]pyridin-4-yl)oxy)phenyl)-1-(2-phenylpyrrolidin-1-yl)propan-1-one | 1E-b/rac-2-phenyl-pyrrolidine | Diastereoisomer B<br>$^1$H NMR (400 MHz, d6-DMSO) δ 11.38 (s, 1H), 8.00-7.96 (m, 1H), 7.38-6.99 (m, 7H), 6.52-6.46 (m, 1H), 6.15-6.08 (m, 1H), 5.29-4.99 (m, 1H), 3.89-3.75 (m, 1H), 3.67-3.52 (m, 1H), 3.30-3.23 (m, 1H), 2.86 (dd, J = 6.7, 13.4 Hz, 1H), 2.70 (dd, J = 7.6, 13.2 Hz, 1H), 2.40-2.36 (m, 5H), 2.12-2.02 (m, 1H), 1.84-1.67 (m, 4H). | Rt = 2.93 min, m/z 459.3 [M + H]$^+$ (Method 1) |
| 86 | 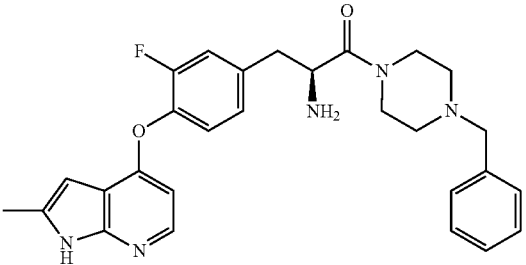<br>(ee % = 79%)<br>(S)-2-amino-1-(4-benzylpiperazin-1-yl)-3-(3-fluoro-4-((2-methyl-1H-pyrrolo[2,3-b]pyridin-4-yl)oxy)phenyl)propan-1-one | 1E-c/1-benzyl-piperazine | $^1$H NMR (400 MHz, d6-DMSO) δ 11.59 (s, 1H), 7.95 (d, J = 5.4 Hz, 1H), 7.34-7.19 (m, 6H), 7.08 (dd, J = 1.4, 8.3 Hz, 1H), 6.33 (d, J = 5.4 Hz, 1H), 5.91 (s, 1H), 3.94 (t, J = 6.9 Hz, 1H), 3.48-3.42 (m, 4H), 3.39-3.25 (m, 4H), 2.80 (dd, J = 6.4, 13.2 Hz, 1H), 2.67 (dd, J = 7.4, 13.1 Hz, 1H), 2.35 (s, 3H), 2.33-2.28 (m, 1H), 2.25-2.19 (m, 1H), 2.14-2.04 (m, 1H), 1.71 (s, 2H). | Rt = 2.09 min, m/z 488.1 [M + H]$^+$ (Method 1) |
| 87 | 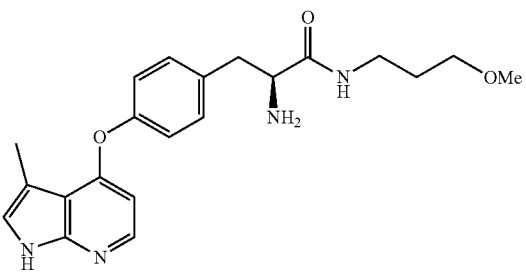<br>(S)-2-amino-N-(3-methoxypropyl)-3-(4-((3-methyl-1H-pyrrolo[2,3-b]pyridin-4-yl)oxy)phenyl)propanamide | 1E-d/3-methoxy-propan-1-amine | $^1$H NMR (400 MHz, d6-DMSO) δ 11.36 (s, 1H), 7.99 (d, J = 5.4 Hz, 1H), 7.82 (t, J = 5.7 Hz, 1H), 7.26 (d, J = 8.5 Hz, 2H), 7.14-7.09 (m, 1H), 7.05 (d, J = 8.6 Hz, 2H), 6.24 (d, J = 5.4 Hz, 1H), 3.40-3.35 (m, 1H), 3.25 (t, J = 6.3 Hz, 2H), 3.20 (s, 3H), 3.16-3.01 (m, 2H), 2.89 (dd, J = 5.6, 13.3 Hz, 1H), 2.67 (dd, J = 7.6, 13.3 Hz, 1H), 2.33-2.33 (m, 3H), 1.72-1.72 (m, 2H), 1.62-1.52 (m, 2H). | Rt = 2.08 min, m/z 383.2 [M + H]$^+$ (Method 1) |

-continued

| Ex | Structure/Name | Intermediate 1E/Amine | 1H NMR | LC-MS |
|---|---|---|---|---|
| 88 | (S)-2-amino-1-(4-benzylpiperazin-1-yl)-3-(4-((3-methyl-1H-pyrrolo[2,3-b]pyridin-4-yl)oxy)phenyl)propan-1-one | 1E-d/1-benzyl-piperazine | $^1$H NMR (400 MHz, d6-DMSO) δ 11.36 (s, 1H), 7.99 (d, J = 5.4 Hz, 1H), 7.34-7.24 (m, 7H), 7.14-7.10 (m, 1H), 7.06 (d, J = 8.6 Hz, 2H), 6.24 (d, J = 5.4 Hz, 1H), 3.91 (t, J = 6.9 Hz, 1H), 3.53-3.45 (m, 1H), 3.41 (s, 2H), 3.40-3.35 (m, 2H), 3.27 (d, J = 3.1 Hz, 1H), 2.77 (dd, J = 7.0, 13.0 Hz, 1H), 2.67 (dd, J = 6.9, 13.0 Hz, 1H), 2.34 (d, J = 1.0 Hz, 3H), 2.33-2.26 (m, 2H), 2.18-2.14 (m, 1H), 1.98-1.92 (m, 1H), 1.70 (s, 2H). | Rt = 1.94 min, m/z 470.3 [M + H]$^+$ (Method 1) |
| 89 | (S)-2-amino-3-(4-((3-methyl-1H-pyrrolo[2,3-b]pyridin-4-yl)oxy)phenyl)-N-(2-(pyridin-4-yl)ethyl)propanamide | 1E-d/2-(pyridin-4-yl)ethan-1-amine | $^1$H NMR (400 MHz, d6-DMSO) δ 11.36 (s, 1H), 8.45 (dd, J = 1.6, 4.4 Hz, 2H), 7.99-7.94 (m, 2H), 7.27-7.18 (m, 4H), 7.14-7.09 (m, 1H), 7.06 (d, J = 18.2 Hz, 2H), 6.24 (d, J = 5.4 Hz, 1H), 3.41-3.30 (m, 2H), 2.88 (dd, J = 5.3, 13.3 Hz, 1H), 2.71 (t, J = 6.9 Hz, 2H), 2.64 (dd, J = 7.2, 13.5 Hz, 1H), 2.33 (s, 3H), 1.76-1.71 (m, 2H). | Rt = 1.67 min, m/z 416.3 [M + H]$^+$ (Method 1) |
| 90 | (S)-2-amino-3-(4-((3-methyl-1H-pyrrolo[2,3-b]pyridin-4-yl)oxy)phenyl)-N-(tetrahydro-2H-pyran-4-yl)propanamide | 1E-d/tetrahydro-2H-pyran-4-amine | $^1$H NMR (400 MHz, d6-DMSO) δ 11.35 (s, 1H), 7.99 (d, J = 5.4 Hz, 1H), 7.71 (d, J = 7.8 Hz, 1H), 7.26 (d, J = 8.6 Hz, 2H), 7.13-7.09 (m, 1H), 7.06-7.03 (m, 2H), 6.24 (d, J = 5.4 Hz, 1H), 3.83-3.69 (m, 3H), 3.42-3.38 (m, 3H), 2.86 (dd, J = 6.2, 13.2 Hz, 1H), 2.69 (dd, J = 7.5, 13.3 Hz, 1H), 2.32 (d, J = 1.0 Hz, 3H), 1.66-1.54 (m, 2H), 1.43-1.22 (m, 2H). | Rt = 2.06 min, m/z 395.0 [M + H]$^+$ (Method 1) |

| Ex | Structure/Name | Intermediate 1E/Amine | 1H NMR | LC-MS |
|---|---|---|---|---|
| 91 | 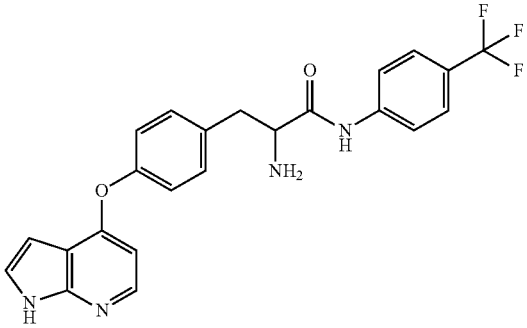<br>Complete racemisation occurred during synthesis<br>3-(4-((1H-pyrrolo[2,3-b]pyridin-4-yl)oxy)phenyl)-2-amino-N-(4-(trifluoromethyl)phenyl)propanamide | 1E-f/4-(trifluoro-methyl)aniline | $^1$H NMR (400 MHz, d6-DMSO) δ 11.69 (s, 1H), 8.02 (d, J = 5.4 Hz, 1H), 7.83 (d, J = 8.4 Hz, 2H), 7.67 (d, J = 8.6 Hz, 2H), 7.32 (d, J = 8.5 Hz, 2H), 7.28 (dd, J = 2.6, 3.3 Hz, 1H), 7.08 (d, J = 8.5 Hz, 2H), 6.32 (d, J = 5.4 Hz, 1H), 6.14 (dd, J = 2.0, 3.5 Hz, 1H), 3.63 (t, J = 6.7 Hz, 1H), 3.00 (dd, J = 5.9, 13.4 Hz, 1H), 2.82 (dd, J = 7.7, 13.4 Hz, 1H). | Rt = 2.78 min, m/z 441.2 [M + H]$^+$ (Method 1) |
| 92 | 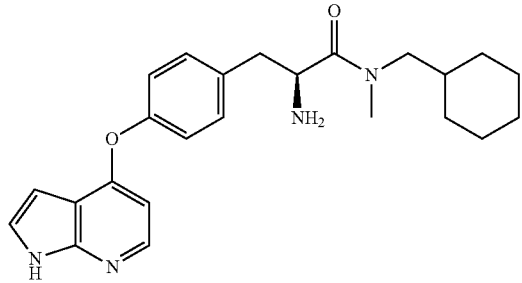<br>(S)-3-(4-((1H-pyrrolo[2,3-b]pyridin-4-yl)oxy)phenyl)-2-amino-N-(cyclohexylmethyl)-N-methylpropanamide | 1E-e/cyclohexyl-N-methyl-methanamine | $^1$H NMR (400 MHz, d6-DMSO) δ 11.72 (s, 1H), 8.08-8.05 (m, 1H), 7.36-7.32 (m, 1H), 7.27 (dd, J = 8.6, 16.0 Hz, 2H), 7.10-7.04 (m, 2H), 6.38-6.35 (m, 1H), 6.19-6.16 (m, 1H), 3.89-3.77 (2 x t, 1H), 3.23 (dd, J = 7.2, 13.0 Hz, 1H), 2.99-2.92 (m, 1H), 2.88 and 2.77 (2 x s, 3H), 2.86-2.78 (m, 1H), 2.71-2.61 (m, 1H), 1.74 (s, 2H), 1.62-1.42 (m, 6H), 1.19-1.02 (m, 3H), 0.96-0.75 (m, 2H). | RT = 2.80 min, m/z 407.3 [M + H]$^+$ (Method 1) |
| 93 | 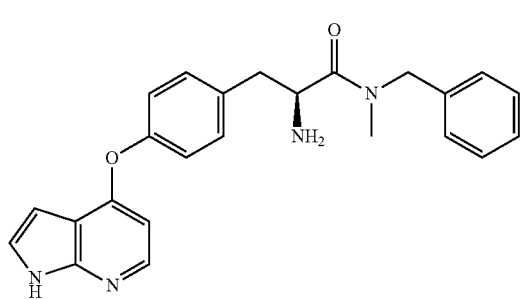<br>(S)-3-(4-((1H-pyrrolo[2,3-b]pyridin-4-yl)oxy)phenyl)-2-amino-N-benzyl-N-methylpropanamide | 1E-e/N-methyl-1-phenyl-methanamine | $^1$H NMR (400 MHz, d6-DMSO) δ 11.72 (s, 1H), 8.08-8.05 (m, 1H), 7.35-7.19 (m, 6H), 7.14-7.03 (m, 4H), 6.40-6.34 (m, 1H), 6.20-6.17 (m, 1H), 4.61-4.29 (m, 2H), 4.03-3.82 (2 x t, 1H), 2.87 (dd, J = 7.0, 13.1 Hz, 1H), 2.82-2.77 (2 x s, 3H), 2.76-2.65 (m, 1H), 2.35 (s, 2H). | Rt = 2.49 min, m/z 401.2 [M + H]$^+$ (Method 1) |

-continued

| Ex | Structure/Name | Intermediate 1E/Amine | 1H NMR | LC-MS |
|---|---|---|---|---|
| 94 | (S)-3-(4-((1H-pyrrolo[2,3-b]pyridin-4-yl)oxy)phenyl)-2-amino-N-(6-chloropyridin-3-yl)propanamide | 1E-e/6-chloropyridin-3-amine | $^1$H NMR (400 MHz, d6-DMSO) δ 11.70 (s, 1H), 8.62 (d, J = 2.7 Hz, 1H), 8.12 (dd, J = 2.8, 8.7 Hz, 1H), 8.03 (d, J = 5.4 Hz, 1H), 7.47 (d, J = 8.7 Hz, 1H), 7.31 (d, J = 8.5 Hz, 2H), 7.29 (dd, J = 2.6, 3.4 Hz, 1H), 7.08 (d, J = 8.6 Hz, 2H), 6.32 (d, J = 5.4 Hz, 1H), 6.14 (dd, J = 2.0, 3.4 Hz, 1H), 3.62 (t, J = 6.9 Hz, 1H), 2.99 (dd, J = 5.9, 13.3 Hz, 1H), 2.82 (dd, J = 7.6, 13.3 Hz, 1H. | Rt = 2.70 min, m/z 408.2 [M + H]$^+$ (Method 3) |
| 95 | (S)-3-(4-((1H-pyrrolo[2,3-b]pyridin-4-yl)oxy)phenyl)-2-amino-N-(2-(dimethylamino)ethyl)propanamide | 1E-e/N,N-dimethyl-ethane-1,2-diamine | $^1$H NMR (400 MHz, d6-DMSO) δ 11.72 (s, 1H), 8.06 (d, J = 5.4 Hz, 1H), 7.79 (t, J = 5.6 Hz, 1H), 7.34 (dd, J = 2.4 ,3.4 Hz, 1H), 7.28 (d, J = 8.5 Hz, 2H), 7.09 (d, J = 8.5 Hz, 2H), 6.39 (d, J = 5.4 Hz, 1H), 6.20 (dd, J = 1.9, 3.4 Hz, 1H), 3.38 (dd, J = 5.2, 7.9 Hz, 1H), 3.17-3.10 (m, 2H), 2.93 (dd, J = 5.2, 13.3 Hz, 1H), 2.67 (dd, J = 7.9, 13.3 Hz, 1H), 2.23 (t, J = 6.7 Hz, 2H), 2.12 (s, 6H), 1.76 (s, 2H). | Rt = 2.89 min, m/z 368.2 [M + H]$^+$ (Method 1) |
| 96 | (R)-3-(4-((1H-pyrrolo[2,3-b]pyridin-4-yl)oxy)phenyl)-2-amino-N-(2-(dimethylamino)ethyl)propanamide | 1E-g/N,N-dimethyl-ethane-1,2-diamine | $^1$H NMR (400 MHz, d6-DMSO) δ 11.71 (s, 1H), 8.06 (d, J = 5.4 Hz, 1H), 7.79 (t, J = 5.6 Hz, 1H), 7.34 (dd, J = 2.5, 3.3 Hz, 1H), 7.28 (d, J = 8.5 Hz, 2H), 7.09 (d, J = 8.5 Hz, 2H), 6.39 (d, J = 5.3 Hz, 1H), 6.20 (dd, J = 1.9, 3.5 Hz, 1H), 3.38 (dd, J = 5.2, 7.9 Hz, 1H), 3.17-3.09 (m, 2H), 2.93 (dd, J = 5.2, 13.4 Hz, 1H), 2.66 (dd, J = 8.0, 13.3 Hz, 1H), 2.23 (t, J = 6.7 Hz, 2H), 2.12 (s, 6H), 1.75 (s, 2H). | Rt = 2.91 min, m/z 368.2 [M + H]$^+$ (Method 1) |
| 97 | (S)-3-(4-((1H-pyrrolo[2,3-b]pyridin-4-yl)oxy)phenyl)-2-amino-N-benzylpropanamide | 1E-e/benzylamine | $^1$H NMR (400 MHz, d6-DMSO) δ 11.71 (s, 1H), 8.33 (t, J = 6.0 Hz, 1H), 8.06 (d, J = 5.4 Hz, 1H), 7.34 (dd, J = 2.5, 3.4 Hz, 1H), 7.31-7.15 (m, 7H), 7.07 (d, J = 8.6 Hz, 2H), 6.39 (d, J = 5.4 Hz, 1H), 6.21 (dd, J = 1.9, 3.5 Hz, 1H), 4.34-4.20 (m, 2H), 3.47 (dd, J = 5.8, 7.5 Hz, 1H), 2.95 (dd, J = 5.7, 13.3 Hz, 1H), 2.72 (dd, J = 7.8, 13.4 Hz, 1H), 1.77 (s, 2H). | Rt = 2.32 mm, m/z 387.2 [M + H]$^+$ (Method 1) |

-continued

| Ex | Structure/Name | Intermediate 1E/Amine | 1H NMR | LC-MS |
|---|---|---|---|---|
| 98 | 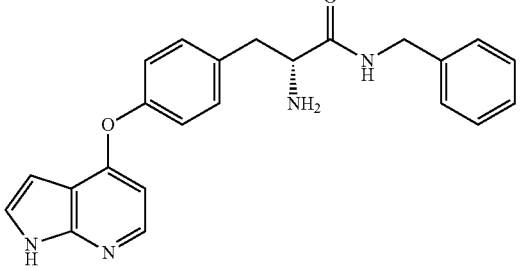<br>(R)-3-(4-((1H-pyrrolo[2,3-b]pyridin-4-yl)oxy)phenyl)-2-amino-N-benzylpropanamide | 1E-g/ benzylamine | $^1$H NMR (400 MHz, d6-DMSO) δ 11.71 (s, 1H), 8.32 (t, J = 6.0 Hz, 1H), 8.06 (d, J = 5.4 Hz, 1H), 7.34 (dd, J = 2.5, 3.4 Hz, 1H), 7.31-7.15 (m, 7H), 7.07 (d, J = 8.6 Hz, 2H), 6.39 (d, J = 5.4 Hz, 1H), 6.21 (dd, J = 1.9, 3.4 Hz, 1H), 4.33-4.20 (m, 2H), 3.47 (dd, J = 5.8, 7.5 Hz, 1H), 2.95 (dd, J = 5.6, 13.3 Hz, 1H), 2.72 (dd, J = 7.7, 13.3 Hz, 1H), 1.77 (s, 2H). | Rt = 2.33 min, m/z 387.2 [M + H]$^+$ (Method 1) |
| 99 | 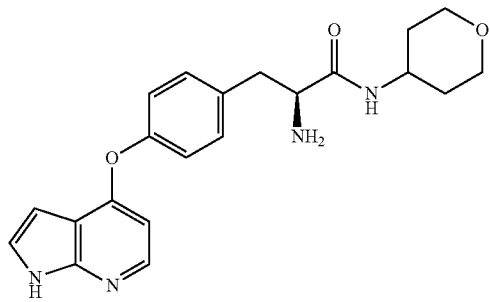<br>(S)-3-(4-((1H-pyrrolo[2,3-b]pyridin-4-yl)oxy)phenyl)-2-amino-N-(tetrahydro-2H-pyran-4-yl)propanamide | 1E-e/ tetrahydro-2H-pyran-4-amine | $^1$H NMR (400 MHz, d6-DMSO) δ 11.71 (s, 1H), 8.06 (d, J = 5.4 Hz, 1H), 7.71 (d, J = 7.8 Hz, 1H), 7.34 (dd, J = 2.4, 3.3 Hz, 1H), 7.27 (d, J = 8.5 Hz, 2H), 7.08 (d, J = 8.5 Hz, 2H), 6.38 (d, J = 5.4 Hz, 1H), 6.22-6.18 (m, 1H), 3.83-3.71 (m, 3H), 3.39-3.28 (m, 3H), 2.87 (dd, J = 6.0, 13.2 Hz, 1H), 2.70 (dd, J = 7.4, 13.2 Hz, 1H), 1.71 (s, 2H), 1.68-1.56 (m, 2H), 1.43-1.26 (m, 2H). | Rt = 1.85 min, m/z 381.2 [M + H]$^+$ (Method 1) |
| 100 | 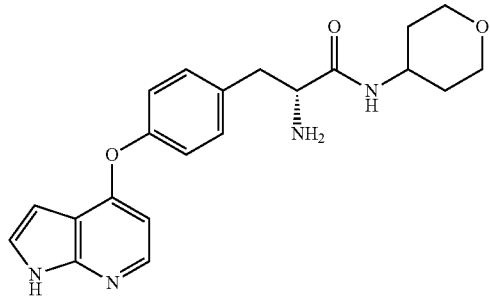<br>(R)-3-(4-((1H-pyrrolo[2,3-b]pyridin-4-yl)oxy)phenyl)-2-amino-N-(tetrahydro-2H-pyran-4-yl)propanamide | 1E-g/ tetrahydro-2H-pyran-4-amine | $^1$H NMR (400 MHz, d6-DMSO) δ 11.71 (s, 1H), 8.06 (d, J = 5.4 Hz, 1H), 7.70 (d, J = 7.8 Hz, 1H), 7.34 (dd, J = 2.5, 3.3 Hz, 1H), 7.27 (d, J = 8.5 Hz, 2H), 7.08 (d, J = 8.6 Hz, 2H), 6.38 (d, J = 5.4 Hz, 1H), 6.21-6.19 (m, 1H), 3.83-3.72 (m, 3H), 3.40-3.27 (m, 3H), 2.87 (dd, J = 6.0, 13.2 Hz, 1H), 2.70 (dd, J = 7.1, 13.0 Hz, 1H), 1.74 (s, 2H), 1.66-1.56 (m, 2H), 1.43-1.26 (m, 2H). | Rt = 1.86 min, m/z 381.2 [M + H]$^+$ (Method 1) |
| 101 | 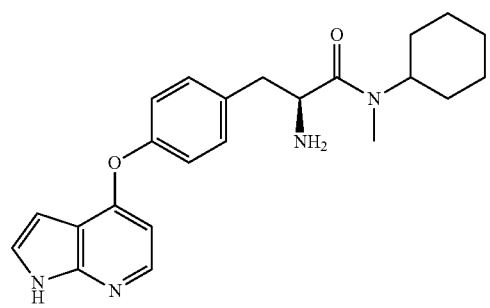<br>(S)-3-(4-((1H-pyrrolo[2,3-b]pyridin-4-yl)oxy)phenyl)-2-amino-N-cyclohexyl-N-methylpropanamide | 1E-e/N-methyl-cyclohexan-amine | $^1$H NMR (400 MHz, d6-DMSO) δ 11.72 (s, 1H), 8.06 (d, J = 5.4 Hz, 1H), 7.37-7.32 (m, 1H), 7.30-7.23 (m, 2H), 7.10-7.05 (m, 2H), 6.37-6.34 (m, 1H), 6.22-6.18 (m, 1H), 4.30-4.16 and 2.83-2.73 (m, 1H), 2.66-2.73 (m, 1H), 2.64 and 2.65 (s, 3H), 1.72 (s, 2H), 1.66-1.56 (m, 4H), 1.49-1.00 (m, 6H). | Rt = 2.50 min, mJz 393.3 [M + H]$^+$ (Method 1) |

-continued

| Ex | Structure/Name | Intermediate 1E/Amine | 1H NMR | LC-MS |
|---|---|---|---|---|
| 102 | 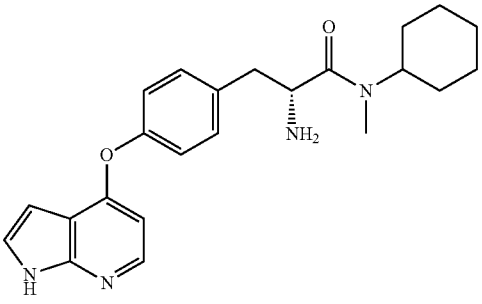<br>(R)-3-(4-((1H-pyrrolo[2,3-b]pyridin-4-yl)oxy)phenyl)-2-amino-N-cyclohexyl-N-methylpropanamide | 1E-g/N-methyl-cyclo-hexanamine | $^1$H NMR (400 MHz, d6-DMSO) δ 11.72 (s, 1H), 8.06 (d, J = 5.4 Hz, 1H), 7.36-7.32 (m, 1H), 7.27-7.30 (m, 2H), 7.10-7.05 (m, 2H), 6.38-6.33 (m, 1H), 6.22-6.18 (m, 1H), 4.29-4.17 and 3.56-3.45 (m, 1H), 3.92-3.82 (m, 1H), 2.83-2.73 (m, 1H), 2.65-2.72 (m, 1H), 2.64-2.66 (s, 3H), 1.72 (s, 2H), 1.66-1.56 (m, 4H), 1.49-1.00 (m, 6H). | Rt = 2.51 min. m/z 393.3 [M + H]$^+$ (Method 1) |
| 103 | 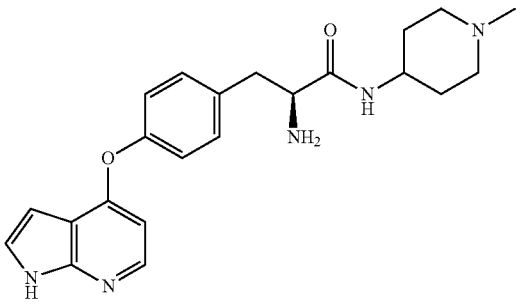<br>(S)-3-(4-((1H-pyrrolo[2,3-b]pyridin-4-yl)oxy)phenyl)-2-amino-N-(1-methylpiperidin-4-yl)propanamide | 1E-e/1-methyl-piperidin-4-amine | $^1$H NMR (400 MHz, d6-DMSO) δ 11.71 (s, 1H), 8.05 (d, J = 5.4 Hz, 1H), 7.62 (d, J = 7.9 Hz, 1H), 7.34 (dd, J = 2.4, 3.3 Hz, 1H), 7.27 (d, J = 8.5 Hz, 2H), 7.08 (d, J = 8.6 Hz, 2H), 6.37 (d, J = 5.4 Hz, 1H), 6.20 (dd, J = 1.8, 3.4 Hz, 1H), 3.52-3.41 (m, 1H), 3.37 (t, J = 6.6 Hz, 1H), 2.86 (dd, J = 5.9, 13.3 Hz, 1H), 2.72-2.58 (m, 3H), 2.12 (s, 3H), 1.95-1.85 (m, 2H), 1.69 (s, 2H), 1.65-1.57 (m, 2H), 1.42-1.25 (m, 2H). | Rt = 2.91 min, m/z 394.2 [M + H]$^+$ (Method 1) |
| 104 | 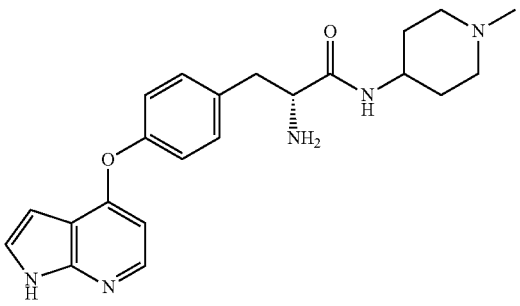<br>(R)-3-(4-((1H-pyrrolo[2,3-b]pyridin-4-yl)oxy)phenyl)-2-amino-N-(1-methylpiperidin-4-yl)propanamide | 1E-g/1-methyl-piperidin-4-amine | $^1$H NMR (400 MHz, d6-DMSO) δ 11.73-11.68 (m, 1H), 8.05 (d, J = 5.4 Hz, 1H), 7.62 (d, J = 7.8 Hz, 1H), 7.34 (dd, J = 2.5, 3.4 Hz, 1H), 7.27 (d, J = 8.4 Hz, 2H), 7.08 (d, J = 8.5 Hz, 2H), 6.37 (d, J = 5.4 Hz, 1H), 6.20 (dd, J=1.9, 3.5 Hz, 1H), 3.52-3.42 (m, 1H), 3.37 (t, J = 6.7 Hz, 1H), 2.86 (dd, J = 6.0, 13.2 Hz, 1H), 2.72-2.59 (m, 3H), 2.12 (s, 3H), 1.95-1.86 (m, 2H), 1.71 (s, 2H), 1.67-1.55 (m, 2H), 1.42-1.25 (m, 2H). | Rt = 2.91 min, m/z 394.2 [M + H]$^+$ (Method 1) |
| 105 | 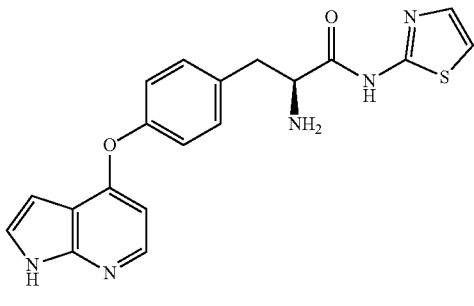<br>(S)-3-(4-((1H-pyrrolo[2,3-b]pyridin-4-yl)oxy)phenyl)-2-amino-N-(thiazol-2-yl)propanamide | 1E-e/2-amino-thiazole | $^1$H NMR (400 MHz, d6-DMSO) δ 11.69 (s, 1H), 8.04 (d, J = 5.4 Hz, 1H), 7.48 (d, J = 3.5 Hz, 1H), 7.32-7.28 (m, 3H), 7.21 (d, J = 3.5 Hz, 1H), 7.07 (d, J = 8.6 Hz, 2H), 6.33 (d, J = 5.4 Hz, 1H), 6.14 (dd, J = 1.8, 3.4 Hz, 1H), 5.27-5.27 (m, 3H), 3.74 (dd, J = 6.1, 7.9 Hz, 1H), 2.99 (dd, J = 5.9, 13.4 Hz, 1H), 2.79 (dd, J = 8.0, 13.4 Hz, 1H). | Rt = 2.00 min. m/z 380.0 [M + H]$^+$ (Method 1) |

| Ex | Structure/Name | Intermediate 1E/Amine | 1H NMR | LC-MS |
|---|---|---|---|---|
| 106 | 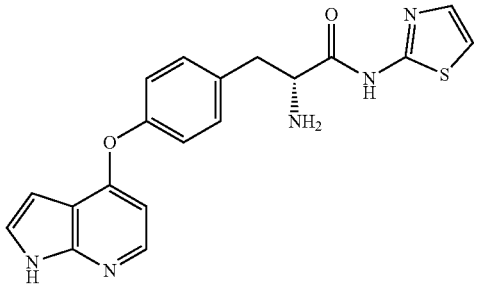<br>(ee % = 83%)<br>(R)-3-(4-((1H-pyrrolo[2,3-b]pyridin-4-yl)oxy)phenyl)-2-amino-N-(thiazol-2-yl)propanamide | 1E-g/2-amino-thiazole | $^1$H NMR (400 MHz, d6-DMSO) δ 11.69 (s, 1H), 8.04 (d, J = 5.4 Hz, 1H), 7.48 (d, J = 3.5 Hz, 1H), 7.30 (d, J = 8.2 Hz, 3H), 7.21 (d, J = 3.5 Hz, 1H), 7.07 (d, J = 8.4 Hz, 2H), 6.33 (d, J = 5.4 Hz, 1H), 6.14 (d, J = 1.7 Hz, 1H), 5.27-5.27 (m, 3H), 3.74 (m, 1H), 2.99 (dd, J = 5.8, 13.4 Hz, 1H), 2.79 (dd, J = 8.0, 13.2 Hz, 1H). | Rt = 2.00 min, m/z 380.1 [M + H]$^+$ (Method 1) |
| 107 | 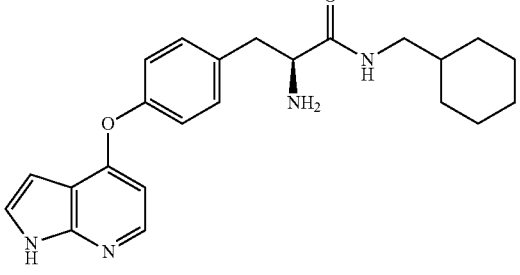<br>(S)-3-(4-((1H-pyrrolo[2,3-b]pyridin-4-yl)oxy)phenyl)-2-amino-N-(cyclohexylmethyl)propanamide | 1E-e/cyclo-hexyl-methanamine | $^1$H NMR (400 MHz, d6-DMSO) δ 11.71 (s, 1H), 8.06 (d, J = 5.4 Hz, 1H), 7.76 (t, J = 5.9 Hz, 1H), 7.34 (dd, J = 2.6, 3.3 Hz, 1H), 7.27 (d, J = 8.5 Hz, 2H), 7.08 (d, J = 8.5 Hz, 2H), 6.38 (d, J = 5.4 Hz, 1H), 6.20 (dd, J = 2.0, 3.5 Hz, 1H), 3.39 (dd, J = 5.9, 7.5 Hz, 1H), 2.96-2.80 (m, 3H), 2.68 (dd, J = 7.4, 13.2 Hz, 1H), 1.78 (s, 2H), 1.67-1.53 (m, 5H), 1.38-1.28 (m, 1H), 1.21-1.05 (m, 3H), 0.84-0.74 (m, 2H). | Rt = 2.59 min, m/z 393.2 [M + H]$^+$ (Method 1) |
| 108 | 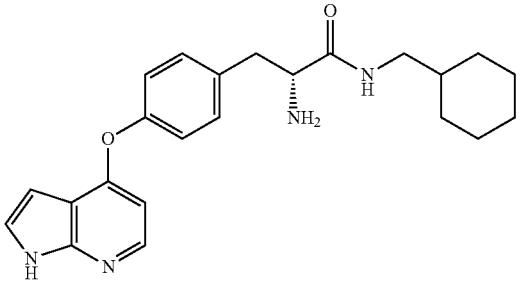<br>(ee % = 83%)<br>(R)-3-(4-((1H-pyrrolo[2,3-b]pyridin-4-yl)oxy)phenyl)-2-amino-N-(cyclohexylmethyl)propanamide | 1E-g/cyclo-hexyl-methanamine | $^1$H NMR (400 MHz, d6-DMSO) δ 11.71 (s, 1H), 8.06 (d, J = 5.4 Hz, 1H), 7.76 (t, J = 5.9 Hz, 1H), 7.34 (dd, J = 2.5, 3.4 Hz, 1H), 7.27 (d, J = 8.6 Hz, 2H), 7.08 (d, J = 8.5 Hz, 2H), 6.38 (d, J = 5.4 Hz, 1H), 6.20 (dd, J = 1.9, 3.5 Hz, 1H), 3.39 (dd, J = 6.0, 7.3 Hz, 1H), 2.96-2.80 (m, 3H), 2.72-2.65 (m, 1H), 1.72 (s, 2H), 1.67-1.55 (m, 5H), 1.37-1.28 (m, 1H), 1.16-1.08 (m, 3H), 0.80 (q, J = 11.4 Hz, 2H). | Rt = 2.55 min, m/z 393.2 [M + H]$^+$ (Method 3) |
| 109 | 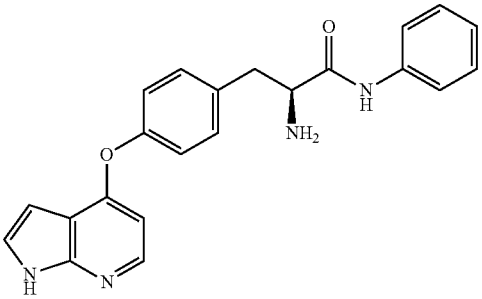<br>(ee % = 85%)<br>(S)-3-(4-((1H-pyrrolo[2,3-b]pyridin-4-yl)oxy)phenyl)-2-amino-N-phenylpropanamide | 1E-e/aniline | $^1$H NMR (400 MHz, d6-DMSO) δ 11.69 (s, 1H), 9.81 (s, 1H), 8.03 (d, J = 5.4 Hz, 1H), 7.60 (dd, J = 1.1, 8.6 Hz, 2H), 7.34-7.26 (m, 5H), 7.11-7.02 (m, 3H), 6.33 (d, J = 5.4 Hz, 1H), 6.15 (dd, J = 2.0, 3.5 Hz, 1H), 3.59 (dd, J = 5.8, 7.7 Hz, 1H), 3.00 (dd, J = 5.7, 13.4 Hz, 1H), 2.79 (dd, J = 7.9, 13.4 Hz, 1H), 1.98-1.98 (m, 2H). | Rt = 2.25 min, m/z 373.2 [M + H]$^+$ (Method 1) |

-continued

| Ex | Structure/Name | Intermediate 1E/Amine | 1H NMR | LC-MS |
|---|---|---|---|---|
| 110 | (ee % = 82%)<br>(R)-3-(4-((1H-pyrrolo[2,3-b]pyridin-4-yl)oxy)phenyl)-2-amino-N-phenylpropanamide | 1E-g/aniline | $^1$H NMR (400 MHz, d6-DMSO) δ 11.69 (s, 1H), 9.82 (s, 1H), 8.03 (d, J = 5.4 Hz, 1H), 7.61-7.59 (m, 2H), 7.34-7.26 (m, 5H), 7.11-7.01 (m, 3H), 6.33 (d, J = 5.4 Hz, 1H), 6.15 (dd, J = 1.9, 3.5 Hz, 1H), 3.59 (dd, J = 6.0, 7.5 Hz, 1H), 3.00 (dd, J = 5.7, 13.3 Hz, 1H), 2.79 (dd, J = 7.8, 13.3 Hz, 1H), 1.94 (s, 2H). | Rt = 2.22 min, m/z 373.2 [M + H]$^+$ (Method 3) |
| 111 | (S)-3-(4-((1H-pyrrolo[2,3-b]pyridin-4-yl)oxy)phenyl)-2-amino-N-cyclohexylpropanamide | 1E-e/cyclohexanamine | $^1$H NMR (400 MHz, d6-DMSO) δ 11.71 (s, 1H), 8.05 (d, J = 5.4 Hz, 1H), 7.58 (d, J = 8.1 Hz, 1H), 7.34 (dd, J = 2.5, 3.4 Hz, 1H), 7.27 (d, J = 8.6 Hz, 2H), 7.08 (d, J = 8.5 Hz, 2H), 6.37 (d, J = 5.4 Hz, 1H), 6.21 (dd, J = 2.0, 3.5 Hz, 1H), 3.55-3.46 (m, 1H), 3.36 (dd, J = 6.1, 7.3 Hz, 1H), 2.86 (dd, J = 5.9, 13.3 Hz, 1H), 2.69 (dd, J = 7.4, 13.4 Hz, 1H), 1.76 (s, 2H), 1.72-1.61 (m, 4H), 1.29-1.02 (m, 6H). | Rt = 2.38 min, m/z 379.2 [M + H]$^+$ (Method 1) |
| 112 | (ee % = 84%)<br>(R)-3-(4-((1H-pyrrolo[2,3-b]pyridin-4-yl)oxy)phenyl)-2-amino-N-cyclohexylpropanamide | 1E-g/cyclohexanamine | $^1$H NMR (400 MHz, d6-DMSO) δ 11.71 (s, 1H), 8.05 (d, J = 5.4 Hz, 1H), 7.57 (d, J = 8.1 Hz, 1H), 7.34 (dd, J = 2.5, 3.3 Hz, 1H), 7.27 (d, J = 8.4 Hz, 2H), 7.08 (d, J = 8.7 Hz, 2H), 6.37 (d, J = 5.4 Hz, 1H), 6.21 (dd, J = 1.9, 3.5 Hz, 1H), 3.56-3.46 (m, 1H), 3.40-3.34 (m, 1H), 2.86 (dd, J = 5.9, 13.2 Hz, 1H), 2.71-2.65 (m, 1H), 1.75-1.58 (m, 6H), 1.57-1.49 (m, 1H), 1.29-1.02 (m, 5H). | Rt = 2.34 min, m/z 379.2 [M + H]$^+$ (Method 3) |
| 113 | 3-(4-((1H-pyrrolo[2,3-b]pyridin-4-yl)oxy)phenyl)-2-amino-N,N-dimethylpropanamide | 1E-f/dimethylamine | $^1$H NMR (400 MHz, d6-DMSO) δ 11.72 (s, 1H), 8.08 (d, J = 5.4 Hz, 1H), 7.35 (dd, J = 2.4, 3.3 Hz, 1H), 7.28 (d, J = 8.7 Hz, 2H), 7.10 (d, J = 8.6 Hz, 2H), 6.39 (d, J = 5.4 Hz, 1H), 6.17 (dd, J = 1.7, 3.4 Hz, 1H), 4.01 (t, J = 6.9 Hz, 1H), 3.83-3.65 (s, 2H), 2.86-2.79 (m, 1H), 2.84 (s, 3H), 2.80 (s, 3H), 2.76-2.69 (m, 1H). | Rt = 1.77 min, m/z 325.1 [M + H]$^+$ (Method 3) |

| Ex | Structure/Name | Intermediate 1E/Amine | 1H NMR | LC-MS |
|---|---|---|---|---|
| 114 | 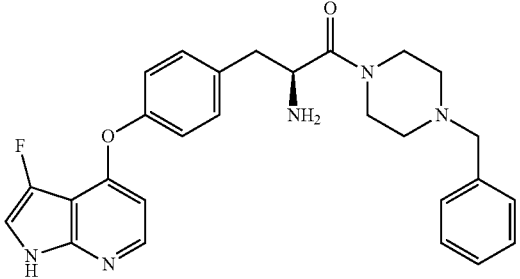<br>(ee % n.d.)<br>(S)-2-amino-1-(4-benzylpiperazin-1-yl)-3-(4-((3-fluoro-1H-pyrrolo[2,3-b]pyridin-4-yl)oxy)phenyl)propan-1-one | 1E-h/1-benzyl-piperazine | $^1$H NMR (400 MHz, d6-DMSO) δ 11.54 (s, 1H), 8.06 (d, J = 5.5 Hz, 1H), 7.36-7.24 (m, 8H), 7.12 (d, J = 8.6 Hz, 2H), 6.29 (d, J = 5.4 Hz, 1H), 3.91 (dd, J = 6.9, 6.9 Hz, 1H), 3.45-3.37 (m, 5H), 3.34-3.21 (m, 2H), 2.81-2.64 (m, 2H), 2.34-2.29 (m, 2H), 2.22-2.18 (m, 1H), 2.00 (d, J = 7.7 Hz, 1H), 1.24 (s, 1H). | Rt = 2.16 min, m/z 474.0 [M + H]$^+$ (Method 1) |
| 115 | 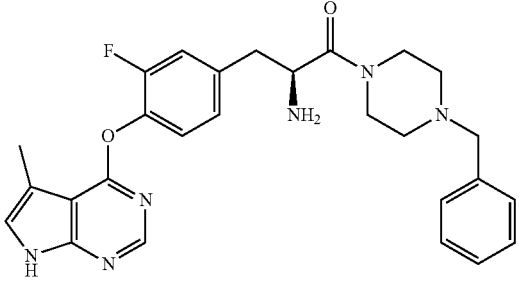<br>(ee % = 87%)<br>(S)-2-amino-1-(4-benzylpiperazin-1-yl)-3-(3-fluoro-4-((5-methyl-7H-pyrrolo[2,3-d]pyrimidin-4-yl)oxy)phenyl)propan-1-one | 1E-i/1-benzyl-piperazine | $^1$H NMR (400 MHz, d6-DMSO) δ 11.90 (s, 1H), 8.19 (s, 1H), 7.33-7.21 (m, 8H), 7.09 (dd, J = 1.4, 8.3 Hz, 1H), 3.93 (t, J = 6.9 Hz, 1H), 3.53-3.37 (m, 6H), 2.79 (dd, J = 6.4, 13.2 Hz, 1H), 2.68 (dd, J = 7.3, 13.1 Hz, 1H), 2.43 (d, J = 1.1 Hz, 3H), 2.36-2.27 (m, 2H), 2.27-2.19 (m, 1H), 2.09-2.03 (m, 1H), 1.70 (s, 2H). | Rt = 2.45 min, m/z 489.3 [M + H]$^+$ (Method 1) |
| 116 | 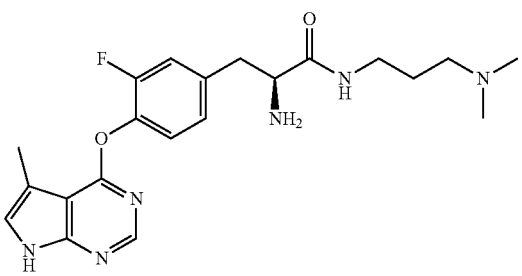<br>(S)-2-amino-N-(3-(dimethylamino)propyl)-3-(3-fluoro-4-((5-methyl-7H-pyrrolo[2,3-d]pyrimidin-4-yl)oxy)phenyl)propanamide | 1E-i/N,N-dimethyl-propoane-1,3-diamine | $^1$H NMR (400 MHz, DMSO) δ 11.90 (s, 1H), 8.20 (s, 1H), 7.88 (t, J = 5.7 Hz, 1H), 7.33-7.19 (m, 3H), 7.10-7.06 (m, 1H), 3.43-3.36 (m, 2H), 3.13-2.99 (m, 3H), 2.92 (dd, J = 5.5, 13.4 Hz, 1H), 2.69 (dd, J = 7.9, 13.4 Hz, 1H), 2.41 (d, J = 1.0 Hz, 3H), 2.16-2.09 (m, 2H), 2.08 (s, 6H), 1.52-1.43 (m, 2H). | Rt = 2.02 min, m/z 415.1 [M + H]$^+$ (Method 1) |

| Ex | Structure/Name | Intermediate 1E/Amine | 1H NMR | LC-MS |
|---|---|---|---|---|
| 117 | 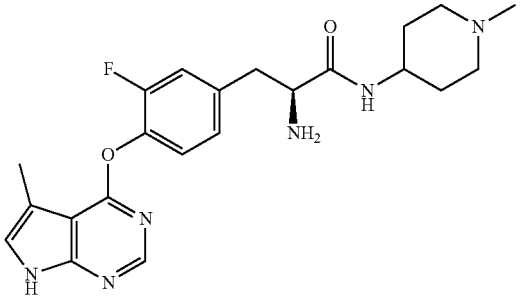<br>(ee % = 81%)<br>(S)-2-amino-3-(3-fluoro-4-((5-methyl-7H-pyrrolo[2,3-d]pyrimidin-4-yl)oxy)phenyl)-N-(1-methylpiperidin-4-yl)propanamide | 1E-i/1-methyl-piperidin-4-amine | $^1$H NMR (400 MHz, DMSO) δ 11.90 (s, 1H), 8.19 (s, 1H), 7.68 (d, J = 7.8 Hz, 1H), 7.30 (t, J = 8.2 Hz, 1H), 7.26-7.18 (m, 2H), 7.10-7.06 (m, 1H), 3.54-3.44 (m, 1H), 3.39 (dd, J = 5.7, 7.7 Hz, 1H), 2.89 (dd, J = 5.5, 13.4 Hz, 1H), 2.72-2.58 (m, 3H), 2.42 (d, J = 1.0 Hz, 3H), 2.13 (s, 3H), 1.97-1.86 (m, 2H), 1.70-1.60 (m, 2H), 1.45-1.31 (m, 2H). | Rt = 2.01 min, m/z 427.1 [M + H]$^+$ (Method 1) |
| 118 | 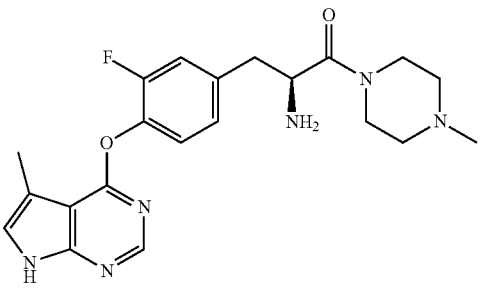<br>(ee % = 66%)<br>(S)-2-amino-3-(3-fluoro-4-((5-methyl-7H-pyrrolo[2,3-d]pyrimidin-4-yl)oxy)phenyl)-1-(4-methylpiperazin-1-yl)propan-1-one | 1E-i/1-methyl-piperazine | $^1$H NMR (400 MHz, DMSO) δ 11.90 (s, 1H), 8.20 (s, 1H), 7.31 (t, J = 8.2 Hz, 1H), 7.27-7.19 (m, 2H), 7.11-7.06 (m, 1H), 3.95 (t, J = 6.9 Hz, 1H), 3.45-3.16 (m, 6H), 2.80 (dd, J = 6.5, 13.2 Hz, 1H), 2.68 (dd, J = 7.3, 13.1 Hz, 1H), 2.41 (s, 3H), 2.33-2.26 (m, 2H), 2.13 (s, 3H), 2.07-1.97 (m, 1H), 1.73 (s, 1H). | Rt = 1.97 min, m/z 413.1 [M + H]$^+$ (Method 1) |
| 119 | 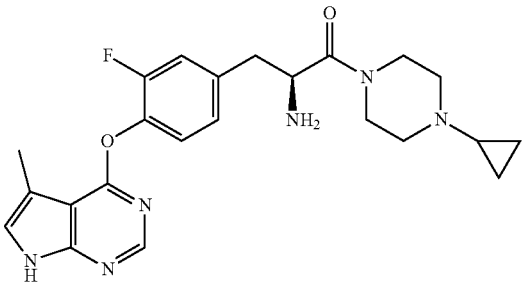<br>(ee % = 26%)<br>(S)-2-amino-1-(4-cyclopropylpiperazin-1-yl)-3-(3-fluoro-4-((5-methyl-7H-pyrrolo[2,3-d]pyrimidin-4-yl)oxy)phenyl)propan-1-one | 1E-i/1-cyclopropyl-piperazine | $^1$H NMR (400 MHz, DMSO) δ 11.89 (s, 1H), 8.18 (s, 1H), 7.31 (t, J = 8.2 Hz, 1H), 7.27-7.20 (m, 2H), 7.09 (dd, J = 1.4, 8.2 Hz, 1H), 3.95 (t, J = 6.9 Hz, 1H), 3.60-3.15 (m, 4H), 2.80 (dd, J = 6.6, 13.1 Hz, 1H), 2.69 (dd, J = 7.1, 13.1 Hz, 1H), 2.48-2.44 (m, 2H), 2.40 (d, J = 1.0 Hz, 3H), 2.38-2.33 (m, 1H), 2.21 (dd, J = 3.8, 7.1 Hz, 1H), 1.74 (s, 2H), 1.59-1.52 (m, 1H), 0.46-0.37 (m, 2H), 0.34-0.28 (m, 2H). | Rt = 2.19 min, m/z 439.1 [M + H]$^+$ (Method 1) |

| Ex | Structure/Name | Intermediate 1E/Amine | 1H NMR | LC-MS |
|---|---|---|---|---|
| 120 | 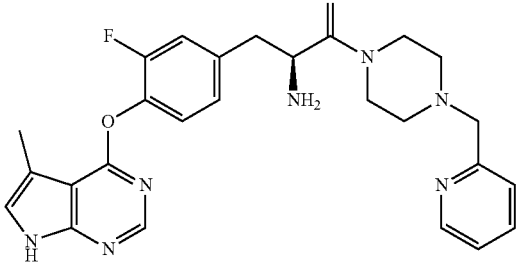<br>(ee % = 64%)<br>(S)-2-amino-3-(3-fluoro-4-((5-methyl-7H-pyrrolo[2,3-d]pyrimidin-4-yl)oxy)phenyl)-1-(4-(pyridin-2-ylmethyl)piperazin-1-yl)propan-1-one | 1E-i/1-(pyridin-2-ylmethyl)piperazine | $^1$H NMR (400 MHz, DMSO) δ 11.90 (s, 1H), 8.49 (dd, J = 0.9, 3.9 Hz, 1H), 8.20 (s, 1H), 7.76 (dt, J = 1.8, 7.7 Hz, 1H), 7.43 (d, J = 7.8 Hz, 1H), 7.33-7.22 (m, 4H), 7.09 (dd, J = 1.4, 8.2 Hz, 1H), 3.97-3.91 (m, 1H), 3.57 (s, 2H), 3.48-3.42 (m, 4H), 2.80 (dd, J = 6.5, 13.2 Hz, 1H), 2.67 (dd, J = 7.4, 13.2 Hz, 1H), 2.42 (d, J = 1.0 Hz, 3H), 2.41-2.24 (m, 3H), 2.19-2.15 (m, 1H), 1.72 (s, 2H). | Rt = 2.24 min, m/z 490.4 [M + H]$^+$ (Method 1) |
| 121 | 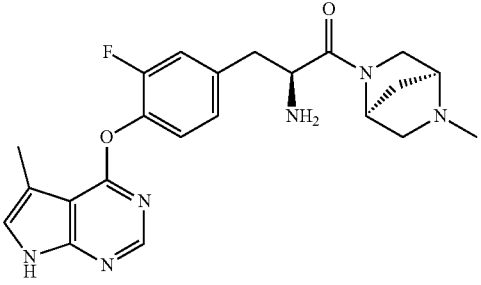<br>(ee % = 69%)<br>2-amino-3-(3-fluoro-4-((5-methyl-7H-pyrrolo[2,3-d]pyrimidin-4-yl)oxy)phenyl)-1-((1S,4S)-5-methyl-2,5-diazabicyclo[2.2.1]heptan-2-yl)propan-1-one | 1E-i/(1S,4S)-2-methyl-2,5-diaza-bicyclo[2.2.1]-heptane | $^1$H NMR (400 MHz, DMSO) δ 11.90 (s, 1H), 8.19-8.17 (m, 1H), 7.33-7.22 (m, 3H), 7.14-7.08 (m, 1H), 4.51 & 4.27 (2xs, 1H), 3.84-3.47 (m, 3H), 3.18-3.08 (m, 1H), 3.02-2.95 (m, 1H), 2.83-2.67 (m, 4H), 2.43-2.39 (m, 3H), 2.31-2.27 (m, 2H), 2.17-2.02 (m, 2H), 1.76-1.67 (m, 1H), 1.52 & 1.36 (2xd, J = 9.6 Hz, 1H). | Rt = 1.97 min, m/z 425.3 [M + H]$^+$ (Method 3) |
| 122 | 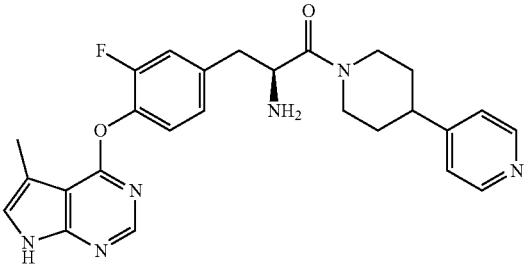<br>(ee % - 65%)<br>(S)-2-amino-3-(3-fluoro-4-((5-methyl-7H-pyrrolo[2,3-d]pyrimidin-4-yl)oxy)phenyl)-1-(4-(pyridin-4-yl)piperidin-1-yl)propan-1-one | 1E-i/4-(piperidin-4-yl)pyridine | $^1$H NMR (400 MHz, DMSO) d 11.91 (s, 1H), 8.47 (d, J = 5.7 Hz, 1H), 8.37 (d, J = 5.7 Hz, 1H), 8.20 & 8.09 (2xs, 1H), 7.36-7.22 (m, 5H), 7.18-7.11 (m, 2H), 4.59-4.53 (m, 1H), 4.11-3.97 (m, 2H), 3.08 & 2.96 (2xt, J=12.7 Hz, 1H), 2.89-2.82 (m, 1H), 2.78-2.70 (m, 1H), 2.68-2.51 (m, 1H), 2.40 (2xs, 3H), 1.87-1.69 (m,4H), 1.68-1.57 & 1.52-1.41 (m, 1H), 1.33-1.23 & 1.09-0.98 (m, 1H). | Rt = 2.24 min, m/z 475.3 [M + H]$^+$ (Method 3) |

| Ex | Structure/Name | Intermediate 1E/Amine | 1H NMR | LC-MS |
|---|---|---|---|---|
| 123 | 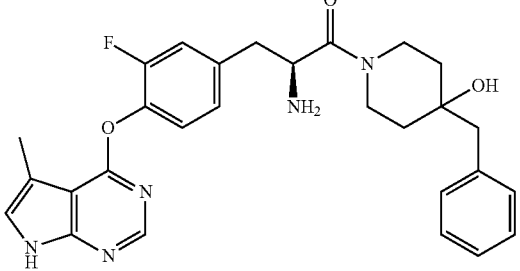<br>(ee % = 49%)<br>(S)-2-amino-1-(4-benzyl-4-hydroxypiperidin-1-yl)-3-(3-fluoro-4-((5-methyl-7H-pyrrolo[2,3-d]pyrimidin-4-yl)oxy)phenyl)propan-1-one | 1E-i/4-benzyl-piperidin-4-ol | $^1$H NMR (400 MHz, CDCl$_3$) δ 9.02 (s, 1H), 8.32 & 8.24 (s, 1H), 7.35-7.27 (m, 3H), 7.24-7.02 (m, 5H), 6.94 (d, J = 10.3 Hz, 1H), 4.47-4.43 & 4.30-4.26 (m, 1H), 4.04-3.95 (m, 1H), 3.57-3.52 (m, 1H), 3.38-2.78 (m, 5H), 2.76 (s, 1H), 2.67 (s, 1H), 2.49 & 2.41 (2xs, 3H), 1.57-1.37 & 0.84-0.77 (m, 6H). | Rt = 3.06 min, m/z 504.2 [M + H]$^+$ (Method 1) |
| 124 | 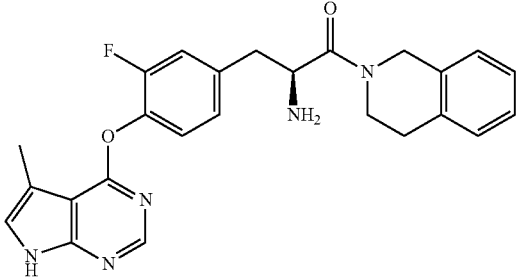<br>(ee % = 59%)<br>(S)-2-amino-1-(3,4-dihydroisoquinolin-2(1H)-yl)-3-(3-fluoro-4-((5-methyl-7H-pyrrolo[2,3-d]pyrimidin-4-yl)oxy)phenyl)propan-1-one | 1E-i/1,2,3,4-tetrahydro-isoquinoline | $^1$H NMR (400 MHz, DMSO) δ 11.89 (s, 1H), 8.11 (d, J = 16.1 Hz, 1H), 7.32-7.05 (m, 8H), 4.77-4.65 (m, 1H), 4.53 (d, J = 16.8 Hz, 1H), 4.07-3.99 (m, 1H), 3.80-3.57 (m, 2H), 2.90-2.67 (m, 4H), 2.42 (d, J = 2.1 Hz, 3H), 1.82-1.82 (m, 2H). | Rt = 3.18 min, m/z 446.3 [M + H]$^+$ (Method 3) |
| 125 | 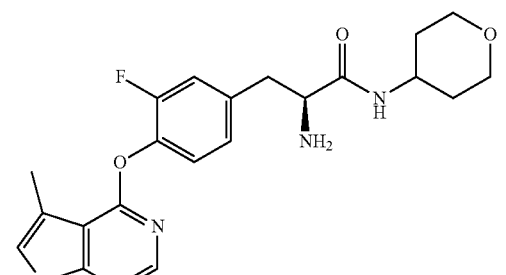<br>(ee % = 49 %)<br>(S)-2-amino-3-(3-fluoro-4-((5-methyl-7H-pyrrolo[2,3-d]pyrimidin-4-yl)oxy)phenyl)-N-(tetrahydro-2H-pyran-4-yl)propanamide | 1E-i/tetrahydro-2H-pyran-4-amine | $^1$H NMR (400 MHz, DMSO) δ 11.90 (s, 1H), 8.19 (s, 1H), 7.76 (d, J = 7.9 Hz, 1H), 7.30 (t, J = 8.3 Hz, 1H), 7.25-7.19 (m, 2H), 7.08 (dd, J = 1.5, 8.3 Hz, 1H), 3.84-3.69 (m, 3H), 3.42-3.33 (m, 3H), 2.90 (dd, J = 5.6, 13.2 Hz, 1H), 2.70 (dd, J = 7.9, 13.2 Hz, 1H), 2.41 (d, J = 0.9 Hz, 3H), 1.79 (s, 2H), 1.69-1.60 (m, 2H), 1.45-1.31 (m, 2H). | Rt = 2.64 min, m/z 414.3 [M + H]$^+$ (Method 3) |

| Ex | Structure/Name | Intermediate 1E/Amine | 1H NMR | LC-MS |
|---|---|---|---|---|
| 126 | 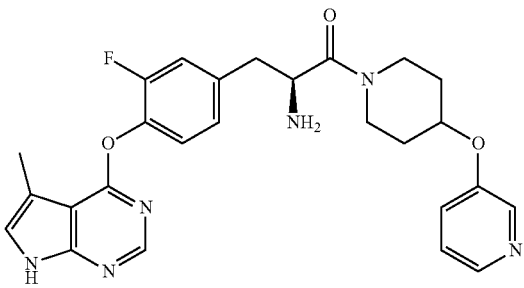<br>(ee % = 71%)<br>(S)-2-amino-3-(3-fluoro-4-((5-methyl-7H-pyrrolo[2,3-d]pyrimidin-4-yl)oxy)phenyl)-1-(4-(pyridin-3-yloxy)piperidin-1-yl)propan-1-one | 1E-i/3-(piperidin-4-yloxy)pyridine | $^1$H NMR (400 MHz, DMSO) δ 11.90 (s, 1H), 8.29 (dd, J = 2.8, 14.6 Hz, 1H), 8.20-8.15 (m, 2H), 7.46-7.41 (m, 1H), 7.34-7.22 (m, 4H), 7.11 (d, J = 8.2 Hz, 1H), 4.69-4.65 (m, 1H), 3.98 (t, J = 6.8 Hz, 1H), 3.91-3.87 (m, 1H), 3.84-3.65 (m, 1H), 3.43-3.19 (m, 3H), 2.84 (dd, J = 6.1, 13.0 Hz, 1H), 2.71-2.64 (m, 1H), 2.42 (s, 3H), 1.99-1.71 (m, 2H), 1.70-1.28 (m, 3H). | Rt = 2.53 min, m/z 491.4 [M + H]$^+$ (Method 3) |
| 127 | 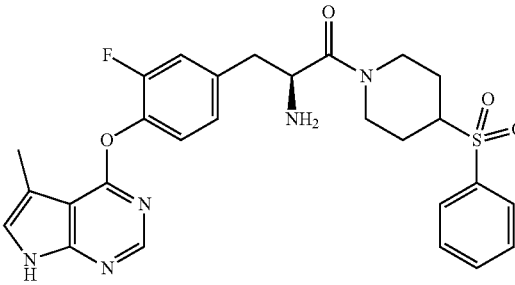<br>(S)-2-amino-3-(3-fluoro-4-((5-methyl-7H-pyrrolo[2,3-d]pyrimidin-4-yl)oxy)phenyl)-1-(4-(phenylsulfonyl)piperidin-1-yl)propan-1-one | 1E-i/4-(benzene-sulfonyl)piperidine | $^1$H NMR (400 MHz, DMSO) δ 11.90 (s, 1H), 8.24-8.16 (m, 1H), 7.87-7.65 (m, 5H), 7.30-7.22 (m, 3H), 7.11-7.03 (m, 1H), 4.55-4.41 (m, 1H), 4.12-4.00 (m, 1H), 3.95-3.90 (m, 1H), 3.58-3.51 (m, 1H), 3.05-2.83 (m, 1H), 2.80 (dd, J = 5.2, 13.3 Hz, 1H), 2.71-2.52 (m, 2H), 2.45-2.40 (m, 3H), 1.93-1.49 (m, 4H), 1.41-1.08 (m, 2H). | Rt = 3.02 min, m/z 538.1 [M + H]$^+$ (Method 1) |
| 128 | 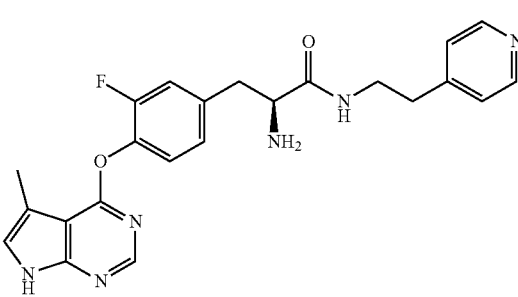<br>(S)-2-amino-3-(3-fluoro-4-((5-methyl-7H-pyrrolo[2,3-d]pyrimidin-4-yl)oxy)phenyl)-N-(2-(pyridin-4-yl)ethyl)propanamide | 1E-i/2-(pyridin-4-yl)ethan-1-amine | $^1$H NMR (400 MHz, DMSO) δ 11.90 (s, 1H), 8.45 (dd, J = 1.6, 4.4 Hz, 2H), 8.17 (s, 1H), 7.99 (t, J = 5.8 Hz, 1H), 7.30 (t, J = 8.2 Hz, 1H), 7.25-7.18 (m, 4H), 7.07 (dd, J = 1.4, 8.2 Hz, 1H), 3.42-3.36 (m, 3H), 2.90 (dd, J = 5.1, 13.4 Hz, 1H), 2.72 (t, J = 7.1 Hz, 2H), 2.64 (dd, J = 8.1, 13.4 Hz, 1H), 2.42 (d, J = 1.1 Hz, 3H), 1.77 (s, 2H). | Rt = 2.09 min, m/z 435.2 [M + H]$^+$ (Method 1) |
| 129 | 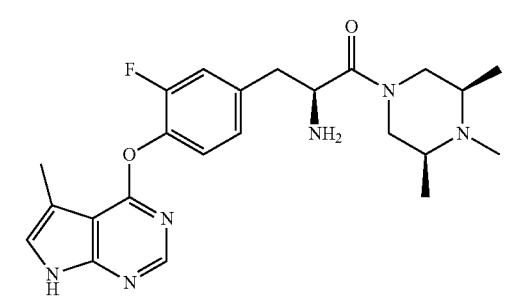<br>(S)-2-amino-3-(3-fluoro-4-((5-methyl-7H-pyrrolo[2,3-d]pyrimidin-4-yl)oxy)phenyl)-1-((3S,5R)-3,4,5-trimethylpiperazin-1-yl)propan-1-one | 1E-i/(2S,6R)-1,2,6-trimethyl-piperazine | $^1$H NMR (400 MHz, DMSO) δ 11.90 (s, 1H), 8.20 (d, J = 3.9 Hz, 1H), 7.34-7.26 (m, 1H), 7.26-7.21 (m, 2H), 7.08 (d, J = 8.1 Hz, 1H), 4.25-4.15 (m, 1H), 4.03-3.96 (m, 1H), 3.81-3.65 (m, 1H), 2.83-2.52 (m, 4H), 2.42-2.40 (m, 3H), 2.26 (dd, J = 11.1, 12.7 Hz, 1H), 2.14 (s, 1H), 2.08-2.05 (m, 3H), 2.00-1.68 (m, 2H), 1.03-0.92 (m, 6H). | Rt = 2.06 min, m/z 441.3 [M + H]$^+$ (Method 1) |

| Ex | Structure/Name | Intermediate 1E/Amine | 1H NMR | LC-MS |
|---|---|---|---|---|
| 130 | 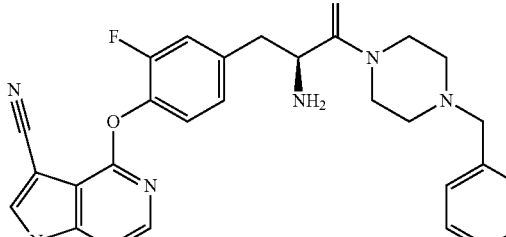<br>(S)-4-(4-(2-amino-3-(4-benzylpiperazin-1-yl)-3-oxopropyl)-2-fluorophenoxy)-7H-pyrrolo[2,3-d]pyrimidine-5-carbonitrile | 1E-j/1-benzyl-piperazine | $^1$H NMR (400 MHz, d6-DMSO) δ 8.43 (s, 1H), 8.37 (s, 1H), 7.40-7.20 (m, 8H), 7.11 (dd, J = 1.3, 8.3 Hz, 1H), 6.40-4.40 (s, 2H), 4.00 (t, J = 6.9 Hz, 1H), 3.39-3.34 (m, 6H), 2.82 (dd, J = 6.4, 13.3 Hz, 1H), 2.70 (dd, J = 7.4, 13.1 Hz, 1H), 2.37-2.27 (m, 2H), 2.27-2.18 (m, 1H), 2.15-2.07 (m, 1H). | Rt = 2.15 min, m/z 500.2 [M + H]$^+$ (Method 1) |

Example 131

Step A. 4-Bromo-1-tosyl-1H-pyrrolo[2,3-b]pyridine (Intermediate 131A-a)

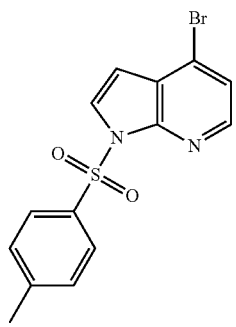 [SMILES: Cc1ccc(S(=O)(=O)n2ccc3c(Br)ccnc32)cc1]

4-Bromo-7-azaindole (5.0 g, 28.90 mmol) was dissolved in DMF (40 mL) and the solution was stirred at RT under a stream of nitrogen. Sodium hydride (60% on mineral oil, 1.50 g, 37.58 mmol) was added portion wise and the reaction was stirred for 30 min. A solution of 4-toluenesulfonyl chloride (5.77 g, 30.37 mmol) in DMF (10 mL) was added dropwise over 10 min, and then the reaction was stirred for a further 2 h. The reaction mixture was carefully poured into cold water (100 mL) and stirred for 30 min. The resulting precipitate was collected by filtration and dried in vacuo. the product was obtained as an off-white solid (9.12 g).

LCMS (Method 6): Rt=1.59 min, m/z 351.1/353.1 [M+H]$^+$

Step B. Methyl (S)-2-((tert-butoxycarbonyl)amino)-3-(4-((tert-butyldimethylsilyl)-oxy)phenyl)propanoate (Intermediate 131B)

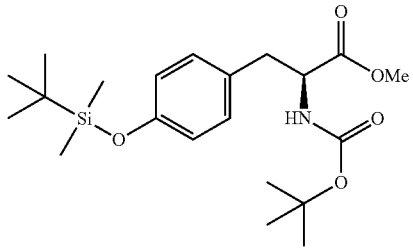 [SMILES: COC(=O)[C@H](Cc1ccc(O[Si](C)(C)C(C)(C)C)cc1)NC(=O)OC(C)(C)C]

A solution of Intermediate 1B-c (500 mg, 1.69 mmol), tert-butyldimethylsilyl chloride (306 mg, 2.03 mmol) and imidazole (288 mg, 5.25 mmol) in DMF (10 mL) was stirred at RT for 18 h. The reaction mixture was partitioned between ethyl acetate (15 mL) and water (15 mL) and the organic layer was separated, washed with water (2×10 mL), dried (Na$_2$SO$_4$) and evaporated to give the desired product as a colourless oil (769 mg).

LCMS (Method 6): Rt=1.89 min, m/z 432.4 [M+Na]$^+$

Step C. Methyl (S)-2-((tert-butoxycarbonyl)(methyl)amino)-3-(4-((tert-butyldimethylsilyl)oxy)phenyl)propanoate (Intermediate 131C)

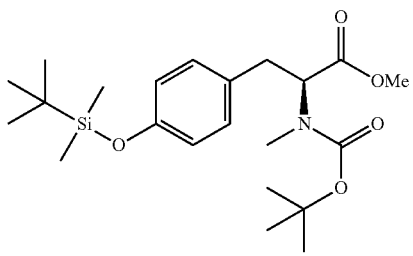 [SMILES: COC(=O)[C@H](Cc1ccc(O[Si](C)(C)C(C)(C)C)cc1)N(C)C(=O)OC(C)(C)C]

Sodium hydride (72 mg, 1.80 mmol) was added to a solution of Intermediate 131B (692 mg, 1.69 mmol) in a mixture of THF (10 mL) and DMF (1 mL). After stirring for 10 min, methyl iodide (316 mg, 5.08 mmol) was added and stirring was continued for 24 h. The reaction mixture was partitioned between ethyl acetate (5 mL) and water (5 mL) and the organic layer was separated, washed with water (2×10 mL), dried (Na$_2$SO$_4$) and evaporated. The product was purified on a Si cartridge (25 g) eluting with 0-25% ethyl acetate in cyclohexane to give the desired product as a yellow oil (436 mg).

LCMS (Method 6): Rt=1.95 min, m/z 424.3 [M+H]$^+$

Step D. Methyl N-(tert-butoxycarbonyl)-N-methyl-L-tyrosinate (Intermediate 131D)

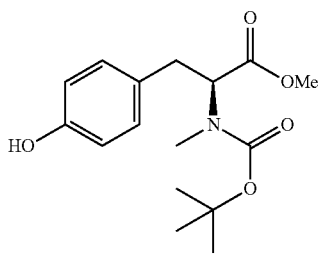 [SMILES: COC(=O)[C@H](Cc1ccc(O)cc1)N(C)C(=O)OC(C)(C)C]

A solution of Intermediate 131C (436 mg, 1.03 mmol) in a mixture of acetic acid (4.45 mL), THF (1.5 mL) and water (1.5 mL) was stirred at RT for 18 h and then at 40° C. for 18 h and at 75° C. for 18 h. The reaction mixture was concentrated in vacuo and the pH adjusted to pH10 by the careful addition of solid potassium carbonate. The product was extracted into ethyl acetate (15 mL) and the organic layer was dried (Na$_2$SO$_4$) and evaporated. The product was purified on a Si cartridge (25 g) eluting with 0-25% ethyl acetate in cyclohexane to give the desired product as a colourless oil which crystallized on standing (110 mg).

LCMS (Method 9): Rt=2.95 min, m/z 332.2 [M+Na]$^+$

Step E. Methyl (S)-2-((tert-butoxycarbonyl)(methyl)amino)-3-(4-((1-tosyl-1H-pyrrolo[2,3-b]pyridin-4-yl)oxy)phenyl)propanoate (Intermediate 131E-a)

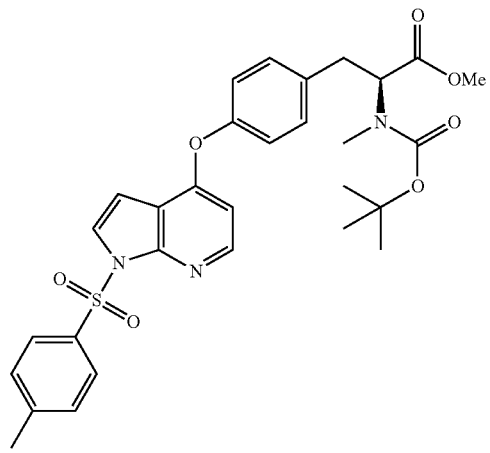 [SMILES: COC(=O)[C@H](Cc1ccc(Oc2ccnc3c2ccn3S(=O)(=O)c2ccc(C)cc2)cc1)N(C)C(=O)OC(C)(C)C]

Intermediate 131E-a was prepared from Intermediate 131A-a and Intermediate 131D using a similar procedure to that used in Step D of Example 1.

LCMS (Method 9): Rt=4.18 min, m/z 580.1 [M+H]$^+$

Step F. (S)-2-((tert-Butoxycarbonyl)(methyl)amino)-3-(4-((1-tosyl-1H-pyrrolo[2,3-b]pyridin-4-yl)oxy)phenyl)propanoic acid (Intermediate 131F-a)

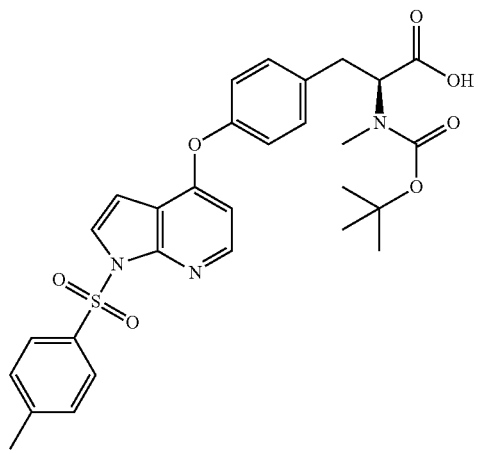 [SMILES: Cc1ccc(S(=O)(=O)n2ccc3c(Oc4ccc(C[C@@H](C(=O)O)N(C)C(=O)OC(C)(C)C)cc4)ccnc32)cc1]

Intermediate 131F-a was prepared from Intermediate 131E-a using a similar procedure to that used in Step E of Example 1.

LCMS (Method 9): Rt=3.77 min, m/z 566.1 [M+H]$^+$

Step G. tert-Butyl (S)-(1-(cyclohexylamino)-1-oxo-3-(4-((1-tosyl-1H-pyrrolo[2,3-b]pyridin-4-yl)oxy)phenyl)propan-2-yl)(methyl)carbamate (Intermediate 131G-a)

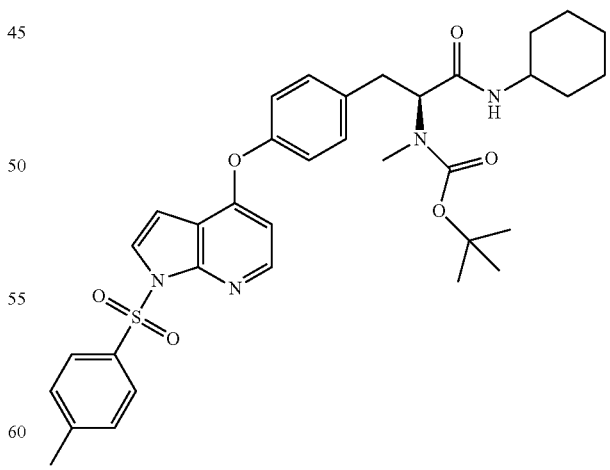

Intermediate 131G-a was prepared from Intermediate 131F-a and cyclohexylmethanamine using a similar procedure to that used in Step F of Example 1.

LCMS (Method 9): Rt=4.39 min, m/z 647.2 [M+H]$^+$

Step H. (S)-3-(4-((1H-pyrrolo[2,3-b]pyridin-4-yl)oxy)phenyl)-N-cyclohexyl-2-(methylamino)propanamide (Example 131)

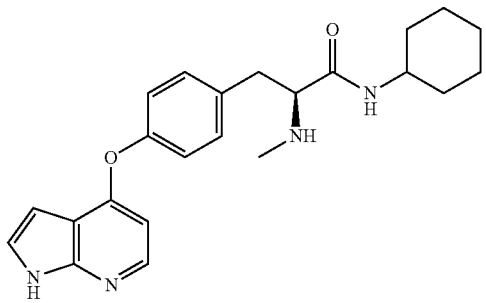 [SMILES: CN[C@@H](Cc1ccc(Oc2ccnc3[nH]ccc23)cc1)C(=O)NC1CCCCC1]

Intermediate 131G-a (118 mg, 0.182 mmol) was dissolved in a mixture of DCM (4 mL) and TFA (4 mL) and the solution was stirred at RT for 1 h. The mixture was poured onto an SCX-2 cartridge (10 g). After flushing with methanol, the product was eluted with 2M methanolic ammonia and the volatiles were evaporated. The residue was dissolved in dioxane (4 mL) and 4M sodium hydroxide (4 mL) was added. The mixture was stirred at 80° C. for 4 h. The reaction mixture was diluted with DCM/IPA (10:1) (10 mL) and washed with brine. The aqueous was extracted further with DCM (3×10 mL) and the combined extracts were dried (Na$_2$SO$_4$) and evaporated. The product was purified by HPLC eluting with a gradient of 0-80% acetonitrile in water (0.1% NH$_4$OH added) to give a white solid (27 mg).

Rt=2.47 min, m/z 393.3 [M+H]$^+$ (Method 1)

$^1$H NMR (400 MHz, d6-DMSO) δ 11.72 (s, 1H), 8.05 (d, J=5.4 Hz, 1H), 7.58 (d, J=8.1 Hz, 1H), 7.34 (dd, J=2.6, 3.3 Hz, 1H), 7.25 (d, J=8.6 Hz, 2H), 7.06 (d, J=8.6 Hz, 2H), 6.36 (d, J=5.4 Hz, 1H), 6.21 (dd, J=1.9, 3.5 Hz, 1H), 3.57-3.47 (m, 1H), 3.10 (t, J=6.9 Hz, 1H), 2.76 (d, J=6.9 Hz, 2H), 2.18 (s, 3H), 1.87 (s, 1H), 1.69-1.48 (m, 4H), 1.29-0.99 (m, 6H).

ee %=38%

Examples 132 to 144

The following Examples were prepared in a similar way to Example 131 by replacing at each step the suitable starting materials.

Preparation of Intermediate 131A-b

The following intermediate was prepared in a similar manner to Intermediate 131A-a from the indicated starting material.

| Intermediate | Structure | Starting materials | LC-MS |
|---|---|---|---|
| 131A-b | 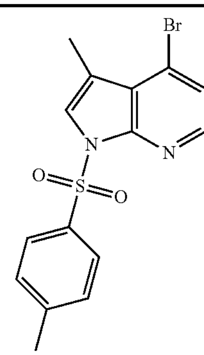 | 4-Bromo-3-methyl-7-azaindole | Rt = 1.71 min, m/z 365.0/367.0 [M + H]$^+$ (Method 6) |

Preparation of Intermediates from 131E-b to 131E-e

The following intermediates were prepared in a similar manner to Intermediate 131E-a from the indicated starting materials according to the method used in Step D of Example 1.

| Intermediate | Structure | Starting materials | LC-MS |
|---|---|---|---|
| 131E-b | 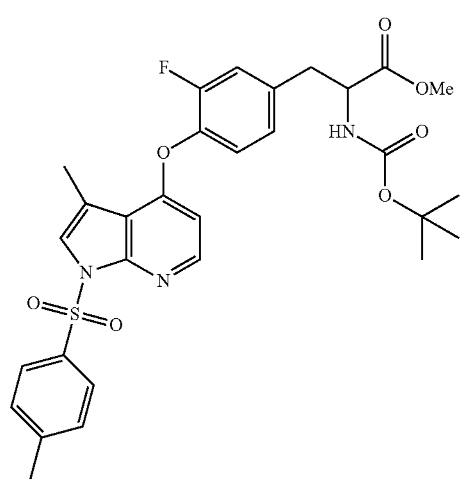 [SMILES: COC(=O)C(Cc1ccc(Oc2ccnc3c2c(C)cn3S(=O)(=O)c2ccc(C)cc2)c(F)c1)NC(=O)OC(C)(C)C] | 131A-b and 1B-b | Rt = 1.74 min, m/z 598.2 [M+ H]$^+$ (Method 6) |

| Intermediate | Structure | Starting materials | LC-MS |
|---|---|---|---|
| 131E-c | 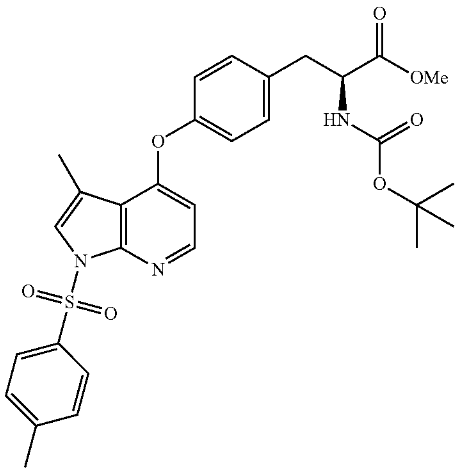 [SMILES: COC(=O)[C@H](Cc1ccc(Oc2ccnc3c2c(C)cn3S(=O)(=O)c2ccc(C)cc2)cc1)NC(=O)OC(C)(C)C] | 131A-b and 1B-c | Rt = 1.79 min, m/z 580.2 [M + H]+ (Method 6) |
| 131E-d | 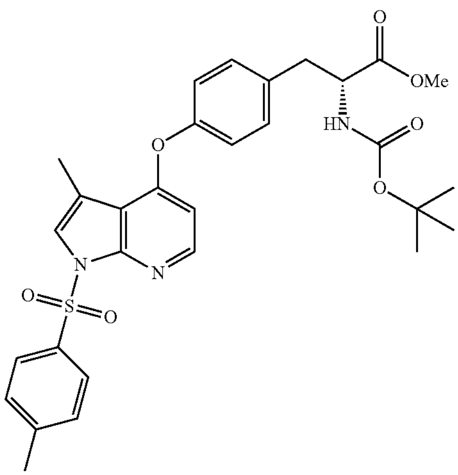 [SMILES: COC(=O)[C@@H](Cc1ccc(Oc2ccnc3c2c(C)cn3S(=O)(=O)c2ccc(C)cc2)cc1)NC(=O)OC(C)(C)C] | 131A-b and 1B-d | Rt = 1.79 min, m/z 580.2 [M + H]+ (Method 6) |
| 131E-e | 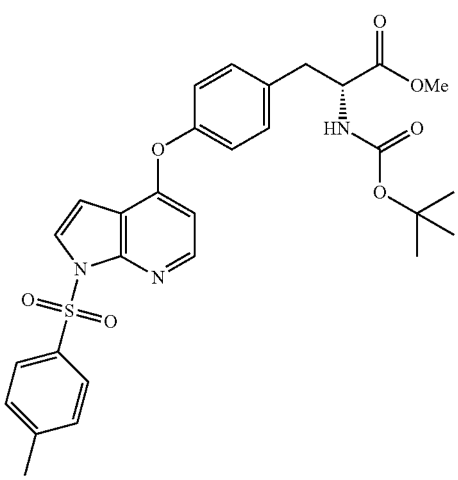 [SMILES: COC(=O)[C@@H](Cc1ccc(Oc2ccnc3c2ccn3S(=O)(=O)c2ccc(C)cc2)cc1)NC(=O)OC(C)(C)C] | 131A-a and 1B-d | Rt = 4.03 min, m/z 566.1 [M + H]+ (Method 9) |

Preparation of Intermediates from 131F-b to 131F-e

The following intermediates were prepared from the indicated starting materials according to the method used in Step E of Example 1.

| Intermediate | Structure | Starting materials | LC-MS |
| --- | --- | --- | --- |
| 131F-b | 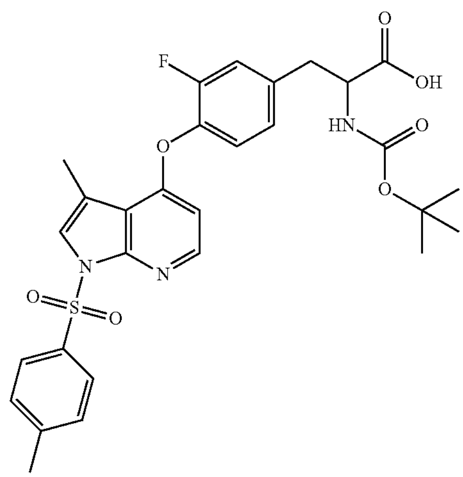 [SMILES: Cc1ccc(S(=O)(=O)n2cc(C)c3c(Oc4ccc(CC(NC(=O)OC(C)(C)C)C(=O)O)cc4F)ccnc32)cc1] | 131E-b | Rt = 1.71 min, m/z 584.2 [M + H]+ (Method 6) |
| 131F-c | 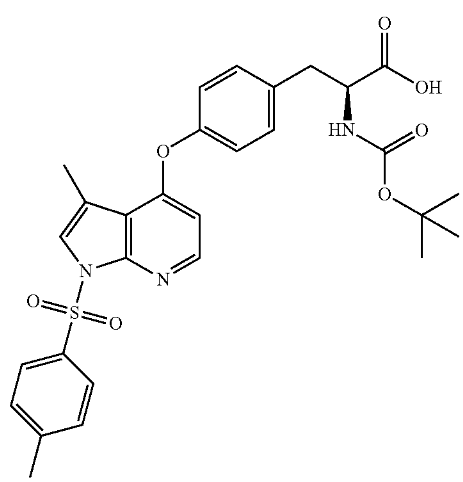 [SMILES: Cc1ccc(S(=O)(=O)n2cc(C)c3c(Oc4ccc(C[C@H](NC(=O)OC(C)(C)C)C(=O)O)cc4)ccnc32)cc1] | 131E-c | Rt = 1.69 min, m/z 566.2 [M + H]+ (Method 6) |
| 131F-d | 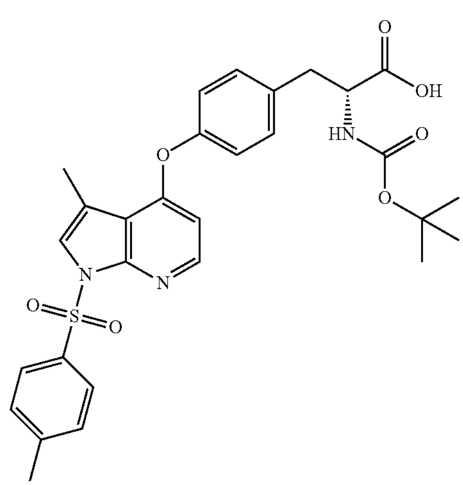 [SMILES: Cc1ccc(S(=O)(=O)n2cc(C)c3c(Oc4ccc(C[C@@H](NC(=O)OC(C)(C)C)C(=O)O)cc4)ccnc32)cc1] | 131E-d | Rt = 1.68 min, m/z 566.2 [M + H]+ (Method 6) |

-continued

| Intermediate | Structure | Starting materials | LC-MS |
|---|---|---|---|
| 131F-e | [structure] | 131E-e | Rt = 3.68 min, m/z 552.1 [M + H]⁺ (Method 9) |

Preparation of Examples

The following examples were prepared using the same synthetic sequence as for Example 131, by replacing in Step G the indicated Intermediate 131F and an amine.

| Ex | Structure | Intermediate 131F/ Amine | 1H NMR | LC-MS |
|---|---|---|---|---|
| 132 | [structure] 2-amino-1-(4-benzylpiperazin-1-yl)-3-(3-fluoro-4-((3-methyl-1H-pyrrolo[2,3-b]pyridin-4-yl)oxy)phenyl)propan-1-one | 131F-b/1-benzyl-piperazine | $^1$H NMR (400 MHz, d6-DMSO) δ 11.41 (s, 1H), 7.98 (d, J = 5.4 Hz, 1H), 7.34-7.22 (m, 7H), 7.16-7.13 (m, 1H), 7.10 (dd, J = 1.4, 8.2 Hz, 1H), 6.16 (d, J = 5.4 Hz, 1H), 3.96-3.91 (m, 1H), 3.54-3.46 (m, 1H), 3.43 (s, 2H), 3.42-3.29 (m, 3H), 2.79 (dd, J = 6.5, 13.1 Hz, 1H), 2.68 (dd, J = 7.0, 13.3 Hz, 1H), 2.39 (d, J = 1.0 Hz, 3H), 2.38-2.30 (m, 2H), 2.21-2.12 (m, 1H), 2.05-1.96 (m, 1H), 1.77-1.76 (m, 2H). | Rt = 2.11 min, m/z 488.4 [M + H]⁺ (Method 1) |
| 133 | [structure] 1-(4-acetylpiperazin-1-yl)-2-amino-3-(3-fluoro-4-((3-methyl-1H-pyrrolo[2,3-b]pyridin-4-yl)oxy)phenyl)propan-1-one | 131F-b/1-(piperazin-1-yl)ethan-1-one | $^1$H NMR (400 MHz, d6-DMSO) δ 11.40 (s, 1H), 7.96 (d, J = 5.4 Hz, 1H), 7.34 (dd, J = 1.7, 11.9 Hz, 1H), 7.27-7.20 (m, 1H), 7.15-7.10 (m, 2H), 6.14-6.09 (m, 1H), 3.98-3.93 (m, 1H), 3.50-3.37 (m, 6H), 3.21-3.17(m, 1H), 2.83 (dd, J = 6.1, 13.3 Hz, 1H), 2.69 (dd, J = 7.5, 13.2 Hz, 1H), 2.61-2.51 (m, 1H), 2.37 (d, J = 0.9 Hz, 3H), 2.01 (s, 3H), 1.77-1.77 (m, 2H). | Rt = 2.07 min, m/z 440.3 [M + H]⁺ (Method 1) |

| Ex | Structure | Intermediate 131F/Amine | 1H NMR | LC-MS |
|---|---|---|---|---|
| 134 | (S)-2-amino-N-cyclohexyl-N-methyl-3-(4-((3-methyl-1H-pyrrolo[2,3-b]pyridin-4-yl)oxy)phenyl)propanamide | 131F-c/N-methylcyclohexan-amine | $^1$H NMR (400 MHz, d6-DMSO) δ 11.36 (s, 1H), 7.99 (dd, J = 1.8, 5.4 Hz, 1H), 7.28-7.23 (m, 2H), 7.13-7.10 (m, 1H), 7.07-7.01 (m, 2H), 6.22 (dd, J = 5.4, 10.9 Hz, 1H), 4.27-4.16 & 3.51-3.40 (2xm, 1H), 3.90-3.80 (m, 1H), 2.79-2.67 (m, 2H), 2.65 (d, J = 1.8 Hz, 3H), 2.33-2.31 (m, 3H), 1.77-1.22 (m, 10H), 1.20-0.95 (m, 2H). | Rt = 2.68 min, m/z 407.3 [M + H]$^+$ (Method 1) |
| 135 | (ee % = 79%) (S)-2-amino-N-benzyl-3-(4-((3-methyl-1H-pyrrolo[2,3-b]pyridin-4-yl)oxy)phenyl)propanamide | 131F-c/benzylamine | $^1$H NMR (400 MHz, d6-DMSO) δ 11.35 (s, 1H), 8.32 (t, J = 6.0 Hz, 1H), 7.99 (d, J = 5.4 Hz, 1H), 7.28-7.12 (m, 8H), 7.04 (d, J = 8.5 Hz, 2H), 6.23 (d, J = 5.4 Hz, 1H), 4.34-4.19 (m, 2H), 3.46 (dd, J = 5.9, 7.5 Hz, 1H), 2.94 (dd, J = 5.7, 13.3 Hz, 1H), 2.72 (dd, J = 7.6, 13.3 Hz, 1H), 2.34 (d, J = 1.1 Hz, 3H), 1.92 (s, 2H). | Rt = 2.48 min, m/z 401.2 [M + H]$^+$ (Method 1) |
| 136 | (ee % = 72%) (R)-2-amino-N-benzyl-3-(4-((3-methyl-1H-pyrrolo[2,3-b]pyridin-4-yl)oxy)phenyl)propanamide | 131F-d/benzylamine | $^1$H NMR (400 MHz, d6-DMSO) δ 11.37 (s, 1H), 8.32 (t, J = 6.0 Hz, 1H), 7.99 (d, J = 5.5 Hz, 1H), 7.32-7.09 (m, 8H), 7.06-7.02 (m, 2H), 6.23 (d, J = 5.4 Hz, 1H), 4.35-4.19 (m, 2H), 3.46 (dd, J = 6.0, 7.4 Hz, 1H), 2.94 (dd, J = 5.8, 13.3 Hz, 1H), 2.72 (dd, J = 7.6, 13.3 Hz, 1H), 2.34 (d, J = 1.0 Hz, 3H), 1.80 (s, 2H). | Rt = 2.50 min, m/z 401.2 [M + H]$^+$ (Method 1) |
| 137 | (S)-2-amino-3-(4-((3-methyl-1H-pyrrolo[2,3-b]pyridin-4-yl)oxy)phenyl)-N-phenylpropanamide | 131F-c/aniline | $^1$H NMR (400 MHz, d6-DMSO) δ 11.34 (s, 1H), 9.84 (s, 1H), 7.95 (d, J = 5.4 Hz, 1H), 7.60-7.58 (m, 2H), 7.34-7.28 (m, 4H), 7.13-7.08 (m, 1H), 7.05 (d, J = 23.5 Hz, 3H), 6.17 (d, J = 5.4 Hz, 1H), 3.60 (dd, J = 5.9, 7.7 Hz, 1H), 3.01 (dd, J = 5.7, 13.4 Hz, 2H), 2.79 (dd, J = 7.6, 13.0 Hz, 2H), 2.31-2.30 (m, 3H). | Rt = 2.47 min, m/z 387.2 [M + H]$^+$ (Method 1) |

| Ex | Structure | Intermediate 131F/Amine | 1H NMR | LC-MS |
|---|---|---|---|---|
| 138 | (ee % = 80%)<br>(R)-2-amino-3-(4-((3-methyl-1H-pyrrolo[2,3-b]pyridin-4-yl)oxy)phenyl)-N-phenylpropanamide | 131F-d/aniline | $^1$H NMR (400 MHz, d6-DMSO) δ 11.34 (s, 1H), 9.79 (s, 1H), 7.95 (d, J = 5.4 Hz, 1H), 7.61-7.58 (m, 2H), 7.34-7.27 (m, 4H), 7.12-7.09 (m, 1H), 7.08-7.01 (m, 3H), 6.17 (d, J = 5.4 Hz, 1H), 3.58 (dd, J = 5.7, 7.8 Hz, 1H), 3.00 (dd, J = 5.7, 13.3 Hz, 1H), 2.77 (dd, J = 7.9, 13.3 Hz, 1H), 2.31 (d, J = 1.0 Hz, 3H), 2.00-1.94 (s, 2H). | Rt = 2.47 min, m/z 387.2 [M + H]$^+$ (Method 1) |
| 139 | (ee % = 76%)<br>(S)-2-amino-N-(cyclohexylmethyl)-3-(4-((3-methyl-1H-pyrrolo[2,3-b]pyridin-4-yl)oxy)phenyl)propanamide | 131F-c/cyclohexylmethanamine | $^1$H NMR (400 MHz, d6-DMSO) δ 11.33 (s,1H), 7.98 (d, J = 5.4 Hz, 1H), 7.74 (t, J = 5.9 Hz, 1H), 7.26 (d, J = 8.5 Hz, 2H), 7.11 (dd, J = 1.1, 2.1 Hz, 1H), 7.05 (d, J = 8.5 Hz, 2H), 6.22 (d, J = 5.4 Hz, 1H), 3.39 (t, J = 6.7 Hz, 1H), 2.97-2.77 (m, 3H), 2.69 (dd, J = 7.2,13.4 Hz, 1H), 2.33 (d, J = 1.0 Hz, 3H), 1.74 (s, 2H), 1.66-1.49 (m, 5H), 1.35-1.23 (m, 1H), 1.15-1.07 (m, 3H), 0.90-0.68 (m, 2H). | Rt = 2.73 min, m/z 407.3 [M + H]$^+$ (Method 1) |
| 140 | (ee % = 71%)<br>(R)-2-amino-N-(cyclohexylmethyl)-3-(4-((3-methyl-1H-pyrrolo[2,3-b]pyridin-4-yl)oxy)phenyl)propanamide | 131F-d/cyclohexylmethanamine | $^1$H NMR (400 MHz, d6-DMSO) δ 11.35 (s, 1H), 7.98 (d, J = 5.4 Hz, 1H), 7.75 (t, J = 5.9 Hz, 1H), 7.26 (d, J = 8.5 Hz, 2H), 7.11 (dd, J = 1.2, 2.2 Hz, 1H), 7.05 (d, J = 8.5 Hz, 2H), 6.22 (d, J = 5.4 Hz, 1H), 3.43-3.37 (m, 1H), 2.97-2.76 (m, 4H), 2.69 (dd, J = 7.3, 13.2 Hz, 1H), 2.33 (d, J = 1.0 Hz, 3H), 1.66-1.53 (m, 6H), 1.32-1.07 (m, 4H), 0.84-0.71 (m, 2H). | Rt = 2.74 min, m/z 407.3 [M + H]$^+$ (Method 1) |
| 141 | (ee % = 76%)<br>(S)-2-amino-N-cyclohexyl-3-(4-((3-methyl-1H-pyrrolo[2,3-b]pyridin-4-yl)oxy)phenyl)propanamide | 131F-c/cyclohexanamine | $^1$H NMR (400 MHz, d6-DMSO) δ 11.36 (s, 1H), 7.98 (d, J = 5.4 Hz, 1H), 7.57 (d, J = 8.1 Hz, 1H), 7.26 (d, J = 8.6 Hz, 2H), 7.13-7.09 (m, 1H), 7.04 (d, J = 8.6 Hz, 2H), 6.23 (d, J = 5.4 Hz, 1H), 3.54-3.45 (m, 1H), 2.85 (dd, J = 5.9, 13.3 Hz, 1H), 2.67 (dd, J = 7.4, 13.3 Hz, 1H), 2.32 (d, J = 1.0 Hz, 3H), 2.06-2.05 (s, 2H), 1.68-1.49 (m, 5H), 1.30-1.00(m, 6H). | Rt = 2.58 min, m/z 393.3 [M + H]$^+$ (Method 1) |

-continued

| Ex | Structure | Intermediate 131F/Amine | 1H NMR | LC-MS |
|---|---|---|---|---|
| 142 | 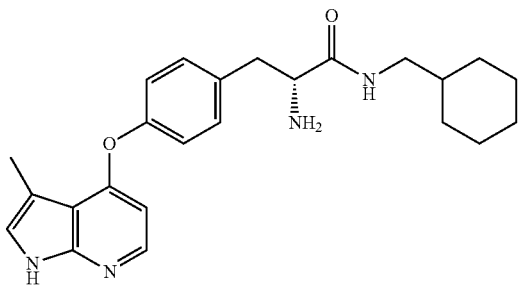<br>(ee % = 72%)<br>(R)-2-amino-N-cyclohexyl-3-(4-((3-methyl-1H-pyrrolo[2,3-b]pyridin-4-yl)oxy)phenyl)propanamide | 131F-d/cyclo-hexanamine | $^1$H NMR (400 MHz, d6-DMSO) δ 11.35 (s, 1H), 7.98 (d, J = 5.4 Hz, 1H), 7.57 (d, J = 8.1 Hz, 1H), 7.26 (d, J = 8.6 Hz, 2H), 7.12 (dd, J = 1.2, 2.1 Hz, 1H), 7.04 (d, J = 8.5 Hz, 2H), 6.23 (d, J = 5.4 Hz, 1H), 3.53-3.45 (m, 1H), 3.29-3.33(m, 1H), 2.85 (dd, J = 5.9, 13.2 Hz, 1H), 2.67 (dd, J = 7.5, 13.2 Hz, 1H), 2.32 (d, J = 1.0 Hz, 3H), 1.80 (s, 2H), 1.69-1.49 (m, 6H), 1.29-1.01 (m,4H). | Rt = 2.59 min, m/z 393.2 [M + H]$^+$ (Method 1) |
| 143 | 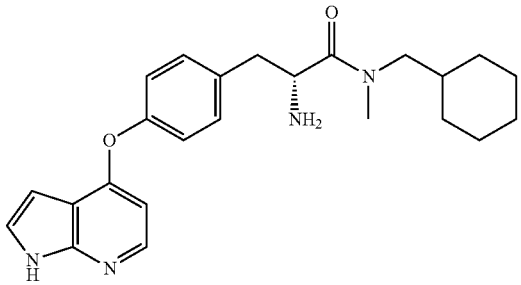<br>(R)-3-(4-((1H-pyrrolo[2,3-b]pyridin-4-yl)oxy)phenyl)-2-amino-N-(cyclohexylmethyl)-N-methylpropanamide | 131F-e/cyclohexyl-N-methylmethan-amine | $^1$H NMR (400 MHz, d6-DMSO) δ 11.72 (s, 1H), 8.08-8.05 (m, 1H), 7.36-7.32 (m, 1H), 7.28 (dd, J = 8.4, 16.1 Hz, 2H), 7.09-7.05 (m, 2H), 6.38-6.35 (m, 1H), 6.19-6.16 (m, 1H), 3.90-3.76 (2 x t, 1H), 3.23 (dd, J = 7.2, 13.1 Hz, 1H), 2.99-2.92 (m, 1H), 2.87 and 2.77 (2 x s, 3H), 2.86-2.78 (m, 1H), 2.71-2.61 (m, 1H), 1.92 (m, 2H), 1.63-1.42 (m, 6H), 1.17-1.05 (m, 3H), 0.90-0.75 (m, 2H). | Rt = 2.78 min, m/z 407.3 [M + H]$^+$ (Method 1) |
| 144 | 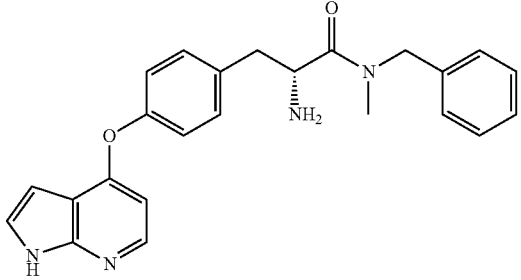<br>(R)-3-(4-((1H-pyrrolo[2,3-b]pyridin-4-yl)oxy)phenyl)-2-amino-N-benzyl-N-methylpropanamide | 131F-e/N-methyl-1-phenylmethan-amine | $^1$H NMR (400 MHz, d6-DMSO) δ 11.72 (s, 1H), 8.08-8.05 (m, 1H), 7.35-7.19 (m, 6H), 7.14-7.03 (m, 4H), 6.40-6.34 (m, 1H), 6.20-6.17 (m, 1H), 4.63-4.33 (m, 2H), 4.00-3.80 (2 x t, 1H), 2.87 (dd, J = 7.0, 13.1 Hz, 1H), 2.83-2.76 (2 x s, 3H), 2.76-2.63 (m, 1H), 1.84 (s, 2H). | Rt = 2.48 min, m/z 401.2 [M + H]$^+$ (Method 1) |

Example 145

Step A. tert-Butyl (S)-(3-(3-fluoro-4-hydroxyphenyl)-1-oxo-1-(phenylamino)propan-2-yl)carbamate (Intermediate 145A-a)

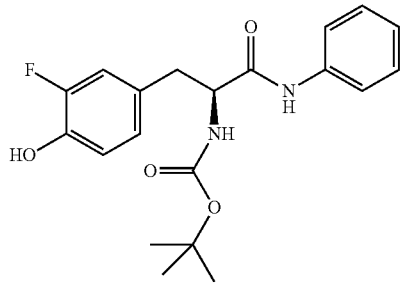 [SMILES: CC(C)(C)OC(=O)N[C@@H](Cc1ccc(O)c(F)c1)C(=O)Nc1ccccc1]

Intermediate 145A-a was prepared from (S)-2-((tert-butoxycarbonyl)amino)-3-(3-fluoro-4-hydroxyphenyl)propanoic acid and aniline using a similar procedure to that used for Step F of Example 1.

LCMS (Method 6): Rt=1.36 min, m/z 373.1 [M−H]−

Step B. tert-Butyl (S)-(3-(3-fluoro-4-((3-methyl-1-tosyl-1H-pyrrolo[2,3-b]pyridin-4-yl)oxy)phenyl)-1-oxo-1-(phenylamino)propan-2-yl)carbamate (Intermediate 145B-a)

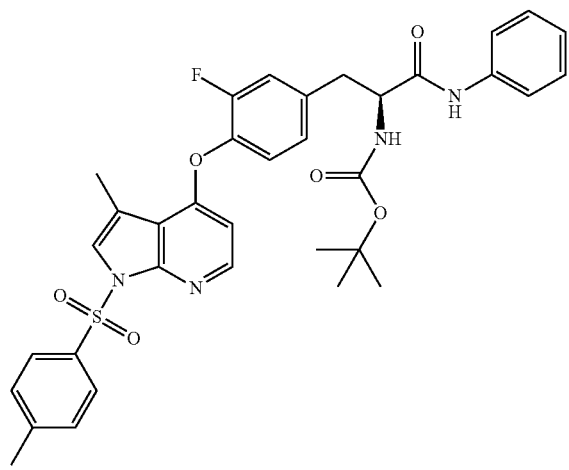 [SMILES: Cc1ccc(S(=O)(=O)n2cc(C)c3c(Oc4ccc(C[C@H](NC(=O)OC(C)(C)C)C(=O)Nc5ccccc5)cc4F)ccnc32)cc1]

Intermediate 145B-a was prepared from Intermediate 145A-a and 131A-b using a similar procedure to that used for Step D of Example 1.

LCMS (Method 6): Rt=1.80 min, m/z 659.3 [M+H]+

Step C. (S)-2-amino-3-(3-fluoro-4-((3-methyl-1H-pyrrolo[2,3-b]pyridin-4-yl)oxy)phenyl)-N-phenylpropanamide (Example 145)

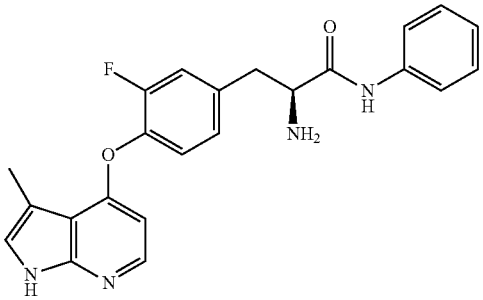 [SMILES: Cc1c[nH]c2nccc(Oc3ccc(C[C@H](N)C(=O)Nc4ccccc4)cc3F)c12]

Intermediate 145B-a (180 mg, 0.274 mmol) was dissolved in DCM (5 mL) and TFA (1 mL) was added. After stirring at RT for 90 min the volatiles were evaporated and the residue was dissolved in methanol. The solution was loaded onto an SCX-2 cartridge (5 g). After flushing with DCM and methanol, the free base was eluted with 2M methanolic ammonia. Evaporation gave a residue which was re-dissolved in methanol (5 mL). Lithium hydroxide hydrate (22 mg, 0.516 mmol) in water (2 mL) was added and the reaction was stirred at RT for 18 h then at 50° C. for 2 h. The methanol was evaporated and the aqueous mixture was extracted with DCM (12 mL). The organic was dried ($Na_2SO_4$) and evaporated. The product was purified by HPLC eluting with a gradient of 10-98% acetonitrile in water (0.1% $NH_4OH$) to give a white solid (14 mg).

Rt=2.62 min, m/z 405.2 [M+H]+ (Method 1)

$^1$H NMR (400 MHz, d6-DMSO) δ 11.38 (s, 1H), 9.84 (s, 1H), 7.94 (d, J=5.4 Hz, 1H), 7.60 (d, J=7.5 Hz, 2H), 7.36-7.12 (m, 6H), 7.05 (t, J=7.4 Hz, 1H), 6.08 (d, J=4.9 Hz, 1H), 3.60 (dd, J=5.7, 7.9 Hz, 1H), 3.01 (dd, J=5.5, 13.4 Hz, 1H), 2.79 (dd, J=8.1, 13.4 Hz, 1H), 2.37 (d, J=1.0 Hz, 3H), 2.00 (s, 2H).

Examples 146 to 149

The following Examples were prepared in a similar way to Example 145 by replacing at each step the suitable starting materials.

Preparation of Intermediates 145A-b to 145A-d

The following intermediates were prepared in a similar manner to Intermediate 145A-a by replacing in Step A of Example 145 the tyrosine with the indicated amine.

| Intermediate | Structure | Starting material | LC-MS |
|---|---|---|---|
| 145A-b | 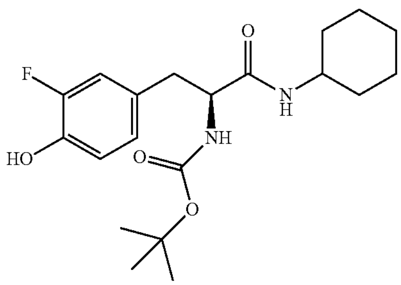 [SMILES: CC(C)(C)OC(=O)N[C@@H](Cc1ccc(O)c(F)c1)C(=O)NC1CCCCC1] | 3-Fluoro-L-tyrosine and cyclohexanamine | Rt = 3.33 min, m/z 381.1 [M + H]+ (Method 7) |
| 145A-c | 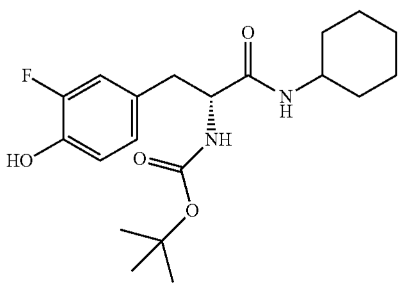 [SMILES: CC(C)(C)OC(=O)N[C@H](Cc1ccc(O)c(F)c1)C(=O)NC1CCCCC1] | 3-Fluoro-D-tyrosine and cyclohexanamine | Rt = 1.15 min, m/z 379.3 [M − H]− (Method 6) |
| 145A-d | 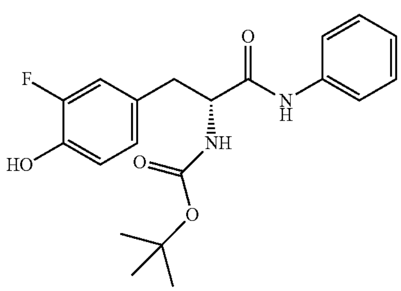 [SMILES: CC(C)(C)OC(=O)N[C@H](Cc1ccc(O)c(F)c1)C(=O)Nc1ccccc1] | 3-Fluoro-D-tyrosine and aniline | Rt = 1.41 min, m/z 373.2 [M − H]− (Method 6) |

Preparation of Intermediates from 145B-b to 145B-e

The following intermediates were prepared in a similar manner to Intermediate 145B-a from the indicated starting materials.

| Intermediate | Structure | Starting materials | LC-MS |
|---|---|---|---|
| 145B-b | 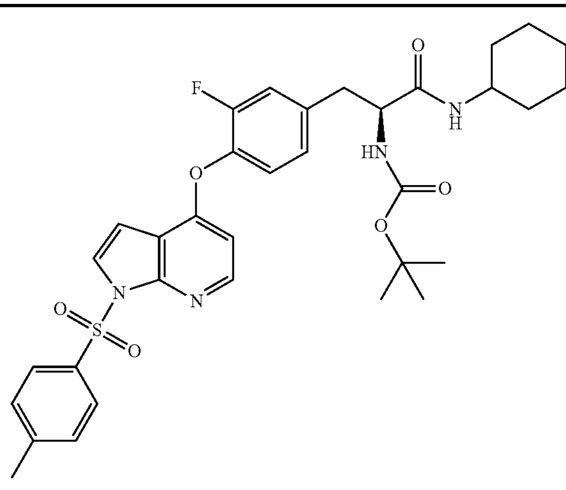 | 145A-b and 131A-a | Rt = 1.75 min, m/z 651.3 [M + H]+ (Method 6) |

-continued

| Intermediate | Structure | Starting materials | LC-MS |
|---|---|---|---|
| 145B-c | 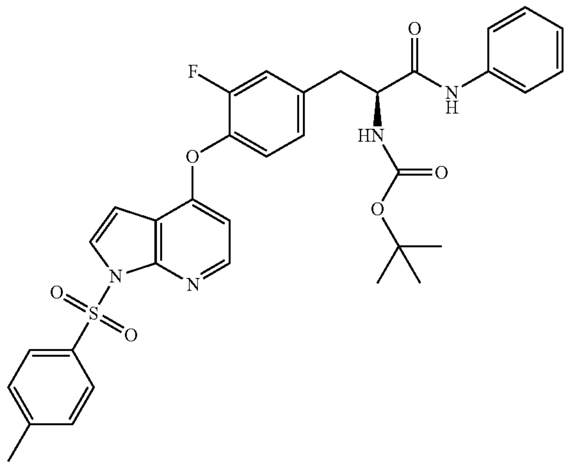 [SMILES: Cc1ccc(S(=O)(=O)n2ccc3c(Oc4ccc(C[C@H](NC(=O)OC(C)(C)C)C(=O)Nc5ccccc5)cc4F)ccnc32)cc1] | 145A-a and 131A-a | Rt = 1.73 min, m/z 645.2 [M + H]+ (Method 6) |
| 145B-d | 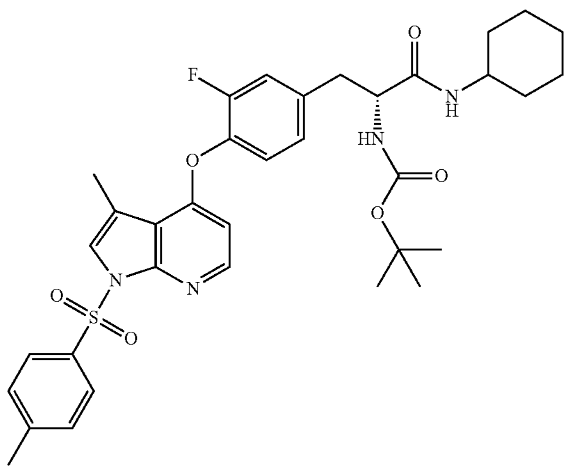 [SMILES: Cc1ccc(S(=O)(=O)n2cc(C)c3c(Oc4ccc(C[C@@H](NC(=O)OC(C)(C)C)C(=O)NC5CCCCC5)cc4F)ccnc32)cc1] | 145A-c and 131A-b | Rt = 1.79 min, m/z 665.3 [M + H]+ (Method 6) |
| 145B-e | 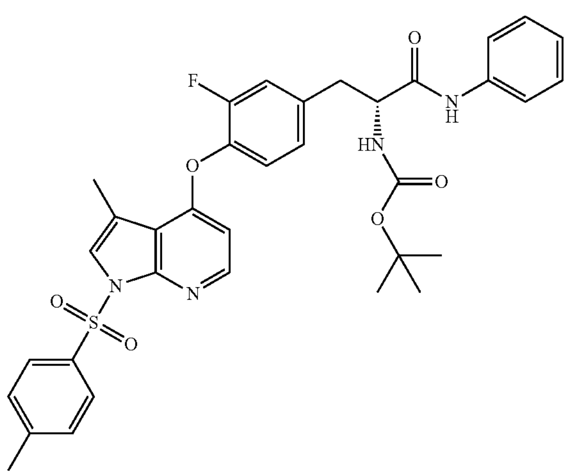 [SMILES: Cc1ccc(S(=O)(=O)n2cc(C)c3c(Oc4ccc(C[C@@H](NC(=O)OC(C)(C)C)C(=O)Nc5ccccc5)cc4F)ccnc32)cc1] | 145A-d and 131A-b | Rt = 1.77 min, m/z 659.2 [M + H]+ (Method 6) |

Preparation of Examples

The following examples were prepared in a similar manner to Example 145, following the same synthetic sequence, by replacing in Step C the indicated Intermediate in the table below.

| Ex | Structure | Intermediate | 1H NMR | LC-MS |
|---|---|---|---|---|
| 146 | (S)-3-(4-((1H-pyrrolo[2,3-b]pyridin-4-yl)oxy)-3-fluorophenyl)-2-amino-N-cyclohexylpropanamide | 145B-b | $^1$H NMR (400 MHz, d6-DMSO) δ 11.76 (s, 1H), 8.05 (d, J = 5.4 Hz, 1H), 7.61 (d, J = 8.1 Hz, 1H), 7.37 (dd, J = 2.1, 3.2 Hz, 1H), 7.29-7.24 (m, 2H), 7.11-7.07 (m, 1H), 6.33 (d, J = 5.5 Hz, 1H), 6.28-6.24 (m, 1H), 3.56-3.47 (m, 1H), 3.38 (t, J = 6.7 Hz, 1H), 2.87 (dd, J = 6.0, 13.2 Hz, 1H), 2.76-2.67 (m, 1H), 1.77 (s, 2H), 1.70-1.57 (m, 4H), 1.30-1.04 (m, 6H). | Rt = 2.50 min, m/z 397.2 [M + H]$^+$ (Method 3) |
| 147 | (S)-3-(4-((1H-pyrrolo[2,3-b]pyridin-4-yl)oxy)-3-fluorophenyl)-2-amino-N-phenylpropanamide | 145B-c | $^1$H NMR (400 MHz, d6-DMSO) δ 11.74 (s, 1H), 9.82 (s, 1H), 8.02 (d, J = 5.3 Hz, 1H), 7.60 (dd, J = 1.1, 8.6 Hz, 2H), 7.37-7.24 (m, 5H), 7.15 (dd, J = 1.5, 8.3 Hz, 1H), 7.05 (tt, J = 1.2, 7.4 Hz, 1H), 6.28 (dd, J = 0.4, 5.4 Hz, 1H), 6.20 (dd, J = 1.9, 3.4 Hz, 1H), 3.61 (t, J = 6.9 Hz, 1H), 3.01 (dd, J = 5.7, 13.3 Hz, 1H), 2.81 (dd, J = 8.0, 13.4 Hz, 1H), 2.01 (s, 2H). | Rt = 2.41 min, m/z 391.2 [M + H]$^+$ (Method 1) |
| 148 | (R)-2-amino-N-cyclohexyl-3-(3-fluoro-4-((3-methyl-1H-pyrrolo[2,3-b]pyridin-4-yl)oxy)phenyl)propanamide | 145B-d | $^1$H NMR (400 MHz, d6-DMSO) δ 11.38 (s, 1H), 7.97 (d, J = 5.4 Hz, 1H), 7.60 (d, J = 8.1 Hz, 1H), 7.28-7.20 (m, 2H), 7.15-7.06 (m, 2H), 6.15 (d, J = 4.8 Hz, 1H), 3.55-3.46 (m, 1H), 3.38 (t, J = 6.7 Hz, 1H), 2.86 (dd, J = 6.0, 13.2 Hz, 1H), 2.71 (dd, J = 27.3, 13.0 Hz, 1H), 2.38 (d, J = 1.0 Hz, 3H), 1.77 (d, J = 1.2 Hz, 2H), 1.69-1.52 (m, 5H), 1.29-1.16 (m, 2H), 1.15-1.02 (m, 3H). | Rt = 2.71 min, m/z 411.2 [M + H]$^+$ (Method 1) |
| 149 | (R)-2-amino-3-(3-fluoro-4-((3-methyl-1H-pyrrolo[2,3-b]pyridin-4-yl)oxy)phenyl)-N-phenylpropanamide | 145B-e | $^1$H NMR (400 MHz, d6-DMSO) δ 11.38 (s, 1H), 9.84 (s, 1H), 7.94 (d, J = 5.4 Hz, 1H), 7.60 (d, J = 7.5 Hz, 2H), 7.36-7.12 (m, 6H), 7.05 (t, J = 7.4 Hz, 1H), 6.08 (d, J = 4.9 Hz, 1H), 3.60 (dd, J = 5.7, 7.9 Hz, 1H), 3.01 (dd, J = 5.5, 13.4 Hz, 1H), 2.79 (dd, J = 8.1, 13.4 Hz, 1H), 2.37 (d, J = 1.0 Hz, 3H), 2.00 (s, 2H). | Rt = 2.62 min, m/z 405.2 [M + H]$^+$ (Method 1) |

Example 150

Step A. Methyl 2-((tert-butoxycarbonyl)amino)-3-(4-hydroxyphenyl)-2-methylpropan-oate (Intermediate 150A)

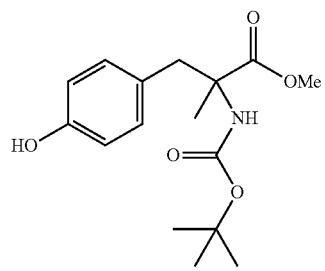 [SMILES: COC(=O)C(C)(Cc1ccc(O)cc1)NC(=O)OC(C)(C)C]

Intermediate 150A was prepared from 2-amino-3-(4-hydroxyphenyl)-2-methylpropanoic acid using similar procedures to those used for Steps A and B of Example 1.

LCMS (Method 6): Rt=1.27 min, m/z 332.1 [M+Na]$^+$

Step B. Methyl 2-((tert-butoxycarbonyl)amino)-2-methyl-3-(4-((1-(phenylsulfonyl)-1H-pyrrolo[2,3-b]pyridin-4-yl)oxy)phenyl)propanoate (Intermediate 150B)

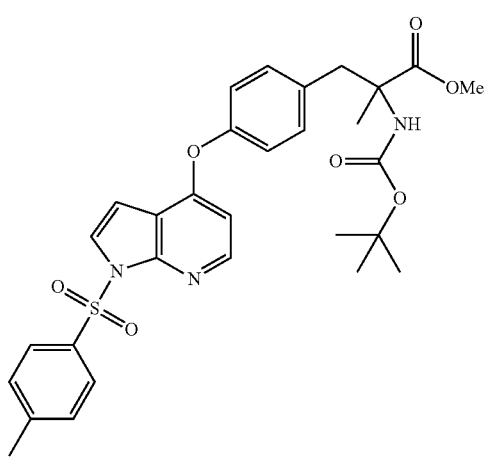 [SMILES: COC(=O)C(C)(Cc1ccc(Oc2ccnc3c2ccn3S(=O)(=O)c2ccc(C)cc2)cc1)NC(=O)OC(C)(C)C]

Intermediate 150B was prepared from Intermediate 150A and Intermediate 131A-a using a similar procedure to that used for Step D of Example 1.

LCMS (Method 6): Rt=1.73 min, m/z 580.2 [M+H]$^+$

Step C. 3-(4-((1H-Pyrrolo[2,3-b]pyridin-4-yl)oxy)phenyl)-2-((tert-butoxycarbonyl)-amino)-2-methylpropanoic acid (Intermediate 150C)

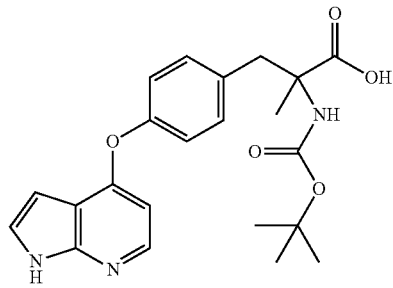 [SMILES: CC(C)(C)OC(=O)NC(C)(Cc1ccc(Oc2ccnc3[nH]ccc23)cc1)C(=O)O]

Intermediate 150B (1.0 g, 1.73 mmol) was dissolved in methanol (10 mL) and 2M lithium hydroxide (1 mL) was added. The reaction was stirred at 60° C. for 3 h. A further portion of 2M lithium hydroxide (1 mL) was added and heating was continued for 4 h. After stirring at RT for a further 18 h, the reaction mixture was evaporated, treated with 1M hydrochloric acid (20 mL) and the product extracted with DCM (30 mL). The organic extract was dried (Na$_2$SO$_4$) and evaporated to give the product as a gum (861 mg).

LCMS (Method 6): Rt=1.13 min, m/z 412.3 [M+H]$^+$

Step D. tert-Butyl (3-(4-((1H-pyrrolo[2,3-b]pyridin-4-yl)oxy)phenyl)-1-(cyclohexylamino)-2-methyl-1-oxopropan-2-yl)carbamate (Intermediate 150D)

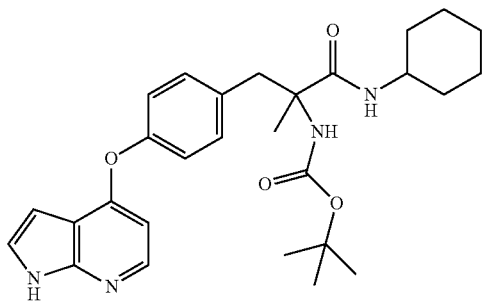 [SMILES: CC(C)(C)OC(=O)NC(C)(Cc1ccc(Oc2ccnc3[nH]ccc23)cc1)C(=O)NC1CCCCC1]

Intermediate 150D was prepared from Intermediate 150C and cyclohexanamine using a method similar to that used in Steps F of Example 1.

LCMS (Method 6): Rt=1.45 min, m/z 493.2 [M+H]$^+$ (Method 1)

Step E. 3-(4-((1H-pyrrolo[2,3-b]pyridin-4-yl)oxy)phenyl)-2-amino-N-cyclohexyl-2-methylpropanamide (Example 150)

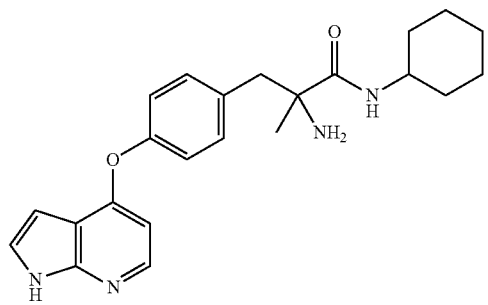 [SMILES: CC(N)(Cc1ccc(Oc2ccnc3[nH]ccc23)cc1)C(=O)NC1CCCCC1]

Example 150 was prepared from Intermediate 150D using a method similar to that used in Step G of Example 1.

LCMS (Method 1): Rt=2.47 min, m/z 393.3 [M+H]$^+$ $^1$H NMR (400 MHz, d6-DMSO) δ 11.71 (s, 1H), 8.05 (d, J=5.4 Hz, 1H), 7.47 (d, J=8.3 Hz, 1H), 7.35-7.32 (m, 1H), 7.23 (d, J=8.6 Hz, 2H), 7.06 (d, J=8.6 Hz, 2H), 6.37 (d, J=5.4 Hz, 1H), 6.19 (dd, J=2.0, 3.5 Hz, 1H), 3.51-3.43 (m, 1H), 3.05 (d, J=12.8 Hz, 1H), 2.63 (d, J=12.8 Hz, 1H), 1.80 (s, 2H), 1.70-1.47 (m, 5H), 1.34-1.22 (m, 2H), 1.21 (s, 3H), 1.19-0.98 (m, 3H).

Preparation of Example 151

Example 151 was prepared from Intermediate 150C in a similar manner to Example 150, following the same synthetic sequence, by replacing in Step D the indicated amine starting material the table below.

| Ex | Structure | Amine | 1H NMR | LC-MS |
|---|---|---|---|---|
| 151 | ![structure] 3-(4-((1H-pyrrolo[2,3-b]pyridin-4-yl)oxy)phenyl)-2-amino-2-methyl-N-(tetrahydro-2H-pyran-4-yl)propanamide | Tetrahydro-2H-pyran-4-amine | $^1$H NMR (400 MHz, d6-DMSO) δ 11.71 (s, 1H), 8.05 (d, J = 5.4 Hz, 1H), 7.57 (d, J = 8.1 Hz, 1H), 7.34 (dd, J = 2.0, 3.2 Hz, 1H), 7.23 (d, J = 8.6 Hz, 2H), 7.07 (d, J = 8.6 Hz, 2H), 6.38 (d, J = 5.4 Hz, 1H), 6.18 (dd, J = 1.3, 3.4 Hz, 1H), 3.82-3.66 (m, 3H), 3.36-3.26 (m, 2H), 3.05 (d, J = 12.8 Hz, 1H), 2.66-2.61 (m, 1H), 1.79 (s, 2H), 1.63-1.24 (m, 4H), 1.22 (s, 3H). | Rt = 1.89 min, m/z 395.2 [M + H]$^+$ (Method 1) |

Example 152

Step A. Benzyl (S)-4-(2-((tert-butoxycarbonyl)amino)-3-(3-fluoro-4-((3-methyl-1-((2-(trimethylsilyl)ethoxy)methyl)-1H-pyrrolo[2,3-b]pyridin-4-yl)oxy)phenyl)propanoyl)piperazine-1-carboxylate (Intermediate 152A)

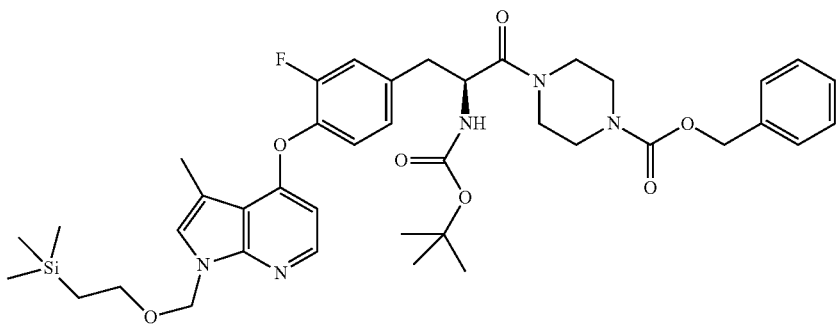 [SMILES: Cc1cn(COCC[Si](C)(C)C)c2nccc(Oc3ccc(C[C@H](NC(=O)OC(C)(C)C)C(=O)N4CCN(C(=O)OCc5ccccc5)CC4)cc3F)c12]

Intermediate 152A was prepared from 1E-a and benzyl piperazine-1-carboxylate using a method similar that used in Step F of Example 1.

LCMS (Method 6): Rt=1.89 min, m/z 762.2 [M+H]$^+$

Step B. tert-Butyl (S)-(3-(3-fluoro-4-((3-methyl-1-((2-(trimethylsilyl)ethoxy)methyl)-1H-pyrrolo[2,3-b]pyridin-4-yl)oxy)phenyl)-1-oxo-1-(piperazin-1-yl)propan-2-yl)carbamate (Intermediate 152B)

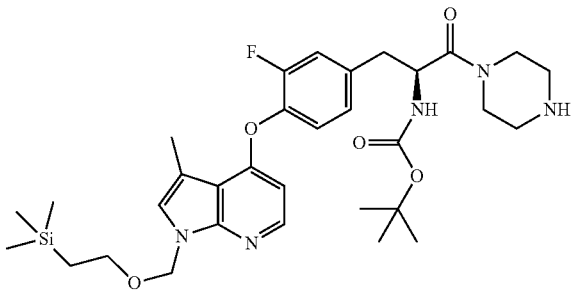 [SMILES: Cc1cn(COCC[Si](C)(C)C)c2nccc(Oc3ccc(C[C@H](NC(=O)OC(C)(C)C)C(=O)N4CCNCC4)cc3F)c12]

Intermediate 152A (1.50 g, 1.97 mmol) was dissolved in IMS (44.6 mL) and 10% palladium on carbon (187 mg) was added. The mixture was stirred under an atmosphere of hydrogen gas provided by a balloon. After 18 h, the mixture was filtered through Celite® and the solvent was evaporated in vacuo. The residue was chromatographed on a 40 g Si cartridge eluting with 0-10% 2M ammonia in methanol in DCM. The product was obtained as a white solid (951 mg).

LCMS (Method 6): Rt=1.39 min, m/z 628.2 [M+H]$^+$

Step C. (S)-2-amino-3-(3-fluoro-4-((3-methyl-1H-pyrrolo[2,3-b]pyridin-4-yl)oxy)phenyl)-1-(piperazin-1-yl)propan-1-one (Example 152)

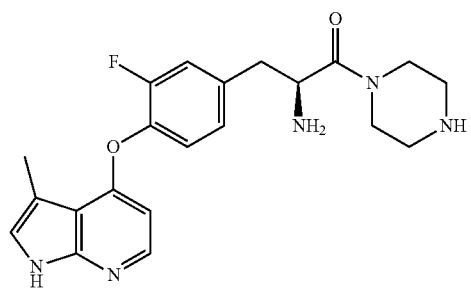 [SMILES: Cc1c[nH]c2nccc(Oc3ccc(C[C@H](N)C(=O)N4CCNCC4)cc3F)c12]

Intermediate 152B (66 mg, 0.11 mmol) was dissolved in DCM (1.2 mL) and TFA (1.2 mL) was added. The solution was stirred at RT for 3 h. The reaction mixture was diluted with methanol and passed down a 5 g SCX-2 cartridge. After flushing with methanol, the product was eluted with 2M ammonia in methanol. Evaporation gave a residue which was dissolved in THF (1.2 mL). 4M aqueous sodium hydroxide (1.2 mL) was added and the reaction was stirred at RT for 1 h. After diluting with water (8 mL), the product was extracted with ethyl acetate (3×10 mL). The combined organic extracts were dried (Na$_2$SO$_4$) and evaporated. The product was purified by HPLC eluting with a gradient of 10-98% acetonitrile in water (0.1% NH$_4$OH added). The desired product was obtained as a beige solid (23 mg).

LCMS (Method 1): Rt=1.57 min, m/z 398.2 [M+H]$^+$ $^1$H NMR (400 MHz, d6-DMSO) δ 11.39 (s, 1H), 8.00-7.96 (m, 1H), 7.34-7.20 (m, 2H), 7.15-7.08 (m, 2H), 6.16-6.10 (m, 1H), 3.96-3.89 (m, 1H), 3.50-3.30 (m, 8H), 2.80 (dd, J=6.2, 13.2 Hz, 1H), 2.72-2.63 (m, 2H), 2.55-2.52 (m, 1H), 2.38-2.36 (m, 4H).

ee % (n.d.)

Example 153

Step A. tert-Butyl (S)-(3-(3-fluoro-4-((3-methyl-1-((2-(trimethylsilyl)ethoxy)methyl)-1H-pyrrolo[2,3-b]pyridin-4-yl)oxy)phenyl)-1-oxo-1-(4-(pyridazin-4-ylmethyl)piperazin-1-yl)propan-2-yl)carbamate (Intermediate 153A)

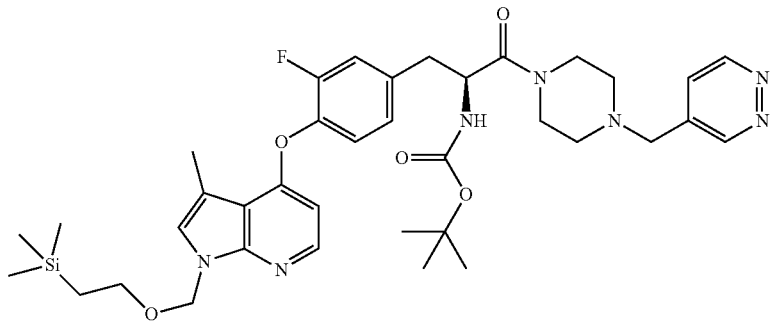 [SMILES: Cc1cn(COCC[Si](C)(C)C)c2nccc(Oc3ccc(C[C@H](NC(=O)OC(C)(C)C)C(=O)N4CCN(Cc5ccnnc5)CC4)cc3F)c12]

A solution of Intermediate 152B (150 mg, 0.24 mmol), pyridazine-4-carbaldehyde (39 mg, 0.36 mmol), and acetic acid (0.05 mL) in DCE (3 mL) was stirred at RT over 4 Å molecular sieves for 2.5 h. Sodium triacetoxyborohydride (127 mg, 0.60 mmol) was added and stirring was continued for a further 1 h. The mixture was diluted with methanol and passed through a 10 g SCX-2 cartridge. After flushing with methanol, the product was eluted with 2M ammonia in methanol. Evaporation gave the desired product (168 mg) which was used without further purification.

LCMS (Method 6): Rt=1.69 min, m/z 720.3 [M+H]$^+$

Step B. (S)-2-amino-3-(3-fluoro-4-((3-methyl-1H-pyrrolo[2,3-b]pyridin-4-yl)oxy)phenyl)-1-(4-(pyridazin-4-ylmethyl)piperazin-1-yl)propan-1-one (Example 153)

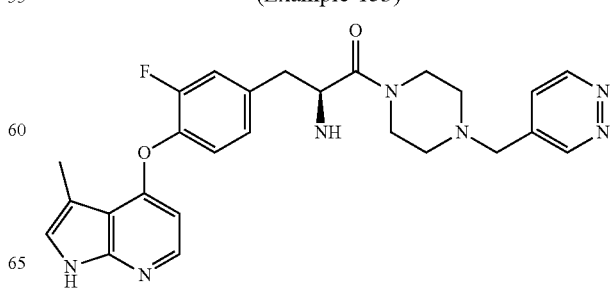

Example 153 was prepared from Intermediate 153A using a method similar to that used for Step G of Example 1.

LCMS (Method 1): Rt=2.07 min, m/z 490.1 [M+H]$^+$ $^1$H NMR (400 MHz, d6-DMSO) δ 11.40 (s, 1H), 9.18-9.15 (m, 2H), 7.99 (d, J=5.4 Hz, 1H), 7.59 (dd, J=2.4, 5.1 Hz, 1H), 7.32 (dd, J=1.9, 11.8 Hz, 1H), 7.24 (dd, J=8.4, 8.4 Hz, 1H), 7.14 (s, 1H), 7.11 (dd, J=1.3, 8.3 Hz, 1H), 6.17 (d, J=5.4 Hz, 1H), 3.93 (dd, J=6.8, 6.8 Hz, 1H), 3.55 (s, 2H), 3.53-3.36 (m, 4H), 2.80 (dd, J=6.2, 13.2 Hz, 1H), 2.67 (dd, J=7.5, 13.2 Hz, 1H), 2.43-2.22 (m, 6H), 2.18-2.10 (m, 1H), 1.63-1.83 (s, 2H).

Examples 154 to 164

The following examples were prepared in a similar manner to Example 153 by replacing in Step A the corresponding aldehyde indicated in the table below.

| Ex | Structure | Aldehyde | 1H NMR | LC-MS |
|---|---|---|---|---|
| 154 | (S)-2-amino-3-(3-fluoro-4-((3-methyl-1H-pyrrolo[2,3-b]pyridin-4-yl)oxy)phenyl)-1-(4-((2-(methylthio)pyrimidin-4-yl)methyl)piperazin-1-yl)propan-1-one | 2-(Methylthio)-pyrimidine-4-carbaldehyde | $^1$H NMR (400 MHz, d6-DMSO) δ 11.40 (s, 1H), 8.58 (d, J = 5.1 Hz, 1H), 7.99 (d, J = 5.4 Hz, 1H), 7.32 (dd, J = 1.9, 11.8 Hz, 1H), 7.27-7.21 (m, 2H), 7.15-7.09 (m, 2H), 6.17 (d, J = 5.0 Hz, 1H), 3.95 (dd, J = 6.9, 6.9 Hz, 1H), 3.54 (s, 3H), 3.51-3.38 (m, 3H), 2.80 (dd, J = 6.4, 13.2 Hz, 1H), 2.72-2.64 (m, 1H), 2.46-2.42 (m, 5H), 2.39 (d, J = 0.9 Hz, 3H), 2.34-2.22 (m, 1H), 2.20-2.10 (m, 1H), 1.75 (s, 2H). | Rt = 2.39 min, m/z 536.1 [M + H]$^+$ (Method 1) |
| 155 | (S)-2-amino-3-(3-fluoro-4-((3-methyl-1H-pyrrolo[2,3-b]pyridin-4-yl)oxy)phenyl)-1-(4-(pyrazin-2-ylmethyl)piperazin-1-yl)propan-1-one | Pyrazine-2-carbaldehyde | $^1$H NMR (400 MHz, d6-DMSO) δ 11.40 (s, 1H), 8.69 (d, J = 1.4 Hz, 1H), 8.59-8.54 (m, 2H), 7.99 (d, J = 5.4 Hz, 1H), 7.31 (dd, J = 1.8, 11.8 Hz, 1H), 7.24 (t, J = 8.4 Hz, 1H), 7.15-7.09 (m, 2H), 6.17 (d, J = 5.2 Hz, 1H), 3.94 (t, J = 6.9 Hz, 1H), 3.65 (s, 2H), 3.50-3.36 (m, 4H), 2.80 (dd, J = 6.4, 13.1 Hz, 1H), 2.68 (dd, J = 7.3, 13.2 Hz, 1H), 2.47-2.41 (m, 2H), 2.39 (d, J = 0.8 Hz, 3H), 2.34-2.25 (m, 1H), 2.19-2.10 (m, 1H), 1.74 (s, 2H). | Rt = 2.00 min, m/z 490.1 [M + H]$^+$ (Method 1) |
| 156 | (S)-2-amino-3-(3-fluoro-4-((3-methyl-1H-pyrrolo[2,3-b]pyridin-4-yl)oxy)phenyl)-1-(4-((1-methyl-1H-imidazol-2-yl)methyl)piperazin-1-yl)propan-1-one | 1-Methyl-1H-imidazole-2-carbaldehyde | $^1$H NMR (400 MHz, d6-DMSO) δ 11.39 (s, 1H), 8.01 (d, J = 5.4 Hz, 1H), 7.31 (dd, J = 2.0, 11.9 Hz, 1H), 7.24 (t, J = 8.5 Hz, 1H), 7.16-7.12 (m, 1H), 7.12-7.08 (m, 1H), 7.08 (d, J = 1.1 Hz, 1H), 6.75 (d, J = 1.2 Hz, 1H), 6.17 (d, J = 4.9 Hz, 1H), 3.97-3.90 (m, 1H), 3.64 (s, 3H), 3.49 (s, 2H), 3.47-3.35 (m, 4H), 2.79 (dd, J = 6.4, 13.2 Hz, 1H), 2.67 (dd, J = 7.4, 13.2 Hz, 1H), 2.38 (d, J = 1.0 Hz, 3H), 2.37-2.33 (m, 2H), 2.24-2.14 (m, 1H), 2.10-2.04 (m, 1H), 1.72 (s, 2H). | Rt = 1.85 min, m/z 492.1 [M + H]$^+$ (Method 1) |

-continued

| Ex | Structure | Aldehyde | 1H NMR | LC-MS |
|---|---|---|---|---|
| 157 | (S)-2-amino-3-(3-fluoro-4-((3-methyl-1H-pyrrolo[2,3-b]pyridin-4-yl)oxy)phenyl)-1-(4-((2-methylthiazol-4-yl)methyl)piperazin-1-yl)propan-1-one | 2-Methylthiazole-4-carbaldehyde | $^1$H NMR (400 MHz, d6-DMSO) δ 11.39 (s, 1H), 7.99 (d, J = 5.4 Hz, 1H), 7.31 (dd, J = 2.1, 11.8 Hz, 1H), 7.24 (s, 1H), 7.24 (t, J = 8.5 Hz, 1H), 7.16-7.12 (m, 1H), 7.12-7.08 (m, 1H), 6.16 (d, J = 4.8 Hz, 1H), 3.94 (t, J = 6.9 Hz, 1H), 3.51 (s, 2H), 3.50-3.34 (m, 4H), 2.79 (dd, J = 6.4, 13.2 Hz, 1H), 2.67 (dd, J = 7.3, 13.3 Hz, 1H), 2.62-2.62 (m, 3H), 2.45-2.40 (m, 1H), 2.39 (d, J = 1.0 Hz, 3H), 2.34-2.24 (m, 1H), 2.18-2.07 (m, 1H), 1.73 (s, 2H). | Rt = 3.42 min, m/z 509.1 [M + H]$^+$ (Method 2) |
| 158 | (S)-2-amino-3-(3-fluoro-4--((3-methyl-1H-pyrrolo[2,3-b]pyridin-4-yl)oxy)phenyl)-1-(4-((1-methyl-1H-imidazol-5-yl)methyl)piperazin-1-yl)propan-1-one | 1-Methyl-1H-imidazole-5-carbaldehyde | $^1$H NMR (400 MHz, d6-DMSO) δ 11.40 (s, 1H), 7.98 (d, J = 5.4 Hz, 1H), 7.54 (s, 1H), 7.31 (dd, J = 1.9, 11.9 Hz, 1H), 7.25 (t, J = 8.4 Hz, 1H), 7.16-7.13 (m, 1H), 7.13-7.08 (m, 1H), 6.73-6.72 (m, 1H), 6.16 (d, J = 4.9 Hz, 1H), 3.94 (t, J = 6.9 Hz, 1H), 3.60 (s, 3H), 3.53-3.34 (m, 6H), 2.79 (dd, J = 6.4, 13.2 Hz, 1H), 2.68 (dd, J = 7.3, 13.1 Hz, 1H), 2.38 (d, J = 1.0 Hz, 3H), 2.36-2.26 (m, 2H), 2.23-2.11 (m, 1H), 2.05-1.92 (m, 1H), 1.77 (s, 2H). | Rt = 3.08 min, m/z 492.2 [M + H]$^+$ (Method 2) |
| 159 | (S)-2-amino-3-(3-fluoro-4-((3-methyl-1H-pyrrolo[2,3-b]pyridin-4-yl)oxy)phenyl)-1-(4-(quinoxalin-2-ylmethyl)piperazin-1-yl)propan-1-one | Quinoxaline-2-carbaldehyde | $^1$H NMR (400 MHz, d6-DMSO) δ 11.40 (s, 1H), 9.03 (s, 1H), 8.12-8.05 (m, 2H), 8.02 (d, J = 5.4 Hz, 1H), 7.87-7.82 (m, 2H), 7.32 (dd, J = 1.9, 12.0 Hz, 1H), 7.25 (t, J = 8.4 Hz, 1H), 7.17-7.13 (m, 1H), 7.13-7.08 (m, 1H), 6.18 (d, J = 5.0 Hz, 1H), 3.95 (t, J = 6.9 Hz, 1H), 3.84 (s, 2H), 3.58-3.37 (m, 4H), 2.81 (dd, J = 6.4, 13.2 Hz, 1H), 2.68 (dd, J = 7.3, 13.2 Hz, 1H), 2.48-2.43 (m, 2H), 2.40 (d, J = 0.9 Hz, 3H), 2.37-2.28 (m, 1H), 2.25-2.13 (m, 1H), 1.79-1.74 (m, 2H). | Rt = 3.67 min, m/z 540.2 [M + H]$^+$ (Method 2) |

-continued

| Ex | Structure | Aldehyde | 1H NMR | LC-MS |
|---|---|---|---|---|
| 160 | (S)-2-amino-1-(4-(4-(3-(dimethylamino)propoxy)benzyl)piperazin-1-yl)-3-(3-fluoro-4-((3-methyl-1H-pyrrolo[2,3-b]pyridin-4-yl)oxy)phenyl)propan-1-one | 4-(3-(Dimethylamino)propoxy)-benzaldehyde | ¹H NMR (400 MHz, d6-DMSO) δ 11.40 (s, 1H), 7.98 (d, J = 5.4 Hz, 1H), 7.30 (dd, J = 1.9, 12.0 Hz, 1H), 7.24 (t, J = 8.5 Hz, 1H), 7.17 (d, J = 8.5 Hz, 2H), 7.15-7.13 (m, 1H), 7.12-7.07 (m, 1H), 6.86 (d, J = 8.7 Hz, 2H), 6.16 (d, J = 4.9 Hz, 1H), 3.98-3.92 (m, 3H), 3.55-3.30 (m, 6H), 2.79 (dd, J = 6.5, 13.1 Hz, 1H), 2.67 (dd, J = 7.3, 13.1 Hz, 1H), 2.39 (d, J = 1.1 Hz, 3H), 2.36-2.27 (m, 4H), 2.18-2.14 (m, 1H), 2.13 (s, 6H), 2.01-1.92 (m, 1H), 1.87-1.77 (m, 2H), 1.72-1.72 (m, 2H). | Rt = 3.90 min, m/z 589.3 [M + H]⁺ (Method 2) |
| 161 | (S)-2-amino-3-(3-fluoro-4-((3-methyl-1H-pyrrolo[2,3-b]pyridin-4-yl)oxy)phenyl)-1-(4-((1-(methylsulfonyl)piperidin-4-yl)methyl)piperazin-1-yl)propan-1-one | 1-(Methanesulfonyl)piperidine-4-carbaldehyde | ¹H NMR (400 MHz, d6-DMSO) δ 11.41 (s, 1H), 7.98 (d, J = 5.4 Hz, 1H), 7.30 (dd, J = 1.9, 11.9 Hz, 1H), 7.24 (t, J = 8.4 Hz, 1H), 7.16-7.12 (m, 1H), 7.12-7.07 (m, 1H), 6.16 (d, J = 5.4 Hz, 1H), 3.95 (t, J = 6.9 Hz, 1H), 3.59-3.48 (m, 3H), 3.45-3.32 (m, 3H), 2.83 (s, 3H), 2.78 (dd, J = 7.2, 13.1 Hz, 1H), 2.74-2.61 (m, 3H), 2.38 (d, J = 0.9 Hz, 3H), 2.37-2.28 (m, 2H), 2.13-2.04 (m, 3H), 1.97-1.85 (m, 1H), 1.81-1.68 (m, 4H), 1.67-1.53 (m, 1H), 1.17-1.04 (m, 2H). | Rt = 3.42 min, m/z 573.2 [M + H]⁺ (Method 2) |
| 162 | (S)-2-amino-3-(3-fluoro-4-((3-methyl-1H-pyrrolo[2,3-b]pyridin-4-yl)oxy)phenyl)-1-(4-(pyrimidin-5-ylmethyl)piperazin-1-yl)propan-1-one | Pyrimidine-5-carbaldehyde | ¹H NMR (400 MHz, d6-DMSO) δ 11.40 (s, 1H), 9.10 (s, 1H), 8.72 (s, 2H), 7.99 (d, J = 5.4 Hz, 1H), 7.32 (dd, J = 1.8, 11.9 Hz, 1H), 7.24 (t, J = 8.4 Hz, 1H), 7.17-7.13 (m, 1H), 7.13-7.08 (m, 1H), 6.16 (d, J = 5.4 Hz, 1H), 3.93 (t, J = 6.8 Hz, 1H), 3.52 (s, 2H), 3.50-3.36 (m, 4H), 2.80 (dd, J = 6.2, 13.2 Hz, 1H), 2.67 (dd, J = 7.5, 13.2 Hz, 1H), 2.38 (d, J = 1.0 Hz, 3H), 2.37-2.21 (m, 3H), 2.20-2.08 (m, 1H), 1.75-1.75 (m, 2H). | Rt = 3.06 min, m/z 490.1 [M + H]⁺ (Method 2) |

| Ex | Structure | Aldehyde | 1H NMR | LC-MS |
|---|---|---|---|---|
| 163 | (S)-2-amino-3-(3-fluoro-4-((3-methyl-1H-pyrrolo[2,3-b]pyridin-4-yl)oxy)phenyl)-1-(4-((1-methyl-1H-pyrazol-4-yl)methyl)piperazin-1-yl)propan-1-one | 1-Methyl-1H-pyrazole-4-carbaldehyde | $^1$H NMR (400 MHz, d6-DMSO) δ 11.40 (s, 1H), 7.97 (d, J = 5.4 Hz, 1H), 7.53 (s, 1H), 7.33-7.21 (m, 3H), 7.13 (s, 1H), 7.10 (dd, J = 1.3, 8.3 Hz, 1H), 6.15 (d, J = 5.4 Hz, 1H), 3.92 (dd, J = 6.8, 6.8 Hz, 1H), 3.78 (s, 3H), 3.49-3.34 (m, 4H), 3.29 (s, 2H), 2.78 (dd, J = 6.3, 13.2 Hz, 1H), 2.66 (dd, J = 7.3, 13.1 Hz, 1H), 2.38 (d, J = 1.0 Hz, 3H), 2.34-2.26 (m, 2H), 2.17-2.11 (m, 1H), 2.08-2.02 (m, 1H), 1.79-1.64 (s, 2H). | Rt = 1.74 min, m/z 492.1 [M + H]$^+$ (Method 1) |
| 164 | (S)-1-(4-((1,2,3-thiadiazol-4-yl)methyl)piperazin-1-yl)-2-amino-3-(3-fluoro-4-((3-methyl-1H-pyrrolo[2,3-b]pyridin-4-yl)oxy)phenyl)propan-1-one | 1,2,3-Thiadiazole-4-carbaldehyde | $^1$H NMR (400 MHz, d6-DMSO) δ 11.40 (s, 1H), 9.05 (s, 1H), 7.98 (d, J = 5.4 Hz, 1H), 7.31 (dd, J = 2.2, 12.2 Hz, 1H), 7.23 (dd, J = 8.4, 8.4 Hz, 1H), 7.14-7.08 (m, 2H), 6.16 (d, J = 5.4 Hz, 1H), 4.02 (s, 2H), 3.93 (dd, J = 6.9, 6.9 Hz, 1H), 3.54-3.35 (m, 4H), 2.80 (dd, J = 6.2, 13.2 Hz, 1H), 2.69-2.62 (m, 1H), 2.47-2.41 (m, 2H), 2.38 (d, J = 1.0 Hz, 3H), 2.36-2.30 (m, 1H), 2.25-2.17 (m, 1H), 1.77 (s, 2H). | Rt = 2.09 min, m/z 496.0 [M + H]$^+$ (Method 1) |

Example 165

Step A. Methyl (S)-3-((4-(2-((tert-butoxycarbonyl)amino)-3-(3-fluoro-4-((3-methyl-1-((2-(trimethylsilyl)ethoxy)methyl)-1H-pyrrolo[2,3-b]pyridin-4-yl)oxy)phenyl)propanoyl)piperazin-1-yl)methyl)benzoate (Intermediate 165A)

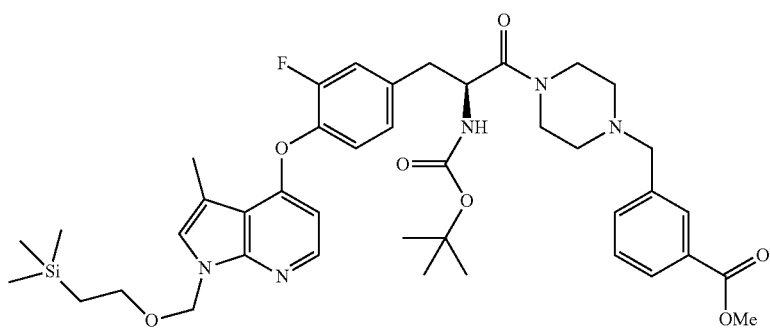 [SMILES: COC(=O)c1cccc(CN2CCN(C(=O)[C@H](Cc3ccc(Oc4ccnc5c4c(C)cn5COCC[Si](C)(C)C)c(F)c3)NC(=O)OC(C)(C)C)CC2)c1]

Intermediate 165A was prepared from Intermediate 152B and methyl 3-formylbenzoate using a method similar to that used for Step A of Example 153.

LCMS (Method 4): Rt=1.51 min, m/z 776.4 [M+H]$^+$

Step B. (S)-3-((4-(2-((tert-Butoxycarbonyl)amino)-3-(3-fluoro-4-((3-methyl-1-((2-(trimethylsilyl)ethoxy)methyl)-1H-pyrrolo[2,3-b]pyridin-4-yl)oxy)phenyl)propanoyl)piperazin-1-yl)methyl)benzoic acid (Intermediate 165B)

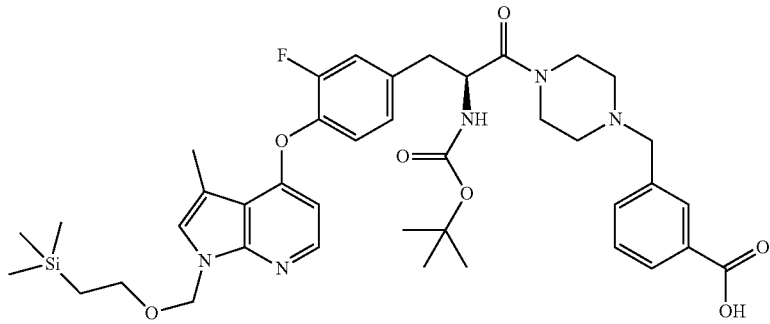 [SMILES: Cc1cn(COCC[Si](C)(C)C)c2nccc(Oc3ccc(C[C@H](NC(=O)OC(C)(C)C)C(=O)N4CCN(Cc5cccc(C(=O)O)c5)CC4)cc3F)c12]

Intermediate 165B was prepared from Intermediate 165A using a method similar to that used in Step E of Example 1. LCMS (Method 4): Rt=1.42 min, m/z 762.5 [M+H]$^+$ Step C. tert-Butyl (S)-(3-(3-fluoro-4-((3-methyl-1-((2-(trimethylsilyl)ethoxy)methyl)-1H-pyrrolo[2,3-b]pyridin-4-yl)oxy)phenyl)-1-(4-(3-(methylcarbamoyl)benzyl)piperazin-1-yl)-1-oxopropan-2-yl)carbamate (Intermediate 165C)

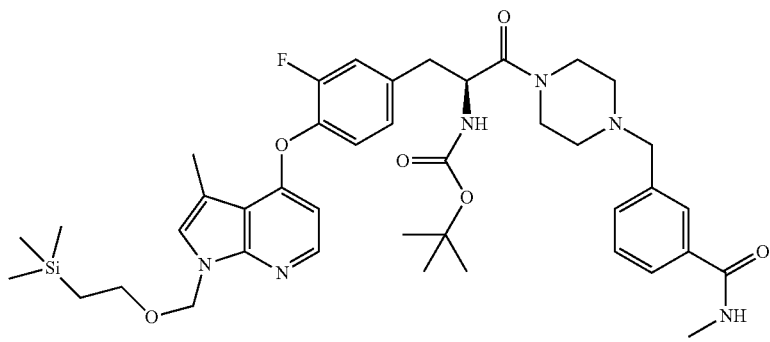 [SMILES: CNC(=O)c1cccc(CN2CCN(C(=O)[C@H](Cc3ccc(Oc4ccnc5c4c(C)cn5COCC[Si](C)(C)C)c(F)c3)NC(=O)OC(C)(C)C)CC2)c1]

Intermediate 165C was prepared from Intermediate 165B and methylamine using a method similar to that used in Step F of Example 1.
LCMS (Method 4): Rt=1.37 min, m/z 775.5 [M+H]$^+$ Step D. (S)-3-((4-(2-amino-3-(3-fluoro-4-((3-methyl-1H-pyrrolo[2,3-b]pyridin-4-yl)oxy)phenyl)propanoyl)piperazin-1-yl)methyl)-N-methylbenzamide (Example 165)

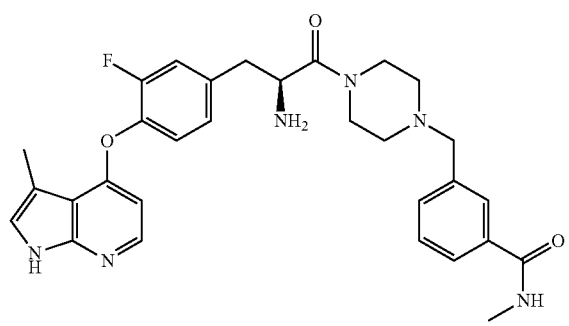 [SMILES: CNC(=O)c1cccc(CN2CCN(C(=O)[C@@H](N)Cc3ccc(Oc4ccnc5[nH]cc(C)c45)c(F)c3)CC2)c1]

Example 165 was prepared from Intermediate 165C using a method similar to that used for in Step G of Example 1.

LCMS (Method 1): Rt=1.93 min, m/z 545.2 [M+H]$^+$ $^1$H NMR (400 MHz, DMSO) δ 11.41 (s, 1H), 8.42-8.38 (m, 1H), 7.98 (d, J=5.4 Hz, 1H), 7.75 (s, 1H), 7.73-7.69 (m, 1H), 7.41 (d, J=6.5 Hz, 2H), 7.31 (dd, J=2.1, 12.0 Hz, 1H), 7.24 (dd, J=8.4, 8.4 Hz, 1H), 7.14-7.08 (m, 2H), 6.16 (d, J=5.4 Hz, 1H), 3.93 (dd, J=6.6, 6.6 Hz, 1H), 3.49 (s, 3H), 3.46-3.41 (m, 3H), 2.84-2.76 (m, 4H), 2.67 (dd, J=7.4, 13.1 Hz, 1H), 2.38 (s, 3H), 2.37-2.30 (m, 2H), 2.23-2.18 (m, 1H), 2.06 (dd, J=7.4, 7.4 Hz, 1H), 1.70 (s, 2H).

Example 166

The following example was prepared using a similar method of Example 165 by replacing in Step A the aldehyde with that indicated in table below.

| Ex | Structure | Aldehyde | 1H NMR | LC-MS |
|---|---|---|---|---|
| 166 | 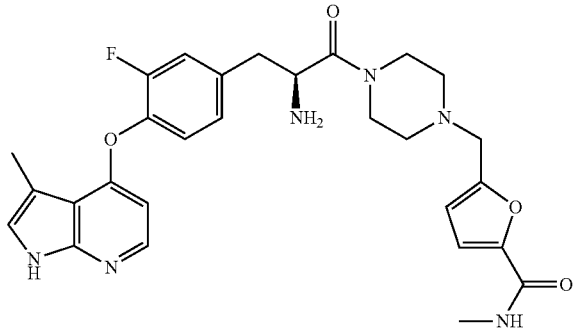 [SMILES: CNC(=O)c1ccc(CN2CCN(C(=O)[C@@H](N)Cc3ccc(Oc4ccnc5[nH]cc(C)c45)c(F)c3)CC2)o1]<br>(S)-5-((4-(2-amino-3-(3-fluoro-4-((3-methyl-1H-pyrrolo[2,3-b]pyridin-4-yl)oxy)phenyl)propanoyl)piperazin-1-yl)methyl)-N-methylfuran-2-carboxamide | Methyl 5-formyl-furan-2-carboxylate | $^1$H NMR (400 MHz, DMSO) δ 11.39 (s, 1H), 8.18 (q, J = 4.5 Hz, 1H), 7.98 (d, J = 5.4 Hz, 1H), 7.32 (dd, J = 1.7, 11.8 Hz, 1H), 7.23 (dd, J = 8.4, 8.4 Hz, 1H), 7.14-7.08 (m, 2H), 6.99 (d, J = 3.3 Hz, 1H), 6.41 (d, J = 3.4 Hz, 1H), 6.16 (d, J = 5.4 Hz, 1H), 3.93 (dd, J = 6.8, 6.8 Hz, 1H), 3.51 (s, 2H), 3.49-3.38 (m, 4H), 2.80 (dd, J = 6.1, 13.3 Hz, 1H), 2.72 (d, J = 4.6 Hz, 3H), 2.69-2.62 (m, 1H), 2.39-2.22 (m, 6H), 2.19-2.11 (m, 1H), 1.70 (s, 2H). | Rt = 1.95 min, m/z 535.2 [M + H]$^+$ (Method 1) |

Example 167

Step A. tert-Butyl (S)-(1-(4-benzoylpiperazin-1-yl)-3-(3-fluoro-4-((3-methyl-1-((2-(trimethylsilyl)ethoxy)methyl)-1H-pyrrolo[2,3-b]pyridin-4-yl)oxy)phenyl)-1-oxopropan-2-yl)carbamate (Intermediate 167A)

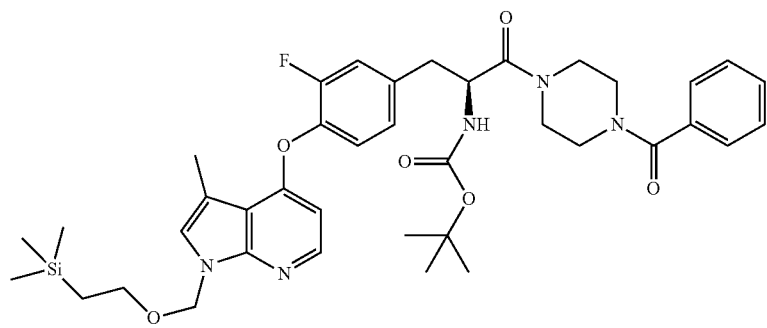 [SMILES: Cc1cn(COCC[Si](C)(C)C)c2nccc(Oc3ccc(C[C@H](NC(=O)OC(C)(C)C)C(=O)N4CCN(C(=O)c5ccccc5)CC4)cc3F)c12]

Intermediate 167A was prepared from Intermediate 152B and benzoic acid using conditions similar to those used in Step F of Example 1.

LCMS (Method 6): Rt=1.81 min, m/z 732.3 [M+H]$^+$

Step B. (S)-2-amino-1-(4-benzoylpiperazin-1-yl)-3-(3-fluoro-4-((3-methyl-1H-pyrrolo[2,3-b]pyridin-4-yl)oxy)phenyl)propan-1-one (Example 167)

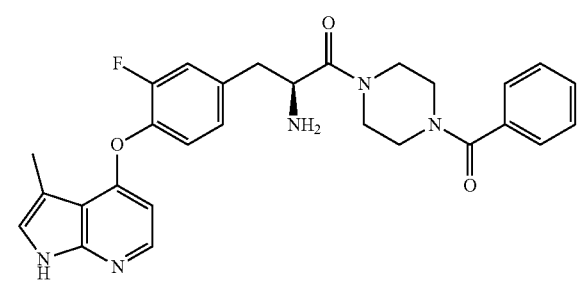 [SMILES: Cc1c[nH]c2nccc(Oc3ccc(C[C@H](N)C(=O)N4CCN(C(=O)c5ccccc5)CC4)cc3F)c12]

Example 167 was prepared from Intermediate 167A using a method similar to Step G of Example 1.

LCMS (Method 2): Rt=3.51 min, m/z 502.0 [M+H]$^+$ $^1$H NMR (400 MHz, d6-DMSO) δ 11.40 (s, 1H), 7.96 (d, J=5.4 Hz, 1H), 7.47-7.38 (m, 5H), 7.35 (d, J=11.8 Hz, 1H), 7.24 (t, J=8.4 Hz, 1H), 7.14-7.10 (m, 2H), 6.13 (d, J=5.4 Hz, 1H), 3.94-3.94 (m, 1H), 3.71-3.37 (m, 7H), 3.26-3.01 (m, 1H), 2.84 (dd, J=5.8, 13.2 Hz, 1H), 2.72-2.65 (m, 1H), 2.38 (s, 3H), 1.75 (s, 2H).

Example 168 to 177

The following examples were prepared in a similar manner to Example 167 by replacing in Step A the corresponding carboxylic acid with those indicated in the table below.

| Ex | Structure | Acid | 1H NMR | LC-MS |
|---|---|---|---|---|
| 168 | 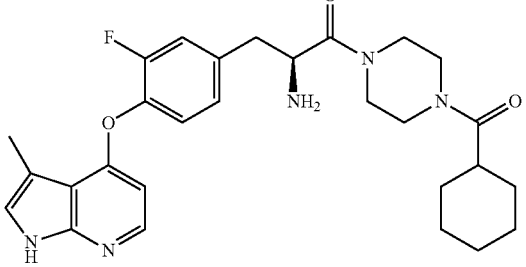<br>(S)-2-amino-1-(4-(cyclohexanecarbonyl)piperazin-1-yl)-3-(3-fluoro-4-((3-methyl-1H-pyrrolo[2,3-b]pyridin-4-yl)oxy)phenyl)propan-1-one | Cyclohexane-carboxylic acid | $^1$H NMR (400 MHz, d6-DMSO) δ 11.40 (s, 1H), 7.95 (d, J = 5.5 Hz, 1H), 7.34 (d, J = 11.7 Hz, 1H), 7.28-7.20 (m, 1H), 7.15-7.10 (m, 2H), 6.13-6.08 (m, 1H), 3.97-3.92 (m, 1H), 3.54-3.38 (m, 6H), 3.21-3.13 (m, 1H), 2.82 (dd, J = 6.2, 13.1 Hz, 1H), 2.70 (dd, J = 7.2, 13.1 Hz, 1H), 2.61-2.53 (m, 1H), 2.37 (d, J = 0.9 Hz, 3H), 1.80-1.61 (m, 7H), 1.30-1.15 (m, 6H). | Rt = 3.78 min, m/z 508.1 [M + H]$^+$ (Method 2) |
| 169 | 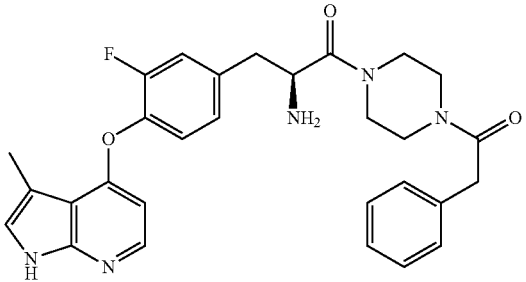 [SMILES: Cc1c[nH]c2nccc(Oc3ccc(C[C@H](N)C(=O)N4CCN(C(=O)Cc5ccccc5)CC4)cc3F)c12]<br>(S)-2-amino-3-(3-fluoro-4-((3-methyl-1H-pyrrolo[2,3-b]pyridin-4-yl)oxy)phenyl)-1-(4-(2-phenylacetyl-)piperazin-1-yl)propan-1-one | 2-Phenylacetic acid | $^1$H NMR (400 MHz, d6-DMSO) δ 11.40 (s, 1H), 7.96 (d, J = 5.4 Hz, 1H), 7.34-7.19 (m, 7H), 7.14-7.09 (m, 2H), 6.14-6.12 (m, 1H), 3.99-3.89 (m, 1H), 3.74 (s, 2H), 3.54-3.33 (m, 7H), 3.28-3.19 (m, 1H), 2.82 (dd, J = 6.0, 13.4 Hz, 1H), 2.70-2.62 (m, 1H), 2.38 (s, 3H), 1.70 (s, 2H). | Rt = 3.62 min, m/z 516.1 [M + H]$^+$ (Method 2) |
| 170 | 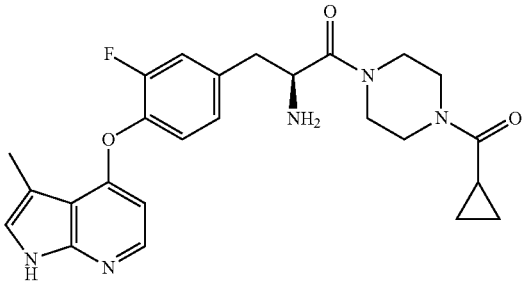 [SMILES: Cc1c[nH]c2nccc(Oc3ccc(C[C@H](N)C(=O)N4CCN(C(=O)C5CC5)CC4)cc3F)c12]<br>(S)-2-amino-1-(4-(cyclopropanecarbonyl)piperazin-1-yl)-3-(3-fluoro-4-((3-methyl-1H-pyrrolo[2,3-b]pyridin-4-yl)oxy)phenyl)propan-1-one | Cyclopropane-carboxylic acid | $^1$H NMR (400 MHz, d6-DMSO) δ 11.40 (s, 1H), 7.95 (d, J = 5.4 Hz, 1H), 7.34 (dd, J = 1.6, 11.9 Hz, 1H), 7.24 (t, J = 8.4 Hz, 1H), 7.15-7.10 (m, 2H), 6.11 (d, J = 5.0 Hz, 1H), 3.97 (t, J = 6.8 Hz, 1H), 3.74-3.36 (m, 7H), 3.28-3.12 (m, 1H), 2.83 (dd, J = 6.3, 13.2 Hz, 1H), 2.70 (dd, J = 7.4, 13.2 Hz, 1H), 2.38 (d, J = 0.9 Hz, 3H), 2.01-1.92 (m, 1H), 1.76 (s, 2H), 0.74-0.69 (m, 4H). | Rt = 3.25 min, m/z 466.1 [M + H]$^+$ (Method 2) |
| 171 | 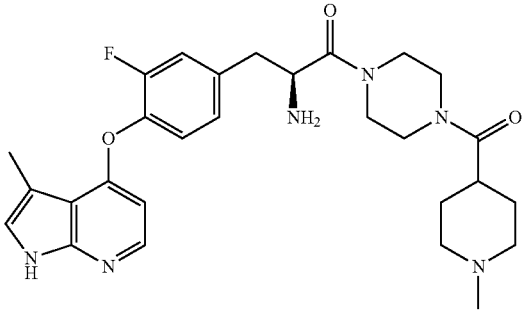 [SMILES: Cc1c[nH]c2nccc(Oc3ccc(C[C@H](N)C(=O)N4CCN(C(=O)C5CCN(C)CC5)CC4)cc3F)c12]<br>(S)-2-amino-3-(3-fluoro-4-((3-methyl-1H-pyrrolo[2,3-b]pyridin-4-yl)oxy)phenyl)-1-(4-(1-methylpiperidine-4-carbonyl)piperazin-1-yl)propan-1-one | 1-Methyl-piperidine-4-carboxylic acid | $^1$H NMR (400 MHz, d6-DMSO) δ 11.40 (s, 1H), 7.96 (d, J = 5.4 Hz, 1H), 7.33 (d, J = 11.7 Hz, 1H), 7.28-7.22 (m, 1H), 7.15-7.11 (m, 2H), 6.11 (s, 1H), 3.96-3.96 (m, 1H), 3.55-3.41 (m, 6H), 3.20-3.15 (m, 1H), 2.87-2.65 (m, 4H), 2.37 (d, J = 0.8 Hz, 3H), 2.13 (s, 3H), 1.92-1.82 (m, 2H), 1.76 (s, 2H), 1.55-1.50 (m, 6H). | Rt = 1.84 min, m/z 523.1 [M + H]$^+$ (Method 1) |

| Ex | Structure | Acid | 1H NMR | LC-MS |
|---|---|---|---|---|
| 172 | (S)-2-amino-1-(4-(4-((dimethylamino)methyl)benzoyl)piperazin-1-yl)-3-(3-fluoro-4-((3-methyl-1H-pyrrolo[2,3-b]pyridin-4-yl)oxy)phenyl)propan-1-one | 4-((Dimethylamino)methyl) benzoic acid | $^1$H NMR (400 MHz, d6-DMSO) δ 11.41 (d, J = 1.7 Hz, 1H), 7.97 (d, J = 5.4 Hz, 1H), 7.40-7.37 (m, 5H), 7.27 (dd, J = 8.4, 8.4 Hz, 1H), 7.15-7.11 (m, 2H), 6.15 (d, J = 5.4 Hz, 1H), 4.13 (s, 2H), 3.56-3.42 (m, 11H), 2.91 (dd, J = 5.7, 13.4 Hz, 1H), 2.78 (d, J = 7.5 Hz, 1H), 2.38 (s, 3H), 2.16 (s, 6H). | Rt = 1.91 min, m/z 559.2 [M + H]$^+$ (Method 1) |
| 173 | (S)-2-amino-1-(4-(3-((dimethylamino)methyl)benzoyl)piperazin-1-yl)-3-(3-fluoro-4-((3-methyl-1H-pyrrolo[2,3-b]pyridin-4-yl)oxy)phenyl)propan-1-one | 3-((Dimethylamino)methyl) benzoic acid | $^1$H NMR (400 MHz, d6-DMSO) δ 11.44 (d, J = 1.9 Hz, 1H), 7.98 (d, J = 5.2 Hz, 1H), 7.56-7.46 (m, 3H), 7.46-7.38 (m, 2H), 7.32 (dd, J = 8.3, 8.3 Hz, 1H), 7.17 (d, J = 11.5 Hz, 2H), 6.20 (d, J = 5.4 Hz, 1H), 4.67 (s, 1H), 3.90-3.47 (m, 11H), 3.18-3.01 (m, 3H), 2.46 (s, 6H), 2.38 (s, 3H). | Rt = 1.95 min, m/z 559.2 [M + H]$^+$ (Method 1) |
| 174 | (S)-2-amino-3-(3-fluoro-4-((3-methyl-1H-pyrrolo[2,3-b]pyridin-4-yl)oxy)phenyl)-1-(4-nicotinoylpiperazin-1-yl)propan-1-one | Pyridine-3-carboxylic acid | $^1$H NMR (400 MHz, DMSO) δ 11.40 (s, 1H), 8.67 (dd, J = 1.7, 4.9 Hz, 1H), 8.63 (d, J = 1.5 Hz, 1H), 7.97 (d, J = 5.4 Hz, 1H), 7.87-7.82 (m, 1H), 7.49 (dd, J = 4.9, 7.8 Hz, 1H), 7.35 (d, J = 12.1 Hz, 1H), 7.24 (dd, J = 8.3, 8.3 Hz, 1H), 7.16-7.10 (m, 2H), 6.14 (d, J = 5.3 Hz, 1H), 3.97 (s, 2H), 3.59-3.50 (m, 7H), 2.87-2.81 (m, 1H), 2.73-2.66 (m, 1H), 2.38 (s, 3H). | Rt = 2.11 min, m/z 503.2 [M + H]$^+$ (Method 1) |

| Ex | Structure | Acid | 1H NMR | LC-MS |
|---|---|---|---|---|
| 175 | (S)-2-amino-3-(3-fluoro-4-((3-methyl-1H-pyrrolo[2,3-b]pyridin-4-yl)oxy)phenyl)-1-(4-(1-methyl-1H-pyrazole-4-carbonyl)piperazin-1-yl)propan-1-one | 1-Methyl-1H-pyrazole-4-carboxylic acid | $^1$H NMR (400 MHz, DMSO) δ 11.38 (s, 1H), 8.07 (s, 1H), 7.94 (d, J = 5.4 Hz, 1H), 7.67 (s, 1H), 7.35 (dd, J = 2.1, 12.1 Hz, 1H), 7.25 (dd, J = 8.4, 8.4 Hz, 1H), 7.13 (dd, J = 4.2, 4.2 Hz, 2H), 6.12 (d, J = 5.4 Hz, 1H), 3.97 (dd, J = 6.7, 6.7 Hz, 1H), 3.85 (s, 3H), 3.66-3.42 (m, 8H), 2.85 (dd, J = 6.0, 13.3 Hz, 1H), 2.70 (dd, J = 7.5, 13.2 Hz, 1H), 2.37 (s, 3H). | Rt = 2.17 min, m/z 506.3 [M + H]$^+$ (Method 3) |
| 176 | (S)-2-amino-3-(3-fluoro-4-((3-methyl-1H-pyrrolo[2,3-b]pyridin-4-yl)oxy)phenyl)-1-(4-(1-methyl-1H-imidazole-4-carbonyl)piperazin-1-yl)propan-1-one | 1-Methyl-1H-imidazole-4-carboxylic acid | $^1$H NMR (400 MHz, DMSO) δ 11.39 (s, 1H), 7.66 (d, J = 0.9 Hz, 2H), 7.36 (dd, J = 1.9, 12.1 Hz, 1H), 7.24 (dd, J = 8.4, 8.4 Hz, 1H), 7.13 (dd, J = 1.2, 6.4 Hz, 2H), 6.11 (d, J = 5.2 Hz, 1H), 4.27-3.86 (m, 3H), 3.69 (s, 3H), 3.57-3.45 (m, 6H), 2.83 (dd, J = 6.4, 13.2 Hz, 1H), 2.71 (dd, J = 7.4, 13.2 Hz, 1H), 2.37 (s, 3H. | Rt = 2.06 min, m/z 506.3 [M + H]$^+$ (Method 3) |
| 177 | (S)-2-amino-3-(3-fluoro-4-((3-methyl-1H-pyrrolo[2,3-b]pyridin-4-yl)oxy)phenyl)-1-(4-(thiazole-2-carbonyl)piperazin-1-yl)propan-1-one | Thiazole-2-carboxylic acid | $^1$H NMR (400 MHz, DMSO) δ 11.38 (s, 1H), 8.07-8.02 (m, 2H), 7.91 (dd, J = 4.8, 27.6 Hz, 1H), 7.36 (dd, J = 1.7, 11.9 Hz, 1H), 7.24 (dd, J = 8.4, 8.4 Hz, 1H), 7.14 (d, J = 9.2 Hz, 2H), 6.12 (d, J = 5.1 Hz, 1H), 4.34-4.00 (m, 3H), 3.73-3.48 (m, 6H), 2.89-2.83 (m, 1H), 2.72-2.67 (m, 1H), 2.38-2.34 (m, 3H), 1.83-1.83 (m, 2H). | Rt = 2.45 min, m/z 509.3 [M + H]$^+$ (Method 3) |

Example 178

Step A. tert-Butyl 3-((3-(4-((1H-pyrrolo[2,3-b]pyridin-4-yl)oxy)phenyl)-1-(dimethylamino)-1-oxopropan-2-yl)carbamoyl)pyrrolidine-1-carboxylate (Intermediate 178A)

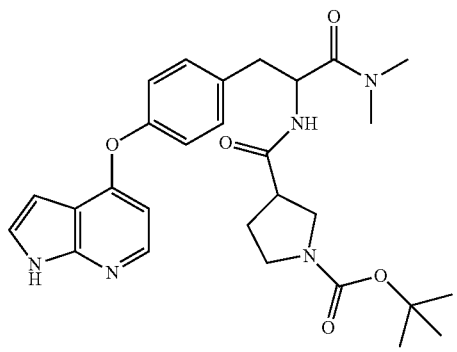 [SMILES: CN(C)C(=O)C(Cc1ccc(Oc2ccnc3[nH]ccc23)cc1)NC(=O)C1CCN(C(=O)OC(C)(C)C)C1]

Example 113 (45 mg, 0.139 mmol), racemic 1-(tert-butoxycarbonyl)pyrrolidine-3-carboxylic acid (33 mg, 0.153 mmol) and DIPEA (72 µL, 0.419 mmol) were dissolved in a mixture of DMF (2 mL) and DCM (5 mL). HATU (63 mg, 0.166 mmol) was added and the reaction was stirred at RT overnight. Evaporation gave a residue which was used without further purification (82 mg).

LCMS (Method 6): Rt=1.08 and 1.09 min, m/z 522.3 [M+H]$^+$

Step B. N-(3-(4-((1H-pyrrolo[2,3-b]pyridin-4-yl)oxy)phenyl)-1-(dimethylamino)-1-oxopropan-2-yl)pyrrolidine-3-carboxamide (Example 178)

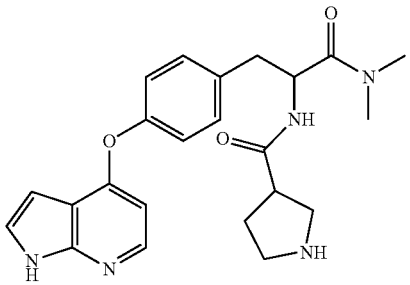 [SMILES: CN(C)C(=O)C(Cc1ccc(Oc2ccnc3[nH]ccc23)cc1)NC(=O)C1CCNC1]

Intermediate 178A (72 mg, crude) was dissolved in DCM (3 mL) and TFA (1 mL) was added. The reaction was stirred at RT overnight and then the volatiles were evaporated. The residue was dissolved in methanol and loaded on to 2 g SCX-2 cartridge which had been conditioned with methanol. After flushing with methanol, the product was eluted with 2M ammonia in methanol. After evaporation of the solvent, the residue was purified by HPLC eluting with a gradient of 10-98% acetonitrile in water (0.1% formic acid added). The desired product was obtained as an off-white solid (24 mg).

LCMS (Method 3): Rt=1.93 min, m/z 422.3 [M+H]$^+$ $^1$H NMR (400 MHz, d6-DMSO) δ 11.72 (s, 1H), 8.45 (d, J=8.4 Hz, 1H), 8.33 (s, 1H), 8.07 (d, J=5.4 Hz, 1H), 7.33-7.30 (m, 3H), 7.10-7.07 (m, 2H), 6.36 (d, J=5.4 Hz, 1H), 6.14 (d, J=2.9 Hz, 1H), 4.96-4.88 (m, 1H), 3.07-2.96 (m, 2H), 2.95 (s, 3H), 2.93-2.88 (m, 2H), 2.87-2.77 (m, 2H), 2.82 (s, 3H), 2.74 (dd, J=6.5, 10.5 Hz, 1H), 1.97-1.73 (m, 2H).

Examples 179 to 180

The following examples were prepared in a similar manner to Example 178 by replacing the appropriate starting material as indicated in the table below

Preparation of Intermediates 179A to 180A

The following intermediates were prepared in a similar manner to Example 1 by replacing in Step 1 the intermediate 1E-a and amine with the corresponding starting materials indicated in the table below.

| Intermediate | Structure | Starting materials | LC-MS |
|---|---|---|---|
| 179A | 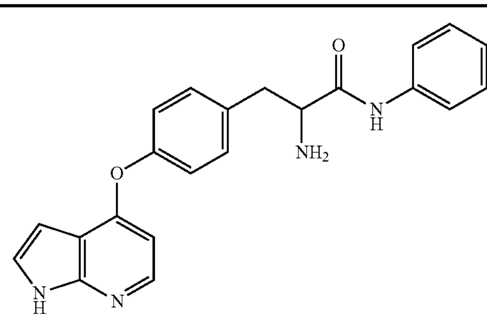 | 1E-f and aniline | Rt = 2.28 min, m/z 373.0 [M + H]$^+$ (Method 3) |

| Intermediate | Structure | Starting materials | LC-MS |
|---|---|---|---|
| 180A | 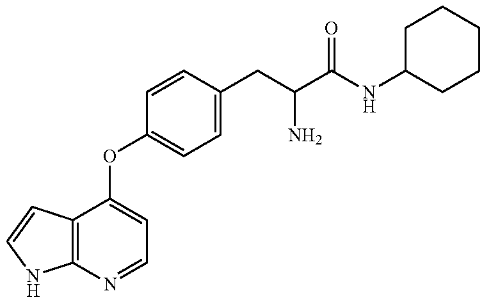 [SMILES: NC(Cc1ccc(Oc2ccnc3[nH]ccc23)cc1)C(=O)NC1CCCCC1] | 1E-f and cyclohexanamine | Rt = 2.40 min, m/z 379.1 [M + H]⁺ (Method 3) |

Preparation of Examples

The following examples were prepared in a similar manner to Example 178 by replacing in Step A the starting material indicated in the table below.

| Ex | Structure | Starting material | 1H NMR | LC-MS |
|---|---|---|---|---|
| 179 | N-(3-(4-((1H-pyrrolo[2,3-b]pyridin-4-yl)oxy)phenyl)-1-oxo-1-(phenylamino)propan-2-yl)pyrrolidine-3-carboxamide | Intermediate 179A | $^1$H NMR (400 MHz, d6-DMSO) δ 11.72 (s, 1H), 10.23-10.19 (m, 1H), 8.61-8.53 (m, 1H), 8.35 (s, 1H), 8.04 (d, J = 5.4 Hz, 1H), 7.59 (d, J = 7.6 Hz, 2H), 7.40-7.28 (m, 5H), 7.12-7.04 (m, 3H), 6.33-6.30 (m, 1H), 6.14-6.10 (m, 1H), 4.77-4.67 (m, 1H), 3.11-2.89 (m, 6H), 2.77 (dd, J = 6.5, 10.9 Hz, 1H), 2.00-1.79 (m, 2H). | Rt = 2.38 min, m/z 470.3 [M + H]⁺ (Method 3) |
| 180 | N-(3-(4-((1H-pyrrolo[2,3-b]pyridin-4-yl)oxy)phenyl)-1-(cyclohexylamino)-1-oxopropan-2-yl)pyrrolidine-3-carboxamide | Intermediate 180A | $^1$H NMR (400 MHz, d6-DMSO) δ 11.73 (s, 1H), 8.39-8.30 (m, 2H), 8.06 (dd, J = 1.3, 5.4 Hz, 1H), 7.96-7.89 (m, 1H), 7.36-7.32 (m, 1H), 7.30 (dd, J = 2.3, 8.5 Hz, 2H), 7.08 (d, J = 8.5 Hz, 2H), 6.35 (dd, J = 5.5, 6.6 Hz, 1H), 6.17 (t, J = 3.0 Hz, 1H), 4.59-4.48 (m, 1H), 3.18-2.91 (m, 6H), 2.84-2.73 (m, 1H), 2.00-1.79 (m, 1H), 1.73-1.50 (m, 6H), 1.27-1.05 (m, 6H). | Rt = 2.47/2.50 min, m/z 476.3 [M + H]⁺ (Method 3) |

Example 181

Step A. Methyl 2-((tert-butoxycarbonyl)amino)-3-(4-((1-tosyl-1H-pyrrolo[2,3-b]pyridin-4-yl)oxy)phenyl)propanoate (Intermediate 181A)

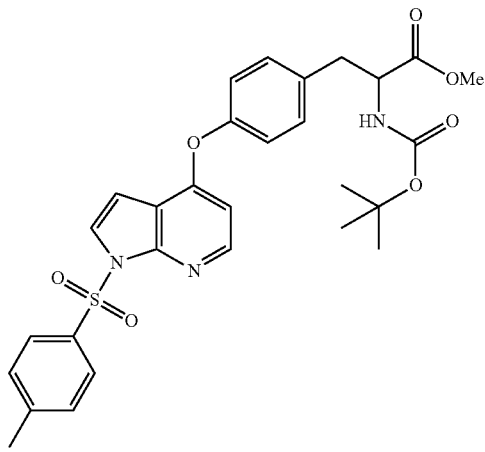 [SMILES: COC(=O)C(Cc1ccc(Oc2ccnc3c2ccn3S(=O)(=O)c2ccc(C)cc2)cc1)NC(=O)OC(C)(C)C]

Intermediate 181A was prepared from Intermediate 131A-a and methyl (tert-butoxycarbonyl)tyrosinate using a method similar to that used in Step D of Example 1.

LCMS (Method 6): Rt=1.69 min, m/z 566.2 [M+H]$^+$

Step B. Methyl 2-amino-3-(4-((1-tosyl-1H-pyrrolo[2,3-b]pyridin-4-yl)oxy)phenyl)propanoate (Intermediate 181B)

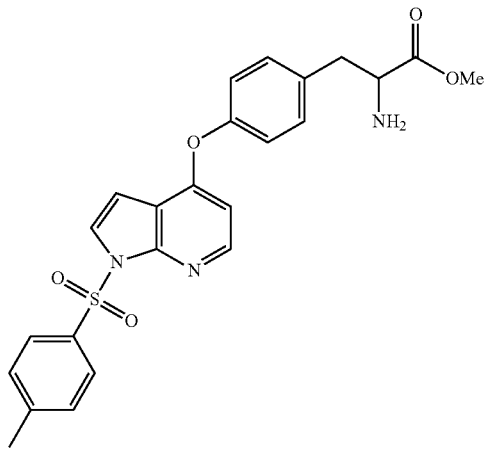 [SMILES: COC(=O)C(N)Cc1ccc(Oc2ccnc3c2ccn3S(=O)(=O)c2ccc(C)cc2)cc1]

Intermediate 181A (2.31 g, 4.09 mmol) was dissolved in DCM (10 mL) and TFA (2 mL) was added. The reaction was stirred at RT for 6 h and then the volatiles were evaporated. The residue was chromatographed on a 24 g Si cartridge eluting with 0-10% methanol in DCM to give the product as a beige solid (2.03 g)

LCMS (Method 6): Rt=1.07 min, m/z 466.2 [M+H]$^+$

Step C. Methyl 2-(cyclohexanecarboxamido)-3-(4-((1-tosyl-1H-pyrrolo[2,3-b]pyridin-4-yl)oxy)phenyl)propanoate (Intermediate 181C)

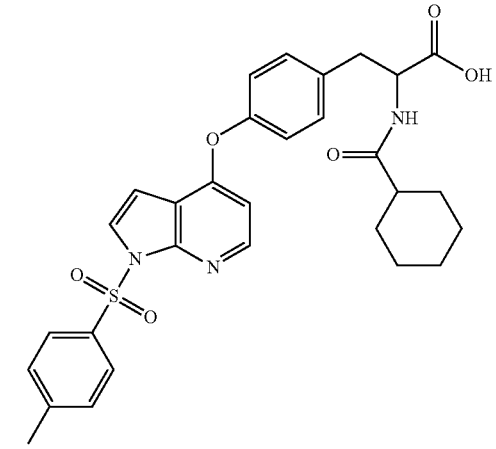 [SMILES: Cc1ccc(S(=O)(=O)n2ccc3c(Oc4ccc(CC(NC(=O)C5CCCCC5)C(=O)O)cc4)ccnc32)cc1]

Intermediate 181B (250 mg, 0.538 mmol) was dissolved in DCM (10 mL) and DIPEA (140 μL, 0.806 mmol) and cyclohexanecarbonyl chloride (87 μL, 0.646 mmol) were added. The reaction was stirred at RT for 18 h and then diluted with DCM (20 mL). The solution was washed with saturated ammonium chloride solution (10 mL) and brine (10 mL), dried (Na$_2$SO$_4$) and evaporated. The product was obtained as a solid (290 mg)

LCMS (Method 5): Rt=1.64 min, m/z 576.3 [M+H]$^+$

Step D. 2-(Cyclohexanecarboxamido)-3-(4-((1-tosyl-1H-pyrrolo[2,3-b]pyridin-4-yl)oxy)phenyl)propanoic acid (Intermediate 181D)

Intermediate 181C (290 mg, 0.504 mmol) was dissolved in methanol (5 mL) and a solution of lithium hydroxide hydrate (32 mg, 0.762 mmol) in water (1 mL) was added. The reaction was stirred at RT overnight. The methanol was evaporated and the aqueous was adjusted to pH 5 by the addition of 1N HCl. The product was extracted into DCM (10 mL) and the solution was dried (Na$_2$SO$_4$) and evaporated to give the desired product as a solid (248 mg).

LCMS (Method 5): Rt=1.56 min, m/z 562.2 [M+H]$^+$

Step E. N-(1-((2-(Dimethylamino)ethyl)amino)-1-oxo-3-(4-((1-tosyl-1H-pyrrolo[2,3-b]pyridin-4-yl)oxy)phenyl)propan-2-yl)cyclohexanecarboxamide (Intermediate 181E)

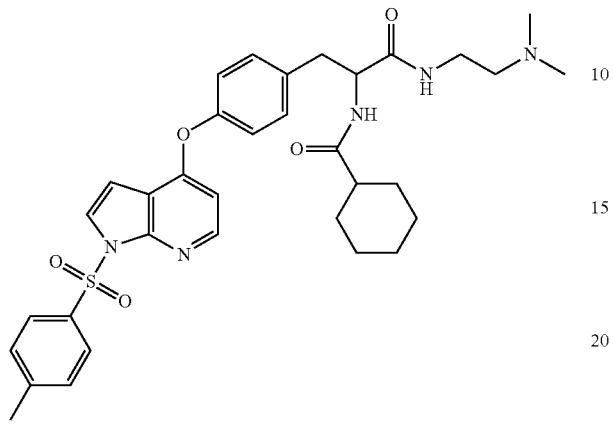

Intermediate 181E was prepared from Intermediate 181D and N,N-dimethylethane-1,2-diamine using a similar method to that used in Step F of Example 1.

LCMS (Method 6): Rt=1.19 min, m/z 632.4 [M+H]$^+$

Step F. N-(3-(4-((1H-pyrrolo[2,3-b]pyridin-4-yl)oxy)phenyl)-1-((2-(dimethylamino)ethyl)amino)-1-oxopropan-2-yl)cyclohexanecarboxamide (Example 181)

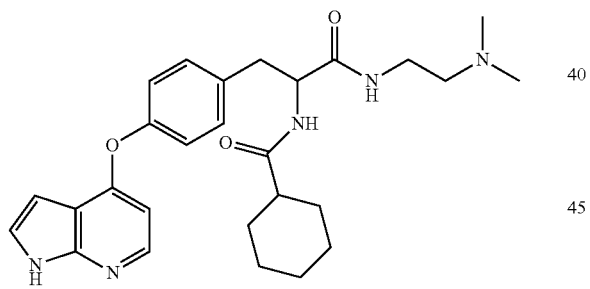

Intermediate 181E (153 mg, 0.267 mmol) was dissolved in methanol (5 mL) and a solution of lithium hydroxide hydrate (22 mg, 0.533 mmol) in water (1.5 mL) was added. The reaction was stirred at RT for 1 h and then THF (3 mL) was added. Stirring was continued at 50° C. for 2 h. The solvents were evaporated and the crude mixture was purified by HPLC eluting with a gradient of 10-98% acetonitrile in water (0.1% NH$_4$OH added). Example 181 was obtained as a white solid (30 mg).

LCMS (Method 1): Rt=2.49 min, m/z 478.3 [M+H]$^+$ $^1$H NMR (400 MHz, DMSO) δ 11.71 (s, 1H), 8.05-8.03 (m, 1H), 7.89 (d, J=8.7 Hz, 1H), 7.82 (dd, J=5.4, 5.4 Hz, 1H), 7.33-7.28 (m, 3H), 7.07 (d, J=8.6 Hz, 2H), 6.34 (d, J=5.4 Hz, 1H), 6.16 (d, J=3.5 Hz, 1H), 4.53-4.45 (m, 1H), 3.18-3.10 (m, 2H), 3.01 (dd, J=4.7, 13.5 Hz, 1H), 2.75 (dd, J=10.1, 13.6 Hz, 1H), 2.28-2.22 (m, 2H), 2.14-2.13 (m, 6H), 1.70-1.54 (m, 4H), 1.50-1.46 (m, 1H), 1.29-1.11 (m, 6H).

Example 182

Step A. Methyl 2-(dimethylamino)-3-(4-((1-tosyl-1H-pyrrolo[2,3-b]pyridin-4-yl)oxy)phenyl)propanoate (Intermediate 182A)

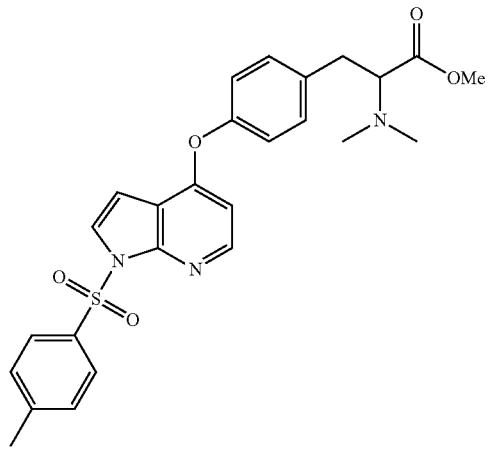 [SMILES: COC(=O)C(Cc1ccc(Oc2ccnc3c2ccn3S(=O)(=O)c2ccc(C)cc2)cc1)N(C)C]

Intermediate 181B (475 mg, 1.022 mmol) was dissolved in IMS (10 mL) and the solution was added to a flask containing 10% palladium on carbon (50 mg). Aqueous paraformaldehyde (37%, 0.61 mL, 8.18 mmol) was added and the vessel was evacuated and back-filled with hydrogen. The reaction was stirred at RT under an atmosphere of hydrogen for 18 h. The mixture was filtered through Celite® and the solvent was evaporated to give the desired product which was used without further purification (603 mg crude).

LCMS (Method 6): Rt=1.13 min, m/z 494.2 [M+H]$^+$

Step B. 3-(4-((1H-Pyrrolo[2,3-b]pyridin-4-yl)oxy)phenyl)-2-(dimethylamino)propanoic acid (Intermediate 182B)

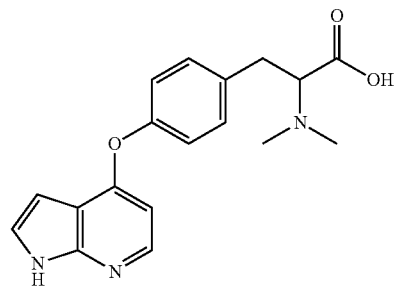 [SMILES: CN(C)C(Cc1ccc(Oc2ccnc3[nH]ccc23)cc1)C(=O)O]

Intermediate 182A (504 mg, 1.02 mmol) was dissolved in methanol (10 mL) and a solution of lithium hydroxide hydrate (86 mg, 2.04 mmol) in water (2 mL) was added. The reaction was stirred at 50° C. for 4 h and then at RT overnight. The solvents were evaporated in vacuo and the crude product was used in the next step without further purification.

LCMS (Method 6): Rt=0.59 min, m/z 326.2 [M+H]$^+$

Step C. 3-(4-((1H-pyrrolo[2,3-b]pyridin-4-yl)oxy)phenyl)-2-(dimethylamino)-N-(tetrahydro-2H-pyran-4-yl)propanamide (Example 182)

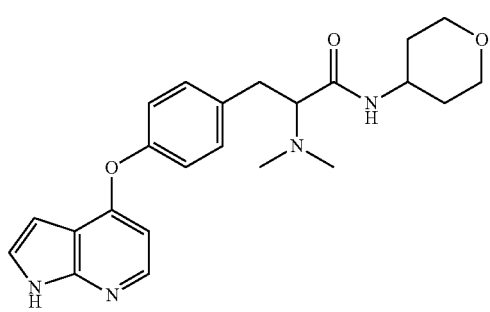 [SMILES: CN(C)C(Cc1ccc(Oc2ccnc3[nH]ccc23)cc1)C(=O)NC1CCOCC1]

Example 182 was prepared from Intermediate 182B and tetrahydro-2H-pyran-4-amine using a method similar to that used in Step F of Example 1.

LCMS (Method 1): Rt=1.95 min, m/z 409.3 [M+H]$^+$ $^1$H NMR (400 MHz, d6-DMSO) δ 11.71 (s, 1H), 8.05 (d, J=5.4 Hz, 1H), 7.72 (d, J=7.8 Hz, 1H), 7.33 (d, J=3.5 Hz, 1H), 7.26 (d, J=8.6 Hz, 2H), 7.06 (d, J=8.6 Hz, 2H), 6.35 (d, J=5.4 Hz, 1H), 6.17 (d, J=3.4 Hz, 1H), 3.82-3.70 (m, 3H), 3.30-3.24 (m, 1H), 3.19-3.12 (m, 2H), 2.96 (dd, J=9.6, 13.0 Hz, 1H), 2.80 (dd, J=5.0, 13.1 Hz, 1H), 2.27 (s, 6H), 1.66-1.59 (m, 1H), 1.50-1.18 (m, 3H).

Example 183

The following example was prepared in a similar manner to Example 182 by replacing in Step C the amine indicated in the table below.

Example 184

Step A. Methyl (S)-2-amino-3-(4-((3-methyl-1-tosyl-1H-pyrrolo[2,3-b]pyridin-4-yl)oxy)phenyl)propanoate (Intermediate 184A)

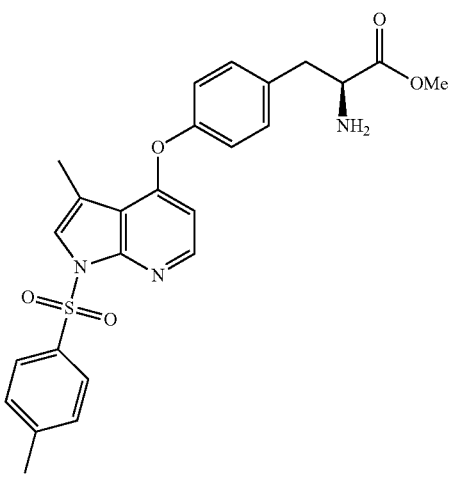 [SMILES: COC(=O)[C@@H](N)Cc1ccc(Oc2ccnc3c2c(C)cn3S(=O)(=O)c2ccc(C)cc2)cc1]

Intermediate 184A was prepared from Intermediate 131E-c using a method similar to that used in Step G of Example 1.

LCMS (Method 8): Rt=1.18 min, m/z 480.2 [M+H]$^+$

| Ex | Structure | Starting materials | 1H NMR | LC-MS |
|----|-----------|-------------------|--------|-------|
| 183 | ![structure] 3-(4-((1H-pyrrolo[2,3-b]pyridin-4-yl)oxy)phenyl)-N-cyclohexyl-2-(dimethylamino)propanamide | Cyclohexanamine | $^1$H NMR (400 MHz, d6-DMSO) δ 11.70 (s, 1H), 8.04 (d, J = 5.4 Hz, 1H), 7.56 (d, J = 8.1 Hz, 1H), 7.32 (d, J = 3.4 Hz, 1H), 7.25 (d, J = 8.6 Hz, 2H), 7.06 (d, J = 8.5 Hz, 2H), 6.34 (d, J = 5.4 Hz, 1H), 6.18 (d, J = 3.4 Hz, 1H), 3.55-3.46 (m, 1H), 3.16 (dd, J = 5.1, 9.6 Hz, 1H), 2.96 (dd, J = 9.7, 13.0 Hz, 1H), 2.77 (dd, J = 5.0, 13.0 Hz, 1H), 2.26 (s, 6H), 1.69-1.47 (m, 5H), 1.27-0.94 (m, 5H). | Rt = 2.48 min, m/z 407.3 [M + H]$^+$ (Method 1) |

Step B. Methyl (S)-2-(dimethylamino)-3-(4-((3-methyl-1-tosyl-1H-pyrrolo[2,3-b]pyridin-4-yl)oxy)phenyl)propanoate (Intermediate 184B)

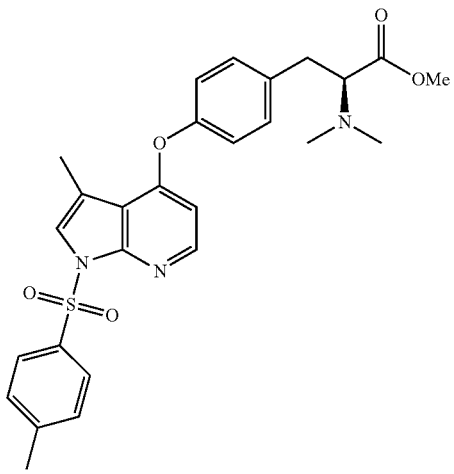 [SMILES: COC(=O)[C@H](Cc1ccc(Oc2ccnc3c2c(C)cn3S(=O)(=O)c2ccc(C)cc2)cc1)N(C)C]

Intermediate 184B was prepared from Intermediate 184A using a method similar to that used for Intermediate 182A.

LCMS (Method 6): Rt=1.17 min, m/z 508.4 [M+H]$^+$

Step C. (S)-2-(Dimethylamino)-3-(4-((3-methyl-1H-pyrrolo[2,3-b]pyridin-4-yl)oxy)phenyl)propanoic acid (Intermediate 184C)

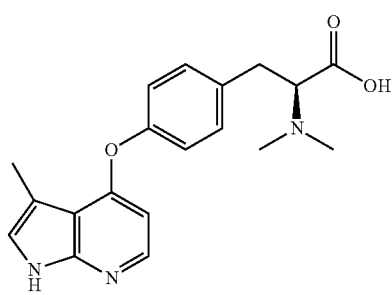 [SMILES: Cc1c[nH]c2nccc(Oc3ccc(C[C@@H](C(=O)O)N(C)C)cc3)c12]

Intermediate 184C was prepared from Intermediate 184E using a method similar to that used for Intermediate 182B.

LCMS (Method 6): Rt=0.71 min, m/z 340.3 [M+H]$^+$

Step D. (S)—N-cyclohexyl-2-(dimethylamino)-3-(4-((3-methyl-1H-pyrrolo[2,3-b]pyridin-4-yl)oxy)phenyl)propanamide (Example 184)

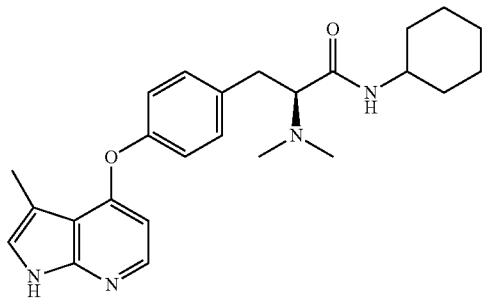 [SMILES: Cc1c[nH]c2nccc(Oc3ccc(C[C@@H](C(=O)NC4CCCCC4)N(C)C)cc3)c12]

Example 184 was prepared from Intermediate 184C and cyclohexanamine using a method similar to that used for amide coupling in step F of Example 1.

LCMS (Method 1): Rt=2.59 min, m/z 421.3 [M+H]$^+$ $^1$H NMR (400 MHz, d6-DMSO) δ 11.35 (s, 1H), 7.98-7.96 (m, 1H), 7.54 (d, J=8.1 Hz, 1H), 7.24 (d, J=8.6 Hz, 2H), 7.12 (s, 1H), 7.02 (d, J=8.5 Hz, 2H), 6.19 (d, J=5.4 Hz, 1H), 3.55-3.46 (m, 1H), 3.17-3.11 (m, 1H), 2.94 (dd, J=9.6, 13.0 Hz, 1H), 2.76 (dd, J=5.1, 13.0 Hz, 1H), 2.31 (d, J=1.0 Hz, 3H), 2.26 (s, 6H), 1.71-1.46 (m, 5H), 1.29-0.93 (m, 5H).

(ee %=75%)

Example 185

Step A. Methyl 2-((cyclohexylmethyl)amino)-3-(4-((1-tosyl-1H-pyrrolo[2,3-b]pyridin-4-yl)oxy)phenyl)propanoate (Intermediate 185A)

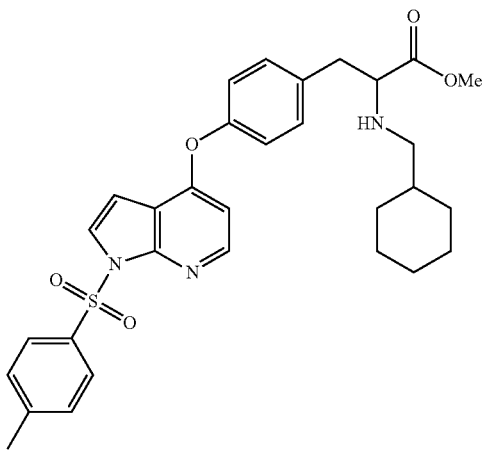 [SMILES: COC(=O)C(Cc1ccc(Oc2ccnc3c2ccn3S(=O)(=O)c2ccc(C)cc2)cc1)NCC1CCCCC1]

Intermediate 181B (250 mg, 0.538 mmol) and cyclohexanecarbaldehyde (72 µl, 0.589 mmol) were dissolved in DCM (5 mL) and sodium triacetoxyborohydride (228 mg, 1.08 mmol) was added. The reaction was stirred at RT for 1 h. The reaction mixture was washed with saturated aqueous ammonium chloride (5 mL) and brine (5 mL), dried (Na$_2$SO$_4$) and evaporated. The product was used in the next reaction without purification (255 mg).

LCMS (Method 5): Rt=1.26 min, m/z 562.3 [M+H]$^+$

Step B. 2-((Cyclohexylmethyl)amino)-3-(4-((1-tosyl-1H-pyrrolo[2,3-b]pyridin-4-yl)oxy)phenyl)propanoic acid (Intermediate 185B)

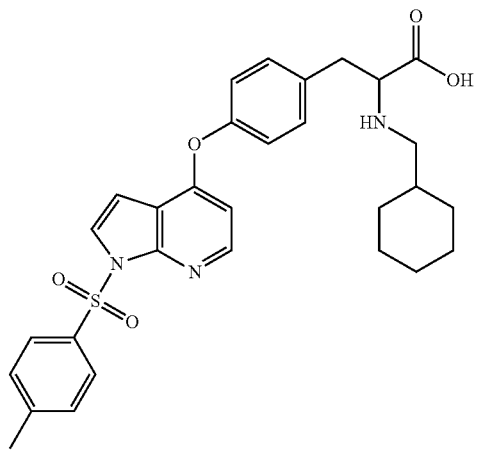 [SMILES: Cc1ccc(S(=O)(=O)n2ccc3c(Oc4ccc(CC(NCC5CCCCC5)C(=O)O)cc4)ccnc32)cc1]

Intermediate 185B was prepared from intermediate 185A using a procedure similar to that used in Step E of Example 1.

LCMS (Method 5): Rt=1.31 min, m/z 548.2 [M+H]$^+$

Step C. 2-((Cyclohexylmethyl)amino)-N-methyl-3-(4-((1-tosyl-1H-pyrrolo[2,3-b]pyridin-4-yl)oxy)phenyl)propanamide (Intermediate 185C)

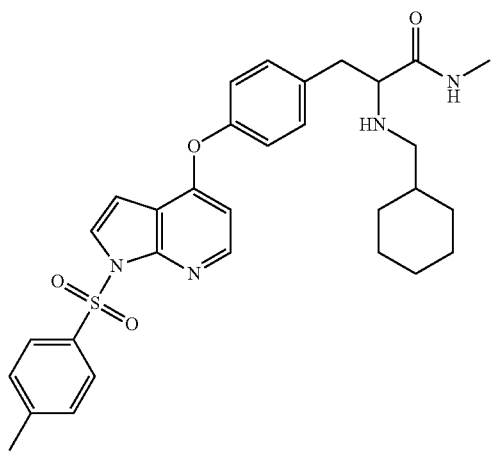 [SMILES: CNC(=O)C(Cc1ccc(Oc2ccnc3c2ccn3S(=O)(=O)c2ccc(C)cc2)cc1)NCC1CCCCC1]

Intermediate 185C was prepared from intermediate 185B and methylamine (2M in THF) using a procedure similar to that used for step F of Example 1.

LCMS (Method 6): Rt=1.19 min, m/z 561.3 [M+H]$^+$

Step D. 3-(4-((1H-pyrrolo[2,3-b]pyridin-4-yl)oxy)phenyl)-2-((cyclohexylmethyl)amino)-N-methylpropanamide (Example 185)

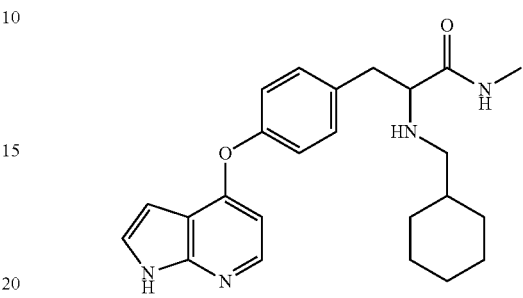

Example 185 was prepared from intermediate 185C using a procedure similar to that used for Step B of Example 182.

LCMS (Method 1): Rt=2.43 min, m/z 407.3 [M+H]$^+$ $^1$H NMR (400 MHz, d6-DMSO) δ 11.71 (s, 1H), 8.06 (d, J=5.4 Hz, 1H), 7.77-7.70 (m, 1H), 7.32 (d, J=3.5 Hz, 1H), 7.27 (d, J=8.4 Hz, 2H), 7.08 (d, J=8.5 Hz, 2H), 6.37 (d, J=5.4 Hz, 1H), 6.14 (d, J=3.4 Hz, 1H), 3.18-3.10 (m, 1H), 2.84 (dd, J=6.0, 13.4 Hz, 1H), 2.70 (dd, J=7.9, 13.4 Hz, 1H), 2.57 (d, J=4.7 Hz, 3H), 2.34-2.21 (m, 1H), 2.17-2.09 (m, 1H), 1.68-1.56 (m, 6H), 1.32-1.20 (m, 1H), 1.19-1.05 (m, 3H), 0.84-0.73 (m, 2H).

Example 186

Step A. tert-Butyl (S)-(1-(cyclohexyl amino)-3-(3-fluoro-4-hydroxyphenyl)-1-oxopropan-2-yl)carbamate (Intermediate 186A)

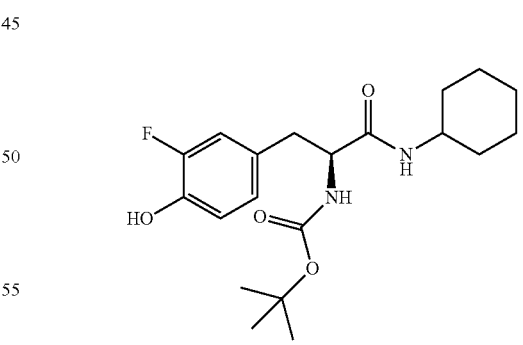

Intermediate 186A was prepared from (S)-2-((tert-butoxycarbonyl)amino)-3-(3-fluoro-4-hydroxyphenyl)propanoic acid and cyclohexanamine using a procedure similar to that for Step F of Example 1.

LCMS (Method 6): Rt=1.35 min, m/z 403.3 [M+Na]$^+$

Step B. tert-Butyl (S)-(1-(cyclohexylamino)-3-(3-fluoro-4-((1-((2-(trimethylsilyl)ethoxy)methyl)-1H-pyrrolo[2,3-b]pyridin-4-yl)oxy)phenyl)-1-oxopropan-2-yl)carbamate (Intermediate 186B)

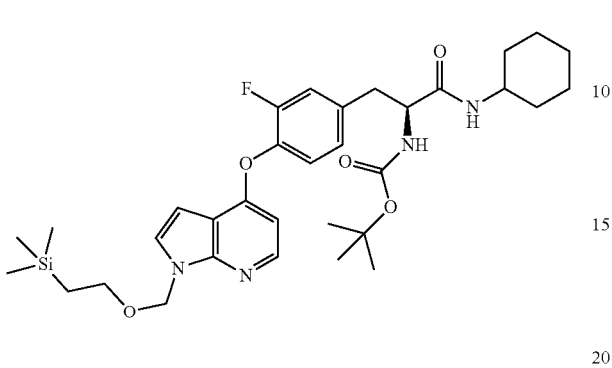

Intermediate 186B was prepared from Intermediate 186A and Intermediate 1C-c using a method similar to that used for Step D of Example 1.

LCMS (Method 6): Rt=1.84 min, m/z 627.4 [M+H]$^+$

Step C. tert-Butyl (S)-(3-(4-((3-bromo-1-((2-(trimethylsilyl)ethoxy)methyl)-1H-pyrrolo[2,3-b]pyridin-4-yl)oxy)-3-fluorophenyl)-1-(cyclohexylamino)-1-oxopropan-2-yl)carbamate (Intermediate 186C)

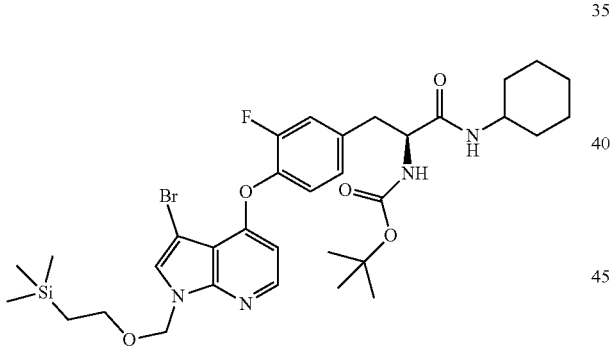

Intermediate 186B (580 mg, 0.927 mmol) was dissolved in acetonitrile (15 mL) and the solution was stirred at 0° C. NBS (173 mg, 0.972 mmol) was added and the reaction was stirred for 30 min at 0° C. Stirring was continued at RT for 1 h and then 1M sodium thiosulfate (15 mL) was added. The product was extracted into ethyl acetate (3×10 mL) and the combined extracts were dried (Na$_2$SO$_4$) and evaporated. The residue was chromatographed on a 12 g Si cartridge eluting with 0-30% ethyl acetate in cyclohexane. The pure product was obtained as a cream solid (351 mg).

LCMS (Method 6): Rt=1.91 min, m/z 705.3/707.3 [M+H]$^+$

Step D. (S)-2-amino-3-(4-((3-bromo-1H-pyrrolo[2,3-b]pyridin-4-yl)oxy)-3-fluorophenyl)-N-cyclohexylpropanamide (Example 186)

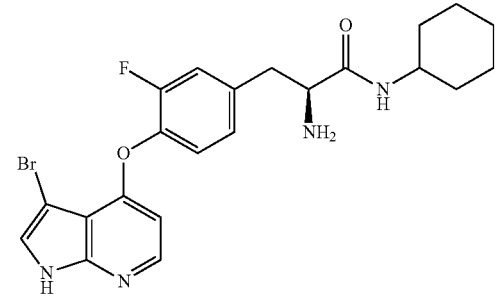 [SMILES: N[C@@H](Cc1ccc(Oc2ccnc3[nH]cc(Br)c23)c(F)c1)C(=O)NC1CCCCC1]

Example 186 was prepared from Intermediate 186C using a similar procedure to that used for Step G of Example 1.

LCMS (Method 1): Rt=3.08 min, m/z 475.1/477.1 [M+H]$^+$ $^1$H NMR (400 MHz, d6-DMSO) δ 12.16 (s, 1H), 8.08 (d, J=5.5 Hz, 1H), 7.62-7.60 (m, 2H), 7.30-7.23 (m, 2H), 7.09 (d, J=8.3 Hz, 1H), 6.27-6.24 (m, 1H), 3.55-3.47 (m, 1H), 3.40-3.35 (m, 1H), 2.88 (dd, J=5.8, 13.2 Hz, 1H), 2.71 (dd, J=7.4, 13.2 Hz, 1H), 1.82 (s, 2H), 1.69-1.49 (m, 5H), 1.32-1.02 (m, 5H).

Example 187

Step A. tert-Butyl (S)-(1-(4-benzylpiperazin-1-yl)-3-(3-fluoro-4-hydroxyphenyl)-1-oxopropan-2-yl)carbamate (Intermediate 187A)

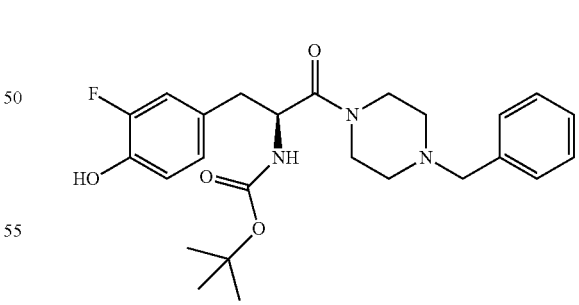

Intermediate 187A was prepared from N-Boc-3-fluoro-L-tyrosine and 1-benzylpiperazine using a method similar to that used for Step F of Example 1.

LCMS (Method 6): Rt=0.94 min, m/z 458.3 [M+H]$^+$

Step B. tert-Butyl (S)-(1-(4-benzylpiperazin-1-yl)-3-(3-fluoro-4-((1-((2-(trimethylsilyl)ethoxy)methyl)-1H-pyrrolo[2,3-b]pyridin-4-yl)oxy)phenyl)-1-oxopropan-2-yl)carbamate (Intermediate 187B)

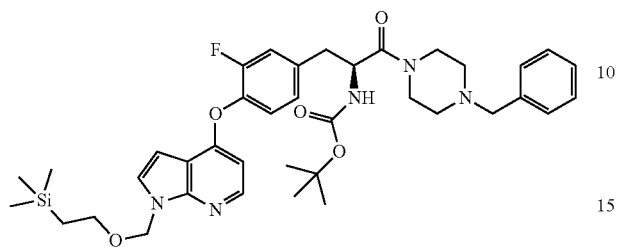

Intermediate 187B was prepared from Intermediate 187A and Intermediate 1C-c using a similar procedure to that used for Step D of Example 1.
LCMS (Method 6): Rt=1.42 min, m/z 704.4 [M+H]$^+$ Step C. tert-Butyl (S)-(1-(4-benzylpiperazin-1-yl)-3-(4-((3-bromo-1-((2-(trimethylsilyl)ethoxy)methyl)-1H-pyrrolo[2,3-b]pyridin-4-yl)oxy)-3-fluorophenyl)-1-oxopropan-2-yl)carbamate (Intermediate 187C)

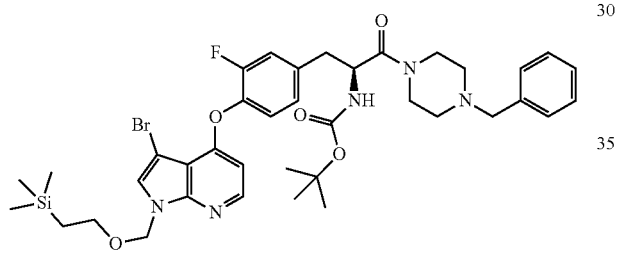

Intermediate 187C was prepared from Intermediate 187B using a similar procedure to that used for Intermediate 186C.
LCMS (Method 6): Rt=1.49 min, m/z 782.3/784.3 [M+H]$^+$ Step D. (S)-2-amino-1-(4-benzylpiperazin-1-yl)-3-(4-((3-bromo-1H-pyrrolo[2,3-b]pyridin-4-yl)oxy)-3-fluorophenyl)propan-1-one (Example 187)

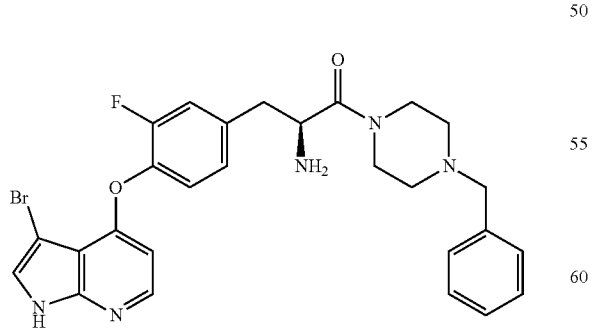

Example 187 was synthesized from Intermediate 187C using a similar procedure to that used for Step G of Example 1.
LCMS (Method 1): Rt=2.42 min, m/z 552.2 [M+H]$^+$ $^1$H NMR (400 MHz, DMSO) δ 12.17 (s, 1H), 8.09 (d, J=5.4 Hz, 1H), 7.63 (s, 1H), 7.35-7.24 (m, 6H), 7.12 (d, J=8.3 Hz, 1H), 6.27-6.25 (m, 1H), 3.94 (t, J=6.9 Hz, 1H), 3.55-3.38 (m, 5H), 2.80 (dd, J=6.4, 13.1 Hz, 1H), 2.68 (dd, J=7.3, 13.3 Hz, 1H), 2.34-2.33 (m, 2H), 2.20-2.16 (m, 1H), 2.04 (m, 1H), 1.78-1.78 (m, 2H).

Example 188

Step A. Methyl (S)-3-(4-((3-bromo-1-((2-(trimethylsilyl)ethoxy)methyl)-1H-pyrrolo[2,3-b]pyridin-4-yl)oxy)phenyl)-2-((tert-butoxycarbonyl)amino)propanoate (Intermediate 188A)

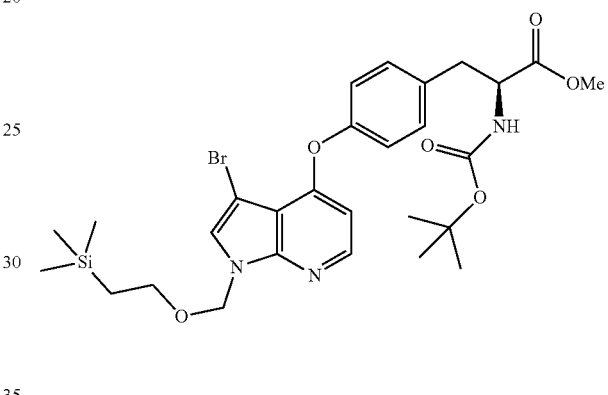

Intermediate 188A was prepared from Intermediate 1D-e using a procedure similar to that of Intermediate 186C.
LCMS (Method 6): Rt=1.88 min, m/z 620.2/622.2 [M+H]$^+$ Step B. (S)-3-(4-((3-Bromo-1-((2-(trimethylsilyl)ethoxy)methyl)-1H-pyrrolo[2,3-b]pyridin-4-yl)oxy)phenyl)-2-((tert-butoxycarbonyl)amino)propanoic acid (Intermediate 188B)

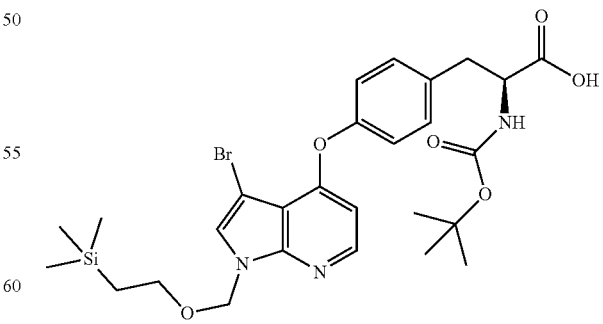

Intermediate 188B was prepared from Intermediate 188A using a procedure similar to that in Step E of Example 1.
LCMS (Method 6): Rt=1.79 min, m/z 606.2/608.2 [M+H]$^+$

Step C. tert-Butyl (S)-(3-(4-((3-bromo-1-((2-(trimethylsilyl)ethoxy)methyl)-1H-pyrrolo[2,3-b]pyridin-4-yl)oxy)phenyl)-1-(cyclohexylamino)-1-oxopropan-2-yl)carbamate (Intermediate 188C)

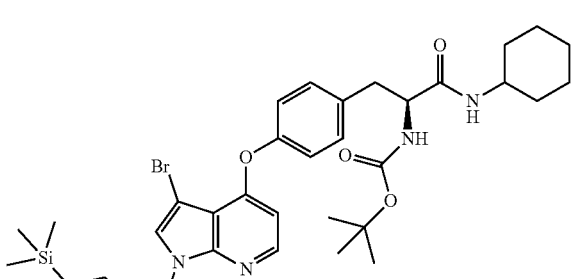

Intermediate 188C was prepared from Intermediate 188B and cyclohexanamine using a procedure similar to that used for Step F of Example 1.

LCMS (Method 6): Rt=1.91 min, m/z 687.3/689.3 [M+H]$^+$

Step D. (S)-2-amino-3-(4-((3-bromo-1H-pyrrolo[2,3-b]pyridin-4-yl)oxy)phenyl)-N-cyclohexylpropanamide (Example 188)

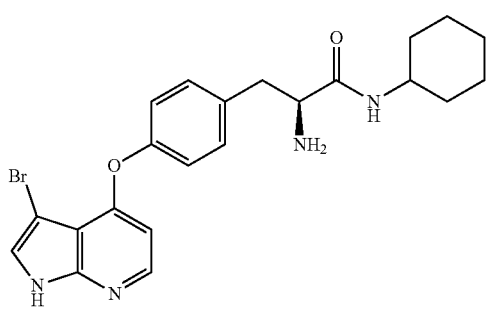

Example 188 was prepared from Intermediate 188C using a similar procedure to that used for Step G of Example 1.

LCMS (Method 1): Rt=3.01 min, m/z 457.1/459.1 [M+H]$^+$ $^1$H NMR (400 MHz, d6-DMSO) δ 12.11 (s, 1H), 8.07 (d, J=5.4 Hz, 1H), 7.60-7.58 (m, 2H), 7.28 (d, J=8.6 Hz, 2H), 7.10-7.07 (m, 2H), 6.29 (d, J=5.4 Hz, 1H), 3.55-3.46 (m, 1H), 3.39-3.35 (m, 1H), 2.87 (dd, J=5.8, 13.2 Hz, 1H), 2.68 (dd, J=7.4, 13.3 Hz, 1H), 1.76-1.75 (m, 2H), 1.69-1.54 (m, 4H), 1.29-1.16 (m, 3H), 1.16-1.02 (m, 3H).

Example 189

Step A. tert-Butyl (S)-(3-(4-((3-bromo-1-((2-(trimethylsilyl)ethoxy)methyl)-1H-pyrrolo[2,3-b]pyridin-4-yl)oxy)phenyl)-1-oxo-1-((tetrahydro-2H-pyran-4-yl)amino)propan-2-yl)carbamate (Intermediate 189A)

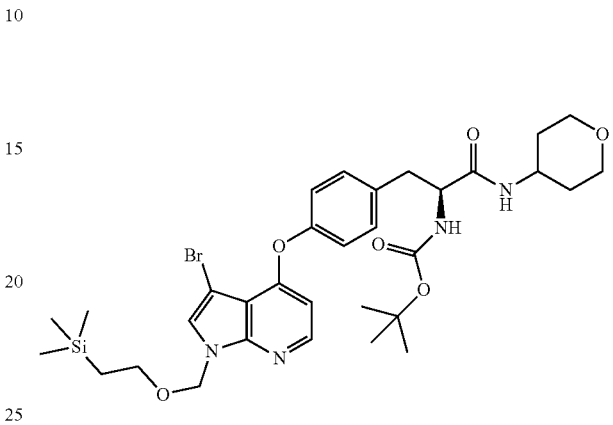

Intermediate 189A was prepared from Intermediate 188B and tetrahydro-2H-pyran-4-amine using a procedure similar to that used for Step F of Example 1.

LCMS (Method 8): Rt=1.76 min, m/z 689.3/691.3 [M+H]$^+$

Step B. (S)-2-amino-3-(4-((3-bromo-1H-pyrrolo[2,3-b]pyridin-4-yl)oxy)phenyl)-N-(tetrahydro-2H-pyran-4-yl)propanamide (Example 189)

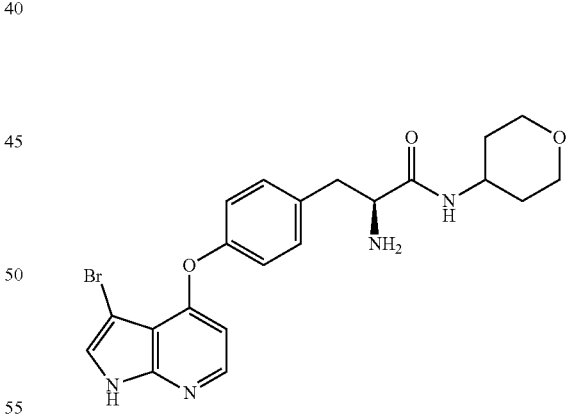

Example 189 was prepared from Intermediate 189A using a similar procedure to that used for deprotection of step G of Example 1.

LCMS (Method 1): Rt=2.49 min, m/z 459.1/461.1

$^1$H NMR (400 MHz, d6-DMSO) δ 12.12 (s, 1H), 8.08 (d, J=5.4 Hz, 1H), 7.73-7.69 (m, 1H), 7.59 (s, 1H), 7.28 (d, J=8.6 Hz, 2H), 7.09 (d, J=8.5 Hz, 2H), 6.30 (d, J=5.4 Hz, 1H), 3.83-3.70 (m, 3H), 3.40-3.34 (m, 3H), 2.87 (dd, J=5.9, 13.2 Hz, 1H), 2.69 (dd, J=7.4, 13.2 Hz, 1H), 1.82 (s, 2H), 1.66-1.55 (m, 2H), 1.43-1.26 (m, 2H).

Example 190. (S)-2-amino-N-cyclohexyl-3-(4-((3-iodo-1H-pyrrolo[2,3-b]pyridin-4-yl)oxy)phenyl)propanamide (Example 190)

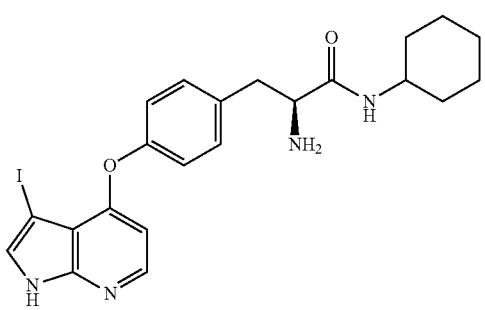 [SMILES: N[C@@H](Cc1ccc(Oc2ccnc3[nH]cc(I)c23)cc1)C(=O)NC1CCCCC1]

Example 190 was prepared similarly to Example 186 by substituting NBS with NIS in Step C.

LCMS (Method 1): Rt=3.03 min, m/z 505.1 [M+H]$^+$ $^1$H NMR (400 MHz, d6-DMSO) δ 12.13 (s, 1H), 8.06 (d, J=5.4 Hz, 1H), 7.60 (s, 1H), 7.58 (d, J=8.3 Hz, 1H), 7.28 (d, J=8.5 Hz, 2H), 7.07 (d, J=8.5 Hz, 2H), 6.29 (d, J=5.4 Hz, 1H), 3.55-3.46 (m, 1H), 3.39-3.34 (m, 1H), 2.87 (dd, J=5.8, 13.2 Hz, 1H), 2.67 (dd, J=7.5, 13.2 Hz, 1H), 1.72-1.52 (m, 6H), 1.30-1.02 (m, 6H).

Example 191. (S)-2-amino-3-(4-((3-chloro-1H-pyrrolo[2,3-b]pyridin-4-yl)oxy)phenyl)-N-cyclohexylpropanamide (Example 191)

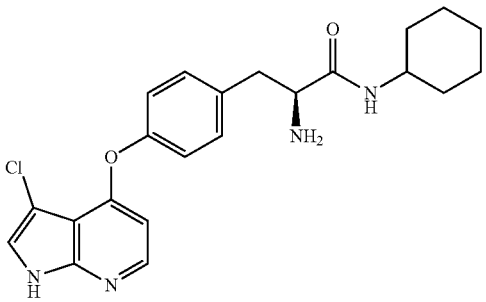 [SMILES: N[C@@H](Cc1ccc(Oc2ccnc3[nH]cc(Cl)c23)cc1)C(=O)NC1CCCCC1]

Example 191 was prepared similarly to Example 186 by substituting in Step C NBS with NCS.

LCMS (Method 1): Rt=2.96 min, m/z 413.2 [M+H]$^+$ $^1$H NMR (400 MHz, d6-DMSO) δ 12.03 (s, 1H), 8.08 (d, J=5.4 Hz, 1H), 7.60-7.55 (m, 2H), 7.28 (d, J=8.6 Hz, 2H), 7.09 (d, J=8.6 Hz, 2H), 6.29 (d, J=5.5 Hz, 1H), 3.55-3.46 (m, 1H), 3.39-3.34 (m, 1H), 2.87 (dd, J=5.8, 13.2 Hz, 1H), 2.68 (dd, J=7.4, 13.3 Hz, 1H), 1.76 (s, 1H), 1.70-1.52 (m, 5H), 1.29-1.05 (m, 6H).

Example 192

Step A. Methyl (S)-2-((tert-butoxycarbonyl)amino)-3-(4-((3-iodo-1-((2-(trimethylsilyl)ethoxy)methyl)-1H-pyrrolo[2,3-b]pyridin-4-yl)oxy)phenyl)propanoate (Intermediate 192A)

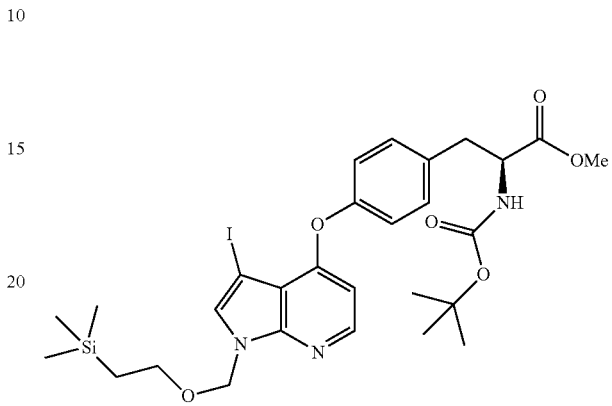

Intermediate 192A was prepared from Intermediate 1D-e in a similar manner to Intermediate 186C using NIS rather than NBS.

LCMS (Method 4): Rt=1.91 min, m/z 668.0 [M+H]$^+$

Step B. (S)-2-((tert-Butoxycarbonyl)amino)-3-(4-((3-iodo-1-((2-(trimethylsilyl)ethoxy)methyl)-1H-pyrrolo[2,3-b]pyridin-4-yl)oxy)phenyl)propanoic acid (Intermediate 192B)

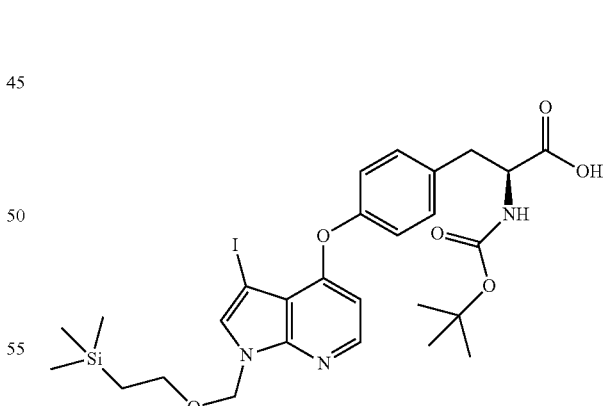

Intermediate 192B was prepared from Intermediate 192A in a similar manner to Step E of Example 1.

LCMS (Method 4): Rt=1.83 min, m/z 654.0 [M+H]$^+$

Step C. tert-Butyl (S)-(1-(4-benzylpiperazin-1-yl)-3-(4-((3-iodo-1-((2-(trimethylsilyl)ethoxy)methyl)-1H-pyrrolo[2,3-b]pyridin-4-yl)oxy)phenyl)-1-oxopropan-2-yl)carbamate (Intermediate 192C)

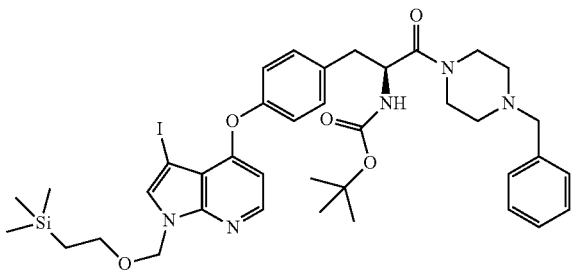 [SMILES: CC(C)(C)OC(=O)N[C@@H](Cc1ccc(Oc2ccnc3c2c(I)cn3COCC[Si](C)(C)C)cc1)C(=O)N1CCN(Cc2ccccc2)CC1]

Intermediate 192C was prepared from Intermediate 192B and 1-benzylpiperazine using the same conditions to those used for Step F of Example 1.
LCMS (Method 4): Rt=2.64 min, m/z 812.1 [M+H]⁺

Step D. (S)-2-amino-1-(4-benzylpiperazin-1-yl)-3-(4-((3-(pyridin-4-yl)-1H-pyrrolo[2,3-b]pyridin-4-yl)oxy)phenyl)propan-1-one (Example 192)

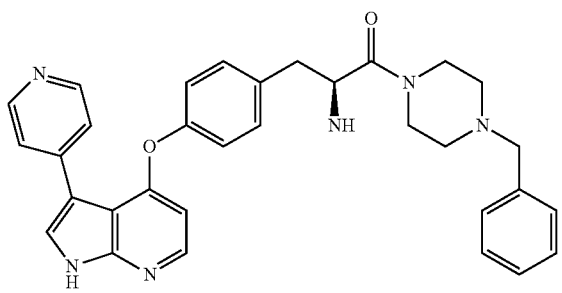 [SMILES: N[C@@H](Cc1ccc(Oc2ccnc3[nH]cc(-c4ccncc4)c23)cc1)C(=O)N1CCN(Cc2ccccc2)CC1]

Intermediate 192C (200 mg, 0.247 mmol), pyridine-4-boronic acid (61 mg, 0.496 mmol), PdCl₂(dppf)₂·CH₂Cl₂ (10 mg, 0.012 mmol), and potassium carbonate (75 mg, 0.543 mmol) in a mixture of DME (3 mL) and water (1 mL) was bubbled with argon for 5 min. The mixture was stirred at 90° C. for 18 h and then allowed to cool to RT. The mixture was applied to a 5 g SCX-2 cartridge which was then flushed with DCM and methanol. The product was eluted with 2M ammonia in methanol and evaporation gave a residue which was taken up into DCM (5 mL). TFA (2 mL) was added and the solution was stirred at RT overnight. After removal of the volatile components in vacuo, the product was purified by HPLC eluting with a gradient of 10-98% acetonitrile in water (0.1% NH₄OH added). The desired compound was obtained as a white solid (53 mg).

LCMS (Method 1): Rt=1.69 min, m/z 533.1 [M+H]⁺

¹H NMR (400 MHz, d6-DMSO) δ 12.25 (s, 1H), 8.47-8.45 (m, 2H), 8.11 (d, J=5.5 Hz, 1H), 7.92 (s, 1H), 7.74-7.71 (m, 2H), 7.32-7.24 (m, 6H), 7.14 (d, J=8.5 Hz, 2H), 6.34 (d, J=5.4 Hz, 1H), 3.91 (dd, J=6.9, 6.9 Hz, 1H), 3.57 (s, 3H), 3.43-3.38 (m, 5H), 2.77 (dd, J=6.7, 13.1 Hz, 1H), 2.70-2.62 (m, 1H), 2.35-2.17 (m, 3H), 2.06-2.02 (m, 1H), 1.71 (s, 1H).

(ee % n.d.)

Examples 193 to 202

The following examples were prepared in a similar manner as Example 192, by replacing in Step D the boronic acid or boronate ester indicated the table below.

| Ex | Structure | Boronic acid | 1H NMR | LC-MS |
|---|---|---|---|---|
| 193 | (S)-2-amino-1-(4-benzylpiperazin-1-yl)-3-(4-((3-(1-ethyl-1H-pyrazol-5-yl)-1H-pyrrolo[2,3-b]pyridin-4-yl)oxy)phenyl)propan-1-one | 1-Ethyl-5-(4,4,5,5-tetramethyl-1,3,2-dioxaborolan-2-yl)-1H-pyrazole | ¹H NMR (400 MHz, d6-DMSO) δ 12.16 (s, 1H), 8.09 (d, J = 5.4 Hz, 1H), 7.55 (s, 1H), 7.37 (d, J = 1.8 Hz, 1H), 7.34-7.21 (m, 6H), 6.99 (d, J = 8.6 Hz, 2H), 6.28-6.24 (m, 2H), 4.09 (q, J = 7.2 Hz, 2H), 3.88 (dd, J = 6.8, 6.8 Hz, 1H), 3.57 (s, 2H), 3.45-3.39 (m, 5H), 2.75 (dd, J = 6.6, 13.1 Hz, 1H), 2.67-2.60 (m, 1H), 2.34-2.28 (m, 2H), 2.23-2.18 (m, 1H), 2.06-2.02 (m, 1H), 1.69 (s, 2H), 1.25 (dd, J = 7.2, 7.2 Hz, 3H). | Rt = 2.16 min, m/z 550.1 [M + H]⁺ (Method 1) |

| Ex | Structure | Boronic acid | 1H NMR | LC-MS |
|---|---|---|---|---|
| 194 | 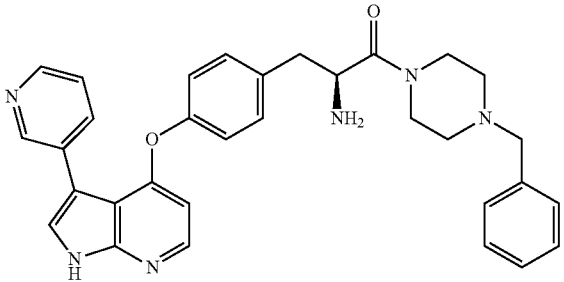 [SMILES: N[C@@H](Cc1ccc(Oc2ccnc3[nH]cc(-c4cccnc4)c23)cc1)C(=O)N1CCN(Cc2ccccc2)CC1]<br>(ee % n.d.)<br>(S)-2-amino-1-(4-benzylpiperazin-1-yl)-3-(4-((3-(pyridin-3-yl)-1H-pyrrolo[2,3-b]pyridin-4-yl)oxy)phenyl)propan-1-one | 3-(4,4,5,5-Tetramethyl-1,3,2-dioxaborolan-2-yl)pyridine | $^1$H NMR (400 MHz, d6-DMSO) δ 12.17 (s, 1H), 8.88 (d, J = 1.6 Hz, 1H), 8.36 (dd, J = 1.6, 4.7 Hz, 1H), 8.11-8.03 (m, 2H), 7.74 (s, 1H), 7.36-7.24 (m, 8H), 7.11 (d, J = 8.6 Hz, 2H), 6.31 (d, J = 5.4 Hz, 1H), 3.90 (dd, J = 6.8, 6.8 Hz, 1H), 3.57 (s, 1H), 3.47-3.39 (m, 5H), 2.77 (dd, J = 6.6, 13.1 Hz, 1H), 2.65 (dd, J = 7.1, 13.1 Hz, 1H), 2.33-2.26 (m, 2H), 2.22-2.18 (m, 1H), 2.06-2.02 (m, 1H), 1.71 (s, 2H). | Rt = 1.86 min, 533.1 m/z [M + H]$^+$ (Method 1) |
| 195 | 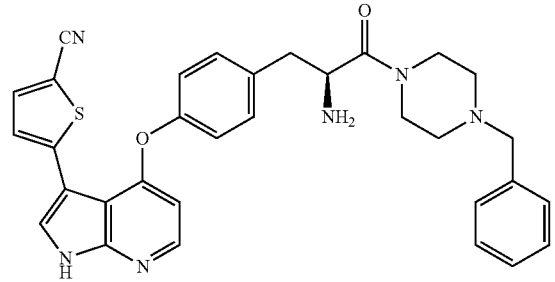 [SMILES: N#Cc1ccc(-c2c[nH]c3nccc(Oc4ccc(C[C@H](N)C(=O)N5CCN(Cc6ccccc6)CC5)cc4)c23)s1]<br>(ee % n.d.)<br>(S)-5-(4-(4-(2-amino-3-(4-benzylpiperazin-1-yl)-3-oxopropyl)phenoxy)-1H-pyrrolo[2,3-b]pyridin-3-yl)thiophene-2-carbonitrile | (5-Cyanothiophen-2-yl)boronic acid | $^1$H NMR (400 MHz, d6-DMSO) δ 12.38 (s, 1H), 8.11 (d, J = 5.4 Hz, 1H), 8.04 (s, 1H), 7.83 (d, J = 4.0 Hz, 1H), 7.53 (d, J = 3.9 Hz, 1H), 7.34-7.28 (m, 4H), 7.25 (d, J = 7.1 Hz, 3H), 7.18 (d, J = 8.6 Hz, 2H), 6.36 (d, J = 5.4 Hz, 1H), 3.92 (dd, J = 6.8, 6.8 Hz, 1H), 3.48-3.39 (m, 5H), 2.79 (dd, J = 6.7, 13.1 Hz, 1H), 2.71-2.64 (m, 1H), 2.53 (d, J = 6.8 Hz, 1H), 2.35-2.30 (m, 2H), 2.18-2.16 (m, 1H), 2.05-2.02 (m, 1H), 1.74 (s, 2H). | Rt = 2.53 min, m/z 563.1 [M + H]$^+$ (Method 1) |
| 196 | 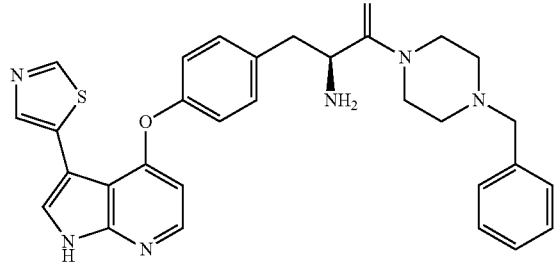<br>(ee % n.d.)<br>(S)-2-amino-1-(4-benzylpiperazin-1-yl)-3-(4-((3-(thiazol-5-yl)-1H-pyrrolo[2,3-b]pyridin-4-yl)oxy)phenyl)propan-1-one | 5-(4,4,5,5-Tetramethyl-1,3,2-dioxaborolan-2-yl)thiazole | $^1$H NMR (400 MHz, d6-DMSO) δ 12.22 (s, 1H), 8.88 (d, J = 0.7 Hz, 1H), 8.12-8.09 (m, 2H), 7.82 (s, 1H), 7.32-7.24 (m, 6H), 7.14 (d, J = 8.6 Hz, 2H), 6.33 (d, J = 5.4 Hz, 1H), 3.91 (dd, J = 6.8, 6.8 Hz, 1H), 3.48-3.38 (m, 7H), 2.78 (dd, J = 6.7, 13.1 Hz, 1H), 2.70-2.63 (m, 1H), 2.36-2.27 (m, 2H), 2.21-2.16 (m, 1H), 2.03 (dd, J = 7.7, 7.7 Hz, 1H), 1.70-1.70 (m, 2H). | Rt = 2.12 min, m/z 539.1 [M + H]$^+$ (Method 1) |

| Ex | Structure | Boronic acid | 1H NMR | LC-MS |
|---|---|---|---|---|
| 197 | (ee % n.d.)<br>(S)-2-amino-1-(4-benzylpiperazin-1-yl)-3-(4-((3-(1-methyl-1H-imidazol-5-yl)-1H-pyrrolo[2,3-b]pyridin-4-yl)oxy)phenyl)propan-1-one | 1-Methyl-5-(4,4,5,5-tetramethyl-1,3,2-dioxaborolan-2-yl)-1H-imidazole | $^1$H NMR (400 MHz, d6-DMSO) δ 12.08 (s, 1H), 8.08 (d, J = 5.4 Hz, 1H), 7.57 (s, 1H), 7.51 (d, J = 1.9 Hz, 1H), 7.34-7.23 (m, 6H), 7.01 (d, J = 8.6 Hz, 2H), 6.89 (d, J = 1.1 Hz, 1H), 6.27 (d, J = 5.5 Hz, 1H), 3.91 (dd, J = 6.8, 6.8 Hz, 1H), 3.57 (s, 3H), 3.49-3.38 (m, 5H), 2.77 (dd, J = 6.4, 13.2 Hz, 1H), 2.68-2.60 (m, 1H), 2.34-2.20 (m, 4H), 2.12-2.05 (m, 2H). | Rt = 1.59 min, m/z 536.2 [M + H]$^+$ (Method 1) |
| 198 | (ee % n.d.)<br>(S)-2-amino-1-(4-benzylpiperazin-1-yl)-3-(4-((3-(isoxazol-4-yl)-1H-pyrrolo[2,3-b]pyridin-4-yl)oxy)phenyl)propan-1-one | 4-(4,4,5,5-tetramethyl-1,3,2-dioxaborolan-2-yl)isoxazole | $^1$H NMR (400 MHz, d6-DMSO) δ 12.09-12.05 (m, 1H), 9.00 (d, J = 16.1 Hz, 2H), 8.08 (d, J = 5.5 Hz, 1H), 7.83 (s, 1H), 7.33-7.24 (m, 7H), 7.19 (d, J = 8.6 Hz, 2H), 6.30 (d, J = 5.4 Hz, 1H), 3.92 (dd, J = 6.9, 6.9 Hz, 1H), 3.46-3.36 (m, 6H), 2.82-2.64 (m, 2H), 2.34-2.27 (m, 2H), 2.15 (dd, J = 7.7, 7.7 Hz, 1H), 1.98 (dd, J = 7.7, 7.7 Hz, 1H. | Rt = 2.14 min, m/z 523.1 [M + H]$^+$ (Method 1) |
| 199 | (ee % n.d.)<br>(S)-2-amino-1-(4-benzylpiperazin-1-yl)-3-(4-((3-phenyl-1H-pyrrolo[2,3-b]pyridin-4-yl)oxy)phenyl)propan-1-one | Phenylboronic acid | $^1$H NMR (400 MHz, d6-DMSO) δ 12.00 (s, 1H), 8.07 (d, J = 5.4 Hz, 1H), 7.69-7.66 (m, 2H), 7.59 (s, 1H), 7.34-7.24 (m, 9H), 7.20-7.14 (m, 1H), 7.08 (d, J = 8.6 Hz, 2H), 6.29 (d, J = 5.4 Hz, 1H), 3.90 (t, J = 6.9 Hz, 1H), 3.47-3.39 (m, 5H), 3.27-3.23 (m, 1H), 2.76 (dd, J = 6.7, 13.1 Hz, 1H), 2.65 (dd, J = 7.0, 13.1 Hz, 1H), 2.34-2.18 (m, 3H), 2.10-2.03 (m, 1H), 1.71 (s, 2H). | Rt = 2.50 min, m/z 532.2 [M + H]$^+$ (Method 1) |

| Ex | Structure | Boronic acid | 1H NMR | LC-MS |
|---|---|---|---|---|
| 200 | 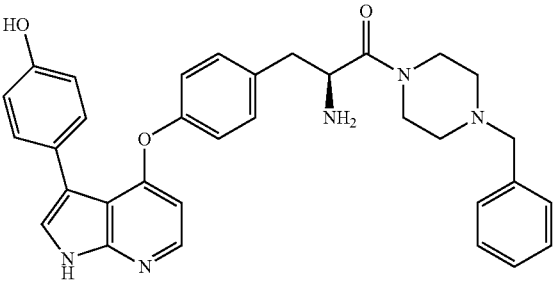 [SMILES: N[C@@H](Cc1ccc(Oc2ccnc3[nH]cc(-c4ccc(O)cc4)c23)cc1)C(=O)N1CCN(Cc2ccccc2)CC1]<br>(ee % n.d.)<br>(S)-2-amino-1-(4-benzylpiperazin-1-yl)-3-(4-((3-(4-hydroxyphenyl)-1H-pyrrolo[2,3-b]pyridin-4-yl)oxy)phenyl)propan-1-one | (4-((tert-Butyldimethyl-silyl)oxy)phenyl)boronic acid | $^1$H NMR (400 MHz, d6-DMSO) δ 11.83 (s, 1H), 9.25 (s, 1H), 8.04 (d, J = 5.4 Hz, 1H), 7.46-7.42 (m, 3H), 7.33-7.23 (m, 6H), 7.06 (d, J = 8.6 Hz, 2H), 6.72-6.69 (m, 2H), 6.26 (d, J = 5.4 Hz, 1H), 3.89 (dd, J = 6.9, 6.9 Hz, 1H), 3.57 (s, 1H), 3.48-3.39 (m, 6H), 2.76 (dd, J = 6.7, 13.1 Hz, 1H), 2.68-2.60 (m, 1H), 2.35-2.27 (m, 2H), 2.21 (d, J = 5.5 Hz, 1H), 2.09-2.04 (m, 1H), 1.68-1.68 (m, 2H). | Rt = 2.06 min, m/z 548.2 [M + H]$^+$ (Method 1) |
| 201 | 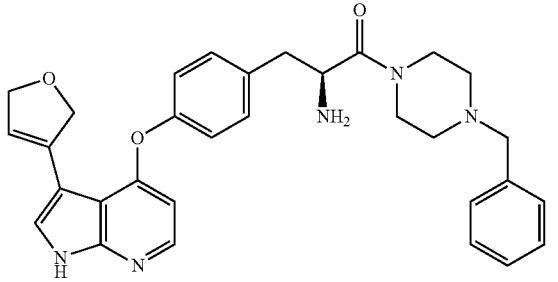 [SMILES: N[C@@H](Cc1ccc(Oc2ccnc3[nH]cc(C4=CCOC4)c23)cc1)C(=O)N1CCN(Cc2ccccc2)CC1]<br>(S)-2-amino-1-(4-benzylpiperazin-1-yl)-3-(4-((3-(2,5-dihydrofuran-3-yl)-1H-pyrrolo[2,3-b]pyridin-4-yl)oxy)phenyl)propan-1-one | 2-(2,5-Dihydrofuran-3-yl)-4,4,5,5-tetramethyl-1,3,2-dioxaborolane | $^1$H NMR (400 MHz, DMSO) δ 11.97 (s, 1H), 8.06 (d, J = 5.5 Hz, 1H), 7.45 (s, 1H), 7.33-7.24 (m, 7H), 7.14 (d, J = 8.6 Hz, 2H), 6.42-6.39 (m, 1H), 6.30 (d, J = 5.4 Hz, 1H), 4.90-4.85 (m, 2H), 4.66-4.61 (m, 2H), 3.92 (dd, J = 6.8, 6.8 Hz, 1H), 3.46-3.36 (m, 6H), 2.82-2.64 (m, 2H), 2.34-2.30 (m, 2H), 2.16 (dd, J = 7.7, 7.7 Hz, 1H), 1.97 (dd, J = 7.9, 7.9 Hz, 1H), 1.72-1.72 (m, 2H). | Rt = 2.12 min, m/z 524.2 [M + H]$^+$ (Method 1) |
| 202 | 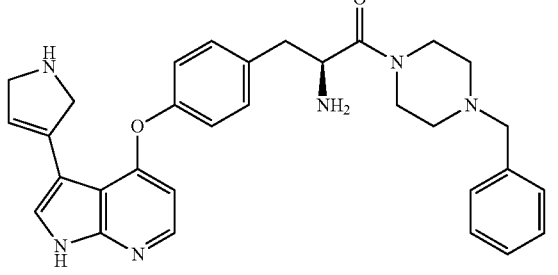<br>(S)-2-amino-1-(4-benzylpiperazin-1-yl)-3-(4-((3-(2,5-dihydro-1H-pyrrol-3-yl)-1H-pyrrolo[2,3-b]pyridin-4-yl)oxy)phenyl)propan-1-one | tert-Butyl 3-(4,4,5,5-tetramethyl-1,3,2-dioxaborolan-2-yl)-2,5-dihydro-1H-pyrrole-1-carboxylate | $^1$H NMR (400 MHz, DMSO) δ 11.92 (s, 1H), 8.04 (dd, J = 4.6, 4.6 Hz, 1H), 7.55-7.37 (m, 1H), 7.34-7.24 (m, 7H), 7.12 (dd, J = 7.6, 7.6 Hz, 2H), 6.37 (s, 1H), 6.28 (d, J = 5.4 Hz, 1H), 4.29 (d, J = 121.7 Hz, 1H), 3.97-3.89 (m, 2H), 3.69 (s, 1H), 3.47-3.37 (m, 8H), 2.81-2.64 (m, 2H), 2.36-2.30 (m, 2H), 2.19-2.17 (m, 1H), 2.02 (s, 1H). | Rt = 1.59 min, m/z 523.2 [M + H]$^+$ (Method 1) |

Example 203. (S)-2-amino-N-cyclohexyl-3-(4-((3-cyclopropyl-1H-pyrrolo[2,3-b]pyridin-4-yl)oxy)phenyl)propanamide (Example 203)

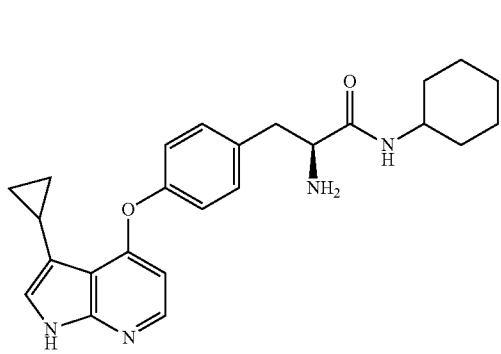 [SMILES: N[C@@H](Cc1ccc(Oc2ccnc3[nH]cc(C4CC4)c23)cc1)C(=O)NC1CCCCC1]

Example 203 was prepared from Intermediate 188C and cyclopropylboronic acid using a method similar to step D of Example 192.

LCMS (Method 1): Rt=2.75 min, m/z 419.3 [M+H]$^+$ $^1$H NMR (400 MHz, d6-DMSO) δ 11.37 (s, 1H), 7.99 (d, J=5.4 Hz, 1H), 7.57 (d, J=8.1 Hz, 1H), 7.25 (d, J=8.6 Hz, 2H), 7.05 (d, J=8.6 Hz, 2H), 7.02 (d, J=2.0 Hz, 1H), 6.26 (d, J=5.4 Hz, 1H), 3.54-3.45 (m, 1H), 3.38-3.34 (m, 1H), 2.85 (dd, J=5.9, 13.2 Hz, 1H), 2.67 (dd, J=7.5, 13.1 Hz, 1H), 2.08-2.02 (m, 1H), 1.72-1.61 (m, 5H), 1.55-1.51 (m, 1H), 1.28-1.01 (m, 6H), 0.77-0.71 (m, 2H), 0.60-0.55 (m, 2H).

ee %=82%

Example 204

Step A. Methyl (S)-2-((tert-butoxycarbonyl)amino)-3-(3-fluoro-4-((1-((2-(trimethylsilyl)ethoxy)methyl)-1H-pyrrolo[2,3-b]pyridin-4-yl)oxy)phenyl)propanoate (Intermediate 204A)

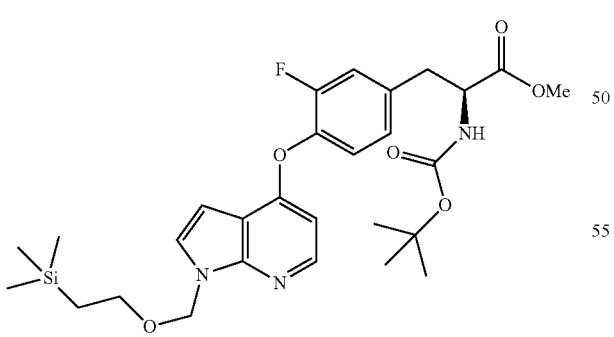

Intermediate 204A was prepared from Intermediate 1C-c and Intermediate 1A-a using a method similar to that of Step D of Example 1.

LCMS (Method 6): Rt=1.99 min, m/z 560.3 [M+H]$^+$

Step B. Methyl (S)-2-((tert-butoxycarbonyl)amino)-3-(3-fluoro-4-((3-iodo-1-((2-(trimethylsilyl)ethoxy)methyl)-1H-pyrrolo[2,3-b]pyridin-4-yl)oxy)phenyl)propanoate (Intermediate 204B)

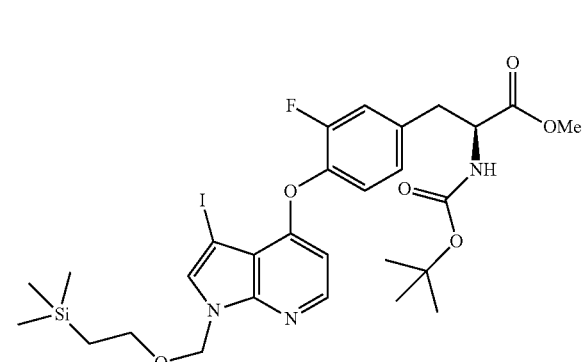

Intermediate 204B was prepared from Intermediate 204A using a procedure similar to that used for Intermediate 186C substituting NBS with NIS.

LCMS (Method 4): Rt=2.09 min, m/z 686.3 [M+H]$^+$

Step C. (S)-2-((tert-butoxycarbonyl)amino)-3-(3-fluoro-4-((3-iodo-1-((2-(trimethylsilyl)ethoxy)methyl)-1H-pyrrolo[2,3-b]pyridin-4-yl)oxy)phenyl)propanoic acid (Intermediate 204C)

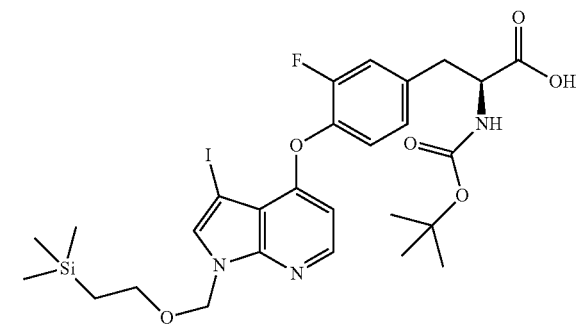 [SMILES: CC(C)(C)OC(=O)N[C@@H](Cc1ccc(Oc2ccnc3c2c(I)cn3COCC[Si](C)(C)C)c(F)c1)C(=O)O]

Intermediate 204C was prepared from Intermediate 204B using the same method as that used in Step E of Example 1.

LCMS (Method 9): Rt=2.70 min, m/z 672.1 [M+H]$^+$

Step D. tert-butyl (S)-(3-(3-fluoro-4-((3-iodo-1-((2-(trimethylsilyl)ethoxy)methyl)-1H-pyrrolo[2,3-b]pyridin-4-yl)oxy)phenyl)-1-((1-methylpiperidin-4-yl)amino)-1-oxopropan-2-yl)carbamate (Intermediate 204D)

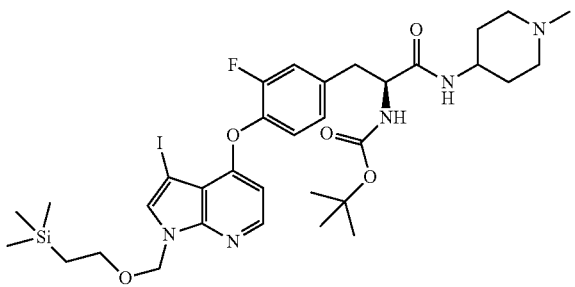

Intermediate 204D was prepared from Intermediate 204C and 1-methylpiperidin-4-amine using a procedure similar to that used in Step F of Example 1.
LCMS (Method 4): Rt=1.51 min, m/z 768.3 [M+H]+

Step E. tert-Butyl (S)-(3-(3-fluoro-4-((3-phenyl-1-((2-(trimethylsilyl)ethoxy)methyl)-1H-pyrrolo[2,3-b]pyridin-4-yl)oxy)phenyl)-1-((1-methylpiperidin-4-yl)amino)-1-oxopropan-2-yl)carbamate (Intermediate 204E)

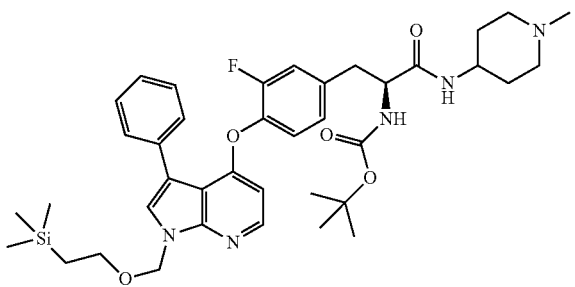

A mixture of Intermediate 204D (500 mg, 0.651 mmol), 4,4,5,5-tetramethyl-2-phenyl-1,3,2-dioxaborolane (266 mg, 1.30 mmol), Pd$_2$Cl$_2$(dppf).CH$_2$Cl$_2$ (27 mg, 0.033 mmol), potassium carbonate (198 mg, 1.43 mmol), DME (4 mL) and water (0.4 mL) was heated at 95° C. for 19 h. After cooling, the mixture was filtered through Celite®. The solution was diluted with ethyl acetate (20 mL), washed with water (10 mL) and dried (Na$_2$SO$_4$). Evaporation gave a crude product which was chromatographed on a Si cartridge (24 g) eluting with 0-100% ethyl acetate in cyclohexane then 0-10% methanol in DCM. Pure product was obtained a colorless foam (180 mg).
LCMS (Method 4): Rt=1.35 min, m/z 718.5 [M+H]+

Step F. (S)-2-amino-3-(3-fluoro-4-((3-phenyl-1H-pyrrolo[2,3-b]pyridin-4-yl)oxy)phenyl)-N-(1-methylpiperidin-4-yl)propanamide (Example 204)

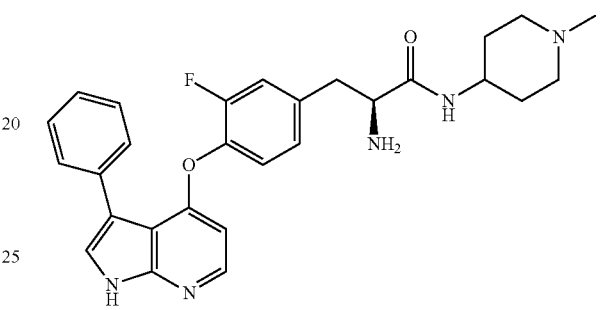

Example 204 was prepared from Intermediate 204E using a method similar to that used for Step G of Example 1.
LCMS (Method 1): Rt=2.21 min, m/z 488.2 [M+H]+
$^1$H NMR (400 MHz, DMSO) δ 12.04 (s, 1H), 8.07 (d, J=5.4 Hz, 1H), 7.70-7.60 (m, 4H), 7.36-7.18 (m, 5H), 7.07 (dd, J=1.3, 8.4 Hz, 1H), 6.24 (d, J=5.2 Hz, 1H), 3.51-3.43 (m, 1H), 3.37 (t, J=6.7 Hz, 1H), 2.85 (dd, J=6.1, 13.2 Hz, 1H), 2.73-2.54 (m, 3H), 2.12 (s, 3H), 1.94-1.87 (m, 2H), 1.75 (s, 2H), 1.62-1.54 (m, 2H), 1.42-1.24 (m, 2H).

Example 205

The following example was prepared from Intermediate 204D and the boronate ester given using a procedure similar to that used for Example 204, by replacing the boronate ester given in Step E.

| Ex | Structure | Boronic acid | 1H NMR | LC-MS |
|---|---|---|---|---|
| 205 | ![structure] (S)-2-amino-3-(3-fluoro-4-((3-(thiazol-5-yl)-1H-pyrrolo[2,3-b]pyridin-4-yl)oxy)phenyl)-N-(1-methylpiperidin-4-yl)propanamide | 5-(4,4,5,5-Tetramethyl-1,3,2-dioxaborolan-2-yl)thiazole | $^1$H NMR (400 MHz, DMSO) δ 12.22 (s, 1H), 8.92 (d, J = 0.7 Hz, 1H), 8.12-8.09 (m, 2H), 7.83 (s, 1H), 7.65 (d, J = 7.9 Hz, 1H), 7.36-7.25 (m, 2H), 7.11 (dd, J = 1.3, 8.2 Hz, 1H), 6.28 (dd, J = 0.8, 5.5 Hz, 1H), 3.53-3.43 (m, 1H), 3.41-3.36 (m, 1H), 2.88 (dd, J = 5.9, 13.2 Hz, 1H), 2.72 (dd, J = 7.6, 13.1 Hz, 1H), 2.66-2.57 (m, 2H), 2.54 (s, 1H), 2.12 (s, 3H), 1.96-1.85 (m, 3H), 1.68-1.56 (m, 2H), 1.43-1.23 (m, 2H). | Rt = 2.95 min, m/z 495.3 [M + H]+ (Method 2) |

Example 206

Step A. 4-Bromo-1-(4-methoxybenzyl)-1H-pyrrolo[2,3-b]pyridine (Intermediate 206A)

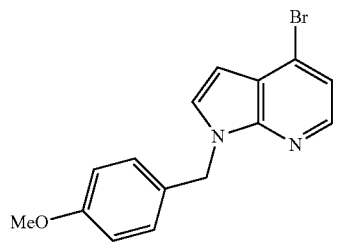 [SMILES: COc1ccc(Cn2ccc3c(Br)ccnc32)cc1]

4-Bromo-7-azaindole (2.5 g, 12.69 mmol) was dissolved in DMF (20 mL) and the solution was cooled in an ice bath under a stream of nitrogen. Sodium hydride (60% in mineral oil, 635 mg, 15.88 mmol) was added and the mixture was stirred for 30 min. 4-Methoxybenzyl bromide (2.81 g, 13.96 mmol) was then added and the reaction was stirred at RT for 2 h. After that time, the mixture was quenched by the careful addition of water (30 mL) and the product was extracted into ethyl acetate (3×20 mL). The combined extracts were dried (Na$_2$SO$_4$) and evaporated. The crude product was chromatographed on an 80 g Si cartridge eluting with 0-30% ethyl acetate in cyclohexane. The pure product was obtained as a cream solid (3.62 g).

LCMS (Method 4): Rt=1.61 min, m/z 316.9/318.9 [M+H]$^+$

Step B. Methyl (S)-2-((tert-butoxycarbonyl)amino)-3-(4-((1-(4-methoxybenzyl)-1H-pyrrolo[2,3-b]pyridin-4-yl)oxy)phenyl)propanoate (Intermediate 206B)

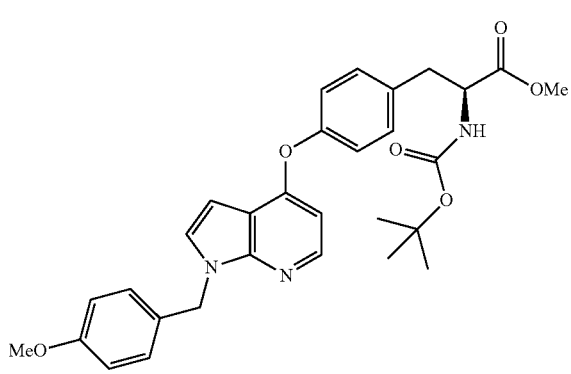 [SMILES: COC(=O)[C@H](Cc1ccc(Oc2ccnc3c2ccn3Cc2ccc(OC)cc2)cc1)NC(=O)OC(C)(C)C]

Intermediate 206B was prepared from Intermediate 206A and 1B-c according to the procedure used Step D of Example 1.

LCMS (Method 4): Rt=1.65 min, m/z 532.1 [M+H]$^+$

Step C. Methyl (S)-2-((tert-butoxycarbonyl)amino)-3-(4-((3-iodo-1-(4-methoxybenzyl)-1H-pyrrolo[2,3-b]pyridin-4-yl)oxy)phenyl)propanoate (Intermediate 206C)

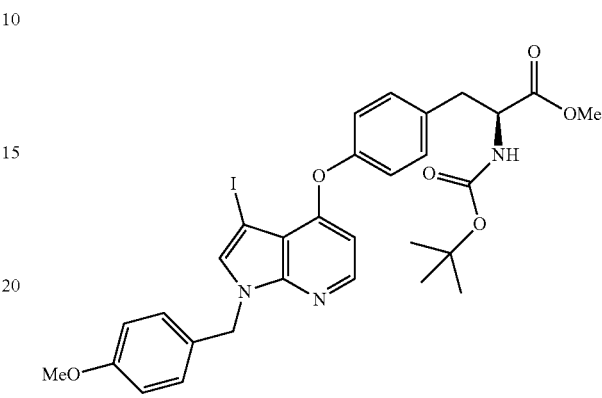

Intermediate 206C was prepared from Intermediate 206B and NIS using a procedure similar to Intermediate 186C replacing NBS with NIS.

LCMS (Method 4): Rt=1.75 min, m/z 658.0 [M+H]$^+$

Step D. (S)-2-((tert-Butoxycarbonyl)amino)-3-(4-((3-iodo-1-(4-methoxybenzyl)-1H-pyrrolo[2,3-b]pyridin-4-yl)oxy)phenyl)propanoic acid (Intermediate 206D)

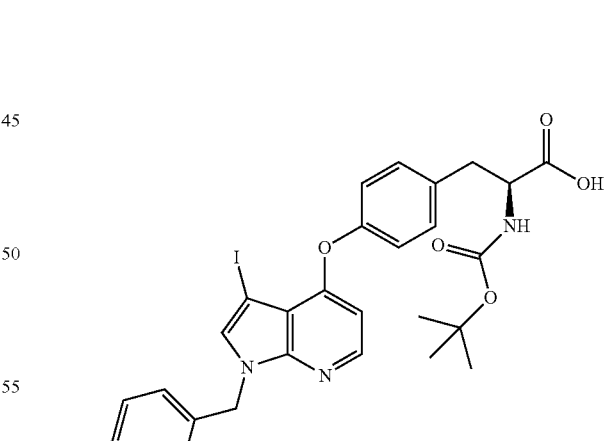

Intermediate 206D was prepared from Intermediate 206C using a procedure similar to that used for Step E of Example 1.

LCMS (Method 4): Rt=1.68 min, m/z 644.0 [M+H]$^+$

Step E. tert-Butyl (S)-(3-(4-((3-iodo-1-(4-methoxy-benzyl)-1H-pyrrolo[2,3-b]pyridin-4-yl)oxy)phenyl)-1-oxo-1-((2-(pyridin-4-yl)ethyl)amino)propan-2-yl)carbamate (Intermediate 206E)

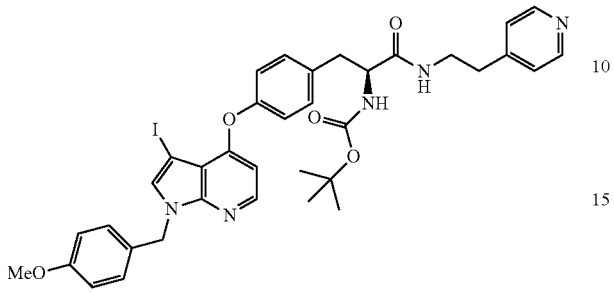

Intermediate 206E was prepared from Intermediate 206D and 2-(pyridin-4-yl)ethan-1-amine using a procedure similar to that used for Step F of Example 1.

LCMS (Method 4): Rt=1.27 min, m/z 748.0 [M+H]+

Step F. (S)-2-amino-3-(4-((3-(4-hydroxyphenyl)-1H-pyrrolo[2,3-b]pyridin-4-yl)oxy)phenyl)-N-(2-(pyridin-4-yl)ethyl)propanamide (Example 206)

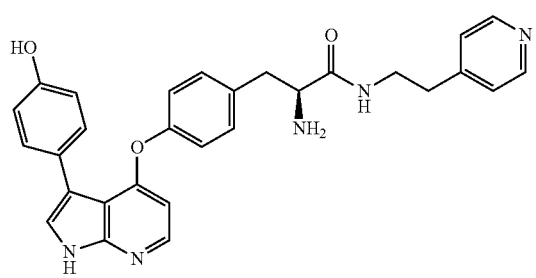 [SMILES: N[C@@H](Cc1ccc(Oc2ccnc3[nH]cc(-c4ccc(O)cc4)c23)cc1)C(=O)NCCc1ccncc1]

A mixture of Intermediate 206E (170 mg, 0.228 mmol), (4-((tert-butyldimethylsilyl)oxy)phenyl)boronic acid (115 mg, 0.456 mmol), Pd$_2$Cl$_2$(dppf).CH$_2$Cl$_2$ (9 mg, mmol), potassium carbonate (69 mg, mmol), DME (3 mL) and water (1 mL) was heated at 90° C. for 19 h. Evaporation gave a crude product which was chromatographed on a Si cartridge (24 g) eluting with 0-10% methanol in DCM. The product was dissolved in TFA (2 mL) and stirred at 90° C. for 18 h. Trifluoromethanesulfonic acid (34 mg, 0.288 mmol) was added and heating was continued at 65° C. for 3 h. The reaction was allowed to cool and the poured onto an SCX-2 cartridge (5 g). After flushing with DCM and methanol, the product was eluted with 2M methanolic ammonia. Evaporation gave a crude product which was purified by HPLC eluting with a gradient of 10-98% acetonitrile in water (0.1% NH$_4$OH added) to give a white solid (7 mg).

LCMS (Method 1): Rt=1.74 min, m/z 494.1 [M+H]+

$^1$H NMR (400 MHz, d6-DMSO) δ 11.82 (s, 1H), 9.24 (s, 1H), 8.46-8.43 (m, 2H), 8.02 (d, J=5.5 Hz, 1H), 7.95 (dd, J=5.8, 5.8 Hz, 1H), 7.45-7.40 (m, 3H), 7.26-7.19 (m, 4H), 7.06 (d, J=8.6 Hz, 2H), 6.71-6.68 (m, 2H), 6.25 (d, J=5.4 Hz, 1H), 3.39-3.27 (m, 3H), 2.88 (dd, J=5.1, 13.3 Hz, 1H), 2.70 (dd, J=7.1, 7.1 Hz, 2H), 2.60 (q, J=7.4 Hz, 1H), 1.69 (s, 2H). ee % (n.d.)

Example 207

Step A. 4-Bromo-1-((2-(trimethylsilyl)ethoxy)methyl)-1H-pyrrolo[2,3-b]pyridine-3-carbaldehyde (Intermediate 207A)

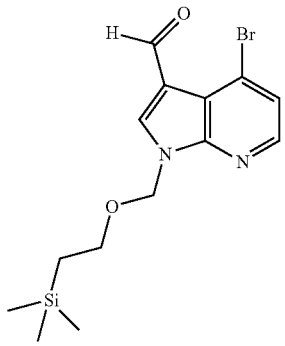 [SMILES: C[Si](C)(C)CCOCn1cc(C=O)c2c(Br)ccnc21]

Intermediate 207A was prepared from 3-formyl-4-bromo-7-azaindole using a procedure similar to that used for the preparation of Intermediate 1C-a.

LCMS (Method 4): Rt=1.91 min, m/z 355.1/357.1 [M+H]+

Step B. Methyl (S)-2-((tert-butoxycarbonyl)amino)-3-(3-fluoro-4-((3-formyl-1-((2-(trimethylsilyl)ethoxy)methyl)-1H-pyrrolo[2,3-b]pyridin-4-yl)oxy)phenyl)propanoate (Intermediate 207B)

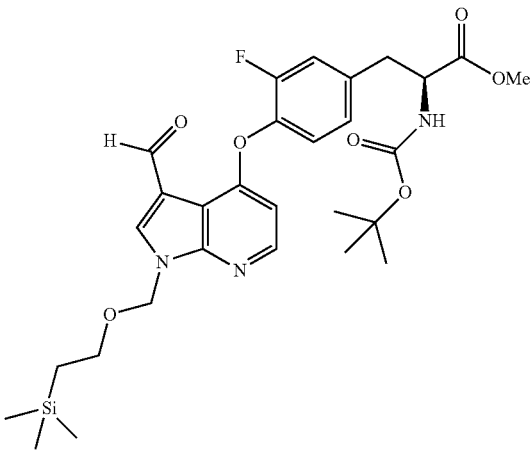 [SMILES: COC(=O)[C@H](Cc1ccc(Oc2ccnc3c2c(C=O)cn3COCC[Si](C)(C)C)c(F)c1)NC(=O)OC(C)(C)C]

Intermediate 207B was prepared from Intermediate 207A and Intermediate 1B-a according to the procedure in Step D of Example 1.

LCMS (Method 6): Rt=1.76 min, m/z 588.4 [M+H]+

Step C. (S)-2-((tert-Butoxycarbonyl)amino)-3-(3-fluoro-4-((3-formyl-1-((2-(trimethylsilyl)ethoxy)methyl)-1H-pyrrolo[2,3-b]pyridin-4-yl)oxy)phenyl)propanoic acid (Intermediate 207C)

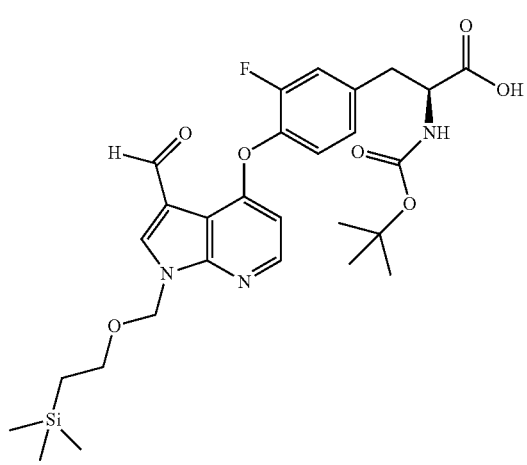 [SMILES: CC(C)(C)OC(=O)N[C@@H](Cc1ccc(Oc2ccnc3c2c(C=O)cn3COCC[Si](C)(C)C)c(F)c1)C(=O)O]

Intermediate 207C was prepared from Intermediate 207B using a similar procedure in Step E of Example 1, LCMS (Method 6): Rt=1.69 min, m/z 574.3 [M+H]$^+$ Step D. (S)-2-((tert-Butoxycarbonyl)amino)-3-(3-fluoro-4-((3-(hydroxymethyl)-1-((2-(trimethylsilyl)ethoxy)methyl)-1H-pyrrolo[2,3-b]pyridin-4-yl)oxy)phenyl)propanoic acid (Intermediate 207D)

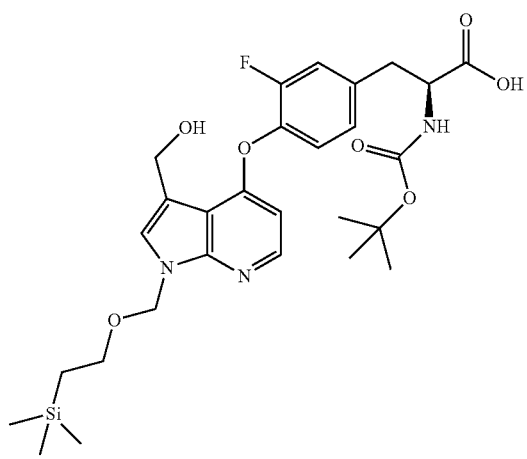 [SMILES: CC(C)(C)OC(=O)N[C@@H](Cc1ccc(Oc2ccnc3c2c(CO)cn3COCC[Si](C)(C)C)c(F)c1)C(=O)O]

Intermediate 207C (386 mg, 0.674 mmol) was dissolved in a mixture of DCM (10 mL) and methanol (1 mL) and sodium borohydride (26 mg, 0.684 mmol) was added. The reaction was stirred at RT overnight. A further portion of sodium borohydride (52 mg, 1.37 mmol) was added and stirring was continued for 2 h. The reaction mixture was washed with water (10 mL), dried (Na$_2$SO$_4$) and evaporated. The product was obtained as a cream solid (346 mg).

LCMS (Method 6): Rt=1.59 min, m/z 576.3 [M+H]$^+$

Step E. tert-Butyl (S)-(1-(4-benzylpiperazin-1-yl)-3-(3-fluoro-4-((3-(hydroxymethyl)-1-((2-(trimethylsilyl)ethoxy)methyl)-1H-pyrrolo[2,3-b]pyridin-4-yl)oxy)phenyl)-1-oxopropan-2-yl)carbamate (Intermediate 207E)

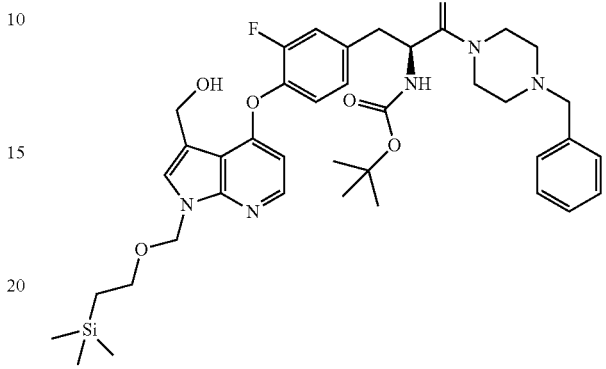

Intermediate 207E was prepared from Intermediate 207D and 1-benzylpiperazine using a procedure similar to that used for step F of Example 1.

LCMS (Method 6): Rt=1.30 min, m/z 734.5 [M+H]$^+$

Step F. (S)-2-amino-1-(4-benzylpiperazin-1-yl)-3-(3-fluoro-4-((3-(hydroxymethyl)-1H-pyrrolo[2,3-b]pyridin-4-yl)oxy)phenyl)propan-1-one (Example 207)

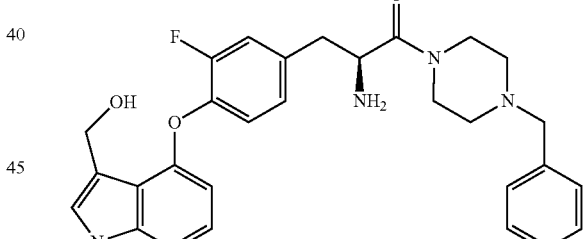

Example 207 was prepared from Intermediate 207E using a procedure similar to that used for Step G of Example 1.

LCMS (Method 2): Rt=3.23 min, m/z 504.4 [M+H]$^+$ $^1$H NMR (400 MHz, d6-DMSO) δ 11.55 (s, 1H), 8.00 (d, J=5.5 Hz, 1H), 7.34-7.22 (m, 9H), 7.11 (dd, J=1.3, 8.3 Hz, 1H), 6.17 (d, J=5.4 Hz, 1H), 4.79-4.76 (m, 3H), 3.94 (t, J=6.8 Hz, 1H), 3.46-3.42 (m, 5H), 2.80 (dd, J=6.3, 13.1 Hz, 1H), 2.67 (dd, J=7.4, 13.1 Hz, 1H), 2.39-2.29 (m, 2H), 2.25-2.14 (m, 1H), 2.11-2.01 (m, 1H), 1.72-1.71 (m, 2H).

Examples 208 to 215

The following examples were prepared in a similar manner example to 207 by replacing 1-benzylpiperazine in Step E with the amine shown below.

| Ex | Structure | Amine | 1H NMR | LC-MS |
|---|---|---|---|---|
| 208 | (S)-2-amino-N-cyclohexyl-3-(3-fluoro-4-((3-(hydroxymethyl)-1H-pyrrolo[2,3-b]pyridin-4-yl)oxy)phenyl)-propanamide | Cyclo-hexanamine | $^1$H NMR (400 MHz, d6-DMSO) δ 1.57 (s, 1H), 7.99 (d, J = 5.4 Hz, 1H), 7.61 (d, J = 8.0 Hz, 1H), 7.31-7.20 (m, 3H), 7.12-7.07 (m, 1H), 6.17 (d, J = 5.4 Hz, 1H), 4.78-4.73 (m, 3H), 3.55-3.47 (m, 1H), 3.40-3.35 (m, 1H), 2.87 (dd, J = 5.9, 13.2 Hz, 1H), 2.71 (dd, J = 7.3, 13.3 Hz, 1H), 1.78 (s, 2H), 1.70-1.61 (m, 4H), 1.53 (d, J = 12.2 Hz, 1H), 1.31-1.06 (m, 5H). | Rt = 3.11 min, m/z 427.4 [M + H]$^+$ (Method 2) |
| 209 | (ee % n.d.) (S)-2-amino-3-(3-fluoro-4-((3-(hydroxymethyl)-1H-pyrrolo[2,3-b]pyridin-4-yl)oxy)phenyl)-N-(tetrahydro-2H-pyran-4-yl)propanamide | Tetrahydro-2H-pyran-4-amine | $^1$H NMR (400 MHz, DMSO) δ 11.54 (s, 1H), 8.00 (d, J = 5.4 Hz, 1H), 7.75 (d, J = 7.8 Hz, 1H), 7.29-7.22 (m, 3H), 7.09 (dd, J = 1.3, 8.3 Hz, 1H), 6.17 (dd, J = 0.9, 5.4 Hz, 1H), 4.78-4.73 (m, 3H), 3.83-3.71 (m, 3H), 3.42-3.35 (m, 2H), 2.88 (dd, J = 5.9, 13.2 Hz, 1H), 2.72 (dd, J = 7.5, 13.2 Hz, 1H), 1.76 (s, 2H), 1.66-1.57 (m, 2H), 1.44-1.22 (m, 2H). | Rt = 1.74 min, m/z 429.0 [M + H]$^+$ (Method 1) |
| 210 | (S)-2-amino-3-(3-fluoro-4-((3-(hydroxymethyl)-1H-pyrrolo[2,3-b]pyridin-4-yl)oxy)phenyl)-N-(1-methylpiperidin-4-yl)propanamide | 1-Methyl-piperidin-4-amine | $^1$H NMR (400 MHz, DMSO) δ 11.56 (d, J = 1.5 Hz, 1H), 8.00 (d, J = 5.4 Hz, 1H), 7.75 (d, J = 7.8 Hz, 1H), 7.29-7.23 (m, 3H), 7.09 (dd, J = 1.3, 8.3 Hz, 1H), 6.18 (dd, J = 0.8, 5.5 Hz, 1H), 4.75 (s, 3H), 3.52-3.42 (m, 2H), 2.90 (dd, J = 6.1, 13.3 Hz, 1H), 2.79-2.60 (m, 3H), 2.15 (s, 3H), 1.99-1.91 (m, 2H), 1.68-1.56 (m, 2H), 1.46-1.23 (m, 2H). | Rt = 2.44 min, m/z 442.2 [M + H]$^+$ (Method 2) |
| 211 | (S)-2-amino-3-(3-fluoro-4-((3-(hydroxymethyl)-1H-pyrrolo[2,3- | (1S,4S)-2-Methyl-2,5-diazabicyclo[2.2.1]heptane | $^1$H NMR (400 MHz, DMSO) δ 11.58-11.53 (m, 1H), 8.01 (dd, J = 3.1, 5.4 Hz, 1H), 7.37-7.22 (m, 3H), 7.13 (dd, J = 2.0, 8.2 Hz, 1H), 6.25-6.14 (m, 1H), 4.79-4.72 (m, 3H), 4.50-4.22 (m, 1H), 3.78-3.50 (m, 1H), 3.38-3.35 (m, 2H), 3.15-3.00 (m, 1H), 2.81-2.65 (m, 3H), 2.27 (s, 1H), 2.15 (s, 3H), 1.72 (dd, J = 8.9, 8.9 Hz, 1H), 1.50-1.28 (m, 1H). | Rt = 2.29 min, m/z 440.2 [M + H]$^+$ (Method 2) |

| Ex | Structure | Amine | 1H NMR | LC-MS |
|---|---|---|---|---|
| | b]pyridin-4-yl)oxy)phenyl)-1-((1S,4S)-5-methyl-2,5-diazabicyclo[2.2.1]-heptan-2-yl)propan-1-one | | | |
| 212 | 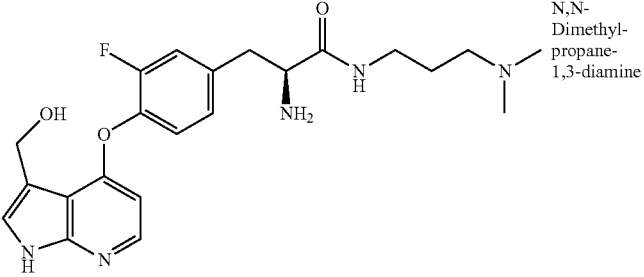<br>(S)-2-amino-N-(3-(dimethylamino)-propyl)-3-(3-fluoro-4-((3-(hydroxymethyl)-1H-pyrrolo[2,3-b]pyridin-4-yl)oxy)phenyl)propanamide | N,N-Dimethyl-propane-1,3-diamine | $^1$H NMR (400 MHz, DMSO) δ 11.55 (d, J = 1.2 Hz, 1H), 8.00 (d, J = 5.4 Hz, 1H), 7.87 (dd, J = 5.7, 5.7 Hz, 1H), 7.29-7.22 (m, 3H), 7.10 (dd, J = 1.3, 8.3 Hz, 1H), 6.18-6.16 (m, 1H), 4.75 (s, 3H), 3.43-3.37 (m, 2H), 3.12-3.00 (m, 2H), 2.92 (dd, J = 5.7, 13.3 Hz, 1H), 2.75-2.67 (m, 1H), 2.17-2.10 (m, 3H), 2.09 (s, 6H), 1.51-1.42 (m, 2H). | Rt = 2.42 min, m/z 430.2 [M + H]$^+$ (Method 2) |
| 213 | 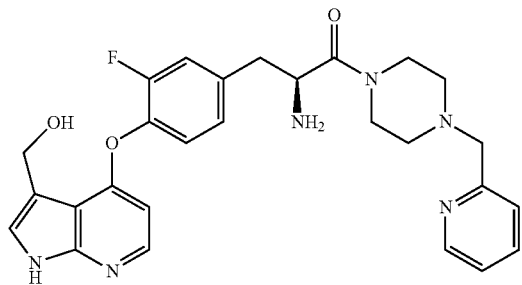 [SMILES: N[C@@H](Cc1ccc(Oc2ccnc3[nH]cc(CO)c23)c(F)c1)C(=O)N1CCN(Cc2ccccn2)CC1]<br>(S)-2-amino-3-(3-fluoro-4-((3-(hydroxymethyl)-1H-pyrrolo[2,3-b]pyridin-4-yl)oxy)phenyl)-1-(4-(pyridin-2-ylmethyl)piperazin-1-yl)propan-1-one | 1-(Pyridin-2-ylmethyl)piperazine | $^1$H NMR (400 MHz, d6-DMSO) δ 11.56-11.56 (m, 1H), 8.49 (dd, J = 0.9, 4.9 Hz, 1H), 8.01 (d, J = 5.4 Hz, 1H), 7.79-7.74 (m, 1H), 7.44 (d, J = 7.8 Hz, 1H), 7.34-7.22 (m, 4H), 7.11 (dd, J = 1.3, 8.3 Hz, 1H), 6.19-6.17 (m, 1H), 4.82-4.74 (m, 3H), 3.94 (dd, J = 6.9, 6.9 Hz, 1H), 3.58 (s, 2H), 3.54-3.37 (m, 4H), 2.80 (dd, J = 6.4, 13.2 Hz, 1H), 2.71-2.64 (m, 1H), 2.42-2.23 (m, 3H), 2.18-2.07 (m, 1H), 1.79-1.75 (m, 2H). | Rt = 1.57 min, m/z 505.2 [M + H]$^+$ (Method 1) |
| 214 | 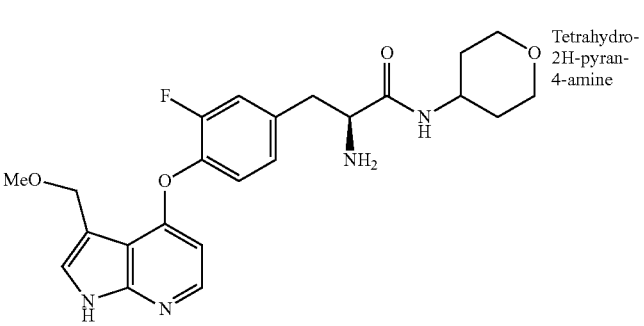<br>Isolated from the preparation of Example 211<br>(ee % n.d.)<br>(S)-2-amino-3-(3-fluoro-4-((3-(methoxymethyl)-1H-pyrrolo[2,3-b]pyridin-4-yl)oxy)phenyl)-N-(tetrahydro-2H-pyran-4-yl)propanamide | Tetrahydro-2H-pyran-4-amine | $^1$H NMR (400 MHz, DMSO) δ 11.73 (s, 1H), 8.24 (s, 1H), 8.03 (d, J = 5.4 Hz, 1H), 7.82 (d, J = 7.8 Hz, 1H), 7.41 (d, J = 2.1 Hz, 1H), 7.30-7.22 (m, 2H), 7.09 (dd, J = 1.2, 8.3 Hz, 1H), 6.22 (d, J = 4.8 Hz, 1H), 4.61 (s, 2H), 3.82-3.70 (m, 4H), 3.45 (dd, J = 6.8, 6.8 Hz, 1H), 3.38-3.28 (m, 3H), 3.25 (s, 3H), 2.90 (dd, J = 6.1, 13.3 Hz, 1H), 2.76 (dd, J = 7.4, 13.3 Hz, 1H), 1.69-1.54 (m, 2H), 1.44-1.23 (m, 2H). | Rt = 2.07 min, m/z 443.1 [M + H]$^+$ (Method 1) |

| Ex | Structure | Amine | 1H NMR | LC-MS |
|---|---|---|---|---|
| 215 | 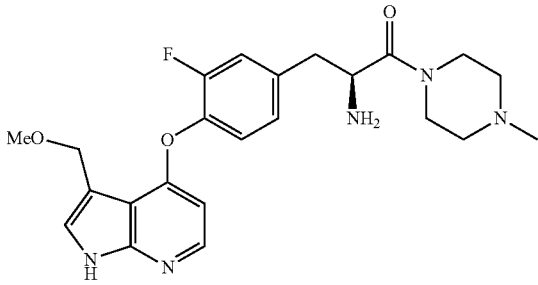 [SMILES: COCc1c[nH]c2nccc(Oc3ccc(C[C@H](N)C(=O)N4CCN(C)CC4)cc3F)c12]<br>Isolated product when synthesizing hydroxyalkyl derivative on R₁<br>(ee % n.d.)<br>(S)-2-amino-3-(3-fluoro-4-((3-(methoxymethyl)-1H-pyrrolo[2,3-b]pyridin-4-yl)oxy)phenyl)-1-(4-methylpiperazin-1-yl)propan-1-one | 1-Methyl-piperazine | ¹H NMR (400 MHz, DMSO) d 11.70 (s, 1H), 8.03 (d, J = 5.5 Hz, 1H), 7.40 (s, 1H), 7.31 (dd, J = 2.1, 12.0 Hz, 1H), 7.24 (dd, J = 8.4, 8.4 Hz, 1H), 7.11 (dd, J = 1.4, 8.3 Hz, 1H), 6.23-6.21 (m, 1H), 4.61 (s, 2H), 3.95 (dd, J = 6.9, 6.9 Hz, 1H), 3.56-3.49 (m, 1H), 3.46-3.36 (m, 3H), 3.25 (s, 3H), 2.80 (dd, J = 6.6, 13.2 Hz, 1H), 2.72-2.65 (m, 1H), 2.28 (dd, J = 3.5, 10.4 Hz, 2H), 2.14 (s, 3H), 2.10-1.89 (m, 2H), 1.74 (s, 2H). | Rt = 1.56 min, m/z 442.1 [M + H]⁺ (Method 1) |

Example 213 (Alternative Method)

Step A. (4-Bromo-1-((2-(trimethylsilyl)ethoxy)methyl)-1H-pyrrolo[2,3-b]pyridin-3-yl)methanol (Intermediate 213A)

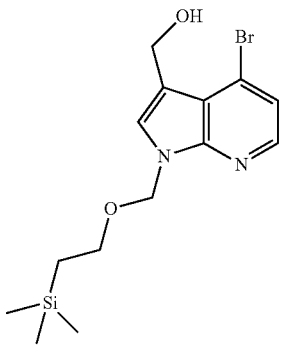 [SMILES: C[Si](C)(C)CCOCn1cc(CO)c2c(Br)ccnc21]

Intermediate 213A was prepared from Intermediate 207A using a procedure similar to that used for the preparation of Intermediate 207D.

LCMS (Method 4): Rt=1.58 min, m/z 357.1/359.1 [M+H]⁺

Step B. 4-Bromo-3-(((tert-butyldimethylsilyl)oxy)methyl)-1-((2-(trimethylsilyl)ethoxy)methyl)-1H-pyrrolo[2,3-b]pyridine (Intermediate 213B)

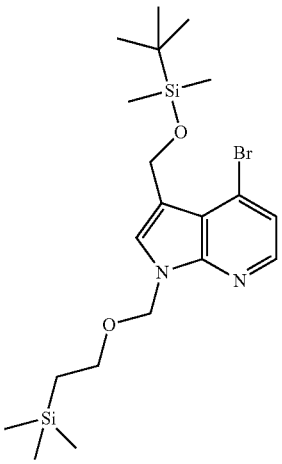 [SMILES: CC(C)(C)[Si](C)(C)OCc1cn(COCC[Si](C)(C)C)c2nccc(Br)c12]

Intermediate 213A (204 mg, 0.57 mmol) in DCM (6.5 mL) was treated with imidazole (78 mg, 1.14 mmol). tert-Butyldimethylsilyl chloride (102 mg, 0.68 mmol) was added and the reaction was stirred at RT overnight. The reaction mixture was diluted with water (10 mL) and the DCM layer was separated. The aqueous was further extracted with DCM (10 mL) and the combined extracts were dried (Na₂SO₄) and evaporated. The residue was chromatographed on a 25 g Si cartridge eluting with 0-30% ethyl acetate in cyclohexane to give the desired product as colourless oil (240 mg).

LCMS (Method 4): Rt=2.19 min, m/z 471.2/473.2 [M+H]⁺

Step C. Methyl (S)-2-((tert-butoxycarbonyl)amino)-3-(4-((3-(((tert-butyldimethylsilyl)oxy)methyl)-1-((2-(trimethylsilyl)ethoxy)methyl)-1H-pyrrolo[2,3-b]pyridin-4-yl)oxy)-3-fluorophenyl)propanoate (Intermediate 213C)

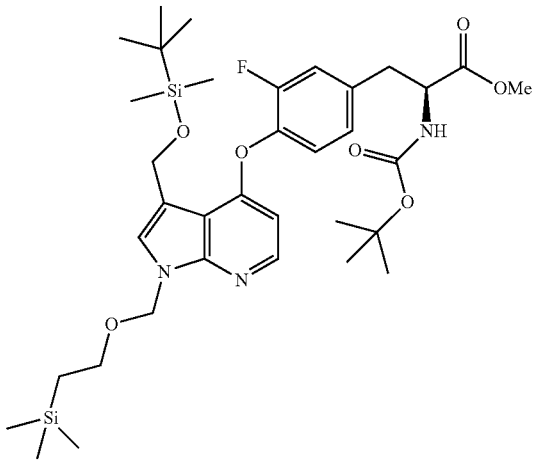 [SMILES: COC(=O)[C@H](Cc1ccc(Oc2ccnc3c2c(CO[Si](C)(C)C(C)(C)C)cn3COCC[Si](C)(C)C)c(F)c1)NC(=O)OC(C)(C)C]

Intermediate 213C was prepared from Intermediate 213B and Intermediate 1B-a according to the procedure in Step D of Example 1.

LCMS (Method 4): Rt=4.55 min, m/z 704.5 [M+H]$^+$

Step D. (S)-2-((tert-Butoxycarbonyl)amino)-3-(4-((3-(((tert-butyldimethylsilyl)oxy)methyl)-1-((2-(trimethylsilyl)ethoxy)methyl)-1H-pyrrolo[2,3-b]pyridin-4-yl)oxy)-3-fluorophenyl)propanoic acid (Intermediate 213D)

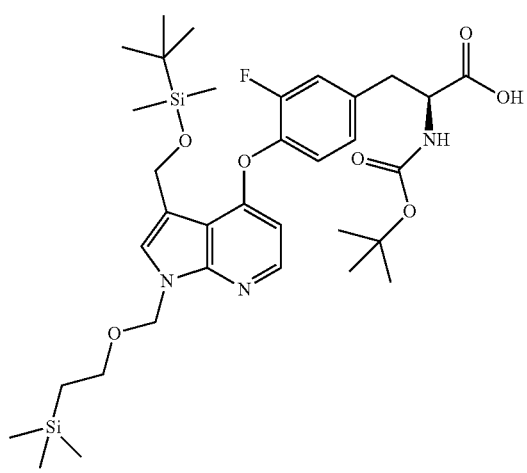 [SMILES: CC(C)(C)OC(=O)N[C@@H](Cc1ccc(Oc2ccnc3c2c(CO[Si](C)(C)C(C)(C)C)cn3COCC[Si](C)(C)C)c(F)c1)C(=O)O]

Intermediate 213D was prepared from Intermediate 213C using a procedure in Step E of Example 1.

LCMS (Method 4): Rt=4.39 min, m/z 690 [M+H]$^+$

Step E. tert-Butyl (S)-(3-(4-((3-(((tert-butyldimethylsilyl)oxy)methyl)-1-((2-(trimethylsilyl)ethoxy)methyl)-1H-pyrrolo[2,3-b]pyridin-4-yl)oxy)-3-fluorophenyl)-1-oxo-1-(4-(pyridin-2-ylmethyl)piperazin-1-yl)propan-2-yl)carbamate (Intermediate 213E)

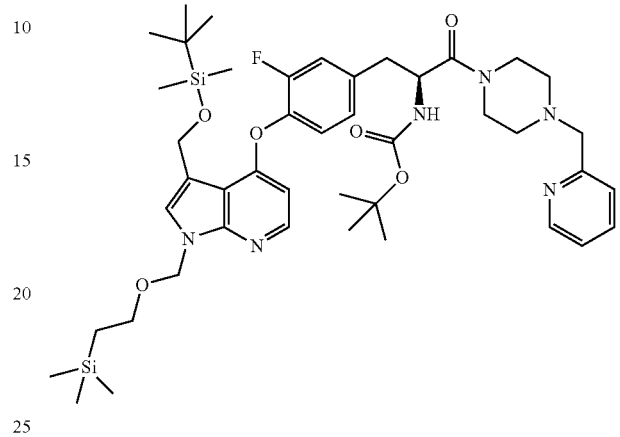

Intermediate 213E was prepared from Intermediate 213D and 1-(pyridin-2-ylmethyl)piperazine using a procedure similar to that used for Step F of Example 1.

LCMS (Method 4): Rt=3.33 min, m/z 849.5 [M+H]$^+$

Step F. (S)-2-Amino-3-(3-fluoro-4-((3-(hydroxymethyl)-1H-pyrrolo[2,3-b]pyridin-4-yl)oxy)phenyl)-1-(4-(pyridin-2-ylmethyl)piperazin-1-yl)propan-1-one (Example 213)

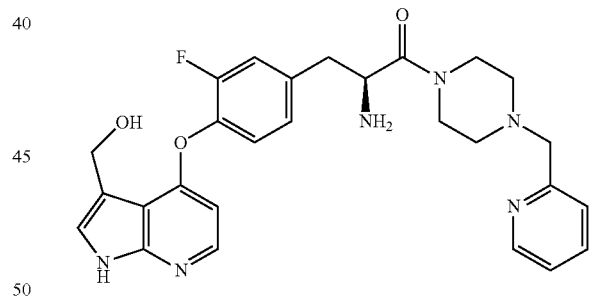

Example 213 was prepared from Intermediate 213E using a procedure similar to that used for Step G of Example 1.

LCMS (Method 1): Rt=1.57 min, m/z 505.2 [M+H]$^+$ $^1$H NMR (400 MHz, d6-DMSO) δ 11.56-11.56 (m, 1H), 8.49 (dd, J=0.9, 4.9 Hz, 1H), 8.01 (d, J=5.4 Hz, 1H), 7.79-7.74 (m, 1H), 7.44 (d, J=7.8 Hz, 1H), 7.34-7.22 (m, 4H), 7.11 (dd, J=1.3, 8.3 Hz, 1H), 6.19-6.17 (m, 1H), 4.82-4.74 (m, 3H), 3.94 (dd, J=6.9, 6.9 Hz, 1H), 3.58 (s, 2H), 3.54-3.37 (m, 4H), 2.80 (dd, J=6.4, 13.2 Hz, 1H), 2.71-2.64 (m, 1H), 2.42-2.23 (m, 3H), 2.18-2.07 (m, 1H), 1.79-1.75 (m, 2H).

Example 216

Step A. Methyl 2-(4-bromo-1-((2-(trimethylsilyl)ethoxy)methyl)-1H-pyrrolo[2,3-b]pyridin-3-yl)acetate (Intermediate 216A)

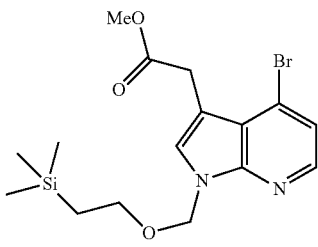 [SMILES: COC(=O)Cc1cn(COCC[Si](C)(C)C)c2nccc(Br)c12]

Intermediate 216A was prepared from methyl 2-(4-bromo-1H-pyrrolo[2,3-b]pyridin-3-yl)acetate using a method similar to that used for Intermediate 1C-a.
LCMS (Method 4): Rt=1.70 min, m/z 399.1/401.1 [M+H]$^+$

Step B. 2-(4-bromo-1-((2-(trimethylsilyl)ethoxy)methyl)-1H-pyrrolo[2,3-b]pyridin-3-yl)ethan-1-ol (Intermediate 216B)

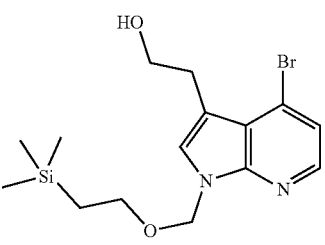 [SMILES: C[Si](C)(C)CCOCn1cc(CCO)c2c(Br)ccnc21]

Intermediate 216B was prepared from Intermediate 216A using a method similar to that used in the preparation of Intermediate 207D.
LCMS (Method 4): Rt=1.64 min, m/z 371.0/373.0 [M+H]$^+$

Step C. 4-Bromo-3-(2-((tert-butyldimethylsilyl)oxy)ethyl)-1-((2-(trimethylsilyl)ethoxy)methyl)-1H-pyrrolo[2,3-b]pyridine (Intermediate 216C)

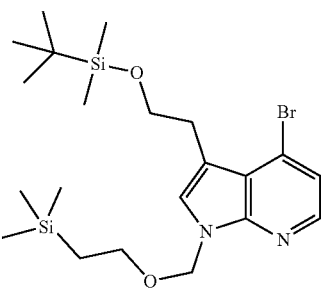 [SMILES: CC(C)(C)[Si](C)(C)OCCc1cn(COCC[Si](C)(C)C)c2nccc(Br)c12]

Intermediate 216C was prepared from Intermediate 216B using a method similar to that used in the preparation of Intermediate 213B.
LCMS (Method 4): Rt=2.27 min, m/z 485.0/487.0 [M+H]$^+$

Step D. Methyl (S)-2-((tert-butoxycarbonyl)amino)-3-(4-((3-(2-((tert-butyldimethyl-silyl)oxy)ethyl)-1-((2-(trimethylsilyl)ethoxy)methyl)-1H-pyrrolo[2,3-b]pyridin-4-yl)oxy)phenyl)propanoate (Intermediate 216D)

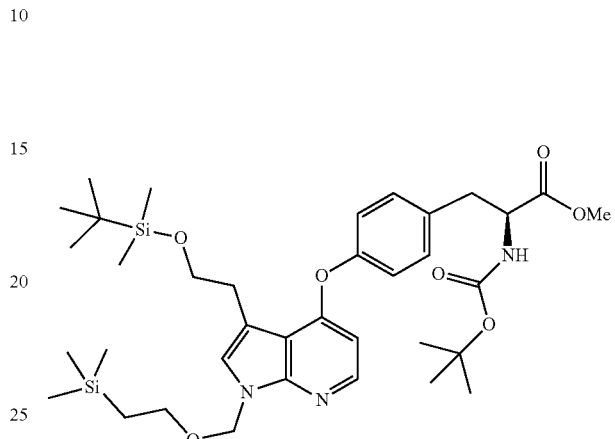

Intermediate 216D was prepared from Intermediate 216C and Intermediate 1B-c using a procedure similar to Step D of Example 1.
LCMS (Method 4): Rt=2.11 min, m/z 700.5 [M+H]$^+$

Step E. (S)-2-((tert-butoxycarbonyl)amino)-3-(4-((3-(2-((tert-butyldimethylsilyl)oxy)ethyl)-1-((2-(trimethylsilyl)ethoxy)methyl)-1H-pyrrolo[2,3-b]pyridin-4-yl)oxy)phenyl)propanoic acid (Intermediate 216E)

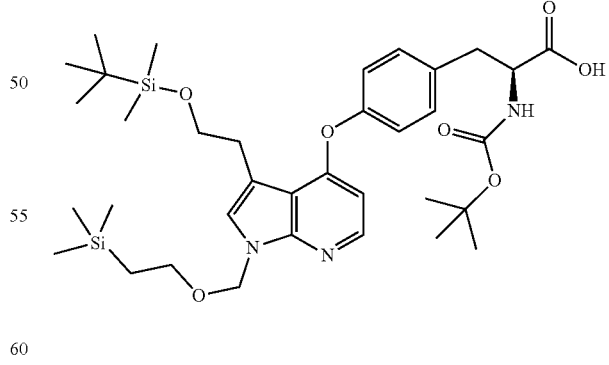

Intermediate 216E was prepared from Intermediate 216D using a procedure analogous to that used in Step E of Example 1.
LCMS (Method 4): Rt=2.08 min, m/z 686.5 [M+H]$^+$

Step F. tert-Butyl (S)-(1-(4-benzylpiperazin-1-yl)-3-(4-((3-(2-hydroxyethyl)-1-((2-(trimethylsilyl)ethoxy)methyl)-1H-pyrrolo[2,3-b]pyridin-4-yl)oxy)phenyl)-1-oxopropan-2-yl)carbamate (Intermediate 216F)

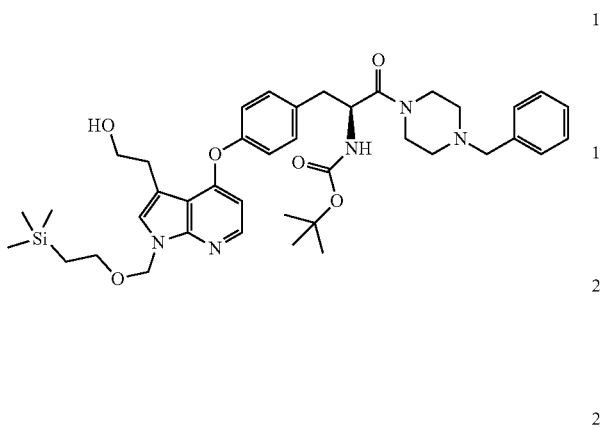

Intermediate 216F was prepared from Intermediate 216E and 1-benzylpiperazine using a method similar to that of Step D of Example 1.

LCMS (Method 4): Rt=2.29 min, m/z 730.7 [M+H]$^+$

Step G. (S)-2-amino-1-(4-benzylpiperazin-1-yl)-3-(4-((3-(2-hydroxyethyl)-1H-pyrrolo[2,3-b]pyridin-4-yl)oxy)phenyl)propan-1-one (Example 216)

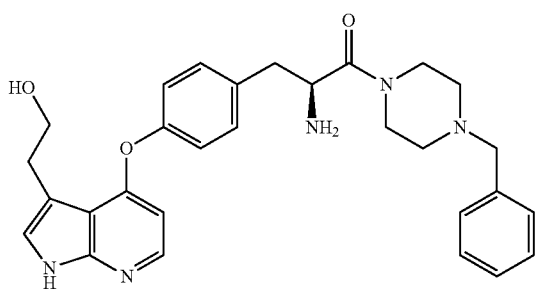 [SMILES: N[C@@H](Cc1ccc(Oc2ccnc3[nH]cc(CCO)c23)cc1)C(=O)N1CCN(Cc2ccccc2)CC1]

Example 216 was synthesized from Intermediate 216F as described for Step G of Example 1.

LCMS (Method 1): Rt=1.71 min, m/z 500.2 [M+H]$^+$ $^1$H NMR (400 MHz, DMSO) δ 11.42 (s, 1H), 7.98 (d, J=5.4 Hz, 1H), 7.33-7.24 (m, 7H), 7.16 (d, J=2.2 Hz, 1H), 7.08 (d, J=8.5 Hz, 2H), 6.21 (d, J=5.4 Hz, 1H), 4.53 (dd, J=5.2, 5.2 Hz, 1H), 3.91 (dd, J=6.8, 6.8 Hz, 1H), 3.71-3.63 (m, 2H), 3.45-3.42 (m, 6H), 2.95-2.89 (m, 2H), 2.78 (dd, J=6.8, 13.1 Hz, 1H), 2.66 (dd, J=6.6, 12.7 Hz, 1H), 2.35-2.29 (m, 2H), 2.22-2.17 (m, 1H), 2.03 (s, 1H), 1.77 (s, 2H).

Example 217

Step A. tert-Butyl (S)-(1-(cyclohexylamino)-1-oxo-3-(4-((1-((2-(trimethylsilyl)ethoxy)methyl)-1H-pyrrolo[2,3-b]pyridin-4-yl)oxy)phenyl)propan-2-yl)carbamate (Intermediate 217A)

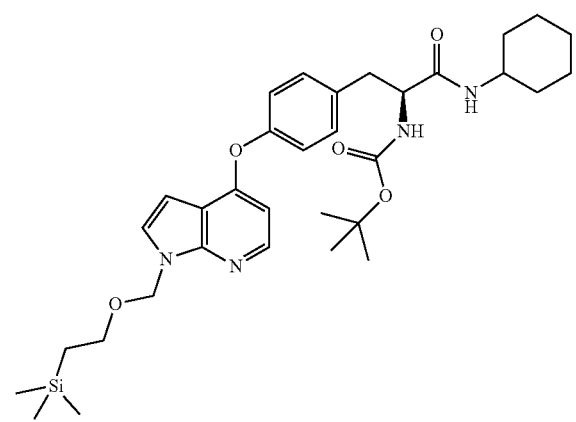 [SMILES: CC(C)(C)OC(=O)N[C@@H](Cc1ccc(Oc2ccnc3c2ccn3COCC[Si](C)(C)C)cc1)C(=O)NC1CCCCC1]

Intermediate 217A was prepared from Intermediate 1E-e and cyclohexanamine using the same procedure as for Step F of Example 1.

LCMS (Method 5): Rt=1.91 min, m/z 609.4 [M+H]$^+$

Step B. tert-Butyl (S)-(1-(cyclohexylamino)-3-(4-((3-iodo-1-((2-(trimethylsilyl)ethoxy)methyl)-1H-pyrrolo[2,3-b]pyridin-4-yl)oxy)phenyl)-1-oxopropan-2-yl)carbamate (Intermediate 217B)

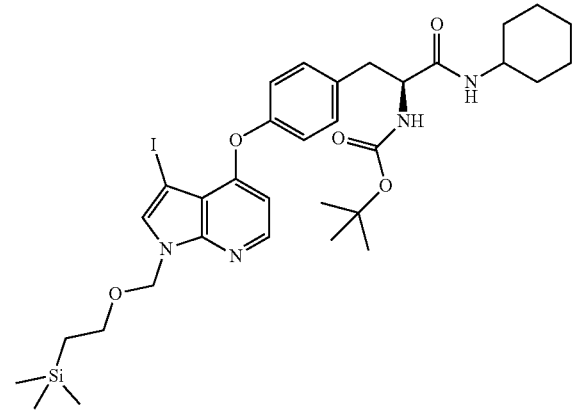 [SMILES: CC(C)(C)OC(=O)N[C@@H](Cc1ccc(Oc2ccnc3c2c(I)cn3COCC[Si](C)(C)C)cc1)C(=O)NC1CCCCC1]

Intermediate 217B was prepared from Intermediate 217A using the same procedure as for Intermediate 186C by substituting NBS with NIS.

LCMS (Method 4): Rt=2.27 min, m/z 735.4 [M+H]$^+$

Step C. tert-Butyl (S)-(3-(4-((3-(3-((tert-butyldimethylsilyl)oxy)prop-1-yn-1-yl)-1-((2-(trimethylsilyl)ethoxy)methyl)-1H-pyrrolo[2,3-b]pyridin-4-yl)oxy)phenyl)-1-(cyclohexylamino)-1-oxopropan-2-yl) carbamate (Intermediate 217C)

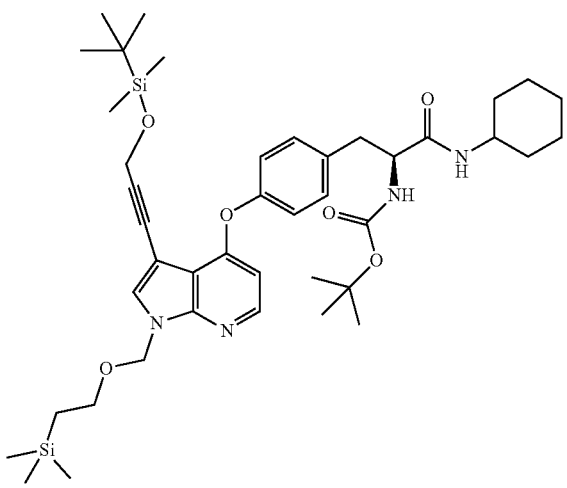 [SMILES: CC(C)(C)OC(=O)N[C@@H](Cc1ccc(Oc2ccnc3c2c(C#CCO[Si](C)(C)C(C)(C)C)cn3COCC[Si](C)(C)C)cc1)C(=O)NC1CCCCC1]

Intermediate 217B (390 mg, 0.531 mmol), tert-butyldimethyl(prop-2-yn-1-yloxy)silane (181 mg, 1.06 mmol), PdCl$_2$(dppf)$_2$.CH$_2$Cl$_2$ (22 mg, 0.027 mmol), copper (I) iodide (10 mg, 0.053 mmol) and trimethylamine (739 mL, 5.32 mmol) in THF (10 mL) were sealed in a reaction tube and the vessel was purged with argon for 5 min. The mixture was heated at 90° C. overnight and then allowed to cool to RT. The mixture was concentrated in vacuo and chromatographed on a 24 g Si cartridge eluting with 0-30% ethyl acetate in cyclohexane. The product was obtained as a cream solid (410 mg)

LCMS (Method 6): Rt=2.18 min, m/z 777.6 [M+H]$^+$

Step D. (S)-2-amino-N-cyclohexyl-3-(4-((3-(3-hydroxyprop-1-yn-1-yl)-1H-pyrrolo[2,3-b]pyridin-4-yl)oxy)phenyl)propanamide (Example 217)

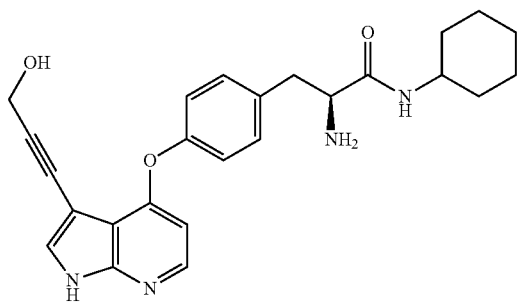 [SMILES: N[C@@H](Cc1ccc(Oc2ccnc3[nH]cc(C#CCO)c23)cc1)C(=O)NC1CCCCC1]

Example 217 was prepared from Intermediate 217C using a procedure similar to that used for Step G of Example 1.

LCMS (Method 2): Rt=3.25 min, m/z 433.1 [M+H]$^+$ $^1$H NMR (400 MHz, d6-DMSO) δ d 12.09 (s, 1H), 8.07 (d, J=5.5 Hz, 1H), 7.69 (s, 1H), 7.59 (d, J=8.1 Hz, 1H), 7.27 (d, J=8.6 Hz, 2H), 7.07 (d, J=8.5 Hz, 2H), 6.32 (d, J=5.4 Hz, 1H), 5.16 (s, 1H), 4.20 (s, 2H), 3.55-3.47 (m, 1H), 3.36 (dd, J=5.8, 7.4 Hz, 1H), 2.87 (dd, J=5.7, 13.3 Hz, 1H), 2.67 (dd, J=7.8, 13.2 Hz, 1H), 1.84 (s, 2H), 1.72-1.48 (m, 4H), 1.29-1.05 (m, 6H).

Example 218

Step A. tert-Butyl (S)-(3-(4-((3-cyano-1-((2-(trimethylsilyl)ethoxy)methyl)-1H-pyrrolo[2,3-b]pyridin-4-yl)oxy)phenyl)-1-oxo-1-((tetrahydro-2H-pyran-4-yl)amino)propan-2-yl)carbamate (Intermediate 218A)

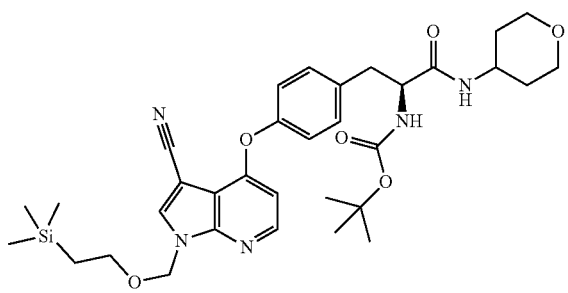 [SMILES: CC(C)(C)OC(=O)N[C@@H](Cc1ccc(Oc2ccnc3c2c(C#N)cn3COCC[Si](C)(C)C)cc1)C(=O)NC1CCOCC1]

Intermediate 189A (122 mg, 0.177 mmol), zinc cyanide (13 mg, 0.111 mmol), Pd$_2$(dba)$_3$ (8 mg, 0.009 mmol), 1,1'-ferrocenediylbis(diphenylphosphine) (12 mg, 0.022 mmol), and water (5 drops) in DMF (3 mL) was heated at 125° C. overnight. The mixture was allowed to cool and then partitioned between ethyl acetate (10 mL) and brine (8 mL). The organic layer was separated, dried (Na$_2$SO$_4$) and evaporated. The crude product (160 mg) was used in the next step without further purification.

LCMS (Method 8): Rt=1.65 min, m/z 636.4 [M+H]$^+$

Step B. (S)-2-amino-3-(4-((3-cyano-1H-pyrrolo[2,3-b]pyridin-4-yl)oxy)phenyl)-N-(tetrahydro-2H-pyran-4-yl)propanamide (Example 218)

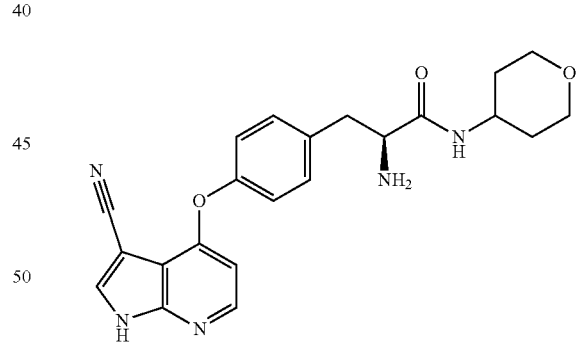

Example 218 was prepared from Intermediate 218A using a procedure similar to that for Step G of Example 1.

LCMS (Method 1): Rt=2.26 min, m/z 406.2 [M+H]$^+$ $^1$H NMR (400 MHz, DMSO) δ 8.38 (s, 1H), 8.19 (d, J=5.5 Hz, 1H), 7.72 (d, J=7.8 Hz, 1H), 7.32 (d, J=8.6 Hz, 2H), 7.16 (d, J=8.6 Hz, 2H), 6.40 (d, J=5.5 Hz, 1H), 3.83-3.71 (m, 3H), 3.41-3.36 (m, 3H), 2.89 (dd, J=5.8, 13.2 Hz, 1H), 2.72 (dd, J=7.6, 13.2 Hz, 1H), 1.67-1.55 (m, 2H), 1.43-1.27 (m, 2H).

Examples 219 to 222

The following examples were prepared in two step synthesis in a similar manner of Example 218 from the starting materials shown.

| Ex | Structure | Starting material | 1H NMR | LC-MS |
|---|---|---|---|---|
| 219 | (ee % = 87%)<br>(S)-2-amino-3-(4-((3-cyano-1H-pyrrolo[2,3-b]pyridin-4-yl)oxy)phenyl)-N-cyclohexylpropanamide | Intermediate 217B | $^1$H NMR (400 MHz, d6-DMSO) δ 8.37 (s, 1H), 8.18 (d, J = 5.5 Hz, 1H), 7.59 (d, J = 8.1 Hz, 1H), 7.32 (d, J = 8.6 Hz, 2H), 7.16 (d, J = 8.6 Hz, 2H), 6.39 (d, J = 5.5 Hz, 1H), 3.55-3.47 (m, 1H), 3.41-3.35 (m, 1H), 2.89 (dd, J = 5.7, 13.2 Hz, 1H), 2.70 (dd, J = 7.6, 13.3 Hz, 1H), 1.70-1.57 (m, 4H), 1.55-1.47 (m, 1H), 1.30-1.16 (m, 2H), 1.14-1.03 (m, 3H). | Rt = 2.79 min, m/z 404.3 [M + H]$^+$ (Method 1) |
| 220 | (ee % n.d.)<br>(S)-4-(4-(2-amino-3-(4-benzylpiperazin-1-yl)-3-oxopropyl)-2-fluorophenoxy)-1H-pyrrolo[2,3-b]pyridine-3-carbonitrile | Intermediate 187C | $^1$H NMR (400 MHz, DMSO) δ 8.42 (s, 1H), 8.20 (d, J = 5.5 Hz, 1H), 7.37-7.29 (m, 6H), 7.29-7.23 (m, 2H), 7.16 (dd, J = 1.2, 8.3 Hz, 1H), 6.39 (d, J = 4.8 Hz, 1H), 3.95 (t, J = 6.9 Hz, 1H), 3.54-3.39 (m, 8H), 2.82 (dd, J = 6.1, 13.2 Hz, 1H), 2.69 (dd, J = 7.5, 112 Hz, 1H), 2.39-2.29 (m, 2H), 2.24-2.15 (m, 1H), 2.12-2.02 (m, 1H). | Rt = 2.15 min, m/z 499.3 [M + H]$^+$ (Method 1) |
| 221 | (S)-2-amino-3-(4-((3-cyano-1H-pyrrolo[2,3-b]pyridin-4-yl)oxy)-3-fluorophenyl)-N-cyclohexylpropanamide | Intermediate 186C | $^1$H NMR (400 MHz, d6-DMSO) δ 8.42 (s, 1H), 8.20 (d, J = 5.6 Hz, 1H), 7.63 (d, J = 8.1 Hz, 1H), 7.36 (t, J = 8.4 Hz, 1H), 7.31 (dd, J = 1.9, 11.7 Hz, 1H), 7.14 (dd, J = 1.2, 8.3 Hz, 1H), 6.39 (d, J = 4.8 Hz, 1H), 3.56-3.47 (m, 1H), 3.44-137 (m, 2H), 2.90 (dd, J = 5.8, 13.2 Hz, 1H), 2.73 (dd, J = 7.5, 13.2 Hz, 1H), 1.70-1.49 (m, 6H), 1.30-1.07 (m, 6H). | Rt = 2.79 min, m/z 422.2 [M + H]$^+$ (Method 1) |
| 222 | (S)-2-amino-3-(4-((3-cyano-1H-pyrrolo[2,3-b]pyridin-4-yl)oxy)-3- | Intermediate 204D | $^1$H NMR (400 MHz, DMSO) δ 8.39 (s, 1H), 8.18 (d, J = 5.5 Hz, 1H), 7.66 (d, J = 7.9 Hz, 1H), 7.37-7.28 (m, 2H), 7.13 (dd, J = 1.3, 8.3 Hz, 1H), 6.38 (dd, J = 0.8, 5.5 Hz, 1H), 3.53-3.44 (m, 1H), 3.39 (dd, J = 6.0, 7.4 Hz, 2H), 2.89 (dd, J = 5.8, 13.3 Hz, 1H), 2.72 (dd, J = 7.6, 13.3 Hz, 1H), 2.66-2.58 (m, 2H), 2.12 (s, 3H), 1.96-1.87 (m, 2H), 1.68-1.57 (m, 2H), 1.43-1.23 (m, 2H). | Rt = 1.74 min, m/z 437.1 [M + H]$^+$ (Method 1) |

| Ex | Structure | Starting material 1H NMR | LC-MS |
|---|---|---|---|
|  | fluorophenyl)-N-(1-methylpiperidin-4-yl)propanamide |  |  |

Examples 223 to 224

Preparation of Intermediates 223A to 224B

The following intermediates were prepared from Intermediate 204C and the amine indicated in a similar way as reported for Step F of Example 1.

| Intermediate | Structure | Amine | LC-MS |
|---|---|---|---|
| 223A | 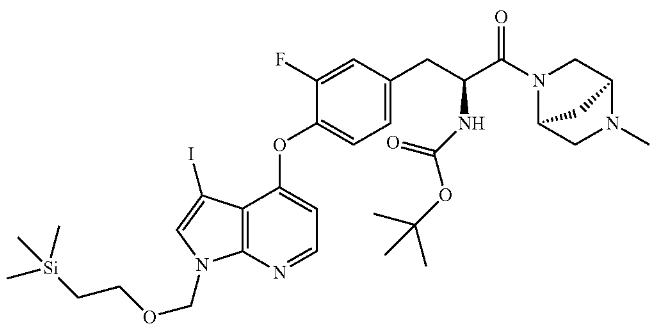 | (1S,4S)-2-methyl-2,5-diazabicyclo[2.2.1]-heptane | Rt = 2.83 min, m/z 766.1 [M + H]$^+$ (Method 9) |
| 224A | 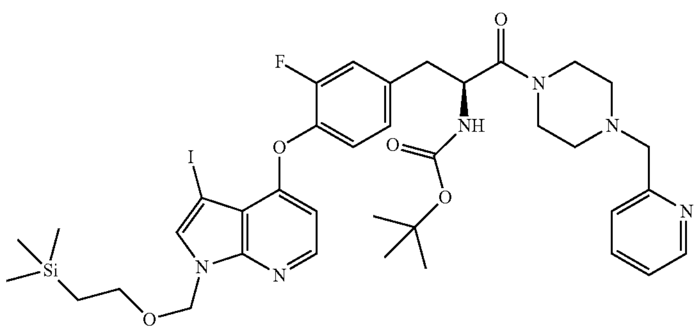 [SMILES: CC(C)(C)OC(=O)N[C@@H](Cc1ccc(Oc2ccnc3c2c(I)cn3COCC[Si](C)(C)C)c(F)c1)C(=O)N1CCN(Cc2ccccn2)CC1] | 1-(pyridin-2-ylmethyl)piperazine | Rt = 3.19 min, m/z 831.3 [M + H]$^+$ (Method 9) |

Preparation of Examples

The following examples were prepared in two step synthesis in a similar manner of Example 218 from the starting materials shown.

| Ex | Structure | Amine | 1H NMR | LC-MS |
|---|---|---|---|---|
| 223 | 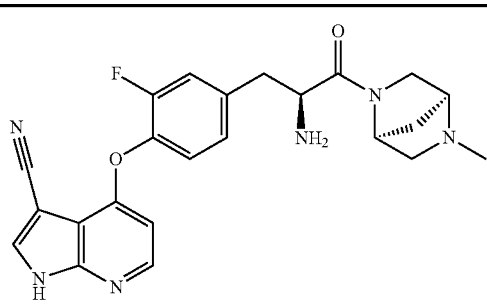 | Intermediate 223A | $^1$H NMR (400 MHz, DMSO) δ 8.41 (d, J = 2.7 Hz, 1H), 8.23-8.20 (m, 1H), 7.41-7.31 (m, 2H), 7.19-7.14 (m, 1H), 6.47-6.34 (2 × m, 1H), 4.51-31 (2 × s, 1H), 3.70-3.55 (2 × t, J = 7.2 Hz, 1H), 3.39-3.33 (m, 4H), 3.14-3.00 (2 × d, J = 10.1 Hz, 1H), 2.84-2.65 (m, 3H), 2.28-2.26 (2 × s, 3H), 1.76-4.68 (m, 1H), 1.57-1.25 (m, 1H). | Rt = 1.73 min, m/z 435.0 [M + H]$^+$ (Method 1) |

| Ex | Structure | Amine | 1H NMR | LC-MS |
|----|-----------|-------|--------|-------|
| 224 | 4-(4-((S)-2-amino-3-((1S,4S)-5-methyl-2,5-diazabicyclo[2.2.1]heptan-2-yl)-3-oxopropyl)-2-fluorophenoxy)-1H-pyrrolo[2,3-b]pyridine-3-carbonitrile<br><br>(S)-4-(4-(2-amino-3-oxo-3-(4-(pyridin-2-ylmethyl)piperazin-1-yl)propyl)-2-fluorophenoxy)-1H-pyrrolo[2,3-b]pyridine-3-carbonitrile | Intermediate 224A | $^1$H NMR (400 MHz, DMSO) δ 8.50-8.48 (m, 1H), 8.42 (s, 1H), 8.22 (d, J = 5.6 Hz, 1H), 7.79-7.74 (m, 1H), 7.44 (d, J = 7.8 Hz, 1H), 7.40-7.33 (m, 2H), 7.29-7.24 (m, 1H), 7.16 (dd, J = 1.1, 8.3 Hz, 1H), 6.40 (d, J = 5.1 Hz, 1H), 3.96 (dd, J = 6.8, 6.8 Hz, 1H), 3.59 (s, 2H), 3.56-3.40 (m, 5H), 2.84 (dd, J = 6.0, 13.2 Hz, 1H), 2.72-2.64 (m, 1H), 2.47-2.21 (m, 5H). | Rt = 1.96 min, m/z 500.3 [M + H]$^+$ (Method 1) |

Example 225

Step A. 4-Bromo-7-tosyl-7H-pyrrolo[2,3-d]pyrimidine (Intermediate 225A)

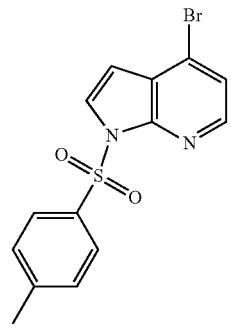 [SMILES: Cc1ccc(S(=O)(=O)n2ccc3c(Br)ccnc32)cc1]

Intermediate 225A was prepared similarly to Intermediate 131A-a from 4-bromo-7H-pyrrolo[2,3-d]pyrimidine.

LCMS (Method 7): Rt=3.82 min, m/z 351.9/353.9 [M+H]$^+$

Step B. Methyl (S)-2-((tert-butoxycarbonyl)amino)-3-(4-((7-tosyl-7H-pyrrolo[2,3-d]pyrimidin-4-yl)oxy)phenyl)propanoate (Intermediate 225B)

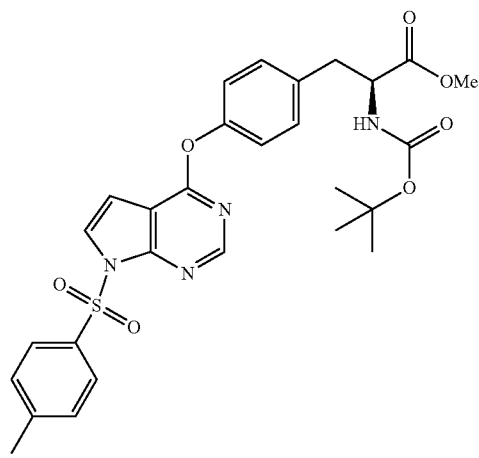 [SMILES: COC(=O)[C@H](Cc1ccc(Oc2ncnc3c2ccn3S(=O)(=O)c2ccc(C)cc2)cc1)NC(=O)OC(C)(C)C]

Intermediate 225B was prepared from Intermediate 225A and 1B-c using a method similar to that used in Step D of Example 1.

LCMS (Method 5): Rt=1.73 min, m/z 567.3 [M+H]$^+$

Step C. (S)-2-tert-Butoxycarbonylamino-3-{4-[7-(toluene-4-sulfonyl)-7H-pyrrolo[2,3-d]pyrimidin-4-yloxy]phenyl}propionic acid (Intermediate 225C)

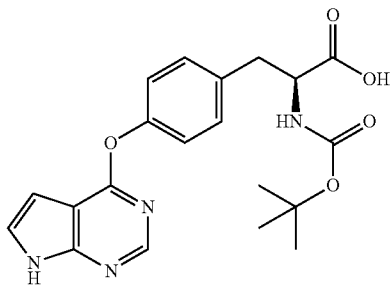 [SMILES: CC(C)(C)OC(=O)N[C@@H](Cc1ccc(Oc2ncnc3[nH]ccc23)cc1)C(=O)O]

Intermediate 225B (406 mg, 1.02 mmol) was dissolved in methanol and 2M lithium hydroxide solution was added. The reaction was stirred at RT overnight. The methanol was evaporated in vacuo and the resulting aqueous solution was acidified to pH 5 by the addition of 1N HCl. The product was extracted into DCM (3×8 mL) and the combined extracts were dried (Na$_2$SO$_4$) and evaporated. The product was obtained as a cream solid (299 mg).

LCMS (Method 5): Rt=1.29 min, m/z 399.2 [M+H]$^+$

Step D. tert-Butyl (S)-(3-(4-((7H-pyrrolo[2,3-d]pyrimidin-4-yl)oxy)phenyl)-1-(cyclohexylamino)-1-oxopropan-2-yl)carbamate (Intermediate 225D)

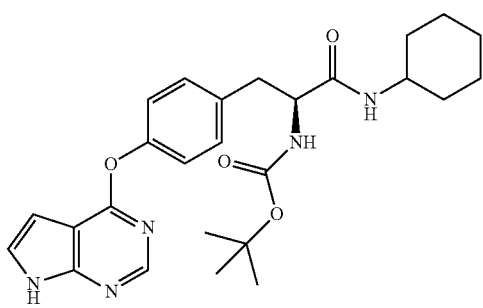 [SMILES: CC(C)(C)OC(=O)N[C@@H](Cc1ccc(Oc2ncnc3[nH]ccc23)cc1)C(=O)NC1CCCCC1]

Intermediate 225D was prepared from Intermediate 225C and cyclohexanamine using a procedure similar to step F of Example 1.
LCMS (Method 6): Rt=1.43 min, m/z 480.4 [M+H]⁺

Step E. (S)-3-(4-((7H-pyrrolo[2,3-d]pyrimidin-4-yl)oxy)phenyl)-2-amino-N-cyclohexylpropanamide (Example 225)

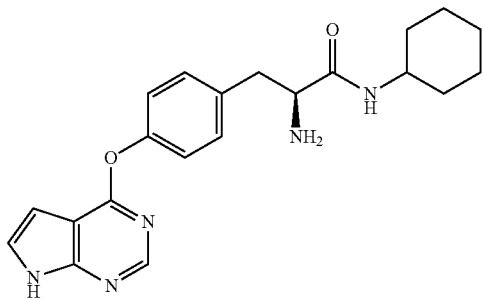 [SMILES: N[C@@H](Cc1ccc(Oc2ncnc3[nH]ccc23)cc1)C(=O)NC1CCCCC1]

Example 225 was prepared from Intermediate 225D using a procedure similar to Step G of Example 1.

LCMS (Method 1): Rt=2.82 min, m/z 380.2 [M+H]⁺

¹H NMR (400 MHz, d6-DMSO) δ 12.19 (s, 1H), 8.28 (s, 1H), 7.63 (d, J=8.1 Hz, 1H), 7.44 (d, J=3.5 Hz, 1H), 7.27 (d, J=8.6 Hz, 2H), 7.14 (d, J=8.6 Hz, 2H), 6.41 (d, J=3.5 Hz, 1H), 3.57-3.47 (m, 1H), 3.40-3.35 (m, 1H), 2.90 (dd, J=5.5, 13.3 Hz, 1H), 2.66 (dd, J=7.8, 13.3 Hz, 1H), 1.72-1.62 (m, 5H), 1.54 (dd, J=3.6, 8.9 Hz, 1H), 1.29-1.05 (m, 6H).

Example 226

The following example was prepared in a similar way of Example 225, by replacing the amine in Step D with that indicated in the table below.

| Ex | Structure | Amine | 1H NMR | LC-MS |
|---|---|---|---|---|
| 226 | (S)-3-(4-((7H-pyrrolo[2,3-d]pyrimidin-4-yl)oxy)phenyl)-2-amino-1-(4-benzylpiperazin-1-yl)propan-1-one | 1-Benzyl-piperazine | ¹H NMR (400 MHz, d6-DMSO) δ 12.20 (s, 1H), 8.28 (s, 1H), 7.45 (d, J = 3.5 Hz, 1H), 7.35-7.21 (m, 7H), 7.14 (d, J = 8.6 Hz, 2H), 6.44 (d, J = 3.5 Hz, 1H), 3.92 (t, J = 6.9 Hz, 1H), 3.47-3.41 (m, 6H), 2.79 (dd, J = 6.7, 13.1 Hz, 1H), 2.67 (dd, J = 7.2, 13.2 Hz, 1H), 2.32-2.24 (m, 3H), 2.12-2.05 (m, 1H), 1.77-1.77 (m, 2H). | Rt = 2.08 min, m/z 457.3 [M + H]⁺ (Method 1) |

Example 227

Step A. Methyl (S)-2-((tert-butoxycarbonyl)amino)-3-(5-hydroxypyridin-2-yl)propanoate (Intermediate 227A)

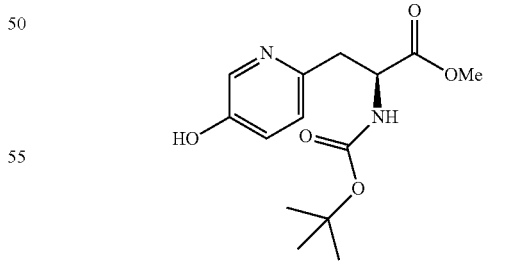

Intermediate 227A was prepared from methyl (S)-2-amino-3-(5-hydroxypyridin-2-yl)propanoate hydrochloride using a method similar to that of Step B of Example 1.
LCMS (Method 6): Rt=0.86 min, m/z 297.1 [M+H]⁺

Step B. 6-Chloro-4-nitro-1-((2-(trimethylsilyl)ethoxy)methyl)-1H-pyrrolo[2,3-b]pyridine (Intermediate 227B)

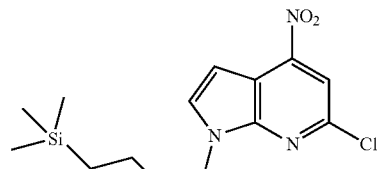

Intermediate 227B was prepared from 6-chloro-4-nitro-1H-pyrrolo[2,3-b]pyridine using a method similar to that of Step C of Example 1.

LCMS (Method 6): Rt=4.71 min $^1$H NMR (400 MHz, DMSO) δ 7.99 (s, 1H), 7.68 (d, J=3.5 Hz, 1H), 7.24 (d, J=3.5 Hz, 1H), 5.75 (s, 2H), 3.60 (m, 2H), 0.98 (m, 2H), 0.00 (s, 9H).

Step C. Methyl (S)-2-((tert-butoxycarbonyl)amino)-3-(5-((6-chloro-1-((2-(trimethylsilyl)ethoxy)methyl)-1H-pyrrolo[2,3-b]pyridin-4-yl)oxy)pyridin-2-yl)propanoate (Intermediate 227C)

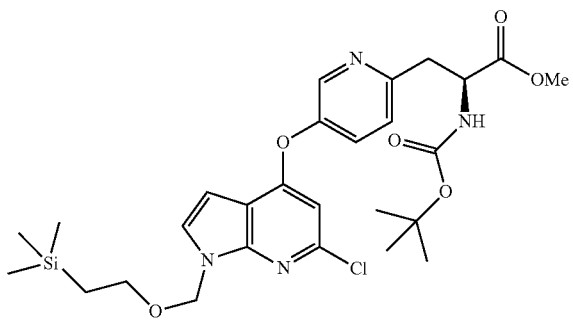 [SMILES: COC(=O)[C@H](Cc1ccc(Oc2cc(Cl)nc3c2ccn3COCC[Si](C)(C)C)cn1)NC(=O)OC(C)(C)C]

Intermediate 227B (302 mg, 0.924 mmol), Intermediate 227A (273 mg, 0.922 mmol) and potassium carbonate (382 mg, 2.77 mmol) were heated at 120° C. in DMSO (5 mL) for 2 h. The reaction mixture was allowed to cool and then poured into water (15 mL). The product was extracted into ethyl acetate (3×10 mL) and the combined extracts were dried (Na$_2$SO$_4$) and evaporated. Pure product was obtained by chromatography on a Si cartridge (24 g) eluting with 0-40% ethyl acetate in cyclohexane. The product was a cream solid (320 mg).

LCMS (Method 6): Rt=1.85 min, m/z 577.3 [M+H]$^+$

Step D. Methyl (S)-2-((tert-butoxycarbonyl)amino)-3-(5-((1-((2-(trimethylsilyl)ethoxy)methyl)-1H-pyrrolo[2,3-b]pyridin-4-yl)oxy)pyridin-2-yl)propanoate (Intermediate 227D)

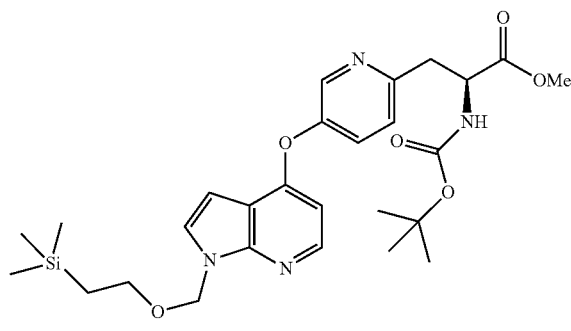 [SMILES: COC(=O)[C@H](Cc1ccc(Oc2ccnc3c2ccn3COCC[Si](C)(C)C)cn1)NC(=O)OC(C)(C)C]

A solution of Intermediate 227C (320 mg, 0.556 mmol) and trimethylamine (93 μL, 0.663 mmol) in IMS (20 mL) was stirred over 10% palladium on carbon (32 mg) under a blanket of hydrogen gas. After 18 h at RT the mixture was filtered through Celite® and the solvent was evaporated to give the desired product as a cream solid (309 mg).

LCMS (Method 4): Rt=1.96 min, m/z 543.3 [M+H]$^+$

Step E. (S)-2-((tert-Butoxycarbonyl)amino)-3-(5-((1-((2-(trimethylsilyl)ethoxy)methyl)-1H-pyrrolo[2,3-b]pyridin-4-yl)oxy)pyridin-2-yl)propanoic acid (Intermediate 227E)

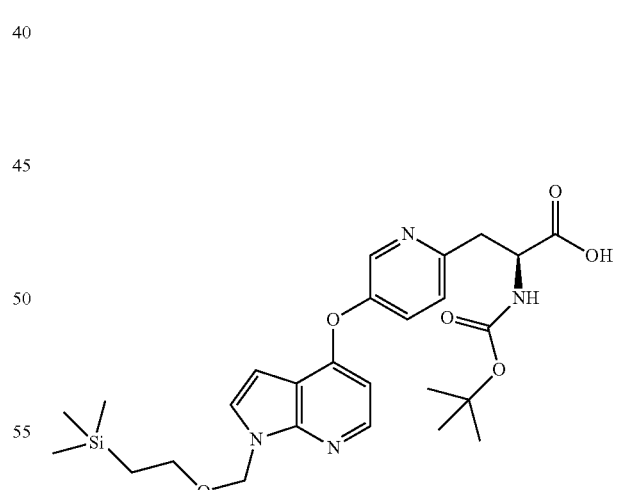

Intermediate 227E was prepared from Intermediate 227D according to the procedure described in Step E of Example 1.

LCMS (Method 6): Rt=1.65 min, m/z 529.3 [M+H]$^+$

Step F. tert-Butyl (S)-(1-(cyclohexylamino)-1-oxo-3-(5-((1-((2-(trimethylsilyl)ethoxy)methyl)-1H-pyrrolo[2,3-b]pyridin-4-yl)oxy)pyridin-2-yl)propan-2-yl)carbamate (Intermediate 227F)

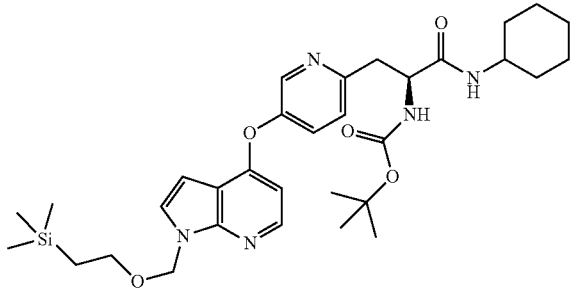 [SMILES: CC(C)(C)OC(=O)N[C@@H](Cc1ccc(Oc2ccnc3c2ccn3COCC[Si](C)(C)C)cn1)C(=O)NC1CCCCC1]

Intermediate 227F was prepared from Intermediate 227E and cyclohexanamine using a method analogous to in Step F of Example 1.
LCMS (Method 6): Rt=1.79 min, m/z 610.4 [M+H]$^+$ Step G. (S)-3-(5-((1H-pyrrolo[2,3-b]pyridin-4-yl)oxy)pyridin-2-yl)-2-amino-N-cyclohexylpropanamide (Example 227)

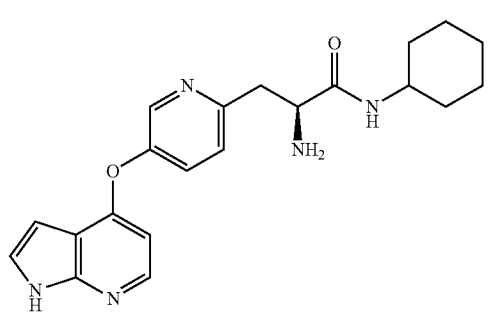 [SMILES: N[C@@H](Cc1ccc(Oc2ccnc3[nH]ccc23)cn1)C(=O)NC1CCCCC1]

Example 227 was prepared from Intermediate 227F using a method analogous to that used for Step G of Example 1.
LCMS (Method 1): Rt=2.36 min, m/z 380.2 [M+H]$^+$ $^1$H NMR (400 MHz, DMSO) δ 11.80 (s, 1H), 8.42 (d, J=2.7 Hz, 1H), 8.09 (d, J=5.4 Hz, 1H), 7.67 (d, J=8.1 Hz, 1H), 7.56 (dd, J=2.9, 8.5 Hz, 1H), 7.38 (d, J=3.6 Hz, 1H), 7.33 (d, J=8.5 Hz, 1H), 6.43 (d, J=5.4 Hz, 1H), 6.24 (d, J=3.5 Hz, 1H), 3.57-3.47 (m, 2H), 3.05 (dd, J=5.3, 13.4 Hz, 1H), 2.83 (dd, J=8.2, 13.4 Hz, 1H), 1.83 (s, 2H), 1.72-1.59 (m, 3H), 1.58-1.49 (m, 1H), 1.28-1.06 (m, 6H).

Example 228

The following example was prepared in a similar way of Example 227, by replacing in Step F the amine indicated in the table below.

| Ex | Structure | Amine | 1H NMR | LC-MS |
|---|---|---|---|---|
| 228 | (S)-3-(5-((1H-pyrrolo[2,3-b]pyridin-4-yl)oxy)pyridin-2-yl)-2-amino-1-(4-benzylpiperazin-1-yl)propan-1-one | 1-Benzyl-piperazine | $^1$H NMR (400 MHz, DMSO) δ 11.81 (s, 1H), 8.42 (d, J = 2.7 Hz, 1H), 8.10 (d, J = 5.4 Hz, 1H), 7.56 (dd, J = 2.9, 8.5 Hz, 1H), 7.41-7.36 (m, 1H), 7.36-7.22 (m, 8H), 6.44 (d, J = 5.4 Hz, 1H), 6.23 (d, J = 2.6 Hz, 1H), 4.10 (dd, J = 5.7, 7.8 Hz, 1H), 3.55-3.37 (m, 4H), 2.96 (dd, J = 5.6, 13.5 Hz, 1H), 2.78 (dd, J = 8.0, 13.5 Hz, 1H), 2.39-2.18 (m, 4H), 1.78 (s, 2H). | Rt = 1.77 min, m/z 457.3 [M + H]$^+$ (Method 1) |

Example 229

Step A. tert-butyl (R)-(1-(Cyclohexylamino)-3-(3,5-difluoro-4-hydroxyphenyl)-1-oxopropan-2-yl)carbamate (Example 229A)

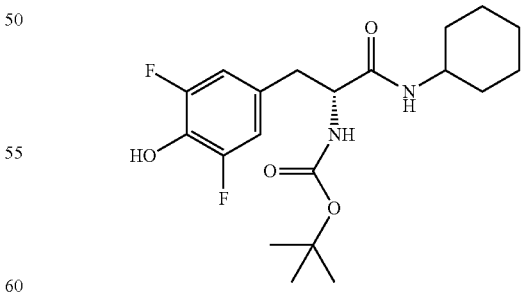

(R)-2-((tert-butoxycarbonyl)amino)-3-(3,5-difluoro-4-hydroxyphenyl)propanoic acid (500 mg, 1.58 mmol) and cyclohexanamine (172 mg, 1.74 mmol), DIPEA (822 μL, 4.74 mmol) and HATU (719 mg, 1.90 mmol) were stirred at RT in a mixture of DMF (2 mL) and DCM (10 mL). After 3 h the reaction mixture was concentrated in vacuo and the residue was partitioned between DCM (20 mL) and saturated sodium bicarbonate solution (15 mL). The organic layer was separated, washed with brine, dried (Na₂SO₄) and evaporated. The crude product was purified by chromatography on a Si cartridge (40 g) eluting with 0-100% ethyl acetate in cyclohexane to give a cream foam (468 mg).

LCMS (Method 6): Rt=1.40 min, m/z 397.1 [M−H]⁻

Step B. tert-Butyl (R)-(3-(4-((6-chloro-1-((2-(trimethylsilyl)ethoxy)methyl)-1H-pyrrolo[2,3-b]pyridin-4-yl)oxy)-3,5-difluorophenyl)-1-(cyclohexylamino)-1-oxopropan-2-yl)carbamate (Example 229B)

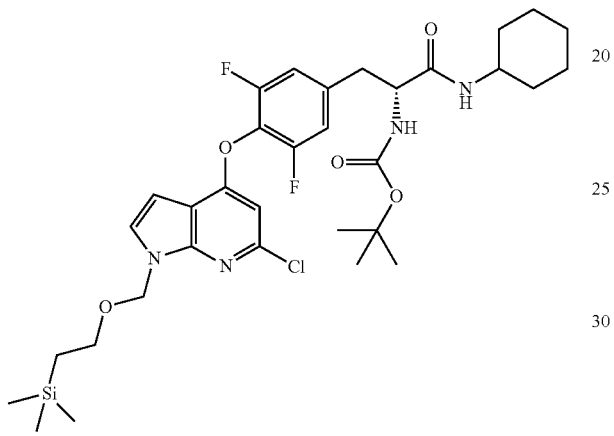

Intermediate 229B was prepared from Intermediate 229A and Intermediate 227B using a procedure similar to that used for Intermediate 227C.

LCMS (Method 6): Rt=1.97 min, m/z 679.3 [M+H]⁺

Step C. tert-Butyl (R)-(1-(cyclohexylamino)-3-(3,5-difluoro-4-((1-((2-(trimethylsilyl)ethoxy)methyl)-1H-pyrrolo[2,3-b]pyridin-4-yl)oxy)phenyl)-1-oxopropan-2-yl)carbamate (Example 229C)

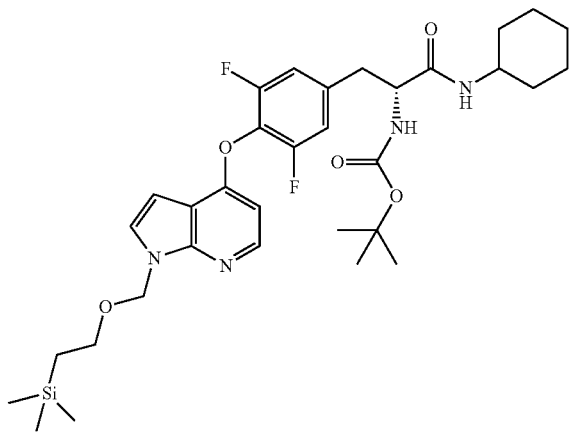 [SMILES: CC(C)(C)OC(=O)N[C@H](Cc1cc(F)c(Oc2ccnc3c2ccn3COCC[Si](C)(C)C)c(F)c1)C(=O)NC1CCCCC1]

Intermediate 229C was prepared from Intermediate 229B using a method analogous to that used for Intermediate 227D.

LCMS (Method 6): Rt=1.87 min, m/z 645.4 [M+H]⁺

Step D. (R)-3-(4-((1H-pyrrolo[2,3-b]pyridin-4-yl)oxy)-3,5-difluorophenyl)-2-amino-N-cyclohexylpropanamide (Example 229)

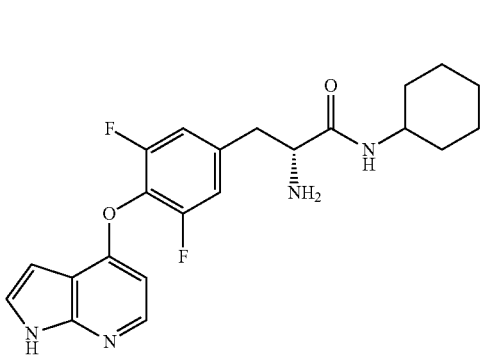 [SMILES: N[C@H](Cc1cc(F)c(Oc2ccnc3[nH]ccc23)c(F)c1)C(=O)NC1CCCCC1]

Intermediate 229C (216 mg, 0.336 mmol) was dissolved in DCM (5 mL) and TFA (1 mL) was added. After stirring at RT for 1 h the volatiles were evaporated and the residue was dissolved in methanol (10 mL). 2M lithium hydroxide (2 mL) was added and the reaction was stirred at RT for 18 h. The methanol was evaporated and the aqueous mixture was extracted with DCM (12 mL). The organic was dried (Na₂SO₄) and evaporated. The product was purified by HPLC eluting with a gradient of 10-98% acetonitrile in water (0.1% formic acid added) to give a white solid (67 mg).

LCMS (Method 1): Rt=2.86 min, m/z 415.2 [M+H]⁺

¹H NMR (400 MHz, DMSO) δ 11.85 (s, 1H), 8.07 (d, J=5.4 Hz, 1H), 7.71 (d, J=8.0 Hz, 1H), 7.41 (dd, J=2.5, 3.4 Hz, 1H), 7.18 (d, J=9.0 Hz, 2H), 6.36 (d, J=5.5 Hz, 1H), 6.34 (dd, J=1.9, 3.4 Hz, 1H), 3.58-3.49 (m, 1H), 3.47 (t, J=6.7 Hz, 1H), 2.91 (dd, J=6.1, 13.2 Hz, 1H), 2.77 (dd, J=7.5, 13.3 Hz, 1H), 1.73-1.49 (m, 6H), 1.32-1.03 (m, 6H).

The following racemic examples were resolved using the conditions given below to give the pure enantiomers.

| Racemate | Separation | Analysis | 1st eluting | 2nd eluting |
|---|---|---|---|---|
| Example 8 Separation 1 | MD SFC<br>YMC Amylose-C<br>30/70 MeOH/MeCN<br>(50/50/0.1% DEA)/$CO_2$<br>100 mL/min<br>40° C.<br>230 nM;<br>column dimensions<br>250 × 20 mm id 5 μm | MD SFC<br>YMC Amylose-C<br>30/70 MeOH/MeCN<br>(50/50/0.1% DEA)/$CO_2$<br>0.95 mL/min<br>40° C.;<br>column dimensions<br>150 × 2 mm, 5 μm | Rt = 5.6 min<br>(further<br>purification<br>required) | Rt = 6.4 min<br>(further<br>purification<br>required) |
| Example 8 Separation 2 First eluting diastereoisomer A | MD SFC<br>YMC Amylose-C<br>30/70 MeOH/MeCN<br>(50/50/0.1% DEA)/$CO_2$<br>100 mL/min<br>40° C.<br>220 nM;<br>column dimensions<br>250 × 20 mm id 5 μm | MD SFC<br>YMC Amylose-C<br>30/70 MeOH/MeCN<br>(50/50/0.1% DEA)/$CO_2$<br>0.95 mL/min<br>40° C.;<br>column dimensions<br>150 × 2 mm, 5 μm | Example 8A<br>Rt = 5.6 mins | |
| Example 8 Separation 2 Second eluting diastereoisomer B | MD SFC<br>YMC Amylose-C<br>30/70 MeOH/MeCN<br>(50/50/0.1% DEA)/$CO_2$<br>100 mL/min<br>40° C.<br>220 nM;<br>column dimensions<br>250 × 20 mm id 5 μm | MD SFC<br>YMC Amylose-C<br>30/70 MeOH/MeCN<br>(50/50/0.1% DEA)/$CO_2$<br>0.95 mL/min<br>40° C.;<br>column dimensions<br>150 × 2 mm, 5 μm | | Example 8B<br>Rt = 6.3 mins |
| Example 132 | MD SFC<br>YMC Amylose-C<br>40/60 IPA(0.1% DEA)/$CO_2$<br>100 mL/min<br>40° C.<br>225 nM;<br>column dimensions<br>250 × 20 mm id 5 μm | MD SFC<br>YMC Amylose-C<br>30/70 IPA(0.1% DEA)/$CO_2$<br>5 mL/min<br>40° C.<br>225 nM;<br>column dimensions<br>250 × 4.6 mm 5 μm | Example 132A<br>Rt = 3.1 min | Example 132B<br>Rt = 3.9 min |
| Example 91 | MD SFC<br>YMC Amylose-C<br>40/60 IPA(0.1% DEA)/$CO_2$<br>70 mL/min<br>40° C.<br>250 nM;<br>column dimensions<br>250 × 20 mm id 5 μm | MD SFC<br>YMC Amylose-C<br>40/60 IPA(0.1% DEA)/$CO_2$<br>5 mL/min<br>40° C.<br>250 nM;<br>column dimensions<br>250 × 4.6 mm 5 μm | Example 91A<br>Rt = 2.1 min | Example 91B<br>Rt = 3.2 min |
| Example 57 | MD SFC<br>YMC Amylose-C<br>30/70 MeOH (0.1% DEA)/$CO_2$<br>100 mL/min<br>40° C.<br>220 nM;<br>column dimensions<br>250 × 20 mm id 5 μm | MD SFC<br>YMC Amylose-C<br>30/70 MeOH (0.1% DEA)/$CO_2$<br>5.0 mL/min<br>40° C.<br>220 nM;<br>column dimensions<br>250 × 4.6 mm 5 μm | Example 57A<br>Rt = 5.0 min | Example 57B<br>Rt = 6.1 min |
| Example 55 | Chiral HPLC (Method A) | Diacel Chiralpak IA, Solvent A $CO_2$ Solvent B IPA (+0.1% DEA) 1.7 mL/min | Example 54<br>Rt = 3.16 min | Example 55<br>Rt = 3.22 min |

| Time | % A | % B |
|---|---|---|
| 0 | 95 | 5 |
| 0.5 | 95 | 5 |
| 2 | 45 | 55 |
| 4.5 | 45 | 55 |
| 4.6 | 95 | 5 |
| 5 | 95 | 5 |

40° C.
400 nM;
column dimensions
100 × 3.0 mm 3 μm

Pharmacological Activity of the Compounds of the Invention.

In Vitro Inhibitory Activity Assay Description

The effectiveness of compounds of the present invention to inhibit Rho kinase activity can be determined in a 10 μl assay containing 40 mM Tris pH7.5, 20 mM $MgCl_2$, 0.1 mg/ml BSA, 50 μM DTT and 2.5 μM peptide substrate (Myelin Basic Protein) using an ADP-Glo kit (Promega). Compounds were dissolved in DMSO such that the final concentration of DMSO was 1% in the assay. All reactions/incubations are performed at 25° C. Compound (2 ul) and either Rho kinase 1 or 2 (4 μl) were mixed and incubated for 30 mins. Reactions were initiated by addition of ATP (4 μl) such that the final concentration of ATP in the assay was 10

µM. After a 1 hour incubation 10 µl of ADP-Glo Reagent was added and after a further 45 minute incubation 20 ul of Kinase Detection Buffer was added and the mixture incubated for a further 30 minutes. The luminescent signal was measured on a luminometer. Controls consisted of assay wells that did not contain compound with background determined using assay wells with no enzyme added. Compounds were tested in dose-response format and the inhibition of kinase activity was calculated at each concentration of compound. To determine the $IC_{50}$ (concentration of compound required to inhibit 50% of the enzyme activity) data were fit to a plot of % inhibition vs $Log_{10}$ compound concentration using a sigmoidal fit with a variable slope and fixing the maximum to 100% and the minimum to 0%. To determine the Ki values the Cheng-Prusoff equation was utilized (Ki=$IC_{50}$/(1+[S]/Km).

Compounds according to the invention showed Ki values lower than 5 µM and for most of the compounds of the invention Ki is even lower that 500 nM. The results for individual compounds are provided below in Table 1 and are expressed as range of activity.

TABLE 1

| Example | Activity ROCK 1 | Activity ROCK 2 |
| --- | --- | --- |
| 1 | +++ | +++ |
| 2 | +++ | +++ |
| 3 | ++ | ++ |
| 4 | +++ | +++ |
| 5 | +++ | +++ |
| 6 | +++ | +++ |
| 7 | +++ | +++ |
| 8 | +++ | +++ |
| 9 | +++ | +++ |
| 10 | +++ | +++ |
| 11 | +++ | +++ |
| 12 | +++ | +++ |
| 13 | +++ | +++ |
| 14 | +++ | +++ |
| 15 | +++ | +++ |
| 16 | +++ | +++ |
| 17 | +++ | +++ |
| 18 | +++ | +++ |
| 19 | +++ | +++ |
| 20 | +++ | +++ |
| 21 | +++ | +++ |
| 22 | +++ | +++ |
| 23 | +++ | +++ |
| 24 | +++ | +++ |
| 25 | +++ | +++ |
| 26 | +++ | +++ |
| 27 | +++ | +++ |
| 28 | +++ | +++ |
| 29 | +++ | +++ |
| 30 | +++ | +++ |
| 31 | +++ | +++ |
| 32 | +++ | +++ |
| 33 | +++ | +++ |
| 34 | +++ | +++ |
| 35 | +++ | +++ |
| 36 | +++ | +++ |
| 37 | +++ | +++ |
| 38 | +++ | +++ |
| 39 | ++ | ++ |
| 40 | ++ | +++ |
| 41 | +++ | +++ |
| 42 | +++ | +++ |
| 43 | +++ | +++ |
| 44 | ++ | +++ |
| 45 | +++ | +++ |
| 46 | +++ | +++ |
| 47 | +++ | +++ |
| 48 | +++ | +++ |
| 49 | +++ | +++ |
| 50 | +++ | +++ |
| 51 | +++ | +++ |
| 52 | +++ | +++ |
| 53 | +++ | +++ |
| 54 | +++ | +++ |
| 55 | ++ | ++ |
| 56 | +++ | +++ |
| 57 | +++ | +++ |
| 58 | +++ | +++ |
| 59 | +++ | +++ |
| 60 | +++ | +++ |
| 61 | +++ | +++ |
| 62 | +++ | +++ |
| 63 | +++ | +++ |
| 64 | ++ | +++ |
| 65 | +++ | +++ |
| 66 | +++ | +++ |
| 67 | +++ | +++ |
| 68 | +++ | +++ |
| 69 | +++ | +++ |
| 70 | +++ | +++ |
| 71 | +++ | +++ |
| 72 | +++ | +++ |
| 73 | +++ | +++ |
| 74 | +++ | +++ |
| 75 | +++ | +++ |
| 76 | +++ | +++ |
| 77 | +++ | +++ |
| 78 | +++ | +++ |
| 79 | +++ | +++ |
| 80 | +++ | +++ |
| 81 | +++ | +++ |
| 82 | +++ | +++ |
| 83 | +++ | +++ |
| 84 | ++ | ++ |
| 85 | ++ | ++ |
| 86 | + | + |
| 87 | +++ | +++ |
| 88 | +++ | +++ |
| 89 | +++ | +++ |
| 90 | +++ | +++ |
| 91 | ++ | +++ |
| 92 | ++ | ++ |
| 93 | ++ | ++ |
| 94 | +++ | +++ |
| 95 | + | + |
| 96 | + | + |
| 97 | ++ | ++ |
| 98 | + | + |
| 99 | ++ | ++ |
| 100 | + | + |
| 101 | ++ | ++ |
| 102 | + | + |
| 103 | ++ | ++ |
| 104 | + | + |
| 105 | ++ | ++ |
| 106 | + | + |
| 107 | +++ | +++ |
| 108 | ++ | ++ |
| 109 | ++ | ++ |
| 110 | + | ++ |
| 111 | ++ | +++ |
| 112 | + | ++ |
| 113 | + | ++ |
| 114 | +++ | +++ |
| 115 | +++ | +++ |
| 116 | ++ | ++ |
| 117 | ++ | ++ |
| 118 | ++ | ++ |
| 119 | +++ | +++ |
| 120 | ++ | +++ |
| 121 | ++ | ++ |
| 122 | ++ | +++ |
| 123 | +++ | +++ |
| 124 | +++ | +++ |
| 125 | ++ | ++ |
| 126 | ++ | ++ |

TABLE 1-continued

| Example | Activity ROCK 1 | Activity ROCK 2 |
|---|---|---|
| 127 | +++ | +++ |
| 128 | +++ | +++ |
| 129 | +++ | +++ |
| 130 | +++ | +++ |
| 131 | ++ | +++ |
| 132 | +++ | +++ |
| 133 | +++ | +++ |
| 134 | +++ | +++ |
| 135 | +++ | +++ |
| 136 | ++ | ++ |
| 137 | +++ | +++ |
| 138 | ++ | ++ |
| 139 | +++ | +++ |
| 140 | ++ | ++ |
| 141 | +++ | +++ |
| 142 | ++ | ++ |
| 143 | + | + |
| 144 | + | + |
| 145 | +++ | +++ |
| 146 | +++ | +++ |
| 147 | ++ | +++ |
| 148 | +++ | +++ |
| 149 | +++ | +++ |
| 150 | ++ | ++ |
| 151 | + | + |
| 152 | +++ | +++ |
| 153 | +++ | +++ |
| 154 | +++ | +++ |
| 155 | +++ | +++ |
| 156 | +++ | +++ |
| 157 | +++ | +++ |
| 158 | +++ | +++ |
| 159 | +++ | +++ |
| 160 | +++ | +++ |
| 161 | +++ | +++ |
| 162 | +++ | +++ |
| 163 | +++ | +++ |
| 164 | +++ | +++ |
| 165 | +++ | +++ |
| 166 | +++ | +++ |
| 167 | +++ | +++ |
| 168 | +++ | +++ |
| 169 | +++ | +++ |
| 170 | +++ | +++ |
| 171 | ++ | ++ |
| 172 | +++ | +++ |
| 173 | +++ | +++ |
| 174 | +++ | +++ |
| 175 | +++ | +++ |
| 176 | ++ | +++ |
| 177 | +++ | +++ |
| 178 | + | + |
| 179 | ++ | ++ |
| 180 | ++ | ++ |
| 181 | + | + |
| 182 | + | + |
| 183 | + | ++ |
| 184 | +++ | +++ |
| 185 | + | + |
| 186 | +++ | +++ |
| 187 | +++ | +++ |
| 188 | +++ | +++ |
| 189 | +++ | +++ |
| 190 | +++ | +++ |
| 191 | +++ | +++ |
| 192 | +++ | +++ |
| 193 | ++ | ++ |
| 194 | +++ | +++ |
| 195 | +++ | +++ |
| 196 | +++ | +++ |
| 197 | +++ | +++ |
| 198 | +++ | +++ |
| 199 | +++ | +++ |
| 200 | +++ | +++ |
| 201 | +++ | +++ |
| 202 | ++ | ++ |
| 203 | +++ | +++ |
| 204 | +++ | +++ |
| 205 | +++ | +++ |
| 206 | +++ | +++ |
| 207 | +++ | +++ |
| 208 | +++ | +++ |
| 209 | ++ | +++ |
| 210 | ++ | ++ |
| 211 | ++ | ++ |
| 212 | ++ | ++ |
| 213 | +++ | +++ |
| 214 | ++ | ++ |
| 215 | ++ | ++ |
| 216 | +++ | +++ |
| 217 | +++ | +++ |
| 218 | +++ | +++ |
| 219 | +++ | +++ |
| 220 | +++ | +++ |
| 221 | +++ | +++ |
| 222 | +++ | +++ |
| 223 | +++ | +++ |
| 224 | +++ | +++ |
| 225 | + | + |
| 226 | ++ | ++ |
| 227 | + | + |
| 228 | + | ++ |
| 229 | ++ | ++ |
| 132A | +++ | +++ |
| 132B | ++ | +++ |
| 8A | +++ | +++ |
| 8B | +++ | +++ |
| 91A | +++ | +++ |
| 91B | ++ | ++ |
| 57A | ++ | +++ |
| 57B | +++ | +++ |

Wherein the compounds are classified in term of potency with respect to their inhibitory activity on ROCK-I and ROCK-II isoforms according to the following classification criterion:

+++:Ki<3 nM

++:Ki in the range 3-30 nM

+:Ki>30 nM

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. A compound of formula (I)

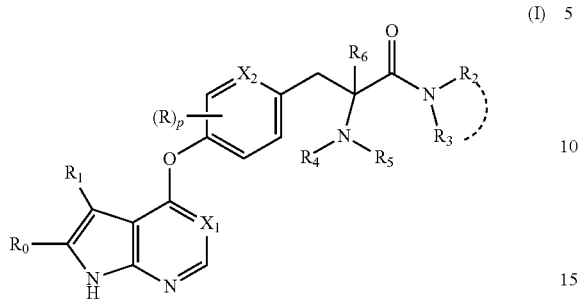

wherein
X₁, and X₂ are in each occurrence independently a CH group or a nitrogen atom;
p is zero or an integer from 1 to 3;
each R, when present, is a halogen;
R₀ and R₁ are independently:
—H,
halogen,
—NR₇R₈,
—CN,
(C₁-C₆) alkyl,
(C₁-C₆) haloalkyl,
(C₁-C₆) hydroxyalkyl,
(C₁-C₆) aminoalkyl,
(C₁-C₆) alkoxy-(C₁-C₆) alkyl
(C₃-C₁₀) cycloalkyl,
(C₂-C₆) alkenyl,
(C₅-C₇) cycloalkenyl,
(C₂-C₆) alkynyl,
(C₂-C₆) hydroxyalkynyl,
aryl,
heteroaryl, or
(C₃-C₆) heterocycloalkyl
wherein each of said aryl, heteroaryl and (C₃-C₆) heterocycloalkyl is optionally and independently substituted with one or more groups selected from the group consisting of:
halogen,
—OH,
—CN,
—NR₇R₈,
—CH₂NR₇R₈,
(C₁-C₆) alkyl,
(C₁-C₆) haloalkyl,
(C₁-C₆) hydroxyalkyl,
(C₂-C₆) alkenyl,
(C₂-C₆) alkynyl, and
(C₂-C₆) hydroxyalkynyl;
R₂ and R₃, are the same or different, and are selected from the group consisting of
—H,
(C₁-C₆) alkyl,
(C₁-C₆) haloalkyl,
(C₁-C₆) hydroxyalkyl,
(C₁-C₆) aminoalkyl,
(C₁-C₆) alkoxy(C₁-C₆) alkyl,
(C₃-C₁₀)cycloalkyl,
(C₃-C₈)heterocycloalkyl,
aryl,
heteroaryl,
aryl(C₁-C₆)alkyl,
heteroaryl(C₁-C₆)alkyl
(C₃-C₈)cycloalkyl(C₁-C₆)alkyl, and
(C₃-C₈)heterocycloalkyl-(C₁-C₆)alkyl
wherein each of said aryl, heteroaryl, cycloalkyl, and heterocycloalkyl is further optionally substituted by one or more group selected independently from the group consisting of halogen, —CN, —OH, (C₁-C₈)alkyl, (C₁-C₆) haloalkyl, (C₁-C₁₀)alkoxy, aryl, aryl(C₁-C₆)alkyl, carbamoyl, (C₁-C₆) aminoalkyl, and (C₁-C₆) hydroxyalkyl; or
R₂ and R₃, in the alternative, taken together with the nitrogen atom to which they are bonded form a mono- or bi-cyclic saturated or partially saturated heterocyclic radical, wherein said heterocyclic radical is optionally further substituted with one or more groups selected from the group consisting of
halogen,
hydroxyl,
—NR₇R₈,
—CH₂NR₇R₈,
(C₁-C₆) alkyl,
(C₁-C₆) haloalkyl,
(C₁-C₆) hydroxyalkyl,
(C₂-C₆) alkenyl,
(C₂-C₆) alkynyl,
(C₂-C₆) hydroxyalkynyl,
(C₁-C₆) alkoxy (C₁-C₆) alkyl,
(C₁-C₆) alkanoyl,
carbamoyl,
(C₃-C₆) cycloalkyl-carbonyl,
(C₃-C₆) heterocycloalkyl-carbonyl,
aryl(C₁-C₆)alkyl,
aryl alkanoyl,
arylsulfonyl,
heteroaryl(C₁-C₆)alkyl,
heteroaryl-carbonyl
heteroaryloxyl,
(C₃-C₆) cycloalkyl,
(C₃-C₈)cycloalkyl(C₁-C₆)alkyl
(C₃-C₆) heterocycloalkyl-(C₁-C₆) alkyl,
aryl, and
heteroaryl
wherein each of said cycloalkyl, aryl, and heteroaryl is further optionally substituted by halogen, (C₁-C₈)alkyl, (C₁-C₁₀)alkoxy, (C₁-C₆)alkylthio, (C₁-C₆) aminoalkyl, (C₁-C₆) aminoalkoxyl, carbamoyl, or (C₁-C₆)alkyl-sulfonyl;
R₄ and R₅ are at each occurrence independently selected from the group consisting of
H,
(C₁-C₆) alkyl,
(C₁-C₆) haloalkyl,
(C₁-C₆) hydroxyalkyl,
(C₁-C₆) aminoalkyl,
(C₁-C₆) alkoxyl,
(C₁-C₆) alkoxy-(C₁-C₆) alkyl,
(C₃-C₆) cycloalkyl-(C₁-C₆) alkyl
(C₃-C₆) heterocycloalkyl-(C₁-C₆) alkyl,
(C₃-C₆) cycloalkyl-carbonyl
(C₃-C₆) heterocycloalkyl-carbonyl
aryl,
heteroaryl, and
(C₃-C₆) heterocycloalkyl;
wherein any of said (C₃-C₆) cycloalkyl, aryl, heteroaryl, and (C₃-C₆) heterocycloalkyl is optionally and independently substituted with one or more groups selected from the group consisting of
halogen,
—OH, and
$(C_1-C_6)$ alkyl;
$R_6$ is selected from the group consisting of —H, $(C_1-C_6)$ alkyl, and $(C_1-C_6)$ haloalkyl;
$R_7$ and $R_8$ are at each occurrence independently selected from the group consisting of
H,
$(C_1-C_6)$ alkyl,
$(C_1-C_6)$ haloalkyl,
$(C_1-C_6)$ hydroxyalkyl,
$(C_1-C_6)$ aminoalkyl,
$(C_1-C_6)$ alkoxyl,
$(C_1-C_6)$ alkoxy-$(C_1-C_6)$ alkyl,
$(C_3-C_6)$ heterocycloalkyl-$(C_1-C_6)$ alkyl,
aryl,
heteroaryl, and $(C_3-C_6)$ heterocycloalkyl;
wherein any of said aryl, heteroaryl, and $(C_3-C_6)$ heterocycloalkyl is optionally and independently substituted with one or more groups selected from the group consisting of
halogen,
—OH, and
$(C_1-C_6)$ alkyl; or
$R_7$ and $R_8$ are taken together with the nitrogen atom to which they are linked, to form a 4 to 6 membered heterocyclic radical, wherein at least one further ring carbon atom in the said heterocyclic radical may be replaced by at least one group selected from N, S, or O, and said heterocyclic radical may be further optionally substituted by a group selected from the group consisting of
H,
—CN,
halogen,
-oxo,
—NR$_7$R$_8$
$(C_1-C_6)$ alkyl,
$(C_1-C_6)$ haloalkyl,
$(C_1-C_6)$ hydroxyalkyl,
$(C_1-C_6)$ aminoalkyl,
$(C_1-C_6)$ alkoxyl,
$(C_1-C_6)$ alkoxy-$(C_1-C_6)$ alkyl, and
alkanoyl;
or pharmaceutically acceptable salt thereof.

2. A compound or pharmaceutically acceptable salt according to claim 1, wherein each of $X_1$ and $X_2$ is a CH group.

3. A compound or pharmaceutically acceptable salt according to claim 1, wherein $R_2$ and $R_3$, taken together with the nitrogen atom to which they are linked, form a piperazine ring, represented by formula Ib:

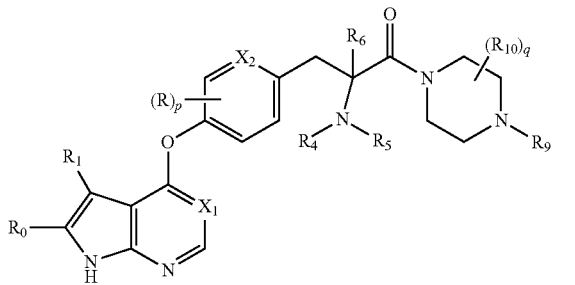

wherein $R_9$ is selected from the group consisting of
$(C_1-C_6)$ alkyl,
$(C_1-C_6)$ alkoxy $(C_1-C_6)$ alkyl,
$(C_1-C_6)$ alkanoyl,
carbamoyl,
$(C_3-C_6)$ cycloalkyl-carbonyl,
$(C_3-C_6)$ heterocycloalkyl-carbonyl,
aryl($C_1-C_6$)alkyl,
aryl alkanoyl,
arylsulfonyl,
heteroaryl($C_1-C_6$)alkyl,
heteroaryl-carbonyl,
heteroaryloxyl,
$(C_3-C_6)$ cycloalkyl,
$(C_3-C_8)$cycloalkyl($C_1-C_6$)alkyl
$(C_3-C_6)$ heterocycloalkyl-$(C_1-C_6)$ alkyl,
aryl, and
heteroaryl
wherein each of said cycloalkyl, heterocycloalkyl, aryl, and heteroaryl is further optionally substituted by one or more substituents selected from the group consisting of halogen, $(C_1-C_8)$alkyl, $(C_1-C_{10})$alkoxy, $(C_1-C_6)$alkylthio, $(C_1-C_6)$ aminoalkyl, $(C_1-C_6)$ aminoalkoxyl, carbamoyl, and $(C_1-C_6)$alkyl-sulfonyl;
and wherein said piperazine ring is further optionally substituted by one or more substituent group $R_{10}$ selected from the group consisting of $(C_1-C_6)$ alkyl, $(C_1-C_6)$ hydroxyalkyl, and aryl.

4. A compound or pharmaceutically acceptable salt according to claim 1, wherein
$X_1$, and $X_2$ are both a CH group;
p is zero or an integer from 1 to 3;
each R, when present, is a halogen;
$R_0$ is —H;
$R_1$ is independently selected from the group consisting of
—CN,
$(C_1-C_6)$ alkyl, and
$(C_1-C_6)$ hydroxyalkyl;
$R_2$ is —H; and
$R_3$, is selected from the group consisting of
$(C_3-C_{10})$cycloalkyl,
$(C_3-C_8)$heterocycloalkyl,
heteroaryl($C_1-C_6$)alkyl;
wherein each of said heteroaryl, cycloalkyl, and heterocycloalkyl is optionally substituted by one or more groups selected from the group consisting of $(C_1-C_8)$alkyl and $(C_1-C_6)$ hydroxyalkyl;
$R_4$ and $R_5$ are both H; and
$R_6$ is —H.

5. A compound or pharmaceutically acceptable salt according to claim 1, wherein
$X_1$, and $X_2$ are at each occurrence independently a CH group or a nitrogen atom;
p is zero or an integer from 1 to 3;
each R, when present, is fluoro;
$R_0$ is —H or methyl;
$R_1$ is independently selected from the group consisting of
—H,
Bromo,
Chloro,
Iodo,
Fluoro
NR$_7$R$_8$,
—CN,
methyl,
$(C_1-C_6)$ haloalkyl, hydroxymethyl,
hydroxyethyl
$(C_1-C_6)$ aminoalkyl,
methoxymethyl,
cyclopropyl,
$(C_2-C_6)$ alkenyl,
$(C_5-C_7)$ cycloalkenyl,
$(C_2-C_6)$ alkynyl,
hydroxypropynyl,
phenyl,
hydroxyphenyl,
isoxazolyl,
N-methylimidazolyl,
pyridinyl,
thiazolyl,
N-ethyl pyrazolyl,
thiopheneyl-carbonitrile,
dihydropyrrolyl, and dihydrofuranyl;

$R_2$ is —H or methyl; and $R_3$, is independently selected from the group consisting of
methyl,
$(C_1-C_6)$ haloalkyl,
$(C_1-C_6)$ hydroxyalkyl,
dimethylaminoethyl,
dimethylaminopropyl,
methoxypropyl,
cyclohexyl,
hydroxymethylcyclohexyl,
hydroxyethylcyclohexyl,
cyano-cyclohexyl,
4-aminocarbonyl-cyclohexane-4yl,
4-dimethylaminomethyl-cyclohexane-4yl,
N-methylpiperidinyl,
(hydroxymethyl)-N-methylpiperidinyl,
N-benzylpiperidinyl,
N-methylazetidin-3-yl,
tetrahydropyranyl,
4-hydroxymethyl-tetrahydropyran-4-yl,
quinuclidinyl,
phenyl,
trifluoromethylphenyl,
dihydroindenyl,
thiazolyl,
pyridinyl,
chloropyridinyl,
isoquinolinyl,
benzyl,
o-hydroxymethylbenzyl,
m-hydroxymethylbenzyl,
p-hydroxymethylbenzyl,
phenethyl,
(pyridinyl)ethyl,
(thiophene-yl)methyl,
(N-phenyl-pyrazolyl)ethyl,
cyclohexylmethyl,
(piperidin-4-yl)methyl,
(N-benzylpiperidinyl)methyl,
(N-methylpiperidin-4-yl)methyl,
N-methylazetidin-3-yl-methyl, and
morpholinopropyl; or $R_2$ and $R_3$, in the alternative, taken together with the nitrogen atom to which they are linked, form a monocyclic group which is piperazin-N-yl, methylpiperazin-N-yl, phenyl-N-methylpiperazin-N-yl, N-phenyl-piperazin-N-yl, trimethylpiperazin-N-yl, 4-benzyl-3,5-dimethylpiperazin-N-yl, (hydroxymethyl)-N-methylpiperazin-N-yl, acetyl(piperazin-N-yl), phenylacetyl(piperazin-N-yl), benzoyl(piperazin-N-yl), 4-(((dimethylamino)methyl)benzoyl)piperazin-1-yl, cyclopropyl(piperazin-N-yl), cyclopropylmethyl(piperazin-N-yl), cyclopropanecarbonyl(piperazin-N-yl), cyclohexanecarbonyl(piperazin-N-yl), N-methylpiperidine-4-carbonyl(piperazin-N-yl), 4-(pyridine-3-carbonyl)piperazin-N-yl, 4-(1methyl-1H-pyrazole-4-carbonyl)piperazin-N-yl, 4-(1methyl-1H-imidazole-4-carbonyl)piperazin-N-yl, 4-(1H-thiazole-4-carbonyl)piperazin-N-yl, 4-dimethylaminocarbonyl(piperazin-N-yl), (phenylsulfonyl)piperazin-N-yl, (pyridinyl)piperazin-N-yl, (pyridinylmethyl)piperazin-N-yl, (methoxyethyl)piperazin-N-yl, (benzyl)piperazin-N-yl, (methoxybenzyl)piperazin-N-yl, (3-(dimethylaminopropoxy)benzyl)piperazin-N-yl, (fluorobenzyl)piperazin-N-yl, (methylbenzyl)piperazin-N-yl, N-(((methylaminocarbonyl)phenyl)methyl)piperazine-N-yl, N-(((methylaminocarbonyl)furanyl)methyl)piperazine-N-yl, (phenethyl)piperazin-N-yl, (pyrimidinylmethyl)piperazin-N-yl, (2(methylthio)pyrimidinylmethyl)piperazin-N-yl, (((methylsulfonyl)piperidin-4-yl)methyl)piperazin-N-yl, ((N-methyl-imidazol-5-yl)methyl)piperazin-N-yl, ((1-methyl-1H-imidazol-2-yl)methyl)piperazin-N-yl, ((methylthiazolyl)methyl)piperazin-N-yl, ((pyrazin-2-yl)methyl)piperazin-N-yl, ((1-methyl-1H-pyrazol-4-yl)methyl)piperazin-N-yl, benzo[d][1,3]dioxol-5-ylmethyl)piperazin-N-yl, (quinoxalin-2-ylmethyl)piperazin-N-yl, ((1,2,3-thiadiazol-4-yl)methyl)piperazin-N-yl, (pyridazin-4-ylmethyl)piperazin-N-yl, pyrrolidin-N-yl, phenylpyrrolidin-N-yl, (pyridinyl)pyrrolidin-N-yl, piperidin-N-yl, (dimethylamino)piperidin-N-yl, 4-((dimethylamino)methyl)piperidin-N-yl, benzylpiperidin-N-yl, benzylhydroxypiperidin-N-yl, pyridinylpiperidin-N-yl, pyridinyloxypiperidin-N-yl, (phenylsulfonyl)piperidin-N-yl, 4-phenyl-5,6-dihydropyridin-1(2H)-yl, phenylmorpholin-N-yl, 3-(dimethylamino)azetidin-N-yl, 3-(dimethylamino)methyl-azetidin-N-yl 3-(dimethylamino)pyrrolidin-N-yl, 3-(3-methyl-1,2,4-oxadiazol-5-yl)pyrrolidin-N-yl, or 3-(dimethylamino)piperidin-N-yl, or a bi-cyclic group which is 5,6-dihydroimidazo[1,5-a]pyrazin-7(8H)-yl, 3,4-dihydro-2,7-naphthyridin-2(1H)-yl), 1H-pyrrolo[3,4-c]pyridin-2(3H)-yl, hexahydropyrazino[2,1-c][1,4]oxazin-8(1H)-yl, 3,4-dihydroisoquinolin-2(1H)-yl, 5-methyl-2,5-diazabicyclo[2.2.1]heptan-2-yl, 5-benzyl-2,5-diazabicyclo[2.2.1]heptan-2-yl, 7,8-dihydropyrido[4,3-d]pyrimidin-6(5H)-yl), 2,6-diazaspiro[3.3]heptan-2-yl, 6-methyl-2,6-diazaspiro[3.3]heptan-2-yl, 7-methyl-2,7-diazaspiro[3.5]nonan-2-yl, 2-methyl-2,9-diazaspiro[5.5]undecan-9-yl, 9-methyl-3,9-diazaspiro[5.5]undecan-3-yl, octahydropyrrolo[3,4-c]pyrrol-2-yl or 5-methyl-octahydropyrrolo[3,4-c]pyrrol-2-yl;

$R_4$ is selected from the group consisting of H, methyl, cyclohexylmethyl, and cyclohexylcarbonyl, and (pyrrolidin-3-yl)carbonyl;

$R_5$ is independently H or methyl; and $R_6$ is —H or methyl.

6. A compound or pharmaceutically acceptable salt according to claim 1, which is a compound selected from the group consisting of:

(S)-2-amino-3-(3-fluoro-4-((3-methyl-1H-pyrrolo[2,3-b]pyridin-4-yl)oxy)phenyl)-N-(1-methylpiperidin-4-yl)propanamide;

(S)-2-amino-1-(7,8-dihydropyrido[4,3-d]pyrimidin-6 (5H)-yl)-3-(3-fluoro-4-((3-methyl-1H-pyrrolo[2,3-b] pyridin-4-yl)oxy)phenyl)propan-1-one;

(S)-2-amino-3-(3-fluoro-4-((3-methyl-1H-pyrrolo[2,3-b] pyridin-4-yl)oxy)phenyl)-1-(6-methyl-2,6-diazaspiro [3.3]heptan-2-yl)propan-1-one;

(2S)-2-amino-3-(3-fluoro-4-((3-methyl-1H-pyrrolo[2,3-b]pyridin-4-yl)oxy)phenyl)-1-(2-phenylmorpholino) propan-1-one;

(S)-2-amino-3-(3-fluoro-4-((3-methyl-1H-pyrrolo[2,3-b] pyridin-4-yl)oxy)phenyl)-1-(4-phenylpiperazin-1-yl) propan-1-one;

(2S)-2-amino-3-(3-fluoro-4-((3-methyl-1H-pyrrolo[2,3-b]pyridin-4-yl)oxy)phenyl)-1-(4-methyl-3-phenylpiperazin-1-yl)propan-1-one;

(S)-2-amino-3-(3-fluoro-4-((3-methyl-1H-pyrrolo[2,3-b] pyridin-4-yl)oxy)phenyl)-1-(4-(phenylsulfonyl)piperidin-1-yl)propan-1-one;

(2S)-2-amino-3-(3-fluoro-4-((3-methyl-1H-pyrrolo[2,3-b]pyridin-4-yl)oxy)phenyl)-1-(3-(3-methyl-1,2,4-oxadiazol-5-yl)pyrrolidin-1-yl)propan-1-one;

(S)-2-amino-1-(4-benzyl-4-hydroxypiperidin-1-yl)-3-(3-fluoro-4-((3-methyl-1H-pyrrolo[2,3-b]pyridin-4-yl) oxy)phenyl)propan-1-one;

(S)-2-amino-1-(3,4-dihydroisoquinolin-2(1H)-yl)-3-(3-fluoro-4-((3-methyl-1H-pyrrolo[2,3-b]pyridin-4-yl) oxy)phenyl)propan-1-one;

(S)-2-amino-3-(3-fluoro-4-((3-methyl-1H-pyrrolo[2,3-b] pyridin-4-yl)oxy)phenyl)-1-(4-(pyridin-3-yloxy)piperidin-1-yl)propan-1-one;

(S)-2-amino-3-(3-fluoro-4-((3-methyl-1H-pyrrolo[2,3-b] pyridin-4-yl)oxy)phenyl)-1-(4-(pyridin-4-yl)piperidin-1-yl)propan-1-one;

(S)-2-amino-1-(4-benzylpiperidin-1-yl)-3-(3-fluoro-4-((3-methyl-1H-pyrrolo[2,3-b]pyridin-4-yl)oxy)phenyl) propan-1-one;

(S)-2-amino-1-(4-(dimethylamino)piperidin-1-yl)-3-(3-fluoro-4-((3-methyl-1H-pyrrolo[2,3-b]pyridin-4-yl) oxy)phenyl)propan-1-one;

(S)-2-amino-N-(3-(dimethylamino)propyl)-3-(3-fluoro-4-((3-methyl-1H-pyrrolo[2,3-b]pyridin-4-yl)oxy)phenyl)propanamide;

(2S)-2-amino-3-(3-fluoro-4-((3-methyl-1H-pyrrolo[2,3-b]pyridin-4-yl)oxy)phenyl)-1-(hexahydropyrazino[2, 1-c][1,4]oxazin-8(1H)-yl)propan-1-one;

(S)-2-amino-3-(3-fluoro-4-((3-methyl-1H-pyrrolo[2,3-b] pyridin-4-yl)oxy)phenyl)-1-((3S,5R)-3,4,5-trimethylpiperazin-1-yl)propan-1-one;

(S)-2-amino-3-(3-fluoro-4-((3-methyl-1H-pyrrolo[2,3-b] pyridin-4-yl)oxy)phenyl)-1-(3,3,4-trimethylpiperazin-1-yl)propan-1-one;

2-amino-3-(3-fluoro-4-((3-methyl-1H-pyrrolo[2,3-b] pyridin-4-yl)oxy)phenyl)-1-(4-(2-methoxyethyl)piperazin-1-yl)propan-1-one;

(S)-2-amino-N-cyclohexyl-3-(3-fluoro-4-((3-methyl-1H-pyrrolo[2,3-b]pyridin-4-yl)oxy)phenyl)propanamide;

(S)-2-amino-3-(3-fluoro-4-((3-methyl-1H-pyrrolo[2,3-b] pyridin-4-yl)oxy)phenyl)-1-(4-phenyl-5,6-dihydropyridin-1(2H)-yl)propan-1-one;

(S)-2-amino-3-(3-fluoro-4-((3-methyl-1H-pyrrolo[2,3-b] pyridin-4-yl)oxy)phenyl)-1-(4-(phenylsulfonyl)piperazin-1-yl)propan-1-one;

(S)-4-(2-amino-3-(3-fluoro-4-((3-methyl-1H-pyrrolo[2, 3-b]pyridin-4-yl)oxy)phenyl)propanoyl)-N,N-dimethylpiperazine-1-carboxamide;

(S)-2-amino-1-((1S,4S)-5-benzyl-2,5-diazabicyclo[2.2.1] heptan-2-yl)-3-(3-fluoro-4-((3-methyl-1H-pyrrolo[2,3-b]pyridin-4-yl)oxy)phenyl)propan-1-one;

(S)-2-amino-3-(3-fluoro-4-((3-methyl-1H-pyrrolo[2,3-b] pyridin-4-yl)oxy)phenyl)-1-((1S,4S)-5-methyl-2,5-diazabicyclo[2.2.1]heptan-2-yl)propan-1-one;

(S)-2-amino-1-((3S,5R)-4-benzyl-3,5-dimethylpiperazin-1-yl)-3-(3-fluoro-4-((3-methyl-1H-pyrrolo[2,3-b]pyridin-4-yl)oxy)phenyl)propan-1-one;

(S)-2-amino-3-(3-fluoro-4-((3-methyl-1H-pyrrolo[2,3-b] pyridin-4-yl)oxy)phenyl)-1-(4-(pyridin-2-ylmethyl) piperazin-1-yl)propan-1-one;

(S)-2-amino-3-(3-fluoro-4-((3-methyl-1H-pyrrolo[2,3-b] pyridin-4-yl)oxy)phenyl)-1-(4-(pyridin-3-ylmethyl) piperazin-1-yl)propan-1-one;

(S)-2-amino-3-(3-fluoro-4-((3-methyl-1H-pyrrolo[2,3-b] pyridin-4-yl)oxy)phenyl)-1-(2,6-diazaspiro[3.3]heptan-2-yl)propan-1-one;

(S)-2-amino-3-(3-fluoro-4-((3-methyl-1H-pyrrolo[2,3-b] pyridin-4-yl)oxy)phenyl)-1-((3aR,6aS)-5-methylhexahydropyrrolo[3,4-c]pyrrol-2(1H)-yl)propan-1-one;

(S)-2-amino-3-(3-fluoro-4-((3-methyl-1H-pyrrolo[2,3-b] pyridin-4-yl)oxy)phenyl)-1-((3 aR,6aS)-hexahydropyrrolo[3,4-c]pyrrol-2(1H)-yl)propan-1-one;

(S)-2-amino-3-(3-fluoro-4-((3-methyl-1H-pyrrolo[2,3-b] pyridin-4-yl)oxy)phenyl)-N-(1-(hydroxymethyl)cyclohexyl)propanamide;

(S)-2-amino-3-(3-fluoro-4-((3-methyl-1H-pyrrolo[2,3-b] pyridin-4-yl)oxy)phenyl)-N-(4-(hydroxymethyl)tetrahydro-2H-pyran-4-yl)propanamide;

(S)-2-amino-N-(1-cyanocyclohexyl)-3-(3-fluoro-4-((3-methyl-1H-pyrrolo[2,3-b]pyridin-4-yl)oxy)phenyl) propanamide;

(S)-1-(2-amino-3-(3-fluoro-4-((3-methyl-1H-pyrrolo[2, 3-b]pyridin-4-yl)oxy)phenyl)propanamido)cyclohexanecarboxamide;

(S)-2-amino-3-(3-fluoro-4-((3-methyl-1H-pyrrolo[2,3-b] pyridin-4-yl)oxy)phenyl)-N-(1-(2-hydroxyethyl)cyclohexyl)propanamide;

(S)-2-amino-3-(3-fluoro-4-((3-methyl-1H-pyrrolo[2,3-b] pyridin-4-yl)oxy)phenyl)-N-(4-(hydroxymethyl)-1-methylpiperidin-4-yl)propanamide;

(S)-2-amino-N-(1-((dimethylamino)methyl)cyclohexyl)-3-(3-fluoro-4-((3-methyl-1H-pyrrolo[2,3-b]pyridin-4-yl)oxy)phenyl)propanamide;

(S)-2-amino-3-(3-fluoro-4-((3-methyl-1H-pyrrolo[2,3-b] pyridin-4-yl)oxy)phenyl)-N-methyl-N-((1-methylpiperidin-4-yl)methyl)propanamide;

(S)-2-amino-3-(3-fluoro-4-((3-methyl-1H-pyrrolo[2,3-b] pyridin-4-yl)oxy)phenyl)-N-((1-methylpiperidin-4-yl) methyl)propanamide;

(S)-2-amino-1-(3-(dimethylamino)azetidin-1-yl)-3-(3-fluoro-4-((3-methyl-1H-pyrrolo[2,3-b]pyridin-4-yl) oxy)phenyl)propan-1-one;

(S)-2-amino-3-(3-fluoro-4-((3-methyl-1H-pyrrolo[2,3-b] pyridin-4-yl)oxy)phenyl)-N-(1-methylazetidin-3-yl) propanamide;

(S)-2-amino-1-((R)-3-(dimethylamino)pyrrolidin-1-yl)-3-(3-fluoro-4-((3-methyl-1H-pyrrolo[2,3-b]pyridin-4-yl)oxy)phenyl)propan-1-one;

(S)-2-amino-3-(3-fluoro-4-((3-methyl-1H-pyrrolo[2,3-b] pyridin-4-yl)oxy)phenyl)-N-methyl-N-(1-methylpiperidin-4-yl)propanamide;

(S)-2-amino-1-(4-((dimethylamino)methyl)piperidin-1-yl)-3-(3-fluoro-4-((3-methyl-1H-pyrrolo[2,3-b]pyridin-4-yl)oxy)phenyl)propan-1-one;

(S)-2-amino-3-(3-fluoro-4-((3-methyl-1H-pyrrolo[2,3-b]pyridin-4-yl)oxy)phenyl)-N-((R)-quinuclidin-3-yl)propanamide;

(S)-2-amino-3-(3-fluoro-4-((3-methyl-1H-pyrrolo[2,3-b]pyridin-4-yl)oxy)phenyl)-N-((1-methylazetidin-3-yl)methyl)propanamide;

(S)-2-amino-1-(3-((dimethylamino)methyl)azetidin-1-yl)-3-(3-fluoro-4-((3-methyl-1H-pyrrolo[2,3-b]pyridin-4-yl)oxy)phenyl)propan-1-one;

(S)-2-amino-1-((S)-3-(dimethylamino)pyrrolidin-1-yl)-3-(3-fluoro-4-((3-methyl-1H-pyrrolo[2,3-b]pyridin-4-yl)oxy)phenyl)propan-1-one;

(S)-2-amino-1-((R)-3-(dimethylamino)piperidin-1-yl)-3-(3-fluoro-4-((3-methyl-1H-pyrrolo[2,3-b]pyridin-4-yl)oxy)phenyl)propan-1-one;

2-amino-3-(3-fluoro-4-((3-methyl-1H-pyrrolo[2,3-b]pyridin-4-yl)oxy)phenyl)-1-(4-(pyridin-4-ylmethyl)piperazin-1-yl)propan-1-one;

2-amino-1-(4-(benzo[d][1,3]dioxol-5-ylmethyl)piperazin-1-yl)-3-(3-fluoro-4-((3-methyl-1H-pyrrolo[2,3-b]pyridin-4-yl)oxy)phenyl)propan-1-one;

2-amino-3-(3-fluoro-4-((3-methyl-1H-pyrrolo[2,3-b]pyridin-4-yl)oxy)phenyl)-1-(4-phenethylpiperazin-1-yl)propan-1-one;

(S)-2-amino-3-(3-fluoro-4-((3-methyl-1H-pyrrolo[2,3-b]pyridin-4-yl)oxy)phenyl)-N-(tetrahydro-2H-pyran-4-yl)propanamide;

(R)-2-amino-3-(3-fluoro-4-((3-methyl-1H-pyrrolo[2,3-b]pyridin-4-yl)oxy)phenyl)-N-(tetrahydro-2H-pyran-4-yl)propanamide;

(S)-2-amino-3-(3-fluoro-4-((3-methyl-1H-pyrrolo[2,3-b]pyridin-4-yl)oxy)phenyl)-N-(2-(1-phenyl-1H-pyrazol-4-yl)ethyl)propanamide;

2-amino-3-(3-fluoro-4-((3-methyl-1H-pyrrolo[2,3-b]pyridin-4-yl)oxy)phenyl)-N-(2-(pyridin-4-yl)ethyl)propanamide;

2-amino-1-(4-(cyclopropylmethyl)piperazin-1-yl)-3-(3-fluoro-4-((3-methyl-1H-pyrrolo[2,3-b]pyridin-4-yl)oxy)phenyl)propan-1-one;

2-amino-3-(3-fluoro-4-((3-methyl-1H-pyrrolo[2,3-b]pyridin-4-yl)oxy)phenyl)-1-(4-methylpiperazin-1-yl)propan-1-one;

2-amino-1-(4-cyclopropylpiperazin-1-yl)-3-(3-fluoro-4-((3-methyl-1H-pyrrolo[2,3-b]pyridin-4-yl)oxy)phenyl)propan-1-one;

2-amino-3-(3-fluoro-4-((3-methyl-1H-pyrrolo[2,3-b]pyridin-4-yl)oxy)phenyl)-N-(thiophen-2-ylmethyl)propanamide;

2-amino-3-(3-fluoro-4-((3-methyl-1H-pyrrolo[2,3-b]pyridin-4-yl)oxy)phenyl)-N-(4-(hydroxymethyl)benzyl)propanamide;

2-amino-N-(2,3-dihydro-1H-inden-2-yl)-3-(3-fluoro-4-((3-methyl-1H-pyrrolo[2,3-b]pyridin-4-yl)oxy)phenyl)propanamide;

2-amino-3-(3-fluoro-4-((3-methyl-1H-pyrrolo[2,3-b]pyridin-4-yl)oxy)phenyl)-1-(2-(hydroxymethyl)-4-methylpiperazin-1-yl)propan-1-one;

2-amino-3-(3-fluoro-4-((3-methyl-1H-pyrrolo[2,3-b]pyridin-4-yl)oxy)phenyl)-1-(1H-pyrrolo[3,4-c]pyridin-2(3H)-yl)propan-1-one;

2-amino-3-(3-fluoro-4-((3-methyl-1H-pyrrolo[2,3-b]pyridin-4-yl)oxy)phenyl)-1-(3-(pyridin-4-yl)pyrrolidin-1-yl)propan-1-one;

2-amino-1-(3,4-dihydro-2,7-naphthyridin-2(1H)-yl)-3-(3-fluoro-4-((3-methyl-1H-pyrrolo[2,3-b]pyridin-4-yl)oxy)phenyl)propan-1-one;

2-amino-3-(3-fluoro-4-((3-methyl-1H-pyrrolo[2,3-b]pyridin-4-yl)oxy)phenyl)-N-(3-methoxypropyl)propanamide;

2-amino-3-(3-fluoro-4-((3-methyl-1H-pyrrolo[2,3-b]pyridin-4-yl)oxy)phenyl)-N-(2-(pyridin-2-yl)ethyl)propanamide;

2-amino-3-(3-fluoro-4-((3-methyl-1H-pyrrolo[2,3-b]pyridin-4-yl)oxy)phenyl)-N-(pyridin-3-yl)propanamide;

2-amino-3-(3-fluoro-4-((3-methyl-1H-pyrrolo[2,3-b]pyridin-4-yl)oxy)phenyl)-N-(pyridin-4-yl)propanamide;

2-amino-3-(3-fluoro-4-((3-methyl-1H-pyrrolo[2,3-b]pyridin-4-yl)oxy)phenyl)-1-(4-(4-methylbenzyl)piperazin-1-yl)propan-1-one;

2-amino-3-(3-fluoro-4-((3-methyl-1H-pyrrolo[2,3-b]pyridin-4-yl)oxy)phenyl)-1-(4-(3-methylbenzyl)piperazin-1-yl)propan-1-one;

2-amino-3-(3-fluoro-4-((3-methyl-1H-pyrrolo[2,3-b]pyridin-4-yl)oxy)phenyl)-1-(4-(4-fluorobenzyl)piperazin-1-yl)propan-1-one;

2-amino-3-(3-fluoro-4-((3-methyl-1H-pyrrolo[2,3-b]pyridin-4-yl)oxy)phenyl)-1-(4-(4-methoxybenzyl)piperazin-1-yl)propan-1-one;

2-amino-3-(3-fluoro-4-((3-methyl-1H-pyrrolo[2,3-b]pyridin-4-yl)oxy)phenyl)-N-phenethylpropanamide;

2-amino-3-(3-fluoro-4-((3-methyl-1H-pyrrolo[2,3-b]pyridin-4-yl)oxy)phenyl)-1-(piperidin-1-yl)propan-1-one;

2-amino-3-(3-fluoro-4-((3-methyl-1H-pyrrolo[2,3-b]pyridin-4-yl)oxy)phenyl)-N-(isoquinolin-5-yl)propanamide;

2-amino-3-(3-fluoro-4-((3-methyl-1H-pyrrolo[2,3-b]pyridin-4-yl)oxy)phenyl)-N-(3-morpholinopropyl)propanamide;

2-amino-3-(3-fluoro-4-((3-methyl-1H-pyrrolo[2,3-b]pyridin-4-yl)oxy)phenyl)-1-(4-(pyridin-2-yl)piperazin-1-yl)propan-1-one;

2-amino-1-(5,6-dihydroimidazo[1,5-a]pyrazin-7(8H)-yl)-3-(3-fluoro-4-((3-methyl-1H-pyrrolo[2,3-b]pyridin-4-yl)oxy)phenyl)propan-1-one;

2-amino-N-((1-benzylpiperidin-4-yl)methyl)-3-(3-fluoro-4-((3-methyl-1H-pyrrolo[2,3-b]pyridin-4-yl)oxy)phenyl)propanamide;

2-amino-N-(1-benzylpiperidin-4-yl)-3-(3-fluoro-4-((3-methyl-1H-pyrrolo[2,3-b]pyridin-4-yl)oxy)phenyl)propanamide;

first eluting rac-diastereoisomer 2-amino-3-(3-fluoro-4-((3-methyl-1H-pyrrolo[2,3-b]pyridin-4-yl)oxy)phenyl)-1-(2-phenylpyrrolidin-1-yl)propan-1-one;

second eluting rac-diastereoisomer 2-amino-3-(3-fluoro-4-((3-methyl-1H-pyrrolo[2,3-b]pyridin-4-yl)oxy)phenyl)-1-(2-phenylpyrrolidin-1-yl)propan-1-one;

(S)-2-amino-1-(4-benzylpiperazin-1-yl)-3-(3-fluoro-4-((2-methyl-1H-pyrrolo[2,3-b]pyridin-4-yl)oxy)phenyl)propan-1-one;

(S)-2-amino-N-(3-methoxypropyl)-3-(4-((3-methyl-1H-pyrrolo[2,3-b]pyridin-4-yl)oxy)phenyl)propanamide;

(S)-2-amino-1-(4-benzylpiperazin-1-yl)-3-(4-((3-methyl-1H-pyrrolo[2,3-b]pyridin-4-yl)oxy)phenyl)propan-1-one;

(S)-2-amino-3-(4-((3-methyl-1H-pyrrolo[2,3-b]pyridin-4-yl)oxy)phenyl)-N-(2-(pyridin-4-yl)ethyl)propanamide;

(S)-2-amino-3-(4-((3-methyl-1H-pyrrolo[2,3-b]pyridin-4-yl)oxy)phenyl)-N-(tetrahydro-2H-pyran-4-yl)propanamide;

3-(4-((1H-pyrrolo[2,3-b]pyridin-4-yl)oxy)phenyl)-2-amino-N-(4-(trifluoromethyl)phenyl)propanamide;
(S)-3-(4-((1H-pyrrolo[2,3-b]pyridin-4-yl)oxy)phenyl)-2-amino-N-(cyclohexylmethyl)-N-methylpropanamide;
(S)-3-(4-((1H-pyrrolo[2,3-b]pyridin-4-yl)oxy)phenyl)-2-amino-N-benzyl-N-methylpropanamide;
(S)-3-(4-((1H-pyrrolo[2,3-b]pyridin-4-yl)oxy)phenyl)-2-amino-N-(6-chloropyridin-3-yl)propanamide;
(S)-3-(4-((1H-pyrrolo[2,3-b]pyridin-4-yl)oxy)phenyl)-2-amino-N-(2-(dimethylamino)ethyl)propanamide;
(R)-3-(4-((1H-pyrrolo[2,3-b]pyridin-4-yl)oxy)phenyl)-2-amino-N-(2-(dimethylamino)ethyl)propanamide;
(S)-3-(4-((1H-pyrrolo[2,3-b]pyridin-4-yl)oxy)phenyl)-2-amino-N-benzylpropanamide;
(R)-3-(4-((1H-pyrrolo[2,3-b]pyridin-4-yl)oxy)phenyl)-2-amino-N-benzylpropanamide;
(S)-3-(4-((1H-pyrrolo[2,3-b]pyridin-4-yl)oxy)phenyl)-2-amino-N-(tetrahydro-2H-pyran-4-yl)propanamide;
(R)-3-(4-((1H-pyrrolo[2,3-b]pyridin-4-yl)oxy)phenyl)-2-amino-N-(tetrahydro-2H-pyran-4-yl)propanamide;
(S)-3-(4-((1H-pyrrolo[2,3-b]pyridin-4-yl)oxy)phenyl)-2-amino-N-cyclohexyl-N-methylpropanamide;
(R)-3-(4-((1H-pyrrolo[2,3-b]pyridin-4-yl)oxy)phenyl)-2-amino-N-cyclohexyl-N-methylpropanamide;
(S)-3-(4-((1H-pyrrolo[2,3-b]pyridin-4-yl)oxy)phenyl)-2-amino-N-(1-methylpiperidin-4-yl)propanamide;
(R)-3-(4-((1H-pyrrolo[2,3-b]pyridin-4-yl)oxy)phenyl)-2-amino-N-(1-methylpiperidin-4-yl)propanamide;
(S)-3-(4-((1H-pyrrolo[2,3-b]pyridin-4-yl)oxy)phenyl)-2-amino-N-(thiazol-2-yl)propanamide;
(R)-3-(4-((1H-pyrrolo[2,3-b]pyridin-4-yl)oxy)phenyl)-2-amino-N-(thiazol-2-yl)propanamide;
(S)-3-(4-((1H-pyrrolo[2,3-b]pyridin-4-yl)oxy)phenyl)-2-amino-N-(cyclohexylmethyl)propanamide;
(R)-3-(4-((1H-pyrrolo[2,3-b]pyridin-4-yl)oxy)phenyl)-2-amino-N-(cyclohexylmethyl)propanamide;
(S)-3-(4-((1H-pyrrolo[2,3-b]pyridin-4-yl)oxy)phenyl)-2-amino-N-phenylpropanamide;
(R)-3-(4-((1H-pyrrolo[2,3-b]pyridin-4-yl)oxy)phenyl)-2-amino-N-phenylpropanamide;
(S)-3-(4-((1H-pyrrolo[2,3-b]pyridin-4-yl)oxy)phenyl)-2-amino-N-cyclohexylpropanamide;
(R)-3-(4-((1H-pyrrolo[2,3-b]pyridin-4-yl)oxy)phenyl)-2-amino-N-cyclohexylpropanamide;
3-(4-((1H-pyrrolo[2,3-b]pyridin-4-yl)oxy)phenyl)-2-amino-N,N-dimethylpropanamide;
(S)-2-amino-1-(4-benzylpiperazin-1-yl)-3-(4-((3-fluoro-1H-pyrrolo[2,3-b]pyridin-4-yl)oxy)phenyl)propan-1-one;
(S)-2-amino-1-(4-benzylpiperazin-1-yl)-3-(3-fluoro-4-((5-methyl-7H-pyrrolo[2,3-d]pyrimidin-4-yl)oxy)phenyl)propan-1-one;
(S)-2-amino-N-(3-(dimethylamino)propyl)-3-(3-fluoro-4-((5-methyl-7H-pyrrolo[2,3-d]pyrimidin-4-yl)oxy)phenyl)propanamide;
(S)-2-amino-3-(3-fluoro-4-((5-methyl-7H-pyrrolo[2,3-d]pyrimidin-4-yl)oxy)phenyl)-N-(1-methylpiperidin-4-yl)propanamide;
(S)-2-amino-3-(3-fluoro-4-((5-methyl-7H-pyrrolo[2,3-d]pyrimidin-4-yl)oxy)phenyl)-1-(4-methylpiperazin-1-yl)propan-1-one;
(S)-2-amino-1-(4-cyclopropylpiperazin-1-yl)-3-(3-fluoro-4-((5-methyl-7H-pyrrolo[2,3-d]pyrimidin-4-yl)oxy)phenyl)propan-1-one;
(S)-2-amino-3-(3-fluoro-4-((5-methyl-7H-pyrrolo[2,3-d]pyrimidin-4-yl)oxy)phenyl)-1-(4-(pyridin-2-ylmethyl)piperazin-1-yl)propan-1-one;
2-amino-3-(3-fluoro-4-((5-methyl-7H-pyrrolo[2,3-d]pyrimidin-4-yl)oxy)phenyl)-1-((1S,4S)-5-methyl-2,5-diazabicyclo[2.2.1]heptan-2-yl)propan-1-one;
(S)-2-amino-3-(3-fluoro-4-((5-methyl-7H-pyrrolo[2,3-d]pyrimidin-4-yl)oxy)phenyl)-1-(4-(pyridin-4-yl)piperidin-1-yl)propan-1-one;
(S)-2-amino-1-(4-benzyl-4-hydroxypiperidin-1-yl)-3-(3-fluoro-4-((5-methyl-7H-pyrrolo[2,3-d]pyrimidin-4-yl)oxy)phenyl)propan-1-one;
(S)-2-amino-1-(3,4-dihydroisoquinolin-2(1H)-yl)-3-(3-fluoro-4-((5-methyl-7H-pyrrolo[2,3-d]pyrimidin-4-yl)oxy)phenyl)propan-1-one;
(S)-2-amino-3-(3-fluoro-4-((5-methyl-7H-pyrrolo[2,3-d]pyrimidin-4-yl)oxy)phenyl)-N-(tetrahydro-2H-pyran-4-yl)propanamide;
(S)-2-amino-3-(3-fluoro-4-((5-methyl-7H-pyrrolo[2,3-d]pyrimidin-4-yl)oxy)phenyl)-1-(4-(pyridin-3-yloxy)piperidin-1-yl)propan-1-one;
(S)-2-amino-3-(3-fluoro-4-((5-methyl-7H-pyrrolo[2,3-d]pyrimidin-4-yl)oxy)phenyl)-1-(4-(phenylsulfonyl)piperidin-1-yl)propan-1-one;
(S)-2-amino-3-(3-fluoro-4-((5-methyl-7H-pyrrolo[2,3-d]pyrimidin-4-yl)oxy)phenyl)-N-(2-(pyridin-4-yl)ethyl)propanamide;
(S)-2-amino-3-(3-fluoro-4-((5-methyl-7H-pyrrolo[2,3-d]pyrimidin-4-yl)oxy)phenyl)-1-((3S,5R)-3,4,5-trimethylpiperazin-1-yl)propan-1-one;
(S)-4-(4-(2-amino-3-(4-benzylpiperazin-1-yl)-3-oxopropyl)-2-fluorophenoxy)-7H-pyrrolo[2,3-d]pyrimidine-5-carbonitrile;
(S)-3-(4-((1H-pyrrolo[2,3-b]pyridin-4-yl)oxy)phenyl)-N-cyclohexyl-2-(methylamino)propanamide;
2-amino-1-(4-benzylpiperazin-1-yl)-3-(3-fluoro-4-((3-methyl-1H-pyrrolo[2,3-b]pyridin-4-yl)oxy)phenyl)propan-1-one;
1-(4-acetylpiperazin-1-yl)-2-amino-3-(3-fluoro-4-((3-methyl-1H-pyrrolo[2,3-b]pyridin-4-yl)oxy)phenyl)propan-1-one;
(S)-2-amino-N-cyclohexyl-N-methyl-3-(4-((3-methyl-1H-pyrrolo[2,3-b]pyridin-4-yl)oxy)phenyl)propanamide;
(S)-2-amino-N-benzyl-3-(4-((3-methyl-1H-pyrrolo[2,3-b]pyridin-4-yl)oxy)phenyl)propanamide;
(R)-2-amino-N-benzyl-3-(4-((3-methyl-1H-pyrrolo[2,3-b]pyridin-4-yl)oxy)phenyl)propanamide;
(S)-2-amino-3-(4-((3-methyl-1H-pyrrolo[2,3-b]pyridin-4-yl)oxy)phenyl)-N-phenylpropanamide;
(R)-2-amino-3-(4-((3-methyl-1H-pyrrolo[2,3-b]pyridin-4-yl)oxy)phenyl)-N-phenylpropanamide;
(S)-2-amino-N-(cyclohexylmethyl)-3-(4-((3-methyl-1H-pyrrolo[2,3-b]pyridin-4-yl)oxy)phenyl)propanamide;
(R)-2-amino-N-(cyclohexylmethyl)-3-(4-((3-methyl-1H-pyrrolo[2,3-b]pyridin-4-yl)oxy)phenyl)propanamide;
(S)-2-amino-N-cyclohexyl-3-(4-((3-methyl-1H-pyrrolo[2,3-b]pyridin-4-yl)oxy)phenyl)propanamide;
(R)-2-amino-N-cyclohexyl-3-(4-((3-methyl-1H-pyrrolo[2,3-b]pyridin-4-yl)oxy)phenyl)propanamide;
(R)-3-(4-((1H-pyrrolo[2,3-b]pyridin-4-yl)oxy)phenyl)-2-amino-N-(cyclohexylmethyl)-N-methylpropanamide;
(R)-3-(4-((1H-pyrrolo[2,3-b]pyridin-4-yl)oxy)phenyl)-2-amino-N-benzyl-N-methylpropanamide;
(S)-2-amino-3-(3-fluoro-4-((3-methyl-1H-pyrrolo[2,3-b]pyridin-4-yl)oxy)phenyl)-N-phenylpropanamide;
(S)-3-(4-((1H-pyrrolo[2,3-b]pyridin-4-yl)oxy)-3-fluorophenyl)-2-amino-N-cyclohexylpropanamide;
(S)-3-(4-((1H-pyrrolo[2,3-b]pyridin-4-yl)oxy)-3-fluorophenyl)-2-amino-N-phenylpropanamide;

(R)-2-amino-N-cyclohexyl-3-(3-fluoro-4-((3-methyl-1H-pyrrolo[2,3-b]pyridin-4-yl)oxy)phenyl)propanamide;
(R)-2-amino-3-(3-fluoro-4-((3-methyl-1H-pyrrolo[2,3-b]pyridin-4-yl)oxy)phenyl)-N-phenylpropanamide;
3-(4-((1H-pyrrolo[2,3-b]pyridin-4-yl)oxy)phenyl)-2-amino-N-cyclohexyl-2-methylpropanamide;
3-(4-((1H-pyrrolo[2,3-b]pyridin-4-yl)oxy)phenyl)-2-amino-2-methyl-N-(tetrahydro-2H-pyran-4-yl)propanamide;
(S)-2-amino-3-(3-fluoro-4-((3-methyl-1H-pyrrolo[2,3-b]pyridin-4-yl)oxy)phenyl)-1-(piperazin-1-yl)propan-1-one;
(S)-2-amino-3-(3-fluoro-4-((3-methyl-1H-pyrrolo[2,3-b]pyridin-4-yl)oxy)phenyl)-1-(4-(pyridazin-4-ylmethyl)piperazin-1-yl)propan-1-one;
(S)-2-amino-3-(3-fluoro-4-((3-methyl-1H-pyrrolo[2,3-b]pyridin-4-yl)oxy)phenyl)-1-(4-((2-(methylthio)pyrimidin-4-yl)methyl)piperazin-1-yl)propan-1-one;
(S)-2-amino-3-(3-fluoro-4-((3-methyl-1H-pyrrolo[2,3-b]pyridin-4-yl)oxy)phenyl)-1-(4-(pyrazin-2-ylmethyl)piperazin-1-yl)propan-1-one;
(S)-2-amino-3-(3-fluoro-4-((3-methyl-1H-pyrrolo[2,3-b]pyridin-4-yl)oxy)phenyl)-1-(4-((1-methyl-1H-imidazol-2-yl)methyl)piperazin-1-yl)propan-1-one;
(S)-2-amino-3-(3-fluoro-4-((3-methyl-1H-pyrrolo[2,3-b]pyridin-4-yl)oxy)phenyl)-1-(4-((2-methylthiazol-4-yl)methyl)piperazin-1-yl)propan-1-one;
(S)-2-amino-3-(3-fluoro-4-((3-methyl-1H-pyrrolo[2,3-b]pyridin-4-yl)oxy)phenyl)-1-(4-((1-methyl-1H-imidazol-5-yl)methyl)piperazin-1-yl)propan-1-one;
(S)-2-amino-3-(3-fluoro-4-((3-methyl-1H-pyrrolo[2,3-b]pyridin-4-yl)oxy)phenyl)-1-(4-(quinoxalin-2-ylmethyl)piperazin-1-yl)propan-1-one;
(S)-2-amino-1-(4-(4-(3-(dimethylamino)propoxy)benzyl)piperazin-1-yl)-3-(3-fluoro-4-((3-methyl-1H-pyrrolo[2,3-b]pyridin-4-yl)oxy)phenyl)propan-1-one;
(S)-2-amino-3-(3-fluoro-4-((3-methyl-1H-pyrrolo[2,3-b]pyridin-4-yl)oxy)phenyl)-1-(4-((1-(methylsulfonyl)piperidin-4-yl)methyl)piperazin-1-yl)propan-1-one;
(S)-2-amino-3-(3-fluoro-4-((3-methyl-1H-pyrrolo[2,3-b]pyridin-4-yl)oxy)phenyl)-1-(4-(pyrimidin-5-ylmethyl)piperazin-1-yl)propan-1-one;
(S)-2-amino-3-(3-fluoro-4-((3-methyl-1H-pyrrolo[2,3-b]pyridin-4-yl)oxy)phenyl)-1-(4-((1-methyl-1H-pyrazol-4-yl)methyl)piperazin-1-yl)propan-1-one;
(S)-1-(4-((1,2,3-thiadiazol-4-yl)methyl)piperazin-1-yl)-2-amino-3-(3-fluoro-4-((3-methyl-1H-pyrrolo[2,3-b]pyridin-4-yl)oxy)phenyl)propan-1-one;
(S)-3-((4-(2-amino-3-(3-fluoro-4-((3-methyl-1H-pyrrolo[2,3-b]pyridin-4-yl)oxy)phenyl)propanoyl)piperazin-1-yl)methyl)-N-methylbenzamide;
(S)-5-((4-(2-amino-3-(3-fluoro-4-((3-methyl-1H-pyrrolo[2,3-b]pyridin-4-yl)oxy)phenyl)propanoyl)piperazin-1-yl)methyl)-N-methylfuran-2-carboxamide;
(S)-2-amino-1-(4-benzoylpiperazin-1-yl)-3-(3-fluoro-4-((3-methyl-1H-pyrrolo[2,3-b]pyridin-4-yl)oxy)phenyl)propan-1-one;
(S)-2-amino-1-(4-(cyclohexanecarbonyl)piperazin-1-yl)-3-(3-fluoro-4-((3-methyl-1H-pyrrolo[2,3-b]pyridin-4-yl)oxy)phenyl)propan-1-one;
(S)-2-amino-3-(3-fluoro-4-((3-methyl-1H-pyrrolo[2,3-b]pyridin-4-yl)oxy)phenyl)-1-(4-(2-phenylacetyl)piperazin-1-yl)propan-1-one;
(S)-2-amino-1-(4-(cyclopropanecarbonyl)piperazin-1-yl)-3-(3-fluoro-4-((3-methyl-1H-pyrrolo[2,3-b]pyridin-4-yl)oxy)phenyl)propan-1-one;
(S)-2-amino-3-(3-fluoro-4-((3-methyl-1H-pyrrolo[2,3-b]pyridin-4-yl)oxy)phenyl)-1-(4-(1-methylpiperidine-4-carbonyl)piperazin-1-yl)propan-1-one;
(S)-2-amino-1-(4-(4-((dimethylamino)methyl)benzoyl)piperazin-1-yl)-3-(3-fluoro-4-((3-methyl-1H-pyrrolo[2,3-b]pyridin-4-yl)oxy)phenyl)propan-1-one;
(S)-2-amino-1-(4-(3-((dimethylamino)methyl)benzoyl)piperazin-1-yl)-3-(3-fluoro-4-((3-methyl-1H-pyrrolo[2,3-b]pyridin-4-yl)oxy)phenyl)propan-1-one;
(S)-2-amino-3-(3-fluoro-4-((3-methyl-1H-pyrrolo[2,3-b]pyridin-4-yl)oxy)phenyl)-1-(4-nicotinoylpiperazin-1-yl)propan-1-one;
(S)-2-amino-3-(3-fluoro-4-((3-methyl-1H-pyrrolo[2,3-b]pyridin-4-yl)oxy)phenyl)-1-(4-(1-methyl-1H-pyrazole-4-carbonyl)piperazin-1-yl)propan-1-one;
(S)-2-amino-3-(3-fluoro-4-((3-methyl-1H-pyrrolo[2,3-b]pyridin-4-yl)oxy)phenyl)-1-(4-(1-methyl-1H-imidazole-4-carbonyl)piperazin-1-yl)propan-1-one;
(S)-2-amino-3-(3-fluoro-4-((3-methyl-1H-pyrrolo[2,3-b]pyridin-4-yl)oxy)phenyl)-1-(4-(thiazole-2-carbonyl)piperazin-1-yl)propan-1-one;
N-(3-(4-((1H-pyrrolo[2,3-b]pyridin-4-yl)oxy)phenyl)-1-(dimethylamino)-1-oxopropan-2-yl)pyrrolidine-3-carboxamide;
N-(3-(4-((1H-pyrrolo[2,3-b]pyridin-4-yl)oxy)phenyl)-1-oxo-1-(phenyl amino)propan-2-yl)pyrrolidine-3-carboxamide;
N-(3-(4-((1H-pyrrolo[2,3-b]pyridin-4-yl)oxy)phenyl)-1-(cyclohexylamino)-1-oxopropan-2-yl)pyrrolidine-3-carboxamide;
N-(3-(4-((1H-pyrrolo[2,3-b]pyridin-4-yl)oxy)phenyl)-1-((2-(dimethylamino)ethyl)amino)-1-oxopropan-2-yl)cyclohexanecarboxamide;
3-(4-((1H-pyrrolo[2,3-b]pyridin-4-yl)oxy)phenyl)-2-(dimethylamino)-N-(tetrahydro-2H-pyran-4-yl)propanamide;
3-(4-((1H-pyrrolo[2,3-b]pyridin-4-yl)oxy)phenyl)-N-cyclohexyl-2-(dimethylamino)propanamide;
(S)-N-cyclohexyl-2-(dimethylamino)-3-(4-((3-methyl-1H-pyrrolo[2,3-b]pyridin-4-yl)oxy)phenyl)propanamide;
3-(4-((1H-pyrrolo[2,3-b]pyridin-4-yl)oxy)phenyl)-2-((cyclohexylmethyl)amino)-N-methylpropanamide;
(S)-2-amino-3-(4-((3-bromo-1H-pyrrolo[2,3-b]pyridin-4-yl)oxy)-3-fluorophenyl)-N-cyclohexylpropanamide;
(S)-2-amino-1-(4-benzylpiperazin-1-yl)-3-(4-((3-bromo-1H-pyrrolo[2,3-b]pyridin-4-yl)oxy)-3-fluorophenyl)propan-1-one;
(S)-2-amino-3-(4-((3-bromo-1H-pyrrolo[2,3-b]pyridin-4-yl)oxy)phenyl)-N-cyclohexylpropanamide;
(S)-2-amino-3-(4-((3-bromo-1H-pyrrolo[2,3-b]pyridin-4-yl)oxy)phenyl)-N-(tetrahydro-2H-pyran-4-yl)propanamide;
(S)-2-amino-N-cyclohexyl-3-(4-((3-iodo-1H-pyrrolo[2,3-b]pyridin-4-yl)oxy)phenyl)propanamide;
(S)-2-amino-3-(4-((3-chloro-1H-pyrrolo[2,3-b]pyridin-4-yl)oxy)phenyl)-N-cyclohexylpropanamide;
(S)-2-amino-1-(4-benzylpiperazin-1-yl)-3-(4-((3-(pyridin-4-yl)-1H-pyrrolo[2,3-b]pyridin-4-yl)oxy)phenyl)propan-1-one;
(S)-2-amino-1-(4-benzylpiperazin-1-yl)-3-(4-((3-(1-ethyl-1H-pyrazol-5-yl)-1H-pyrrolo[2,3-b]pyridin-4-yl)oxy)phenyl)propan-1-one;
(S)-2-amino-1-(4-benzylpiperazin-1-yl)-3-(4-((3-(pyridin-3-yl)-1H-pyrrolo[2,3-b]pyridin-4-yl)oxy)phenyl)propan-1-one;

(S)-5-(4-(4-(2-amino-3-(4-benzylpiperazin-1-yl)-3-oxo-propyl)phenoxy)-1H-pyrrolo[2,3-b]pyridin-3-yl)thiophene-2-carbonitrile;

(S)-2-amino-1-(4-benzylpiperazin-1-yl)-3-(4-((3-(thiazol-5-yl)-1H-pyrrolo[2,3-b]pyridin-4-yl)oxy)phenyl)propan-1-one;

(S)-2-amino-1-(4-benzylpiperazin-1-yl)-3-(4-((3-(1-methyl-1H-imidazol-5-yl)-1H-pyrrolo[2,3-b]pyridin-4-yl)oxy)phenyl)propan-1-one;

(S)-2-amino-1-(4-benzylpiperazin-1-yl)-3-(4-((3-(isoxazol-4-yl)-1H-pyrrolo[2,3-b]pyridin-4-yl)oxy)phenyl)propan-1-one;

(S)-2-amino-1-(4-benzylpiperazin-1-yl)-3-(4-((3-phenyl-1H-pyrrolo[2,3-b]pyridin-4-yl)oxy)phenyl)propan-1-one;

(S)-2-amino-1-(4-benzylpiperazin-1-yl)-3-(4-((3-(4-hydroxyphenyl)-1H-pyrrolo[2,3-b]pyridin-4-yl)oxy)phenyl)propan-1-one;

(S)-2-amino-1-(4-benzylpiperazin-1-yl)-3-(4-((3-(2,5-dihydrofuran-3-yl)-1H-pyrrolo[2,3-b]pyridin-4-yl)oxy)phenyl)propan-1-one;

(S)-2-amino-1-(4-benzylpiperazin-1-yl)-3-(4-((3-(2,5-dihydro-1H-pyrrol-3-yl)-1H-pyrrolo[2,3-b]pyridin-4-yl)oxy)phenyl)propan-1-one;

(S)-2-amino-N-cyclohexyl-3-(4-((3-cyclopropyl-1H-pyrrolo[2,3-b]pyridin-4-yl)oxy)phenyl)propanamide;

(S)-2-amino-3-(3-fluoro-4-((3-phenyl-1H-pyrrolo[2,3-b]pyridin-4-yl)oxy)phenyl)-N-(1-methylpiperidin-4-yl)propanamide;

(S)-2-amino-3-(3-fluoro-4-((3-(thiazol-5-yl)-1H-pyrrolo[2,3-b]pyridin-4-yl)oxy)phenyl)-N-(1-methylpiperidin-4-yl)propanamide;

(S)-2-amino-3-(4-((3-(4-hydroxyphenyl)-1H-pyrrolo[2,3-b]pyridin-4-yl)oxy)phenyl)-N-(2-(pyridin-4-yl)ethyl)propanamide;

(S)-2-amino-1-(4-benzylpiperazin-1-yl)-3-(3-fluoro-4-((3-(hydroxymethyl)-1H-pyrrolo[2,3-b]pyridin-4-yl)oxy)phenyl)propan-1-one;

(S)-2-amino-N-cyclohexyl-3-(3-fluoro-4-((3-(hydroxymethyl)-1H-pyrrolo[2,3-b]pyridin-4-yl)oxy)phenyl)propanamide;

(S)-2-amino-3-(3-fluoro-4-((3-(hydroxymethyl)-1H-pyrrolo[2,3-b]pyridin-4-yl)oxy)phenyl)-N-(tetrahydro-2H-pyran-4-yl)propanamide;

(S)-2-amino-3-(3-fluoro-4-((3-(hydroxymethyl)-1H-pyrrolo[2,3-b]pyridin-4-yl)oxy)phenyl)-N-(1-methylpiperidin-4-yl)propanamide;

(S)-2-amino-3-(3-fluoro-4-((3-(hydroxymethyl)-1H-pyrrolo[2,3-b]pyridin-4-yl)oxy)phenyl)-1-((1S,4S)-5-methyl-2,5-diazabicyclo[2.2.1]heptan-2-yl)propan-1-one;

(S)-2-amino-N-(3-(dimethylamino)propyl)-3-(3-fluoro-4-((3-(hydroxymethyl)-1H-pyrrolo[2,3-b]pyridin-4-yl)oxy)phenyl)propanamide;

(S)-2-amino-3-(3-fluoro-4-((3-(hydroxymethyl)-1H-pyrrolo[2,3-b]pyridin-4-yl)oxy)phenyl)-1-(4-(pyridin-2-ylmethyl)piperazin-1-yl)propan-1-one;

(S)-2-amino-3-(3-fluoro-4-((3-(methoxymethyl)-1H-pyrrolo[2,3-b]pyridin-4-yl)oxy)phenyl)-N-(tetrahydro-2H-pyran-4-yl)propanamide;

(S)-2-amino-3-(3-fluoro-4-((3-(methoxymethyl)-1H-pyrrolo[2,3-b]pyridin-4-yl)oxy)phenyl)-1-(4-methylpiperazin-1-yl)propan-1-one;

(S)-2-amino-1-(4-benzylpiperazin-1-yl)-3-(4-((3-(2-hydroxyethyl)-1H-pyrrolo[2,3-b]pyridin-4-yl)oxy)phenyl)propan-1-one;

(S)-2-amino-N-cyclohexyl-3-(4-((3-(3-hydroxyprop-1-yn-1-yl)-1H-pyrrolo[2,3-b]pyridin-4-yl)oxy)phenyl)propanamide;

(S)-2-amino-3-(4-((3-cyano-1H-pyrrolo[2,3-b]pyridin-4-yl)oxy)phenyl)-N-(tetrahydro-2H-pyran-4-yl)propanamide;

(S)-2-amino-3-(4-((3-cyano-1H-pyrrolo[2,3-b]pyridin-4-yl)oxy)phenyl)-N-cyclohexylpropanamide;

(S)-4-(4-(2-amino-3-(4-benzylpiperazin-1-yl)-3-oxopropyl)-2-fluorophenoxy)-1H-pyrrolo[2,3-b]pyridine-3-carbonitrile;

(S)-2-amino-3-(4-((3-cyano-1H-pyrrolo[2,3-b]pyridin-4-yl)oxy)-3-fluorophenyl)-N-cyclohexylpropanamide;

(S)-2-amino-3-(4-((3-cyano-1H-pyrrolo[2,3-b]pyridin-4-yl)oxy)-3-fluorophenyl)-N-(1-methylpiperidin-4-yl)propanamide;

4-(4-((S)-2-amino-3-((1S,4S)-5-methyl-2,5-diazabicyclo[2.2.1]heptan-2-yl)-3-oxopropyl)-2-fluorophenoxy)-1H-pyrrolo[2,3-b]pyridine-3-carbonitrile;

(S)-4-(4-(2-amino-3-oxo-3-(4-(pyridin-2-ylmethyl)piperazin-1-yl)propyl)-2-fluorophenoxy)-1H-pyrrolo[2,3-b]pyridine-3-carbonitrile;

(S)-3-(4-((7H-pyrrolo[2,3-d]pyrimidin-4-yl)oxy)phenyl)-2-amino-N-cyclohexylpropanamide;

(S)-3-(4-((7H-pyrrolo[2,3-d]pyrimidin-4-yl)oxy)phenyl)-2-amino-1-(4-benzylpiperazin-1-yl)propan-1-one;

(S)-3-(5-((1H-pyrrolo[2,3-b]pyridin-4-yl)oxy)pyridin-2-yl)-2-amino-N-cyclohexylpropanamide;

(S)-3-(5-((1H-pyrrolo[2,3-b]pyridin-4-yl)oxy)pyridin-2-yl)-2-amino-1-(4-benzylpiperazin-1-yl)propan-1-one;

(R)-3-(4-((1H-pyrrolo[2,3-b]pyridin-4-yl)oxy)-3,5-difluorophenyl)-2-amino-N-cyclohexylpropanamide;

first eluting single enantiomer of 2-amino-1-(4-benzylpiperazin-1-yl)-3-(3-fluoro-4-((3-methyl-1H-pyrrolo[2,3-b]pyridin-4-yl)oxy)phenyl)propan-1-one;

second eluting single enantiomer of 2-amino-1-(4-benzylpiperazin-1-yl)-3-(3-fluoro-4-((3-methyl-1H-pyrrolo[2,3-b]pyridin-4-yl)oxy)phenyl)propan-1-one;

first eluting diastereoisomer of (S)-2-amino-3-(3-fluoro-4-((3-methyl-1H-pyrrolo[2,3-b]pyridin-4-yl)oxy)phenyl)-1-(3-(3-methyl-1,2,4-oxadiazol-5-yl)pyrrolidin-1-yl)propan-1-one;

second eluting diastereoisomer of (S)-2-amino-3-(3-fluoro-4-((3-methyl-1H-pyrrolo[2,3-b]pyridin-4-yl)oxy)phenyl)-1-(3-(3-methyl-1,2,4-oxadiazol-5-yl)pyrrolidin-1-yl)propan-1-one;

first eluting enantiomer of 3-(4-((1H-pyrrolo[2,3-b]pyridin-4-yl)oxy)phenyl)-2-amino-N-(4-(trifluoromethyl)phenyl)propanamide;

second eluting enantiomer of 3-(4-((1H-pyrrolo[2,3-b]pyridin-4-yl)oxy)phenyl)-2-amino-N-(4-(trifluoromethyl)phenyl)propanamide;

first eluting enantiomer of 2-amino-3-(3-fluoro-4-((3-methyl-1H-pyrrolo[2,3-b]pyridin-4-yl)oxy)phenyl)-N-(2-(pyridin-4-yl)ethyl)propanamide; and second eluting enantiomer of 2-amino-3-(3-fluoro-4-((3-methyl-1H-pyrrolo[2,3-b]pyridin-4-yl)oxy)phenyl)-N-(2-(pyridin-4-yl)ethyl)propanamide;

or a pharmaceutically acceptable salt of said compound.

7. A pharmaceutical composition comprising a compound or a pharmaceutically acceptable salt according to claim 1, in admixture with one or more pharmaceutically acceptable carrier or excipient.

8. The pharmaceutical composition according to claim 7, further comprising one or more other active ingredients.

9. A method for the prevention and/or treatment of a pulmonary disease selected from the group consisting of asthma, chronic obstructive pulmonary disease, idiopathic pulmonary fibrosis, and pulmonary hypertension, said method comprising administering an effecrtive amount of a compound or salt according to claim 1 to a subject in need thereof.

10. The method according to claim 9, wherein said pulmonary hypertension is pulmonary arterial hypertension.

11. A pharmaceutical composition, comprising a compound or a pharmaceutically acceptable salt according to claim 1 and one or more active ingredients selected from the group consisting of an organic nitrate, an NO donor; inhaled NO; a stimulator of soluble guanylate cyclase (sGC); a prostaciclin analogue, a PGI2 and agonist of prostacyclin receptors; a compound that inhibits the degradation of cyclic guanosine monophosphate (cGMP) and/or cyclic adenosine monophosphate (cAMP); a human neutrophilic elastase inhibitor; a compound inhibiting the signal transduction cascade; an active substance for lowering blood pressure; a neutral endopeptidase inhibitor; an osmotic agent; an ENaC blockers; an anti-inflammatory including corticosteroids and antagonists of chemokine receptors; a bronchodilatory; an antihistamine drug; an anti-tussive drug; antibiotic; an DNase drug substance and selective cleavage agents; an agent that inhibits ALK5 and/or ALK4 phosphorylation of Smad2 and Smad3; a tryptophan hydroylase 1 (TPH1) inhibitor; and a multi-kinase inhibitor.

12. The pharmaceutical composition according to claim 7, which is in a form to be administered by inhalation.

13. The pharmaceutical composition according to claim 12, wherein said form is a powder, a propellant-containing metering aerosol, or a propellant-free inhalable formulation.

14. A device, containing a pharmaceutical composition according to claim 7, wherein said device is a single- or multi-dose dry powder inhaler, a metered dose inhaler and a soft mist nebulizer.

\* \* \* \* \*

UNITED STATES PATENT AND TRADEMARK OFFICE
CERTIFICATE OF CORRECTION

PATENT NO. : 10,501,461 B2
APPLICATION NO. : 15/883729
DATED : December 10, 2019
INVENTOR(S) : Alessandro Accetta et al.

It is certified that error appears in the above-identified patent and that said Letters Patent is hereby corrected as shown below:

On the Title Page

Item (54), Title, Line 2, "RHO-KINASE" should read -- RHO KINASE --

In the Specification

Column 1, Line 2, "RHO-KINASE" should read -- RHO KINASE --

Column 2, Line 50, "Ti," should read -- T., --

Column 3, Line 59, "Biol," should read -- Biol. --

Column 4, Line 18, "Rhokinase" should read -- Rho kinase --

Column 6, Line 57, "atom." should read -- atom; --

Column 7, Line 40, "heteroaryl($C_1$-$C_6$)alkyl" should read -- heteroaryl($C_1$-$C_6$)alkyl, --

Column 8, Line 25, "heteroaryl-carbonyl" should read -- heteroaryl-carbonyl, --

Column 8, Line 28, "($C_3$-$C_8$)cycloalkyl($C_1$-$C_6$)alkyl" should read -- ($C_3$-$C_8$)cycloalkyl($C_1$-$C_6$)alkyl, --

Column 8, Line 39, "H," should read -- —H, --

Column 8, Line 46, "($C_3$-$C_6$) cycloalkyl-($C_1$-$C_6$) alkyl" should read -- ($C_3$-$C_6$) cycloalkyl-($C_1$-$C_6$) alkyl, --

Column 8, Line 48, "($C_3$-$C_6$) cycloalkyl-carbonyl" should read -- ($C_3$-$C_6$) cycloalkyl-carbonyl, --, Signed and Sealed this
Sixteenth Day of February, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,501,461 B2

Column 8, Line 49, "(C$_3$-C$_6$) heterocycloalkyl-carbonyl" should read -- (C$_3$-C$_6$) heterocycloalkyl-carbonyl, --

Column 8, Line 64, "H," should read -- —H, --

Column 9, Line 21, "H," should read -- —H, --

Column 9, Line 25, "—NR$_7$R$_8$" should read -- —NR$_7$R$_8$, --

Column 10, Line 44, "adamantan-yl" should read -- adamantanyl --

Column 11, Lines 11-12, "benzothiopheneyl," should read -- benzothiophenyl, --

Column 11, Line 15, "benzooxazinyl" should read -- benzoxazinyl --

Column 11, Lines 25-26, "Thienyl-ene" should read -- Thienylene --

Column 11, Line 65, "(e.g." should read -- e.g. --

Column 13, Lines 12-13, "(2-(dimethylamino)ethoxy." should read -- 2-(dimethylamino)ethoxy. --

Column 13, Line 25, "(e.g. aryl(C$_1$-C$_6$)alkylC(O)—]" should read -- (e.g. aryl(C$_1$-C$_6$)alkylC(O)—) --

Column 13, Lines 28-29, ""aryl sulfonyl""" should read -- "aryl sulfonyl" --

Column 13, Line 48, "thiazolediyl;" should read -- thiazole-diyl; --

Column 13, Line 49, "isoxazolediyl" should read -- isoxazole-diyl --

Column 16, Line 30, "(C$_3$-C$_8$)cycloalkyl(C$_1$-C$_6$)alkyl" should read -- (C$_3$-C$_8$)cycloalkyl(C$_1$-C$_6$)alkyl, --

Column 16, Line 63, "3" should read -- 3; --

Column 17, Line 25, "Fluoro" should read -- Fluoro, --

Column 17, Line 26, "NR$_7$R$_8$," should read -- —NR$_7$R$_8$, --

Column 17, Line 57, "(C$_3$-C$_3$)heterocycloalkyl" should read -- (C$_3$-C$_8$)heterocycloalkyl --

Column 18, Line 37, "benzo[d][1,3]dioxol-5-ylmethyl)" should read -- ((benzo[d][1,3]dioxol-5-yl)methyl) --

Column 20, Ex. N. 25, Line 2, "[2.2.1]heptan-2-yl)propan-" should read -- [2.2.1]heptan-2-yl)propan- --

Column 23, Ex. N. 87, Line 1, "(3-methoxylpropyl)" should read -- (3-methoxypropyl) --

Column 25, Ex. N. 102, Line 1, "N-eyclohexyl" should read -- N-cyclohexyl --

Column 34, Line 15 (approx.), "that" should read -- than --

Column 34, Line 67 (approx.), "that" should read -- than --

Column 37, Line 2, "R9" should read -- $R_9$ --

Column 37, Line 20, "R9" should read -- $R_9$ --

Column 37, Line 23, "3-(methoxycarbonyl)-phenyl)methyl" should read -- (3-(methoxycarbonyl)-phenyl)methyl --

Column 39, Scheme 3, Line 2 (approx.), "($R_4$ - H)" should read -- ($R_4$ = H) --

Column 42, Scheme 4, Line 6 (approx.), delete "$R_1$" and insert -- X --

Column 45, Line 46, "Rho-kinase" should read -- Rho kinase --

Column 48, Line 10 (approx.), "prostaciclin" should read -- prostacyclin --

Column 48, Line 42 (approx.), "prostaciclin" should read -- prostacyclin --

Column 51, Line 47 (approx.), "detector)" should read -- detector). --

Column 52, Line 23, "☐m" should read -- μm --

Column 52, Line 30, "water)" should read -- water). --

Column 52, Line 34, "☐m" should read -- μm --

Column 52, Lines 40-41, "DMSO+ optional" should read -- DMSO (+optionally --

Column 52, Line 41, "water)" should read -- water). --

Column 52, Line 54, "% ee" should read -- ee % --

Column 53, Line 18 (approx.), "dimethylsuiphoxide" should read -- dimethylsulphoxide --

Column 53, Line 32 (approx.), "$Pd_2(dppf)_2$." should read -- $Pd_2(dppf)_2$ --

Column 53, Lines 40-41, "triisopropylbiphenyl" should read -- triisopropylbiphenyl. --

Column 65, Line 25 (approx.), "1E -b" should read -- 1E-b --

CERTIFICATE OF CORRECTION (continued)
U.S. Pat. No. 10,501,461 B2

Columns 65-66, Structure 1E-c, " 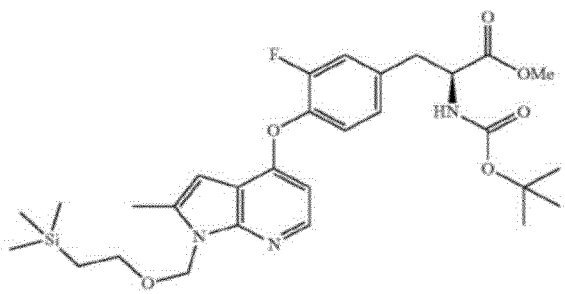 " should read

-- 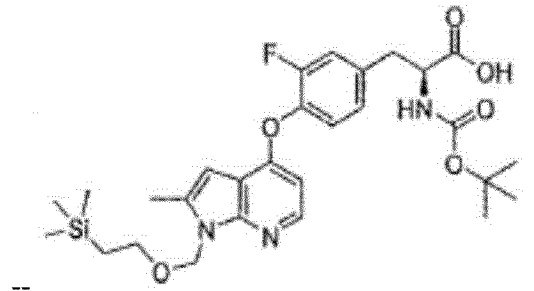 --

Columns 65-66, Structure 1E-d, " 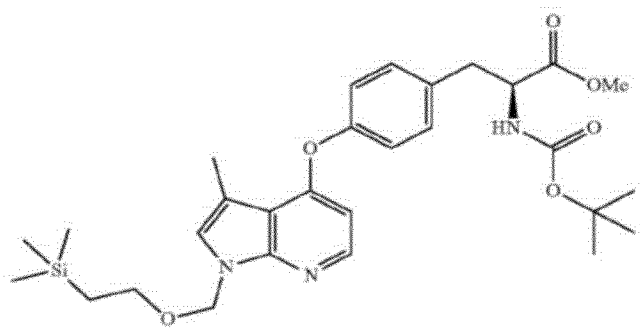 " should read -- 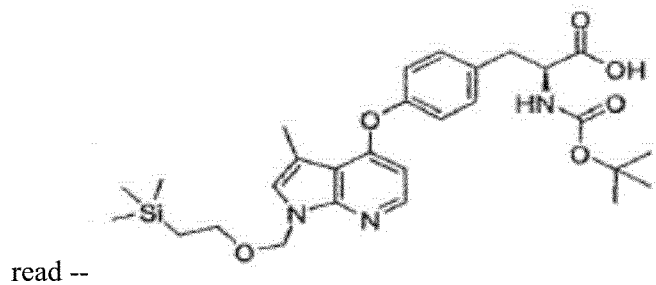 --

Column 86, Structure 29, Line 2, "2,6" should read -- 2,6- --

Column 93, structure 43, " 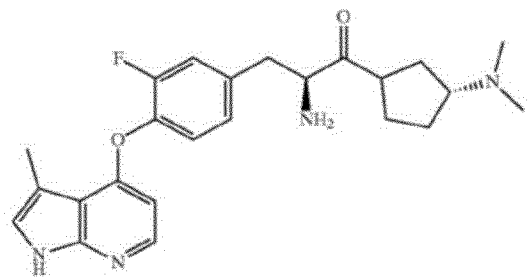 " should read

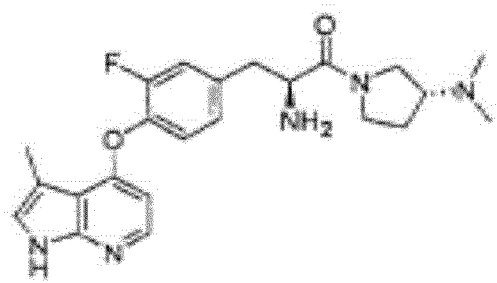 --

Column 94, Structure 44, Line 7 (approx.), "(m,4H)," should read -- (m, 4H), --

Column 98, Structure 50, Line 7 (approx.), "(d J =3.2" should read -- (d, J =3.2 --

Column 100, Structure 54, Line 1 (approx.), "min." should read -- min, --

Column 100, Structure 56, Line 6, "(d,J = 8.1 Hz," should read -- (d, J = 8.1 Hz, --

Column 102, Structure 59, Line 2, "7.31m/z412.2" should read -- 7.31 m/z 412.2 --

Column 102, Structure 59, Line 3, "J =[M + H]+" should read -- J = [M + H]+ --

Column 104, Structure 64, Line 2, "rn/z 442.3" should read -- m/z 442.3 --

Column 112, Structure 81, Line 8, "(br s, 2H)." should read -- (br. s., 2H). --

Column 118, Structure 90, Line 10, "(m,2H)," should read -- (m, 2H), --

Column 122, Structure 94, Line 14, "Hz, 1H." should read -- Hz, 1H). --

Column 122, Structure 97, Line 1, "mm," should read -- min, --

Column 124, Structure 101, Line 2, "mJz 393.3" should read -- m/z 393.3 --

Column 124, Structure 101, Line 6, "and" should read -- and 3.56-3.45 (m, 1H), 3.92-3.82 (m, 1H), --

Column 126, Structure 102, Line 1, "min." should read -- min, --

Column 126, Structure 105, Line 1, "min." should read -- min, --

Column 127, Structure 108, Line 14, "(ee % - 83%)" should read -- (ee % = 83%) --

Column 135, Structure 122, Line 12, "(ee % - 65%)" should read -- (ee % = 65%) --

Column 136, Structure 122, Line 9, "(m,4H)," should read -- (m, 4H), --

Column 137, Structure 125, Line 14, "(ee % - 49 %)" should read -- (ee % = 49%) --

Column 141, Line 62 (approx.), "the" should read -- The --

Column 146, Line 5, "ee %=38%" should read -- (ee % = 38%) --

Column 155, Structure 138, Line 11, "ee % - 80%" should read -- ee % = 80% --

Column 156, Structure 139, Line 2, "(s,lH)," should read -- (s, 1H), --

Column 156, Structure 139, Line 9, "7.2,13.4 Hz," should read -- 7.2, 13.4 Hz, --

Column 166, Structure 147, Line 2, "9.82(s, 1H)," should read -- 9.82 (s, 1H), --

Column 175, Structure 158, Line 14, "4--((3" should read -- 4-((3 --

Column 190, Structure 176, Line 10, "(s, 3H." should read -- (s, 3H). --

Column 192, Line 44, "below" should read -- below. --

Column 195, Line 65 (approx.), "(2.03 g)" should read -- (2.03 g). --

Column 196, Line 27, "☐L," should read -- µL, --

Column 196, Line 32, "mg)" should read -- mg). --

Column 201, Line 65 (approx.), "184E" should read -- 184B --

Column 204, Line 41 (approx.), "(S)-(1-(cyclohexyl amino)-3-(3-" should read -- (S)-(1-(cyclohexylamino)-3-(3- --

Column 216, Structure 194, Lines 3-4, "533.1 m/z" should read -- m/z 533.1 --

Column 218, Structure 198, Line 10, "1H." should read -- 1H). --

Column 227, Line 67, "ee % (n.d.)" should read -- (ee % n.d.) --

Column 229, Line 29 (approx.), "Example 1," should read -- Example 1. --

Column 236, Structure 215, Line 1, "d 11.70" should read -- δ 11.70 --

Column 243, Line 38, "mg)" should read -- mg). --

Column 246, Structure 220, Line 7, "112 Hz," should read -- 13.2 Hz, --

Column 249, Lines 29-41 (approx.), " 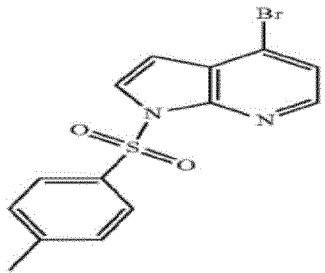 " should read -- 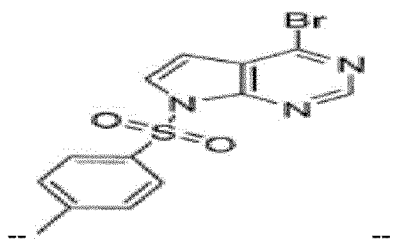 --

Columns 259-260, Example 55, Line 1, "Diacel Chiralpak" should read -- Daicel Chiralpak --

Column 261, Line 17, "Km)." should read -- Km)). --

In the Claims

Column 265, Line 32 (approx.), Claim 1, "($C_1$-$C_6$) alkoxy-($C_1$-$C_6$) alkyl" should read -- ($C_1$-$C_6$) alkoxy ($C_1$-$C_6$) alkyl, --

Column 265, Line 63 (approx.), Claim 1, "($C_1$-$C_6$) alkoxy($C_1$-$C_6$) alkyl," should read -- ($C_1$-$C_6$) alkoxy ($C_1$-$C_6$) alkyl, --

Column 266, Line 2, Claim 1, "heteroaryl($C_1$-$C_6$)alkyl" should read -- heteroaryl($C_1$-$C_6$)alkyl, --

Column 266, Line 38, Claim 1, "heteroaryl-carbonyl" should read -- heteroaryl-carbonyl, --

Column 266, Line 41, Claim 1, "($C_3$-$C_8$)cycloalkyl($C_1$-$C_6$)alkyl" should read -- ($C_3$-$C_8$)cycloalkyl ($C_1$-$C_6$)alkyl, --

Column 266, Line 52, Claim 1, "H," should read -- —H, --

Column 266, Line 61, Claim 1, "($C_3$-$C_6$) cycloalkyl-carbonyl" should read -- ($C_3$-$C_6$) cycloalkyl-carbonyl, --

Column 266, Line 62, Claim 1, "(C$_3$-C$_6$) heterocycloalkyl-carbonyl" should read -- (C$_3$-C$_6$) heterocycloalkyl-carbonyl, --

Column 267, Line 9, Claim 1, "H," should read -- —H, --

Column 267, Line 34, Claim 1, "H," should read -- —H, --

Column 267, Line 38, Claim 1, "—NR$_7$R$_8$" should read -- —NR$_7$R$_8$, --

Column 268, Line 15, Claim 3, "(C$_3$-C$_8$)cycloalkyl(C$_1$-C$_6$)alkyl" should read -- (C$_3$-C$_8$)cycloalkyl(C$_1$-C$_6$)alkyl, --

Column 268, Line 63, Claim 5, "Fluoro" should read -- Fluoro, --

Column 268, Line 64, Claim 5, "NR$_7$R$_8$," should read -- —NR$_7$R$_8$, --

Column 269, Line 2, Claim 5, "hydroxyethyl" should read -- hydroxyethyl, --

Column 269, Line 17, Claim 5, "thiopheneyl" should read -- thiophenyl --

Column 269, Line 53, Claim 5, "(thiophene-yl)methyl," should read -- (thiophenyl)methyl, --

Column 270, Lines 29-30 (approx.), Claim 5, "benzo[d][1,3]dioxol-5-ylmethyl)piperazin-N-yl," should read -- (benzo[d][1,3]dioxol-5-ylmethyl)piperazin-N-yl, --

Column 270, Lines 40-41, Claim 5, "3-(dimethylamino)methyl-azetidin-N-yl" should read -- 3-(dimethylamino)methyl-azetidin-N-yl, --

Column 270, Lines 50-51, Claim 5, "7,8-dihydropyrido[4,3-d]pyrimidin-6(5H)-yl)," should read -- (7,8-dihydropyrido[4,3-d]pyrimidin-6(5H)-yl), --

Column 271, Line 31 (approx.), Claim 6, "(4-(pyridin-3-yloxy)" should read -- (4-(pyridin-3-yl)oxy) --

Column 272, Line 24, Claim 6, "((3 aR,6aS)" should read -- ((3aR,6aS) --

Column 276, Line 2, Claim 6, "((1 S,4S)" should read -- ((1S,4S) --

Column 276, Line 17, Claim 6, "yloxy)" should read -- yl)oxy) --

Column 278, Line 27, Claim 6, "(phenyl amino)" should read -- (phenylamino) --

Column 280, Line 61, Claim 7, "or a" should read -- or --

Column 281, Line 3, Claim 9, "effectrive" should read -- effective --

Column 281, Line 8, Claim 11, "composition," should read -- composition --

Column 281, Line 9, Claim 11, "or a" should read -- or --

Column 281, Line 13, Claim 11, "prostaciclin" should read -- prostacyclin --